US012583923B2

(12) United States Patent
Perez et al.

(10) Patent No.: US 12,583,923 B2
(45) Date of Patent: *Mar. 24, 2026

(54) CHIMERIC ANTIGEN AND T CELL RECEPTORS AND METHODS OF USE

(71) Applicant: Kite Pharma, Inc., Santa Monica, CA (US)

(72) Inventors: Arianne Perez, Woodland Hills, CA (US); Stuart A. Sievers, Van Nuys, CA (US); Ruben Alvarez Rodriguez, Los Angeles, CA (US); Jonathan Belk, Lebanon, NH (US); Jed Wiltzius, Woodland Hills, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/006,997

(22) Filed: Dec. 31, 2024

(65) Prior Publication Data

US 2025/0145707 A1 May 8, 2025

Related U.S. Application Data

(60) Continuation of application No. 18/470,745, filed on Sep. 20, 2023, which is a division of application No. 16/711,180, filed on Dec. 11, 2019, now Pat. No. 11,793,834.

(60) Provisional application No. 62/778,893, filed on Dec. 12, 2018.

(51) Int. Cl.

| | |
|---|---|
| *A61K 40/31* | (2025.01) |
| *A61K 40/11* | (2025.01) |
| *A61K 40/42* | (2025.01) |
| *A61P 35/00* | (2006.01) |
| *C07K 16/28* | (2006.01) |
| *C12N 5/0783* | (2010.01) |
| *C12N 5/10* | (2006.01) |
| *C12N 15/63* | (2006.01) |
| *A61K 39/00* | (2006.01) |

(52) U.S. Cl.
CPC .......... *C07K 16/2803* (2013.01); *A61K 40/11* (2025.01); *A61K 40/31* (2025.01); *A61K 40/4211* (2025.01); *A61K 40/4221* (2025.01); *A61P 35/00* (2018.01); *C07K 16/2887* (2013.01); *C07K 16/2896* (2013.01); *C12N 5/0636* (2013.01); *C12N 5/10* (2013.01); *C12N 15/63* (2013.01); *A61K 2039/505* (2013.01); *A61K 2239/29* (2023.05); *A61K 2239/31* (2023.05); *A61K 2239/38* (2023.05); *C07K 2317/24* (2013.01); *C07K 2317/56* (2013.01); *C07K 2317/565* (2013.01); *C07K 2317/622* (2013.01); *C07K 2317/73* (2013.01); *C07K 2317/76* (2013.01)

(58) Field of Classification Search
CPC .......... A61K 39/3955; A61K 39/39558; A61K 40/11; A61K 40/31; A61K 40/32; A61K 40/33; A61K 40/4211; A61K 40/421; A61K 40/4224; C07K 16/2896; C07K 16/2803; C07K 16/2887; C12N 5/0636; C12N 5/10; C12N 15/63
See application file for complete search history.

(56) References Cited

U.S. PATENT DOCUMENTS

| | | | |
|---|---|---|---|
| 4,946,778 | A | 8/1990 | Ladner et al. |
| 5,091,513 | A | 2/1992 | Huston et al. |
| 5,132,405 | A | 7/1992 | Huston et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,591,827 | A | 1/1997 | Brakenhoff et al. |
| 5,625,126 | A | 4/1997 | Lonberg et al. |
| 5,633,425 | A | 5/1997 | Lonberg et al. |

(Continued)

FOREIGN PATENT DOCUMENTS

| | | |
|---|---|---|
| CN | 103820393 | 5/2014 |
| CN | 106701827 | 5/2017 |

(Continued)

OTHER PUBLICATIONS

Whitlow et al. An improved linker for single-chain Fv with reduced aggregation and enhanced proteolytic stability. Protein Engin 6(8) : 989-995, 1993.*

(Continued)

*Primary Examiner* — Bridget E Bunner
(74) *Attorney, Agent, or Firm* — Sheppard Mullin Richter & Hampton LLP

(57) ABSTRACT

Provided is a chimeric antigen receptor (CAR) or a T cell receptor (TCR) comprising one or more of the antigen binding motifs disclosed herein. Aspects of the disclosure relate to a polynucleotide encoding a chimeric antigen receptor (CAR) or a T cell receptor (TCR) comprising one or more of the antigen binding motifs. Provided are antibodies and antigen binding systems that comprise a binding motif that binds CD20 and optionally a binding motif that binds CD19, and methods of producing and using the same. Antibodies and antigen binding systems of the present disclosure comprise CARs that comprise an anti-CD20 binding motif and an anti-CD19 binding motif. Provided are compositions, such as antibodies and CARs that are or comprise an anti-CD20/anti-CD19 antigen binding system of the present disclosure, and cell therapies comprising the same, are useful, e.g., in the treatment of cancer.

29 Claims, No Drawings
Specification includes a Sequence Listing.

(56) References Cited

U.S. PATENT DOCUMENTS

| | | | |
|---|---|---|---|
| 5,661,016 A | 8/1997 | Lonberg et al. | |
| 5,728,388 A | 3/1998 | Terman | |
| 5,827,642 A | 10/1998 | Riddell et al. | |
| 5,830,462 A | 11/1998 | Crabtree et al. | |
| 5,834,266 A | 11/1998 | Crabtree et al. | |
| 5,869,337 A | 2/1999 | Crabtree et al. | |
| 6,040,177 A | 3/2000 | Riddell et al. | |
| 6,165,787 A | 12/2000 | Crabtree et al. | |
| 6,319,494 B1 | 11/2001 | Capon et al. | |
| 6,410,319 B1 | 6/2002 | Raubitschek et al. | |
| 6,797,514 B2 | 9/2004 | Berenson et al. | |
| 6,867,041 B2 | 3/2005 | Berenson et al. | |
| 6,905,874 B2 | 6/2005 | Berenson et al. | |
| 7,709,226 B2 | 5/2010 | Foote | |
| 7,741,465 B1 | 6/2010 | Eshhar et al. | |
| 8,211,422 B2 | 7/2012 | Eshhar et al. | |
| 8,486,693 B2 | 7/2013 | Park et al. | |
| 8,562,991 B2 | 10/2013 | Igawa et al. | |
| 8,679,492 B2 | 3/2014 | Blein et al. | |
| 9,296,820 B2 | 3/2016 | Umana et al. | |
| 9,834,590 B2 | 12/2017 | Campana et al. | |
| 9,855,298 B2 | 1/2018 | Bot et al. | |
| 9,987,308 B2 | 6/2018 | Riddell et al. | |
| 10,221,245 B2 | 3/2019 | Brogdon et al. | |
| 10,287,350 B2 | 5/2019 | Kochenderfer | |
| 10,493,139 B2 | 12/2019 | Wu et al. | |
| 11,723,923 B2 | 8/2023 | Perez et al. | |
| 11,793,834 B2 | 10/2023 | Perez et al. | |
| 2002/0006409 A1 | 1/2002 | Wood | |
| 2004/0126363 A1 | 7/2004 | Jensen et al. | |
| 2007/0014720 A1 | 1/2007 | Gazit-bornstein et al. | |
| 2010/0104509 A1 | 4/2010 | King et al. | |
| 2011/0286980 A1 | 11/2011 | Brenner | |
| 2012/0093842 A1 | 4/2012 | Eshhar et al. | |
| 2012/0130076 A1 | 5/2012 | Holt et al. | |
| 2012/0213783 A1 | 8/2012 | Rosenberg et al. | |
| 2013/0266551 A1 | 10/2013 | Campana et al. | |
| 2013/0287748 A1 | 10/2013 | June et al. | |
| 2014/0050708 A1 | 2/2014 | Powell et al. | |
| 2014/0099309 A1 | 4/2014 | Powell, Jr. et al. | |
| 2014/0134195 A1 | 5/2014 | Russell | |
| 2014/0154228 A1 | 6/2014 | Volk et al. | |
| 2014/0171649 A1 | 6/2014 | Li et al. | |
| 2014/0227237 A1 | 8/2014 | June et al. | |
| 2014/0271635 A1 | 9/2014 | Brogdon et al. | |
| 2014/0286934 A1 | 9/2014 | Blein et al. | |
| 2014/0286987 A1 | 9/2014 | Spencer et al. | |
| 2015/0038684 A1 | 2/2015 | Jensen | |
| 2015/0202286 A1 | 7/2015 | June et al. | |
| 2015/0266973 A1 | 9/2015 | Jarjour et al. | |
| 2015/0283178 A1 | 10/2015 | June et al. | |
| 2016/0009813 A1 | 1/2016 | Themeli et al. | |
| 2016/0046700 A1 | 2/2016 | Foster et al. | |
| 2017/0173080 A1 | 6/2017 | Lee et al. | |
| 2017/0368098 A1 | 12/2017 | Chen et al. | |
| 2018/0355052 A1 | 12/2018 | Orentas et al. | |
| 2018/0371093 A1 | 12/2018 | Bilic et al. | |
| 2019/0119638 A1 | 4/2019 | Sadelain et al. | |
| 2019/0151361 A1 | 5/2019 | Wiezorek | |
| 2019/0358262 A1 | 11/2019 | Albertson | |
| 2019/0359697 A1 | 11/2019 | Young et al. | |
| 2019/0388471 A1 | 12/2019 | June et al. | |
| 2020/0002400 A1 | 1/2020 | Yao et al. | |
| 2020/0283729 A1 | 9/2020 | Loew et al. | |
| 2021/0145304 A1 | 5/2021 | Visweswara et al. | |
| 2021/0147569 A1 | 5/2021 | Press et al. | |
| 2021/0161959 A1 | 6/2021 | Bot et al. | |
| 2022/0160729 A1 | 5/2022 | Deisher | |
| 2022/0281976 A1 | 9/2022 | Rosenthal et al. | |
| 2022/0387492 A1 | 12/2022 | Bot et al. | |
| 2022/0389449 A1 | 12/2022 | Paul et al. | |
| 2023/0255962 A1 | 8/2023 | Boiko et al. | |
| 2023/0374105 A1 | 11/2023 | Bitter et al. | |
| 2024/0018256 A1 | 1/2024 | Chen et al. | |
| 2024/0058381 A1 | 2/2024 | Wiezorek | |
| 2024/0082307 A1 | 3/2024 | Bot et al. | |
| 2024/0115611 A1 | 4/2024 | Perez et al. | |
| 2024/0252538 A1 | 8/2024 | Brannetti et al. | |
| 2024/0279665 A1 | 8/2024 | Zhao et al. | |
| 2025/0002579 A1 | 1/2025 | Cooper et al. | |

FOREIGN PATENT DOCUMENTS

| | | | |
|---|---|---|---|
| CN | 108384760 A | | 8/2018 |
| WO | WO-9715669 | | 5/1997 |
| WO | WO-2007002223 | | 1/2007 |
| WO | WO-2006130458 | | 2/2007 |
| WO | WO-2008081035 | | 7/2008 |
| WO | WO-2009091826 | | 7/2009 |
| WO | WO-2009054863 | | 9/2009 |
| WO | WO-2010095031 | | 8/2010 |
| WO | WO-2012033885 | | 3/2012 |
| WO | WO-2012079000 | | 6/2012 |
| WO | WO-2012129514 | | 9/2012 |
| WO | WO-2012138475 | | 10/2012 |
| WO | WO-2013123061 | | 8/2013 |
| WO | WO-2013154760 | | 10/2013 |
| WO | WO-2014055657 | | 4/2014 |
| WO | WO-2014127261 | | 8/2014 |
| WO | WO-2014153270 | | 9/2014 |
| WO | WO-2014184744 | | 11/2014 |
| WO | WO-2014186469 | | 11/2014 |
| WO | WO-2015075468 | | 5/2015 |
| WO | WO-2015080981 | | 6/2015 |
| WO | WO-2015090229 | | 6/2015 |
| WO | WO-2015120096 | | 8/2015 |
| WO | WO-2015123642 | | 8/2015 |
| WO | WO-2015142675 | | 9/2015 |
| WO | WO-2015187528 | | 12/2015 |
| WO | WO-2016033570 | | 3/2016 |
| WO | WO-2016044745 | | 3/2016 |
| WO | WO-2016069282 | | 5/2016 |
| WO | WO-2016090369 | | 6/2016 |
| WO | WO-2016100232 | | 6/2016 |
| WO | WO-2016164731 | | 10/2016 |
| WO | WO-2016191755 | | 12/2016 |
| WO | WO-2016191756 | | 12/2016 |
| WO | WO-2016201389 | | 12/2016 |
| WO | WO-2016210293 | | 12/2016 |
| WO | WO-2016210293 A1 * | | 12/2016 |
| WO | WO-2017015783 | | 2/2017 |
| WO | WO-2017025038 | | 2/2017 |
| WO | WO-2017070395 | | 4/2017 |
| WO | WO-2017161353 | | 9/2017 |
| WO | WO-2017189959 | | 11/2017 |
| WO | WO-2017222593 A1 * | | 12/2017 |
| WO | WO-2018067992 | | 4/2018 |
| WO | WO-2018102786 | | 6/2018 |
| WO | WO-2018145648 | | 8/2018 |
| WO | WO-2018161017 | | 9/2018 |
| WO | WO-2018183927 | | 10/2018 |
| WO | WO-2018213337 | | 11/2018 |
| WO | WO-2019058348 | | 3/2019 |
| WO | WO-2019079564 | | 4/2019 |
| WO | WO-2021092290 | | 5/2021 |
| WO | WO-2015157252 | | 10/2025 |

OTHER PUBLICATIONS

Al-Lazikani et al., "Standard conformations for the canonical structures of immunoglobulins" J Mol Bioi 273: 927-948 (1997).

Akbar et al., "A compact vocabulary of paratope-epitope interactions enables predictability of antibody-antigen binding," Cell Reports, 34 pp. 1-21 (Year: 2021).

Albanza et al., "Function of Novel Anti-CD19 Chimeric Antigen Receptors with Human Variable Regions Is Affected by Hinge and Transmembrane Domains," Mol. Ther., 25(11), 2452-2465 (Epub Jul. 27, 2017).

Ando et al., A Safeguard System for Induced Pluripotent Stem Cell-Derived Rejuvenated T Cell Therapy, Stem Cell Reports 2015, vol. 5, pp. 597-608.

Arnon et al., "Monoclonal Antibodies and Cancer Therapy", pp. 243-256, Alan R. Liss, Inc. (1985).

(56)        References Cited

OTHER PUBLICATIONS

Barbas et al., "Recombinant human Fab fragments neutralize human type 1 immunodeficiency virus in vitro", Proc. Natl. Acad. Sci. USA, 89(19): 9339-43 (1992).
Beatty et al., "Mesothelin-specific chimeric antigen receptor mRNA-engineered T cells induce antitumor activity in solid malignancies," Cancer Immunology Research, 2(2), 112-120 (2014).
Brentjens et al., "CD19-targeted T cells rapidly induce molecular remissions in adults with chemotherapy-refractory acute lymphoblastic leukemia," ScienceTranslational Medicine, 5(177), 177ra38 (2013), 19 pages, Author Manuscript.
Brentjens et al., "Eradication of systemic B-cell tumors by genetically targeted human T lymphocytes co-stimulated by COBO and interleukin-15," Nature Medicine, 9(3), 279-286 (2003).
Brentjens et al., "Genetically targeted T cells eradicate systemic acute lymphoblastic leukemia xenografts," Clinical Cancer Research, 13(18), 5426-5435 (2007).
Brentjens et al., "Novel cellular therapies for leukemia: CAR-modified T cells targeted to the CD19 antigen," Hematology. American Society of Hematology. Education Program, 2012, 143-151 (2012).
Brentjens et al., "Safety and persistence of adoptively transferred autologous CD19-targeted T cells in patients with relapsed or chemotherapy refractory B-cell leukemias," Blood, 118 (18), 4817-4828 (2011).
Brudno et al., "Clinical anti-lymphoma activity and toxicity of T cells expressing a novel anti-CD19 chimeric antigen receptor with fully-human variable regions," ASCO Meeting Library, abstract cited in J Clin Oncol., 36, 2018 (suppl; abstr 3052).
Brudno et al., "Toxicities of Chimeric Antigen Receptor T Cells: Recognition and Management," Blood, May 20, 2016 (online), pp. 3321-3330, vol. 127, No. 26.
Burns et al., "Vesicular stomatitis virus G glycoprotein pseudotyped retroviral vectors: concentration to very high titer and efficient gene transfer into mammalian and non mammalian cells," Proc. Natl. Acad. Sci., USA, 90 (17), 8033-8037 (1993).
Cartellieri et al., Chimeric Antigen Receptor-Engineered T Cells for Immunotherapy of Cancer. Journal of Biomedicine and Biotechnology 2010, XP055206629, doi: 10.1155/2010/956304. 13 pages.
Champe et al., "Monoclonal Antibodies That Block the Activity of Leukocyte Function-associated Antigen 1 Recognize Three Discrete Epitopes in the Inserted Domain of CD11a", J Biol Chem, 270(3): 1388-94 (1995).
Chayen, "The role of oil in macromolecular crystallization", Structure, 5(10): 1269-1274 (1997).
Cheadle et al., "Natural expression of the CD19 antigen impacts the long-term engraftment but not antitumor activity of CD19-specific engineered T cells," Journal of Immunology, 184 (4), 1885-1896 (2010).
Chen et al., Discovery of Small-Molecule Inhibitors of HCV NS3-4A Protease as Potential Therapeutic Agents against HCV Infection. Current Medicinal Chemistry 2005, vol. 12, No. 20, doi:10.2174/0929867054864769, pp. 2317-2342, XP009110972.
Cheung et al., "Epitope-specific antibody response to the surface antigen of duck hepatitis B virus in infected ducks", Virology 176(2): 546-552 (1990).
Chothia et al., "Canonical structures for the hypervariable regions of immunoglobulins", J Mol Biol, 196: 901-917 (1987).
Chothia et al., "Structural repertoire of the human VH segments" J Mol Biol, 227: 799-817 (1992).
Cole et al., In: "Monoclonal Antibodies and Cancer Therapy", Alan R. Liss, Inc., pp. 77-96 (1985).
Cooper et al., "T-cell clones can be rendered specific for CD19: toward the selective augmentation of the graft-versus-B-lineage leukemia effect," Blood, 101 (4), 1637-1644 (2003).
Cote et al., Generation of human monoclonal antibodies reactive with cellular antigens, Proc Natl Acad Sci USA, 80 (7): 2026-2030 (1983).

Cunningham et al., "High-resolution epitope mapping of hGH-receptor interactions by alanine-scanning mutagenesis", Science 244(4908): 1081-85 (1989).
Dayhoff et al., "Atlas of Protein Sequence and Structure: A Model of Evolutionary Change in Proteins", 5: 345-352 (1978).
Devereux et al., "A comprehensive set of sequence analysis programs for the VAX", Nucl. Acid Res., 12: 387-395 (1984).
Eshhar et al., "Tumor-specific T-bodies: towards clinical application", Cancer Immunol Immunotherapy, 45(3-4): 131-136 (1997).
Examination Report for New Zealand Application No. 777087 dated Nov. 20, 2023. 3 pages.
Examination Report for Australian Application No. 2019397033 dated Mar. 9, 2023. 5 pages.
Examiner Requisition for Canadian Application No. 3, 122,762 dated Jul. 29, 2022. 4 pages.
Fegan et al. "Chemically controlled protein assembly: techniques and applications", Chem. Rev., 110(6): 3315-3336 (2010).
Finney et al., "Chimeric receptors providing both primary and costimulatory signaling in T cells from a single gene product", Journal of Immunology, 161(6): 2791-2797 (1998).
First Examination Report dated Sep. 2, 2021 in GCC Appl. No. GC 2019-38820.
Fishwild et al., "High-avidity human IgG kappa monoclonal antibodies from a novel strain of minilocus transgenic mice." Nature Biotechnology, 14(7): 845-51 (1996).
Galon et al., Characterization of anti-CD19 chimeric antigen receptor (CAR) T cell-mediated tumor microenvironment immune gene profile in a multicenter trial (ZUMA-1) with axicabtagene ciloleucel (axi-cel, KTE-C19). J. Clin Oncol. 2017;35(15), Abstract 3025. 4 pages.
Gen Bank Accession No. ADM64594.1, published Jun. 11, 2012.
Giege et al., "Crystallogenesis of biological macromolecules: facts and perspectives", Acta Crystallogr D Biol Crystallogr, 50(Pt 4): 339-350 (1994).
Gross et al., "Therapeutic Potential of T Cell Chimeric Antigen Receptors (CARs) in Cancer Treatment: Counteracting Off-Tumor Toxicities for Safe CART Cell Therapy", Annu. Rev. Pharmacol. Toxicol., 56: 59-83 (2016).
Grupp et al., "Chimeric antigen receptor-modified T cells for acute lymphoid leukemia," New England Journal of Medicine, 368 (16), 1509-1518 (2013).
Gust et al., Endothelial Activation and Blood-Brain Barrier Disruption in Neurotoxicity after Adoptive Immunotherapy with CD19 CAR-T Cells. Cancer Discovery 2017, 7(12), pp. 1404-1419.
Hellstrom et al., "Antibodies For Drug Delivery", in Controlled Drug Delivery (2nd Ed.), Robinson et al. (eds.), Marcel Dekker, Inc., 623-53 (1987).
Henikoff et al., "Amino acid substitution matrices from protein blocks", Proc. Natl. Acad. Sci. U.S.A., 89(22): 10915-10919 (1992).
Hermans et al., "The vital assay: a versatile fluorometric technique for assessing CTL- and NKT-mediated cytotoxicity against multiple targets in vitro and in vivo," Journal of Immunological Methods, 285 (1), 25-40 (2004).
Highlights of Prescribing Information for ACTEMRA® (tocilizumab) (Aug. 2017).
Hombach et al., "Costimulation by chimeric antigen receptors revisited the T cell antitumor response benefits from combined CD28-OX40 signalling," International Journal of Cancer, 129 (12), 2935-2944 (2011).
Hoogenboom et al., By-passing immunisation: Human antibodies from synthetic repertoires of germline VH gene segments rearranged in vitro, J. Mol. Biol., 227(2): 381-388 (1991).
Huston et al., "Protein engineering of antibody binding sites: recovery of specific activity in an anti-digoxin single-chain Fv analogue produced in *Escherichia coli*", Proc Nat Acad Sci USA 85(16):5879-5883 (1988).
International Search Report and Written Opinion for International Application No. PCT/US2019/065776 dated Jun. 24, 2020. 21 pages.
Jena et al., Redirecting T-cell specificity by introducing a tumor-specific chimeric antigen receptor. Blood 2010; vol. 116, No. 7, pp. 1035-1044, XP055021403.

(56)                    References Cited

OTHER PUBLICATIONS

Jensen et al., "Antitransgene rejection responses contribute to attenuated persistence of adoptively transferred CD20/CD19-specific chimeric antigen receptor redirected T cells in humans," Biology of Blood and Marrow Transplantation, 16 (9), 1245-1256 (2010).

Kabat et al., "Attempts to locate complementarity-determining residues in the variable positions of light and heavy chains", Ann NY Acad Sci, 190: 382-391 (1971).

Kalos et al., T cells with chimeric antigen receptors have potent antitumor effects and can establish memory in patients with advanced leukemia, Sci. Transl. Med., 3(95): 95ra73 (2011).

Kirkland et al., "Analysis of the fine specificity and cross-reactivity of monoclonal anti-lipid A antibodies", J. Immunol. 137(11): 3614-3619 (1986).

Klein et al., "Epitope interactions of monoclonal antibodies targeting CD20 and their relationship to functional properties," mAbs 5:1, pp. 22-33 (Year: 2013).

Kochenderfer et al., "B-cell depletion and remissions of malignancy along with cytokine-associated toxicity in a clinical trial of anti-CD19 chimeric-antigen-receptor-transduced T cells," Blood, 119(12), 2709-2720 (2012).

Kochenderfer et al., "Chemotherapy-Refractory Diffuse Large B-Cell Lymphoma and Indolent B- Cell Malignancies Can Be Effectively Treated With Autologous T Cells Expressing an Anti-CD19 Chimeric Antigen Receptor", J. Clinical Oncology, pp. 540-549, vol. 33, No. 6 (2015).

Kochenderfer et al., "Construction and Pre-clinical Evaluation of an Anti-CD19 Chimeric Antigen Receptor", J Immunother., 32(7): 689-702 (2009).

Kochenderfer et al., "Eradication of B-lineage cells and regression of lymphoma in a patient treated with autologous T cells genetically engineered to recognize CD19," Blood, 116 (20), 4099-4102 (2010).

Kochenderfer et al., "Treating B-cell cancers with T cells expressing anti CD19 chimeric antigen receptors," Nature Reviews. Clinical Oncology, 10(5), 267-276 (2013).

Kozbor et al., "The production of monoclonal antibodies from human lymphocytes", Immunol Today, 4(3): 72-9 (1983).

Krause et al., "Antigen-dependent CD28 Signaling Selectively Enhances Survival and Proliferation in Genetically Modified Activated Human Primary T Lymphocytes", J. Exp. Med., 188(4): 619-626 (1998).

Lamers et al., "Immune responses to transgene and retroviral vector in patients treated with ex vivo-engineered T cells," Blood, 117 (1), 72-82 (2011).

Latza et al., "The human OX40 homolog: cDNA structure, expression and chromosomal assignment of the ACT35 antigen," European Journal of Immunology, 24 (3), 677-683 (1994).

Lee et al., Current concepts in the diagnosis and management of cytokine release syndrome, Blood 2014, 124(2): pp. 188-195.

Ling et al., "Advances in cancer immunotherapy based on chimeric antigen receptor," Translational Med. J., 4 (3), 97-104 (2015).

Lippow et al., "Computational design of antibody-affinity improvement beyond in vivo maturation," Nature Biotechnology, 25(10) pp. 1171-1176. (Year: 2007).

Littman et al., The isolation and sequence of the gene encoding T8: A molecule defining functional classes of T lymphocytes, Cell 1985, vol. 40, pp. 237-246.

Lo et al., "Conformational epitope matching and prediction," BMC Genomics, 22(Suppl 2) pp. 1-16 (Year: 2021).

Locke et al., "Phase 1 Results of ZUMA-1: A Multicenter Study of KTE-C19 Anti-CD19 CAR T Cell Therapy in Refractory Aggressive Lymphoma", Molecular Therapy, pp. 285-295, vol. 25, No. 1 (2017).

Locke et al., Abstract CT019: Primary results from ZUMA-1: a pivotal trial of axicabtagene ciloleucel (axicel; KTE-C19) in patients with refractory aggressive non-Hodgkin lymphoma (NHL). AACR Annual Meeting 2017. 4 pages.

Locke et al., Updated Phase 1 Results from ZUMA-1: Molecular Therapy, vol. 24, Supplement 1, (Year: 2016). 1 page.

Lonberg et al. "Human antibodies from transgenic mice", Intern. Rev. Immunol., 13(1) 65-93 (1995).

Lonberg et al., "Antigen-specific human antibodies from mice comprising four distinct genetic modifications", Nature, 368(6474): 856-859 (1994).

Lu et al., "A Rapid Cell Expansion Process for Production of Engineered Autologous CAR-T Cell Therapies", Human Gene Therapy Methods, pp. 209-218, vol. 27, No. 6. (2016).

Mannering et al., "A sensitive method for detecting proliferation of rare autoantigen-specific human T cells," Journal of Immunological Methods, 283 (1-2), 173-183 (2003).

Marks et al., "By-passing immunization. Human antibodies from V-gene libraries displayed on phage", J. Mol. Biol., 22(3):581-97 (1991).

Marks et al., "By-passing immunization: building high affinity human antibodies by chain shuffling", Biotechnology, 10(7):779-783 (1992).

McPherson, "Crystallization of Proteins from Polyethylene Glycol", J Biol Chem, 251 (20): 6300-6303 (1976).

McPherson, "Current approaches to macromolecular crystallization", Eur J Biochem, 189: 1-23 (1990).

Moldenhauer et al., Identity of HML-1 Antigen on Intestinal Intraepithelial T Cells and of B-ly7 Antigen on Hairy Cell Leukaemia, Scandinavian Journal of Immunology, 32(2): 77-82 (1990).

Moran et al., "The TNFRs OX40, 4-1 BB, and CD40 as targets for cancer immunotherapy," Current Opinion in Immunology, 25 (2), 230-237 (2013).

Morel et al., "Monoclonal antibodies to bovine serum albumin: affinity and specificity determinations", Mol Immunol, 25(1): 7-15 (1988).

Morrison, "Success in specification", Nature, 368, 812-13 (1994).

Nadler et al., "84, a human B lymphocyte-associated antigen expressed on normal, mitogen-activated, and malignant B lymphocytes," Journal of Immunology, 131 (1), 244-250 (1983).

Neelapu et al., "Axicabtagene Ciloleucel CAR T-Cell Therapy in Refractory Large B-Cell Lymphoma", The New England Journal of Medicine, pp. 2531-2544, vol. 377, No. 26 (2017).

Neuberger, "Generating high-avidity human Mabs in mice", Nature Biotechnology, 14: 826 (1996).

Nicholson et al., "Construction and characterisation of a functional CD19 specific single chain Fv fragment for immunotherapy of B lineage leukaemia and lymphoma," Molecular Immunology, 34 (16-17), 1157-1165 (1997).

Notice of Preliminary Rejection for Korean Application No. 10-2021-7021608 dated Oct. 20, 2024. 4 pages.

Notice of Preliminary Rejection for Korean Application No. 10-2021-7021608 dated Feb. 26, 2024. 6 pages.

Notice of Preliminary Rejection for Korean Application No. 10-2021-7021608 dated Aug. 18, 2023. 17 pages.

Ochi et al., "Functional immunoglobulin M production after transfection of cloned immunoglobulin heavy and light chain genes into lymphoid cells," Proceedings of the National Academy of Sciences of the United States of America, 80 (20), 6351-6355 (1983).

Office Action for Canadian Application No. 3,122,762 dated Nov. 4, 2024. 3 pages.

Office Action for Chinese Application No. 201980091506.9 dated Aug. 7, 2024. 15 pages.

Office Action for Chinese Application No. 201980091506.9 dated Mar. 18, 2024. 19 pages.

Office Action for Canadian Application No. 3,122,762 dated Sep. 18, 2023. 7 pages.

Office Action for Canadian Application No. 3,177,829 dated Feb. 23, 2024. 5 pages.

Office Action for Israeli Application No. 283734 dated Oct. 26, 2023. 5 pages.

Office Action and Search Report for Taiwan Application No. 110125603 dated Oct. 31, 2023. 20 pages.

Office Action for Japanese Application No. 2021-533159 dated Jan. 10, 2023. 4 pages.

Office Action for Japanese Application No. 2021-533159 dated Jul. 5, 2022. 10 pages.

Office Action, issued in TW Application No. 108145595, dated Jan. 13, 2021.

(56) References Cited

OTHER PUBLICATIONS

Park et al., Adoptive Transfer of Chimeric Antigen Receptor Re-directed Cytolytic T Lymphocyte Clones in Patients with Neuroblastoma. Molecular Therapy 2007, vol. 15, No. 4, pp. 825-833.

Patel et al., T-cell killing of heterogenous tumor or viral targets with bispecific chimeric immune receptors. Cancer Gene Therapy 2000, vol. 7, No. 8, pp. 1127-1134, XP055259929.

Pinchera et al. (eds.), "Analysis, Results, And Future Prospective Of The Therapeutic Use Of Radiolabeled Antibody In Cancer Therapy", in Monoclonal Antibodies For Cancer Detection And Therapy, pp. 475-506 (1985).

Porter et al., "Chimeric antigen receptor-modified T cells in chronic lymphoid leukemia", N. Engl. J. Med., 365(8):725-33 (2011).

Porter et al., "Comparison of efficiency of infection of human gene therapy target cells via four different retroviral receptors," Human Gene Therapy, 7 (8), 913-919 (1996).

Raboisson et al., Structure-activity relationship study on a novel series of cyclopentane-containing macrocyclic inhibitors of the hepatitis C virus NS3/4A protease leading to the discovery of TMC435350. Bioorganic & Medicinal Chemistry Letters 2008, vol. 18, No. 17, doi: 10.1016/J.BMCL.2008.07.088, pp. 4853-4858, XP024100116.

Ramos et al., "CAR-T Cell Therapy for Lymphoma," Annu. Rev. Med. 67, pp. 165-183 (Year: 2016).

Ren et al., Multiplex Genome Editing to Generate Universal Car T Cells Resistant to PD1 Inhibition, Clin Cancer Res 2017; 23(9); 2255-2266.

Rosenberg et al., "Adoptive cell transfer as personalized immunotherapy for human cancer", Cancer Immunology and Immunotherapy, 348: 62-68 (2015).

Rubio et al., "Ex vivo identification, isolation and analysis of tumor-cytolytic T cells," Nature Medicine, 9 (11), 1377-1382 (2003).

Ruella et al., "Chimeric Antigen Receptor T cells for B Cell Neoplasms: Choose the Right CAR for You", Curr Hematol Malig Rep, 11: 368-384 (2016).

Sadelain et al., "The Basic Principles of Chimeric Antigen Receptor Design", Cancer Discovery, 3:388-398 (2013).

Sadelain et al., "Targeting Tumors with Genetically Enhanced T Lymphocytes", Nature Rev. Cancer, 3: 35-45 (2003).

Savoldo et al., "CD28 costimulation improves expansion and persistence of chimeric antigen receptor-modified T cells in lymphoma patients," Journal of Clinical Investigation, 121 (5), 1822-1826 (2011).

Schneider et al., Minimizing leukemia escape: implementing a dual anti-CD20- and CD19-scFv-based chimeric antigen receptor (CAR). Journal for Immuno Therapy of Cancer 2015, vol. 3, No. 2, doi: 10.1186/2051-1426-3-S2-P122, XP021235172. 1 page.

Sommermeyer et al., Fully human CD19-specific chimeric antigen receptors for T-cell therapy, Leukemia 31(10): 2191-2199 (2017).

Song et al., "CD27 costimulation augments the survival and antitumor activity of redirected human T cells in vivo", Blood, 119(3): 696-706 (2012).

Stahli et al., "Distinction of epitopes by monoclonal antibodies", Methods in Enzymology, 92: 242-253 (1983).

Tammana et al., 4-1BB and CD28 Signaling Plays a Synergistic Role in Redirecting Umbilical Cord Blood T Cells Against B-Cell Malignancies, Human Gene Therapy 2010 , 21, pp. 75-86.

Thorpe et al., Monoclonal antibodies '84: biological and clinical applications : Proocedings of the International Symposium on Monoclonal antibodies '84 held in Florence, Italy, (Oct. 16-19, 1984).

Thorpe et al., "The preparation and cytotoxic properties of antibody-toxin conjugates", Immunol. Rev., 62: 119-58 (1982).

Tramontano et al., "Framework residue 71 is a major determinant of the position and conformation of the second hypervariable region in the VH domains of immunoglobulins" J Mol Biol, 215(1): 175-82 (1990).

Uniprot KB-P01732 (CD8A Human) (14 pages) Jul. 21, 1986.

Urbanska et al., Targeted cancer immunotherapy via combination of designer bispecific antibody and novel gene-engineered T cells. Journal of Translational Medicine 2014, vol. 12, No. 1, XP021207565. 12 pages.

Venkatraman et al., Macrocyclic inhibitors of HCV NS3 protease. Expert Opinion on Therapeutic Patents 2009, vol. 19, No. 9, doi: 10.1517/13543770903044994, pp. 1277-1303, XP055084885.

Watkins et al., "CD19-targeted Immunotherapies for Treatment of Patients with non-Hodgkin B-cell Lymphomas", Expert Opinion on Investigational Drugs, pp. 601-611, vol. 27, No. 7 (2018).

Weinberg et al., "Science gone translational: the OX40 agonist story," Immunological Reviews, 244 (1), 218-231 (2011), Author Manuscript.

Wong et al., "Ab-Ligity: identifying sequence-dissimilar antibodies that bind to the same epitope," MABS, vol. 13, No. 1 pp. 1-8 (Year: 2021).

Wu et al., "Remote control of therapeutic T cells through a small molecule-gated chimeric receptor", Science, 350:6258 (2014).

Yang et al., "A simplified method for the clinical-scale generation of central memory-like CDS+ T cells after transduction with lentiviral vectors encoding antitumor antigen T-cell receptors," Journal of Immunotherapy, 33 (6), 648-658 (2010).

Zebedee et al., "Human combinatorial antibody libraries to hepatitis B surface antigen", Proc. Natl. Acad. Sci. USA, 89(8): 3175-79 (1992).

Abramson et al., High Durable CR Rates in Relapsed/Refractory (R/R) Aggressive B-NHL Treated with the CD19-Directed Car T Cell Product JCAR017 (Transcend Nhl 001): Defined Composition Allows for Dose-Finding and Definition of Pivotal Cohort, Blood 2017, vol. 130, Supplement 1, p. 581.

Bhojwani et al. (2018), "Inotuzumab ozogamicin in pediatric patients with relapsed/refractory acute lymphoblastic leukemia", Leukemia, Acute lymphoblastic leukemia, accessed at https://doi.org/10.1038/s41375-018-0265-z, 1-9.

Bodogai et al. "Anti-CD20 Antibody Promotes Cancer Escape via Enrichment of Tumor-Evoked Regulatory B Cells Expressing Low Levels of CD20 and CD137L", Cancer Res 73(7): 2127-2138, 2013.

Borowitz et al. (2015), "Prognostic significance of minimal residual disease in high risk B-ALL: a report from Children's Oncology Group study AALL0232", Blood, 126(8), 964-971.

Brudno et al., Allogeneic T Cells That Express an Anti-CD19 Chimeric Antigen Receptor Induce Remissions of B-Cell Malignancies That Progress After Allogeneic Hematopoietic Stem-Cell Transplantation Without Causing Graft-Versus-Host Disease, Journal of Clinical Oncology 2016, vol. 34, No. 10, pp. 1112-1121.

Brudno et al., Chimeric antigen receptor T-cell therapies for lymphoma, Nature Reviews Clinical Oncology 2018, vol. 15, pp. 31-46.

BRÜGGEMANN et al. (2017), "Minimal residual disease in adult ALL: technical aspects and implications for correct clinical interpretation", Blood Advances, 1(25), 2456-2466.

Cannarile et al. (2017), "Colony-stimulating factor 1 receptor (CSF1R) inhibitors in cancer therapy", Journal for Immuno Therapy of Cancer, 5(53), 1-13.

Cao et al., Anti-CD19 Chimeric Antigen Receptor T Cells in Combination With Nivolumab Are Safe and Effective Against Relapsed/Refractory B-Cell Non-hodgkin Lymphoma, Frontiers in Oncology 2019, vol. 9, article 767.

Casan et al. Anti-CD20 monoclonal antibodies: reviewing a revolution. Human Vaccines Immunother 14 (12): 2820-2841, 2018.

Chen et al., Anti-CD19 Chimeric Antigen Receptor T Cells Improve Responses to Chemotherapy-Refractory Mantle Cell Lymphoma: A Case Report, Blood 2016, vol. 128, No. 22: 5393, DOI: 10.1182/blood.V128.22.5393.5393. 2 pages.

Cheson et al. (2007), "Revised Response Criteria for Malignant Lymphoma", Journal of Clinical Oncology, 25(5), 579-586.

Cheson et al. (2014), "Recommendations for Initial Evaluation, Staging, and Response Assessment of Hodgkin and Non-Hodgkin Lymphoma: The Lugano Classification", Journal of Clinical Oncology, 1-10.

Cho et al. Monoclonal Antibody: A New Treatment Strategy against Multiple Myeloma. Antibodies 6: 18, 2017, 22 pages.

(56) References Cited

OTHER PUBLICATIONS

Crotta et al. (2018), "Survival after stem-cell transplant in pediatric and young-adult patients with relapsed and refractory B-cell acute lymphoblastic leukemia", Curr Med Resin, Opin., 34, 1-18.

Deangelo et al. (2017), "32nd Annual Meeting and Pre-Conference Programs of the Society for Immunotherapy of Cancer (SITC 2017): Part One," Journal for Immuno Therapy of Cancer, 5 (Suppl 2)(86), P217.

Decision of Final Rejection for Japanese Application No. 2020-521585 dated Apr. 18, 2023. 9 pages.

Decision of Final Rejection for Japanese Application No. 2023-132752 dated Aug. 5, 2025, 4 pages.

Dolmans et al. (2003), "Photodynamic therapy for cancer", Nature Reviews, Cancer, 3, 380-397.

Enblad et al., A Phase I/IIa Trial Using CD19-Targeted Third-Generation Car T Cells for Lymphoma and Leukemia, Clinical Cancer Research 2018, vol. 24, No. 24, pp. 6185-6194, DOI: 10.1158/1078- 0432.CCR-18-0426.

Examination Report for Australia Patent Application No. 2018351046 dated Nov. 17, 2021. 4 pages.

Examination Report for Australian Application No. 2021282551 dated Dec. 14, 2022.4 pages.

Examination Report for Australian Application No. 2021282551 dated Nov. 7, 2022. 5 pages.

Examination Report for Australian Patent Application No. 2018351046 dated Nov. 16, 2020, 5 pages.

Examination Report for Australian Patent Application No. 2020380366 dated Jun. 7, 2024. 5 pages.

Examination Report for Australian Patent Application No. 2021282551 dated Jul. 29, 2022. 5 pages.

Examination Report for Australian Patent Application No. 2021282551 dated May 9, 2022. 4 pages.

Examination Report issued on Canadian application counterpart 3,084,470, mailed Mar. 23, 2021.

Final Office Action for Japanese Application No. 2023-132752 dated Feb. 12, 2025, 8 pages.

Fraietta et al., Determinants of response and resistance to CD19 chimeric antigen receptor (Car) T cell therapy of chronic lymphocytic leukemia, Nature Medicine 2018, vol. 24, pp. 563-571.

Frey et al. (2019), "Optimizing Chimeric Antigen Receptor T-Cell Therapy for Adults With Acute Lymphoblastic Leukemia", Journal of Clinical Oncology, 1-10.

Gilead Sciences Announces Fourth Quarter and Full Year 2018 Financial Results?Gilead?Feb. 4, 2019?https://s24.q4cdn.com/804398512/files/doc_news/archive/829f46cd-0ddb-43d5-bedb-3771670d8102.pdf.

Guedan et al., "Engineering and Design of Chimeric Antigen Receptors," Molecular Therapy: Methods & Clinical Development, 2019, vol. 12, pp. 145-156.

Gupta et al. (2018), "Flow-cytometric vs. morphologic assessment of remission in childhood acute lymphoblastic leukemia: a report from the Children's Oncology Group (COG)", Leukemia, Springer Nature, accessed at https://doi.org/10.1038/s41375-018-0039-7, 1-10.

Hamilton, "GM-CSF as a target in inflammatory/autoimmune disease: current evidence and future therapeutic potential", Expert Reviews, Clin. Immunol., 2015, Early online, accessed at 10.1586/1744666X.2015.1024110, 1-9.

Hay et al., Chimeric Antigen Receptor (Car) T Cells: Lessons Learned from Targeting of CD19 in B-Cell Malignancies. Drugs 2017, doi 10.1007/s40265-017-0690-8. 16 p. 77 (3) : 237-245.

Highlights of Prescribing Information for YESCARTA (axicabtagene ciloleucel), 2017, 31 pages.

Hirayama et al., The response to lymphodepletion impacts PFS in patients with aggressive non-Hodgkin lymphoma treated with CD19 Car T cells, Blood, 2019, vol. 133, No. 17, pp. 1876-1887.

International Search Report and Written Opinion for International Application No. PCT/US2018/056467 dated Apr. 21, 2020, 11 pages.

International Search Report and Written Opinion for International Application No. PCT/US2020/059285 dated Apr. 12, 2021. 9 pages.

Jaffe et al. "Understanding the New WHO Classification of Lymphoid Malignancies: Why it's Important and How It Will Affect Practice", Biol Blood Marrow Transplant 25 (2019) pg S7-S75.

Jain et al. (2019), "Mantle cell lymphoma: 2019 update on the diagnosis, pathogenesis, prognostication, and management", Annual Clinical Updates in Hematological Malignancies, 94, 710-725.

Jain et al., Axicabtagene ciloleucel (KTE-C19), an anti-CD19 Car T therapy for the treatment of relapsed/refractory aggressive B-cell non-Hodgkin's lymphoma, Therapeutics and Clinical Risk Management 2018, vol. 14, pp. 1007-1017.

Juo, Pei-Show (2002) "Concise dictionary of biomedicine and molecular biology." second edition, Library of Congress Cataloging-in-Publication Data, CRC Press, 1163.

Kantarjian et al. (2017), "Blinatumomab versus Chemotherapy for Advanced Acute Lymphoblastic Leukemia", The New England Journal of Medicine, 376(9), 836-847.

Kapoor et al. Anti-CD20 monoclonal antibody therapy in multiple myeloma. Brit J Haematol 141: 135-148, 2008.

Kite, A Gilead Company, "A Sutdy Evaluating the Safety and Efficacy of Brexucabtagene Autoleucel (KTE-X19) in Adult Subjects with Relapsed/Refractory B-precursor Acute Lymphoblastic Leukemia (ZUMA-3)", ClinicalTrials.gov, Trial No. NCT02614066, Dec. 3, 2018 (Mar. 12, 2018).

Kochenderfer et al. (2017), "Lymphoma Remissions Caused by Anti-CD19 Chimeric Antigen Receptor T Cells Are Associated With High Serum Interleukin-15 Levels", Journal of Clinical Oncology, 35(16), 1803-1813.

Kochenderfer et al., Adoptive transfer of syngeneic T cells transduced with a chimeric antigen receptor that recognizes murine CD19 can eradicate lymphoma and normal B cells. Blood. Nov. 11, 2010;116(19):3875-86.

Lackie et al. (2013)The Dictionary of Cell and Molecular Biology, 5th edition, Academic Press, 748 pages.

Larson et al., Pre-clinical development of gene modification of haematopoietic stem cells with chimeric antigen receptors for cancer immunotherapy, Human Vaccines & Immunotherapeutics 2017, vol. 13, No. 5, 1094-1104.

Lee et al. (2015), "T cells expressing CD19 chimeric antigen receptors for acute lymphoblastic leukaemia in children and young adults: a phase 1 dose-escalation trial", The Lancet, 385, 517-528.

Li et al., A good response of refractory mantel cell lymphoma to haploidentical Car T cell therapy after failure of autologous Car T cell therapy, Journal for ImmunoTherapy of Cancer 2019, vol. 7, No. 51. 7 pages.

Liu et al., Current approaches and advance in mantle cell lymphoma treatment, Stem Cell 2015, 2;18.

Locke et al., Abstract CT019: Primary results from ZUME-1: a pivotal trial of axicabtagene ciloleucel (axicel; KTEC19) in patients with refractory aggressive non-Hodgkin lymphoma (NHL), Cancer Research vol. 77, Supplement 13/CT019. 2017.

Mangogna et al. Rituximab Plus Chemotherapy Provides No. Clinical Benefit in a Peripheral T-Cell Lymphoma not Otherwise Specified with Aberrant Expression of CD20 and CD79a: A Case Report and Review of the Literature. Diagnostic 10: 341, 2020.

Martin et al., "Postibrutinib outcomes in patients with mantle cell lymphoma", Clinical Trials and Observations, Blood, vol. 127, No. 12, Mar. 24, 2016, pp. 1559-1563.

Maude et al. (2018), "Tisagenlecleucel in Children and Young Adults with B-Cell Lymphoblastic Leukemia", The New England Journal of Medicine, 378(5), 439-448.

Neelapu et al. (2018), "Chimeric antigen receptor T-cell therapy assessment and management of toxicities", Nature Reviews, Clinical Oncology, 15, 47-62.

Neelapu et al., "Kte-C19 (anti-CD19 Car T Cells) Induces Complete Remissions in Patients with Refractory Diffuse Large B-Cell Lymphoma (DLBCL): Results from the Pivotal Phase 2 Zuma-1," Blood, 2016, Abstract. 128 (22) : LBA-6.

Neelapu, 2-Year Follow-up and High-Risk Subset Analysis of Zuma-1, the Pivotal Study of Axicabtagene Ciloleucel (Axi-Cel) in Patients with Refractory Large B Cell Lymphoma Sattva S. Neelapu MD Abstracts / Biol Blood Marrow Transplant 25 (2019). S65, #82.

(56) References Cited

OTHER PUBLICATIONS

Nguyen et al. (2008), "Factors influencing survival after relapse from acute lymphoblastic leukemia: a Children's Oncology Group study", Leukemia, 22, 2142-2150.

Notice of Final Rejection for Korean Application No. 10-2020-7013686 dated Oct. 6, 2022. 8 pages.

Notice of Final Rejection Korean for Patent Application No. 10-2020-7013686 dated Jun. 3, 2022. 7.

Notice of Preliminary Rejection for Korean Patent Application No. 10-2020-7013686 dated Oct. 14, 2021.13 pages.

Office Action and Search Report for Chinese Application No. 201880067426.5 dated Feb. 4, 2023. 13 pages.

Office Action for Canadian Patent Application No. 3,084,470 dated Mar. 23, 2022. 4 pages.

Office Action for Japanese Application No. 2020-521585 dated Oct. 25, 2022. 8 pages.

Office Action with Search Report for Taiwan Application No. 107136797 dated Sep. 15, 2022. 12 Pages.

Official Action for Argentinian Patent Application No. 20180103032 dated Feb. 15, 2022. 9 pages.

Oskarsson et al. (2016), "Relapsed childhood acute lymphoblastic leukemia in the Nordic countries: prognostic factors, treatment and outcome", Acute Lymphoblastic Leukemia, Haematologica, 101(1), 68-76.

Partial Supplementary European Search Report for European Application No. 20886085.8 dated Apr. 5, 2024. 23 pages.

Penfold et al., "The FDA grants KTE-C19 Priority Review for the treatment of transplant-ineligible relapsed/refractory Non-Hodgkin Lymphoma," LymphomaHub, 2017, 1 page.

Rheingold et al. (2019), "Prognostic factors for survival after relapsed acute lymphoblastic leukemia (All): A Children's Oncology Group (COG) study", Journal of Clinical Oncology, List of Issues, 37(15), 1- 5.

Ruella et al., The Addition of the BTK Inhibitor Ibrutinib to Anti-CD19 Chimeric Antigen Receptor T Cells (CART19) Improves Responses against Mantle Cell Lymphoma, Clinical Cancer Research, 2016, 22(11):2684-2696.

Sabatino et al., "Production of Anti-CD19 Car T Cells for ZUMA-3 and -4: Phase 1/2 Multicenter Studies Evaluating KTE-C19 in Patients With Relapsed/Refractory B-Precursor Acute Lymphoblastic Leukemia (R/R All)", Blood, 128 (2), "™-6" 1227, 2016.

Sadelain et al., "CD19 Car Therapy for Acute Lymphoblastic Leukemia," American Society of Clinical Oncology Educational Book 2015, e360-e363.

Salles et al. Rituximab in B-Cell hematologic Malignancies: A Review of 20 Years of Clinical Experience. Adv Ther 34: 2232-2273, 2017.

Schrappe et al. (2012), "Outcomes after Induction Failure in Childhood Acute Lymphoblastic Leukemia", The New England Journal of Medicine, 366(15), 1371-1381.

Schuster et al. (2019), "Tisagenlecleucel in Adult Relapsed or Refractory Diffuse Large B-Cell Lymphoma", The New England Journal of Medicine, 380(1), 45-56.

Schuster et al., "Chimeric Antigen Receptor T Cells in Refractory B-Cell Lymphomas," The New England Journal of Medicine, 2017, vol. 377, pp. 2545-2554.

Shah et al., "High Rates of Minimal Residual Disease-Negative (MRD-) Complete Responses (CR) in Adult and Pediatric and Patients with Relapsed/Refractory Acute Lymphoblastic Leukemia (R/R All) Treated with KTE-C19 (anti-CD19 Chimeric Antigen Receptor [Car} T Cells): Preliminary Results of the ZUMA-3 and ZUMA-4 Trials", Blood, 128, Issue 22, p. 2803, http://doi.org/10.1182/blood.V128.22.2803.2803, Dec. 2, 2016 (Feb. 12, 2016).

Shah et al., "End of phase I results of ZUMA-3, a phase 1/2 study of KTE-X19, anti-CD19 chimeric antigen receptor (Car) T cell therapy, in adult patients (pts) with relapsed/refractory (R/R) acute lymphoblastic leukemia (ALL)," 2019, Meeting Abstract: 2019 ASCO Annual Meeting I, Journal of Clinical Oncology, vol. 37, No. 15 Supp., 3 p. 2019.

Shah et al., A Phase 1 Study with Point-of-Care Manufacturing of Dual Targeted, Tandem Anti-CD19, Anti-CD20 Chimeric Antigen Receptor Modified T (Car-T) Cells for Relapsed, Refractory, Non-Hodgkin Lymphoma, Blood 2018, vol. 132, (Supplement 1): 4193, DOI: 10.1182/blood-2018-99-110194. 4 pages.

Sotillo et al. (2015), "Convergence of Acquired Mutations and Alternative Splicing of CD19 Enables Resistance to CART-19 Immunotherapy", Cancer Discovery, OF1-OF14.

Stackelberg et al. (2016), "Phase I/Phase II Study of Blinatumomab in Pediatric Patients With Relapsed/Refractory Acute Lymphoblastic Leukemia", Journal of Clinical Oncology, 34(36), 4381-4389.

Sun et al. (2018), "Outcome of children with multiply relapsed B-cell acute lymphoblastic leukemia: a therapeutic advances in childhood leukemia & lymphoma study", Acute lymphoblastic leukemia, Springer Nature, 32, 2316-2325.

Swerdlow et al. "The 2016 revision of the World Health Organization classification of lymphoid neoplasms", Blood, May 19, 2016, vol. 127, No. 20, pp. 2375-2390.

Topp et al. (2014), "Safety and activity of blinatumomab for adult patients with relapsed or refractory B- precursor acute lymphoblastic leukaemia: a multicentre, single-arm, phase 2 study", The Lancet, 16, 57- 66.

Turtle et al., Immunotherapy of non-Hodgkin lymphoma with a defined ratio of CD8+ and CD4+ CD19- specific chimeric antigen receptor-modified T cells, Science Translational Medicine 2016, vol. 8, No. 355, doi: 10.1126/scitranslmed.aaf8621, 24 pages.

Wang et al. (2017), "Acalabrutinib in relapsed or refractory mantle cell lymphoma (ACE-LY-004): a single-arm, multicentre, phase 2 trial", The Lancet, 1-9.

Wang et al. (2020), "KTE-X19 Car T-Cell Therapy in Relapsed or Refractory Mantle-Cell Lymphoma", The New England Journal of Medicine, 382(14), 1331-1342.

Wang et al., Safety and preliminary efficacy in patients (pts) with relapsed/refractory (R/R) mantle cell lymphoma (MCL) receiving lisocabtagene maraleucel (Liso-cel) in Transcend Nhl 001, Journal of Clinical Oncology, vol. 37, No. 15_suppl, May 26, 2019.

Wang et al., ZUMA-2: A phase 2 multi-center study evaluating the efficacy of KTE-C19 (Anti-CD19 Car T cells) in patients with relapsed/refractory mantle cell lymphoma (R/R Mcl), Annals of Oncology, 2016, vol. 27(Supplement 6): vi326, doi: 10.1093/annonc/mdw375.40. 2 pages.

White et al. Cancer Prevention for the Next Generation. J Adolesc Health 52: S1-S7, 2013.

Wicks et al. (2015), "Targeting GM-CSF in inflammatory diseases", Nature Reviews, Rheumatology, 1- 12.

Zhao et al. Universal CARs, universal T cells, and universal Car T cells. J hematol Oncol 11: 132, 2018, 9 pages.

Park et al. (2018), "Long-Term Follow-up of CD19 Car Therapy in Acute Lymphoblastic Leukemia", The New England Journal of Medicine, 378; 5, 449-459.

"Hematopoietic and Lymphoid Tumors - WHO Classification, 2016 Version," Journal of Clinical Laboratory Medicine, vol. 61., No. 7, 2017, pp. 847-888 with English translation.

Yoon-Hwan, "High-grade B-cell lymphoma," Korean Society for Laboratory Hematology News Letter, 2017, vol. 23, 3 pages with English translation.

European Office Action dated Jan. 19, 2026, for European Patent Application No. 19836733.6, 12 pages.

Schneider et al: "A tandem CD19/CD20 Car lentiviral vector drives on-target and off-target antigen modulation in leukemia cell lines", Journal for Immunotherapy of Cancer, Biomed Central Ltd, London, UK, vol. 5, No. 1, May 16, 2017 (May 16, 2017), pp. 1-17, XP021245145, DOI: 10.1186/S40425-017-0246-1.

Zah et al: "T Cells Expressing CD19/CD20 Bispecific Chimeric Antigen Receptors Prevent Antigen Escape by Malignant B Cells", Cancer Immunology Research, vol. 4, No. 6, Apr. 8, 2016 (Apr. 8, 2016), pp. 498-508, XP055290967, US ISSN: 2326-6066, DOI: 10.1158/2326-6066.CIR-15-0231.

* cited by examiner

CHIMERIC ANTIGEN AND T CELL RECEPTORS AND METHODS OF USE

CROSS-REFERENCE TO RELATED APPLICATIONS

The present application is a continuation of U.S. application Ser. No. 18/470,745, filed Sep. 20, 2023, which is a division of U.S. application Ser. No. 16/711,180, filed Dec. 11, 2019, now U.S. Pat. No. 11,793,834, which claims the priority benefit of U.S. Provisional Application No. 62/778,893, filed Dec. 12, 2018, the contents of each of which are hereby incorporated by reference in their entireties.

REFERENCE TO AN ELECTRONIC SEQUENCE LISTING

The contents of the electronic sequence listing (347485.xml; Size: 466,961 bytes; and Date of Creation: Dec. 27, 2024) is herein incorporated by reference in its entirety.

BACKGROUND OF THE DISCLOSURE

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Current therapies T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen. A need exists for CARs and TCRs for targeting and killing cancer cells.

SUMMARY

In at least a first aspect, the present disclosure comprises an antigen binding system, antibody, or antigen binding fragment thereof comprising an anti-CD20 binding motif, wherein the anti-CD20 binding motif comprises sequences of three heavy chain complementarity determining regions (HCDRs) of any one heavy chain variable region (HCVR) selected from the group consisting of SEQ ID NOs: 1, 23, 45, 67, 89, 111, 133, 155, 177, and 199, and sequences of three light chain CDRs (LCDRs) of any one light chain variable region (LCVR) selected from the group consisting of SEQ ID NOs: 12, 34, 56, 78, 100, 122, 144, 166, 188, and 210. In some embodiments, the anti-CD20 binding motif comprises a first domain comprising three heavy chain complementarity determining regions (HCDR1, HCDR2 and HCDR3) and a second domain comprising three light chain complementarity determining regions (LCDR1, LCDR2 and LCDR3), wherein (i) the HCDR1 has a sequence according to any one of SEQ ID NOs: 3-5, 25-27, 47-49, 69-71, 91-93, 113-115, 135-137, 157-159, 179-181; and 201-203; (ii) the HCDR2 has a sequence according to any one of SEQ ID NOs: 6-8, 28-30, 50-52, 72-74, 94-96, 116-118, 138-140, 160-162, 182-184, and 204-206; (iii) the HCDR3 has a sequence according to any one of SEQ ID NOs: 9-11, 31-33, 53-55, 75-77, 97-99, 119-121, 141-143, 163-165, 185-187, and 207-209; (iv) the LCDR1 has a sequence according to any one of SEQ ID NOs: 14-16, 36-38, 58-60, 80-82, 102-104, 124-126, 146-148, 168-170, 190-192, and 212-214; (v) the LCDR2 has a sequence according to any one of SEQ ID NOs: 17-19, 39-41, 61-63, 83-85, 105-107, 127-129, 149-151, 171-173, 193-195; and 215-217; and (vi) the LCDR3 has a sequence according to any one of SEQ ID NOs: 20-22, 42-44, 64-66, 86-88, 108-110, 130-132, 152-154, 174-176, 196-198, and 218-220. In some embodiments, the HCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; (ii) an HCDR1 according to any of SEQ ID NOs: 25-27; an HCDR2 according to any of SEQ ID NOs: 28-30; an HCDR3 according to any one of SEQ ID NOs: 31-33; (iii) an HCDR1 according to any of SEQ ID NOs: 47-49; an HCDR2 according to any of SEQ ID NOs: 50-52; an HCDR3 according to any one of SEQ ID NOs: 53-55; (iv) an HCDR1 according to any of SEQ ID NOs: 69-71; an HCDR2 according to any of SEQ ID NOs: 72-74; an HCDR3 according to any one of SEQ ID NOs: 75-77; (v) an HCDR1 according to any of SEQ ID NOs: 91-93; an HCDR2 according to any of SEQ ID NOs: 94-96; an HCDR3 according to any one of SEQ ID NOs: 97-99; (vi) an HCDR1 according to any of SEQ ID NOs: 113-115; an HCDR2 according to any of SEQ ID NOs: 116-118; an HCDR3 according to any one of SEQ ID NOs: 119-121; (vii) an HCDR1 according to any of SEQ ID NOs: 135-137; an HCDR2 according to any of SEQ ID NOs: 138-140; an HCDR3 according to any one of SEQ ID NOs: 141-143; (viii) an HCDR1 according to any of SEQ ID NOs: 157-159; an HCDR2 according to any of SEQ ID NOs: 160-162; an HCDR3 according to any one of SEQ ID NOs: 163-165; (ix) an HCDR1 according to any of SEQ ID NOs: 179-181; an HCDR2 according to any of SEQ ID NOs: 182-184; an HCDR3 according to any one of SEQ ID NOs: 185-187; or (x) an HCDR1 according to any of SEQ ID NOs: 201-203; an HCDR2 according to any of SEQ ID NOs: 204-206; an HCDR3 according to any one of SEQ ID NOs: 207-209; and the LCDRs comprise: (i) an LCDR1 according to any of SEQ ID NOs: 14-16; an LCDR2 according to any of SEQ ID NOs: 17-19; an LCDR3 according to any one of SEQ ID NOs: 20-22; (ii) an LCDR1 according to any of SEQ ID NOs: 36-38; an LCDR2 according to any of SEQ ID NOs: 39-41; an LCDR3 according to any one of SEQ ID NOs: 42-44; (iii) an LCDR1 according to any of SEQ ID NOs: 58-60; an LCDR2 according to any of SEQ ID NOs: 61-63; an LCDR3 according to any one of SEQ ID NOs: 64-66; (iv) an LCDR1 according to any of SEQ ID NOs: 80-82; an LCDR2 according to any of SEQ ID NOs: 83-85; an LCDR3 according to any one of SEQ ID NOs: 86-88; (v) an LCDR1 according to any of SEQ ID NOs: 102-104; an LCDR2 according to any of SEQ ID NOs: 105-107; an LCDR3 according to any one of SEQ ID NOs: 108-110; (vi) an LCDR1 according to any of SEQ ID NOs: 124-126; an LCDR2 according to any of SEQ ID NOs: 127-129; an LCDR3 according to any one of SEQ ID NOs: 130-132; (vii) an LCDR1 according to any of SEQ ID NOs: 146-148; an LCDR2 according to any of SEQ ID NOs: 149-151; an LCDR3 according to any one of SEQ ID NOs: 152-154; (viii) an LCDR1 according to any of SEQ ID NOs: 168-170;

an LCDR2 according to any of SEQ ID NOs: 171-173; an LCDR3 according to any one of SEQ ID NOs: 174-176; (ix) an LCDR1 according to any of SEQ ID NOs: 190-192; an LCDR2 according to any of SEQ ID NOs: 193-195; an LCDR3 according to any one of SEQ ID NOs: 196-198; or (x) an LCDR1 according to any of SEQ ID NOs: 212-214; an LCDR2 according to any of SEQ ID NOs: 215-217; an LCDR3 according to any one of SEQ ID NOs: 218-220.

In various embodiments, an antigen binding system, antibody, or antigen binding fragment thereof of the present disclosure comprises a first domain comprising three heavy chain complementarity determining regions (HCDRs) and a second domain comprising three light chain complementarity determining regions (LCDRs), wherein: the HCDRs and LCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; an LCDR1 according to any of SEQ ID NOs: 14-16; an LCDR2 according to any of SEQ ID NOs: 17-19; an LCDR3 according to any one of SEQ ID NOs: 20-22; (ii) an HCDR1 according to any of SEQ ID NOs: 25-27; an HCDR2 according to any of SEQ ID NOs: 28-30; an HCDR3 according to any one of SEQ ID NOs: 31-33; an LCDR1 according to any of SEQ ID NOs: 36-38; an LCDR2 according to any of SEQ ID NOs: 39-41; an LCDR3 according to any one of SEQ ID NOs: 42-44; (iii) an HCDR1 according to any of SEQ ID NOs: 47-49; an HCDR2 according to any of SEQ ID NOs: 50-52; an HCDR3 according to any one of SEQ ID NOs: 53-55; an LCDR1 according to any of SEQ ID NOs: 58-60; an LCDR2 according to any of SEQ ID NOs: 61-63; an LCDR3 according to any one of SEQ ID NOs: 64-66; (iv) an HCDR1 according to any of SEQ ID NOs: 69-71; an HCDR2 according to any of SEQ ID NOs: 72-74; an HCDR3 according to any one of SEQ ID NOs: 75-77; an LCDR1 according to any of SEQ ID NOs: 80-82; an LCDR2 according to any of SEQ ID NOs: 83-85; an LCDR3 according to any one of SEQ ID NOs: 86-88; (v) an HCDR1 according to any of SEQ ID NOs: 91-93; an HCDR2 according to any of SEQ ID NOs: 94-96; an HCDR3 according to any one of SEQ ID NOs: 97-99; an LCDR1 according to any of SEQ ID NOs: 102-104; an LCDR2 according to any of SEQ ID NOs: 105-107; an LCDR3 according to any one of SEQ ID NOs: 108-110; (vi) an HCDR1 according to any of SEQ ID NOs: 113-115; an HCDR2 according to any of SEQ ID NOs: 116-118; an HCDR3 according to any one of SEQ ID NOs: 119-121; an LCDR1 according to any of SEQ ID NOs: 124-126; an LCDR2 according to any of SEQ ID NOs: 127-129; an LCDR3 according to any one of SEQ ID NOs: 130-132; (vii) an HCDR1 according to any of SEQ ID NOs: 135-137; an HCDR2 according to any of SEQ ID NOs: 138-140; an HCDR3 according to any one of SEQ ID NOs: 141-143; an LCDR1 according to any of SEQ ID NOs: 146-148; an LCDR2 according to any of SEQ ID NOs: 149-151; an LCDR3 according to any one of SEQ ID NOs: 152-154; (viii) an HCDR1 according to any of SEQ ID NOs: 157-159; an HCDR2 according to any of SEQ ID NOs: 160-162; an HCDR3 according to any one of SEQ ID NOs: 163-165; an LCDR1 according to any of SEQ ID NOs: 168-170; an LCDR2 according to any of SEQ ID NOs: 171-173; an LCDR3 according to any one of SEQ ID NOs: 174-176; (ix) an HCDR1 according to any of SEQ ID NOs: 179-181; an HCDR2 according to any of SEQ ID NOs: 182-184; an HCDR3 according to any one of SEQ ID NOs: 185-187; an LCDR1 according to any of SEQ ID NOs: 190-192; an LCDR2 according to any of SEQ ID NOs: 193-195; an LCDR3 according to any one of SEQ ID NOs: 196-198; or (x) an HCDR1 according to any of SEQ ID NOs: 201-203; an HCDR2 according to any of SEQ ID NOs: 204-206; an HCDR3 according to any one of SEQ ID NOs: 207-209; an LCDR1 according to any of SEQ ID NOs: 212-214; an LCDR2 according to any of SEQ ID NOs: 215-217; an LCDR3 according to any one of SEQ ID NOs: 218-220. In some embodiments, the antigen binding system, antibody, or antigen binding fragment thereof comprises a first heavy chain variable domain comprising the three HCDRs and a light chain variable domain comprising the three LCDRs, wherein: (i) the heavy chain variable domain is at least 80% identical to SEQ ID NO: 1, SEQ ID NO: 23, SEQ ID NO: 45, SEQ ID NO: 67, SEQ ID NO: 89, SEQ ID NO: 111, SEQ ID NO: 133, SEQ ID NO: 155, SEQ ID NO: 177, or SEQ ID NO: 199; and (ii) the light chain variable domain is at least 80% identical to SEQ ID NO: 12, SEQ ID NO: 34, SEQ ID NO: 56, SEQ ID NO: 78, SEQ ID NO: 100, SEQ ID NO: 122, SEQ ID NO: 144, SEQ ID NO: 166, SEQ ID NO: 188, or SEQ ID NO: 210. In some embodiments, the antigen binding system, antibody, or antigen binding fragment thereof comprises a first heavy chain variable domain comprising the three HCDRs and a light chain variable domain comprising the three LCDRs, wherein: (i) the heavy chain variable domain is at least 80% identical to SEQ ID NO: 1 and the light chain variable domain is at least 80% identical to SEQ ID NO: 12; (ii) the heavy chain variable domain is at least 80% identical to SEQ ID NO: 23 and the light chain variable domain is at least 80% identical to SEQ ID NO: 34; (iii) the heavy chain variable domain is at least 80% identical to SEQ ID NO: 45 and the light chain variable domain is at least 80% identical to SEQ ID NO: 56; (iv) the heavy chain variable domain is at least 80% identical to SEQ ID NO: 67 and the light chain variable domain is at least 80% identical to SEQ ID NO: 78; (v) the heavy chain variable domain is at least 80% identical to SEQ ID NO: 89 and the light chain variable domain is at least 80% identical to SEQ ID NO: 100; (vi) the heavy chain variable domain is at least 80% identical to SEQ ID NO: 111 and the light chain variable domain is at least 80% identical to SEQ ID NO: 122; (vii) the heavy chain variable domain is at least 80% identical to SEQ ID NO: 133 and the light chain variable domain is at least 80% identical to SEQ ID NO: 144; (viii) the heavy chain variable domain is at least 80% identical to SEQ ID NO: 155 and the light chain variable domain is at least 80% identical to SEQ ID NO: 166; (ix) the heavy chain variable domain is at least 80% identical to SEQ ID NO: 177 and the light chain variable domain is at least 80% identical to SEQ ID NO: 188; or (x) the heavy chain variable domain is at least 80% identical to SEQ ID NO: 199 and the light chain variable domain is at least 80% identical to SEQ ID NO: 210.

In some embodiments of the present disclosure comprising the three HCDRs and the three LCDRs, the three HCDRs and the three LCDRs are comprised by a single polypeptide. In some embodiments of the present disclosure comprising the three HCDRs and the three LCDRs, the three HCDRs are comprised by a first polypeptide and the three LCDRs are comprised by a second polypeptide. In some embodiments, the first polypeptide is an antibody heavy chain and the second polypeptide is an antibody light chain.

In some embodiments, the antigen binding system, antibody, or antigen binding fragment thereof further comprises: (i) a binding motif that binds an antigen selected from the group consisting of 5T4, alphafetoprotein, B cell maturation antigen (BCMA), B cell receptor, CA-125, carcinoembryonic antigen, CD19, CD20, CD22, CD23, CD30, CD33, CD40, CD56, CD79, CD78, CD123, CD138, c-Met, CSPG4, IgM, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gpl20, IL-llRalpha, kappa chain, lambda chain, melanoma-associated antigen, mesothelin, MUC-1, mutated p53, mutated ras, prostate-specific antigen, ROR1, VEGFR2, EphA3 (EPH receptor A3), BAFFR (B-cell activating factor receptor), and combinations thereof; and/or (ii) a binding motif that binds an antigen that is characteristic of B-cells, optionally wherein the antigen that is characteristic of B-cells is not CD19 or CD20. In some embodiments, the antigen binding system, antibody, or antigen binding frag-ment thereof further comprises an anti-CD19 binding motif. In some embodiments, the anti-CD19 binding motif com-prises a first domain comprising three HCDRs and a second domain comprising three LCDRs, wherein: the three HCDRs of the anti-CD19 binding motif comprise an HCDR1, an HCDR2, and an HCDR3; the three LCDRs of the anti-CD19 binding motif comprise an LCDR1, an LCDR2, and an LCDR3; and the HCDRs and LCDRs of the anti-CD19 binding motif comprise an HCDR1 according to any of SEQ ID NOs: 223-225; an HCDR2 according to any of SEQ ID NOs: 226-228; an HCDR3 according to any one of SEQ ID NOs: 229-231; an LCDR1 according to any of SEQ ID NOs: 234-236; an LCDR2 according to any of SEQ ID NOs: 237-239; an LCDR3 according to any one of SEQ ID NOs: 240-242. In some embodiments, the anti-CD19 binding motif comprises a first heavy chain variable domain comprising the three HCDRs of the anti-CD19 binding motif and a light chain variable domain comprising the three LCDRs of the anti-CD19 binding motif, wherein the heavy chain variable domain of the anti-CD19 binding motif is at least 80% identical to SEQ ID NO: 221 and the light chain variable domain of the anti-CD19 binding motif is at least 80% identical to SEQ ID NO: 232. In some embodiments, the three HCDRs of the anti-CD19 binding motif and the three LCDRs of the anti-CD19 binding motif are comprised by a single polypeptide. In some embodiments, the three HCDRs of the anti-CD20 binding motif, the three LCDRs of the anti-CD20 binding motif, the three HCDRs of the anti-CD19 binding motif, and the three LCDRs of the anti-CD19 binding motif are together comprised by a single polypeptide. In various embodiments, the antigen binding system, antibody, or antigen binding fragment thereof is, or is comprised by, a chimeric antigen receptor. In some embodi-ments, the antigen binding system, antibody, or antigen binding fragment thereof is a single polypeptide that is, or is comprised by, a chimeric antigen receptor, which chimeric antigen receptor is a bispecific chimeric antigen receptor. In some embodiments, the chimeric antigen receptor comprises a transmembrane domain that is a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD28, CD33, CD37, CD45, CD64, CD80, CD86, CD134, CD137, CD154, or a zeta chain of a T cell receptor, or any combination thereof. In some embodiments, (i) the three HCDRs of the anti-CD20 binding motif and the three LCDRs of the anti-CD20 binding motif are present in a first polypeptide and (ii) the three HCDRs of the anti-CD19 binding motif and the three LCDRs of the anti-CD19 binding motif are together com-prised by a second different polypeptide. In some embodi-ments, the first polypeptide is, or is comprised by, a first chimeric antigen receptor. In some embodiments, the second polypeptide is, or is comprised by, a second chimeric antigen receptor.

In various embodiments, the present disclosure comprises a nucleic acid encoding at least one polypeptide of the present disclosure and/or a vector comprising such a nucleic acid. The present disclosure further comprises a method of generating an engineered cell, the method comprising trans-fecting or transducing a cell with a nucleic acid encoding at least one polypeptide of the present disclosure. Further provided herein is a cell encoding or expressing an antigen binding system, antibody, or antigen binding fragment pro-vided herein, optionally wherein the cell is an immune cell, optionally wherein the cell is a T cell.

The present disclosure further comprises a method of treating cancer in a subject in need thereof, the method comprising administering to the subject a cell therapy com-position comprising one or more cells that encode or com-prise an antigen binding system, antibody, or antigen bind-ing fragment thereof of the present disclosure. Also provided herein is a method of inducing an immune response in a subject or immunizing a subject against a cancer, the method comprising administering to the subject a cell therapy com-position comprising one or more cells that encode or com-prise an antigen binding system, antibody, or antigen bind-ing fragment thereof of the present disclosure. In some embodiments, the cells are CAR-T cells. In various embodi-ments, the cancer is acute lymphoblastic leukemia (ALL) (including non T cell ALL), acute myeloid leukemia, B cell prolymphocytic leukemia, B cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoprolifera-tive conditions, MALT lymphoma, mantle cell lymphoma, Marginal zone lymphoma, monoclonal gammapathy of undetermined significance (MGUS), multiple myeloma, myelodysplasia and myelodysplastic syndrome, non-Hodg-kin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (in-cluding plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, or Waldenstrom macroglobulinemia, Mantle cell lymphoma (MCL), Transformed follicular lymphoma (TFL), Primary mediastinal B cell lymphoma (PMBCL), Multiple myeloma, Hairy cell lymphoma/leukemia, or a combination thereof. In some embodiments, cell therapy is an allogeneic cell therapy or an autologous cell therapy.

At least one aspect of the present disclosure includes a chimeric antigen receptor comprising an anti-CD20 binding motif, the anti-CD20 binding motif comprising three heavy chain complementarity determining regions (HCDRs) con-tained within any one of the heavy chain variable region (HCVR) sequences selected from the group consisting of SEQ ID NOs: 1, 23, 45, 67, 89, 111, 133, 155, 177, and 199, and three light chain CDRs (LCDRs) contained within any one of the light chain variable region (LCVR) sequences selected from the group consisting of SEQ ID NOs: 12, 34, 56, 78, 100, 122, 144, 166, 188, and 210. In some embodiments, a first domain comprising the three heavy chain complementarity determining regions (HCDRs) and a second domain comprising the three light chain complementarity determining regions (LCDRs), wherein (i) the HCDR1 has a sequence according to any one of SEQ ID NOs: 3-5, 25-27, 47-49, 69-71, 91-93, 113-115, 135-137, 157-159, 179-181; and 201-203; (ii) the HCDR2 has a sequence according to any one of SEQ ID NOs: 6-8, 28-30, 50-52, 72-74, 94-96, 116-118, 138-140, 160-162, 182-184; and 204-206; (iii) the HCDR3 has a sequence according to any one of SEQ ID NOs: 9-11, 31-33, 53-55, 75-77, 97-99, 119-121, 141-143, 163-165, 185-187; and 207-209; (iv) the LCDR1 has a sequence according to any one of SEQ ID NOs: 14-16, 36-38, 58-60, 80-82, 102-104, 124-126, 146-148, 168-170, 190-192; and 212-214; (v) the LCDR2 has a sequence according to any one of SEQ ID NOs: 17-19, 39-41, 61-63, 83-85, 105-107, 127-129, 149-151, 171-173, 193-195; and 215-217; and (vi) the LCDR3 has a sequence according to any one of SEQ ID NOs: 20-22, 42-44, 64-66, 86-88, 108-110, 130-132, 152-154, 174-176, 196-198; and 218-220. In some embodiments, the HCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; (ii) an HCDR1 according to any of SEQ ID NOs: 25-27; an HCDR2 according to any of SEQ ID NOs: 28-30; an HCDR3 according to any one of SEQ ID NOs: 31-33; (iii) an HCDR1 according to any of SEQ ID NOs: 47-49; an HCDR2 according to any of SEQ ID NOs: 50-52; an HCDR3 according to any one of SEQ ID NOs: 53-55; (iv) an HCDR1 according to any of SEQ ID NOs: 69-71; an HCDR2 according to any of SEQ ID NOs: 72-74; an HCDR3 according to any one of SEQ ID NOs: 75-77; (v) an HCDR1 according to any of SEQ ID NOs: 91-93; an HCDR2 according to any of SEQ ID NOs: 94-96; an HCDR3 according to any one of SEQ ID NOs: 97-99; (vi) an HCDR1 according to any of SEQ ID NOs: 113-115; an HCDR2 according to any of SEQ ID NOs: 116-118; an HCDR3 according to any one of SEQ ID NOs: 119-121; (vii) an HCDR1 according to any of SEQ ID NOs: 135-137; an HCDR2 according to any of SEQ ID NOs: 138-140; an HCDR3 according to any one of SEQ ID NOs: 141-143; (viii) an HCDR1 according to any of SEQ ID NOs: 157-159; an HCDR2 according to any of SEQ ID NOs: 160-162; an HCDR3 according to any one of SEQ ID NOs: 163-165; (ix) an HCDR1 according to any of SEQ ID NOs: 179-181; an HCDR2 according to any of SEQ ID NOs: 182-184; an HCDR3 according to any one of SEQ ID NOs: 185-187; or (x) an HCDR1 according to any of SEQ ID NOs: 201-203; an HCDR2 according to any of SEQ ID NOs: 204-206; an HCDR3 according to any one of SEQ ID NOs: 207-209; and the LCDRs comprise: (i) an LCDR1 according to any of SEQ ID NOs: 14-16; an LCDR2 according to any of SEQ ID NOs: 17-19; an LCDR3 according to any one of SEQ ID NOs: 20-22; (ii) an LCDR1 according to any of SEQ ID NOs: 36-38; an LCDR2 according to any of SEQ ID NOs: 39-41; an LCDR3 according to any one of SEQ ID NOs: 42-44; (iii) an LCDR1 according to any of SEQ ID NOs: 58-60; an LCDR2 according to any of SEQ ID NOs: 61-63; an LCDR3 according to any one of SEQ ID NOs: 64-66; (iv) an LCDR1 according to any of SEQ ID NOs: 80-82; an LCDR2 according to any of SEQ ID NOs: 83-85; an LCDR3 according to any one of SEQ ID NOs: 86-88; (v) an LCDR1 according to any of SEQ ID NOs: 102-104; an LCDR2 according to any of SEQ ID NOs: 105-107; an LCDR3 according to any one of SEQ ID NOs: 108-110; (vi) an LCDR1 according to any of SEQ ID NOs: 124-126; an LCDR2 according to any of SEQ ID NOs: 127-129; an LCDR3 according to any one of SEQ ID NOs: 130-132; (vii) an LCDR1 according to any of SEQ ID NOs: 146-148; an LCDR2 according to any of SEQ ID NOs: 149-151; an LCDR3 according to any one of SEQ ID NOs: 152-154; (viii) an LCDR1 according to any of SEQ ID NOs: 168-170; an LCDR2 according to any of SEQ ID NOs: 171-173; an LCDR3 according to any one of SEQ ID NOs: 174-176; (ix) an LCDR1 according to any of SEQ ID NOs: 190-192; an LCDR2 according to any of SEQ ID NOs: 193-195; an LCDR3 according to any one of SEQ ID NOs: 196-198; or (x) an LCDR1 according to any of SEQ ID NOs: 212-214; an LCDR2 according to any of SEQ ID NOs: 215-217; an LCDR3 according to any one of SEQ ID NOs: 218-220.

In some embodiments, the chimeric antigen receptor comprises a first domain comprising three heavy chain complementarity determining regions (HCDRs) and a second domain comprising three light chain complementarity determining regions (LCDRs), wherein: the three HCDRs comprise an HCDR1, an HCDR2, and an HCDR3; the three LCDRs comprise an LCDR1, an LCDR2, and an LCDR3; and the HCDRs and LCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; an LCDR1 according to any of SEQ ID NOs: 14-16; an LCDR2 according to any of SEQ ID NOs: 17-19; an LCDR3 according to any one of SEQ ID NOs: 20-22; (ii) an HCDR1 according to any of SEQ ID NOs: 25-27; an HCDR2 according to any of SEQ ID NOs: 28-30; an HCDR3 according to any one of SEQ ID NOs: 31-33; an LCDR1 according to any of SEQ ID NOs: 36-38; an LCDR2 according to any of SEQ ID NOs: 39-41; an LCDR3 according to any of SEQ ID NOs: 42-44; (iii) an HCDR1 according to any of SEQ ID NOs: 47-49; an HCDR2 according to any of SEQ ID NOs: 50-52; an HCDR3 according to any one of SEQ ID NOs: 53-55; an LCDR1 according to any of SEQ ID NOs: 58-60; an LCDR2 according to any of SEQ ID NOs: 61-63; an LCDR3 according to any one of SEQ ID NOs: 64-66; (iv) an HCDR1 according to any of SEQ ID NOs: 69-71; an HCDR2 according to any of SEQ ID NOs: 72-74; an HCDR3 according to any one of SEQ ID NOs: 75-77; an LCDR1 according to any of SEQ ID NOs: 80-82; an LCDR2 according to any of SEQ ID NOs: 83-85; an LCDR3 according to any one of SEQ ID NOs: 86-88; (v) an HCDR1 according to any of SEQ ID NOs: 91-93; an HCDR2 according to any of SEQ ID NOs: 94-96; an HCDR3 according to any one of SEQ ID NOs: 97-99; an LCDR1 according to any of SEQ ID NOs: 102-104; an LCDR2 according to any of SEQ ID NOs: 105-107; an LCDR3 according to any one of SEQ ID NOs: 108-110; (vi) an HCDR1 according to any of SEQ ID NOs: 113-115; an HCDR2 according to any of SEQ ID NOs: 116-118; an HCDR3 according to any one of SEQ ID NOs: 119-121; an LCDR1 according to any of SEQ ID NOs: 124-126; an LCDR2 according to any of SEQ ID NOs: 127-129; an LCDR3 according to any one of SEQ ID NOs: 130-132; (vii) an HCDR1 according to any of SEQ ID NOs: 135-137; an HCDR2 according to any of SEQ ID NOs: 138-140; an HCDR3 according to any one of SEQ ID NOs: 141-143; an LCDR1 according to any of SEQ ID NOs: 146-148; an LCDR2 according to any of SEQ ID NOs: 149-151; an LCDR3 according to any one of SEQ ID NOs: 152-154; (viii) an HCDR1 according to any of SEQ ID NOs: 157-159;

an HCDR2 according to any of SEQ ID NOs: 160-162; an HCDR3 according to any one of SEQ ID NOs: 163-165; an LCDR1 according to any of SEQ ID NOs: 168-170; an LCDR2 according to any of SEQ ID NOs: 171-173; an LCDR3 according to any one of SEQ ID NOs: 174-176; (ix) an HCDR1 according to any of SEQ ID NOs: 179-181; an HCDR2 according to any of SEQ ID NOs: 182-184; an HCDR3 according to any one of SEQ ID NOs: 185-187; an LCDR1 according to any of SEQ ID NOs: 190-192; an LCDR2 according to any of SEQ ID NOs: 193-195; an LCDR3 according to any one of SEQ ID NOs: 196-198; or (x) an HCDR1 according to any of SEQ ID NOs: 201-203; an HCDR2 according to any of SEQ ID NOs: 204-206; an HCDR3 according to any one of SEQ ID NOs: 207-209; an LCDR1 according to any of SEQ ID NOs: 212-214; an LCDR2 according to any of SEQ ID NOs: 215-217; an LCDR3 according to any one of SEQ ID NOs: 218-220. In various embodiments, the chimeric antigen receptor comprises a first heavy chain variable domain comprising the three HCDRs and a light chain variable domain comprising the three LCDRs, wherein: (i) the heavy chain variable domain is at least 80% identical to SEQ ID NO: 1, SEQ ID NO: 23, SEQ ID NO: 45, SEQ ID NO: 67, SEQ ID NO: 89, SEQ ID NO: 111, SEQ ID NO: 133, SEQ ID NO: 155, SEQ ID NO: 177, or SEQ ID NO: 199; and (ii) the light chain variable domain is at least 80% identical to SEQ ID NO: 12, SEQ ID NO: 34, SEQ ID NO: 56, SEQ ID NO: 78, SEQ ID NO: 100, SEQ ID NO: 122, SEQ ID NO: 144, SEQ ID NO: 166, SEQ ID NO: 188, or SEQ ID NO: 210. In some embodiments, the chimeric antigen receptor comprises a first heavy chain variable domain comprising the three HCDRs and a light chain variable domain comprising the three LCDRs, wherein: (i) the heavy chain variable domain is at least 80% identical to SEQ ID NO: 1 and the light chain variable domain is at least 80% identical to SEQ ID NO: 12; (ii) the heavy chain variable domain is at least 80% identical to SEQ ID NO: 23 and the light chain variable domain is at least 80% identical to SEQ ID NO: 34; (iii) the heavy chain variable domain is at least 80% identical to SEQ ID NO: 45 and the light chain variable domain is at least 80% identical to SEQ ID NO: 56; (iv) the heavy chain variable domain is at least 80% identical to SEQ ID NO: 67 and the light chain variable domain is at least 80% identical to SEQ ID NO: 78; (v) the heavy chain variable domain is at least 80% identical to SEQ ID NO: 89 and the light chain variable domain is at least 80% identical to SEQ ID NO: 100; (vi) the heavy chain variable domain is at least 80% identical to SEQ ID NO: 111 and the light chain variable domain is at least 80% identical to SEQ ID NO: 122; (vii) the heavy chain variable domain is at least 80% identical to SEQ ID NO: 133 and the light chain variable domain is at least 80% identical to SEQ ID NO: 144; (viii) the heavy chain variable domain is at least 80% identical to SEQ ID NO: 155 and the light chain variable domain is at least 80% identical to SEQ ID NO: 166; (ix) the heavy chain variable domain is at least 80% identical to SEQ ID NO: 177 and the light chain variable domain is at least 80% identical to SEQ ID NO: 188; or (x) the heavy chain variable domain is at least 80% identical to SEQ ID NO: 199 and the light chain variable domain is at least 80% identical to SEQ ID NO: 210.

In some embodiments comprising three HCDRs and the three LCDRs, the three HCDRs and the three LCDRs are comprised by a single polypeptide. In some embodiments comprising three HCDRs and the three LCDRs, the three HCDRs are comprised by a first polypeptide and the three LCDRs are comprised by a second polypeptide. In some embodiments, the first polypeptide is an antibody heavy chain and the second polypeptide is an antibody light chain. In some embodiments, the chimeric antigen receptor further comprises: (i) a binding motif that specifically binds an antigen selected from the group consisting of 5T4, alphafetoprotein, B cell maturation antigen (BCMA), B cell receptor, CA-125, carcinoembryonic antigen, CD19, CD20, CD22, CD23, CD30, CD33, CD40, CD56, CD79, CD78, CD123, CD138, c-Met, CSPG4, IgM, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gpl20, IL-llRalpha, kappa chain, lambda chain, melanoma-associated antigen, mesothelin, MUC-1, mutated p53, mutated ras, prostate-specific antigen, ROR1, VEGFR2, EphA3 (EPH receptor A3), BAFFR (B-cell activating factor receptor), and combinations thereof; and/or (ii) a binding motif that specifically binds an antigen that is characteristic of B-cells, optionally wherein the antigen that is characteristic of B-cells is not CD19 or CD20. In some embodiments, the chimeric antigen receptor further comprises an anti-CD19 binding motif.

In some embodiments, the anti-CD19 binding motif comprises a first domain comprising three HCDRs and a second domain comprising three LCDRs, wherein: the three HCDRs of the anti-CD19 binding motif comprise an HCDR1, an HCDR2, and an HCDR3; the three LCDRs of the anti-CD19 binding motif comprise an LCDR1, an LCDR2, and an LCDR3; and the HCDRs and LCDRs of the anti-CD19 binding motif comprise an HCDR1 according to any of SEQ ID NOs: 223-225; an HCDR2 according to any of SEQ ID NOs: 226-228; an HCDR3 according to any one of SEQ ID NOs: 229-231; an LCDR1 according to any of SEQ ID NOs: 234-236; an LCDR2 according to any of SEQ ID NOs: 237-239; an LCDR3 according to any one of SEQ ID NOs: 240-242. In some embodiments, the anti-CD19 binding motif comprises a first heavy chain variable domain comprising the three HCDRs of the anti-CD19 binding motif and a light chain variable domain comprising the three LCDRs of the anti-CD19 binding motif, wherein the heavy chain variable domain of the anti-CD19 binding motif is at least 80% identical to SEQ ID NO: 221 and the light chain variable domain of the anti-CD19 binding motif is at least 80% identical to SEQ ID NO: 232. In some embodiments, the three HCDRs of the anti-CD19 binding motif and the three LCDRs of the anti-CD19 binding motif are comprised by a single polypeptide.

In some embodiments, the three HCDRs of the anti-CD20 binding motif, the three LCDRs of the anti-CD20 binding motif, the three HCDRs of the anti-CD19 binding motif, and the three LCDRs of the anti-CD19 binding motif are together comprised by a single polypeptide. In some embodiments, the chimeric antigen receptor comprises a transmembrane domain that is a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD28, CD33, CD37, CD45, CD64, CD80, CD86, CD134, CD137, CD154, or a zeta chain of a T cell receptor, or any combination thereof.

In various embodiments, the present disclosure comprises a bicistronic chimeric antigen receptor comprising a first chimeric antigen receptor of the present disclosure and a second chimeric antigen receptor that comprises a binding motif that specifically binds an antigen selected from the group consisting of 5T4, alphafetoprotein, B cell maturation antigen (BCMA), B cell receptor, CA-125, carcinoembryonic antigen, CD19, CD20, CD22, CD23, CD30, CD33, CD40, CD56, CD79, CD78, CD123, CD138, c-Met, CSPG4, IgM, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MUC-1, mutated p53, mutated ras, prostate-specific antigen, ROR1, VEGFR2, EphA3 (EPH receptor A3), BAFFR (B-cell activating factor receptor), and combinations thereof; and/or a binding motif that specifically binds an antigen that is characteristic of B-cells, optionally wherein the antigen that is characteristic of B-cells is not CD19 or CD20. In some embodiments, the second chimeric antigen receptor comprises an anti-CD19 binding motif.

The present disclosure further provides a nucleic acid encoding at least one polypeptide of the present disclosure and/or a vector comprising such nucleic acid. The present disclosure also comprises a method of generating an engineered cell, the method comprising transfecting or transducing a cell with a nucleic acid of the present disclosure. In various embodiments, the present disclosure comprises a cell encoding or expressing the chimeric antigen receptor provided herein, optionally wherein the cell is an immune cell, optionally wherein the cell is a T cell.

The present disclosure further provides a method of treating cancer in a subject in need thereof, the method comprising administering to the subject a cell therapy composition comprising one or more cells that encode or comprise an chimeric antigen receptor of the present disclosure. The present disclosure further provides a method of inducing an immune response in a subject or immunizing a subject against a cancer, the method comprising administering to the subject a cell therapy composition comprising one or more cells that encode or comprise an chimeric antigen receptor of the present disclosure. In various embodiments, the cells are CAR-T cells. In various embodiments, the cancer is acute lymphoblastic leukemia (ALL) (including non T cell ALL), acute myeloid leukemia, B cell prolymphocytic leukemia, B cell acute lymphoid leukemia ("BALL"), blastic plasmacy-toid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodys-plastic syndrome, non-Hodgkin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (including plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, or Waldenstrom macroglobulinemia, Mantle cell lymphoma (MCL), Transformed follicular lymphoma (TFL), Primary mediastinal B cell lymphoma (PMBCL), Multiple myeloma, Hairy cell lymphoma/leukemia, or a combination thereof. In some embodiments, the cell therapy is an allogeneic cell therapy or an autologous cell therapy.

In at least one aspect, the present disclosure comprises a chimeric antigen receptor comprising an anti-CD20 binding motif and a CD19 binding motif, wherein the anti-CD20 binding motif comprising amino acid sequences selected from the group consisting of SEQ ID NOs: 1, 23, 45, 67, 89, 111, 133, 155, 177, 199, 12, 34, 56, 78, 100, 122, 144, 166, 188, and 210. In some embodiments, the CD19 binding motif comprising amino acid sequences selected from the group consisting of SEQ ID NOs: 221 and 232. In some embodiments, the anti-CD20 binding motif comprising amino acid sequences selected from the group consisting of SEQ ID NOs: 1, 23, 45, 67, 89, 111, 133, 155, 177, 199, 12, 34, 56, 78, 100, 122, 144, 166, 188, and 210; wherein the CD19 binding motif comprising amino acid sequences selected from the group consisting of SEQ ID NOs: 221 and 232. In some embodiments, the anti-CD20 binding motif and the CD19 binding motif are comprised by one polypeptide. In some embodiments, the anti-CD20 binding motif and the CD19 binding motif are comprised by different polypeptides.

In at least one aspect, the present disclosure comprises a polynucleotide encoding amino acid sequences selected from the group consisting of SEQ ID NOs: 1, 23, 45, 67, 89, 111, 133, 155, 177, 199, 12, 34, 56, 78, 100, 122, 144, 166, 188, and 210. In at least one aspect, the present disclosure comprises a pharmaceutical composition comprising a chimeric antigen receptor comprising an anti-CD20 binding motif having amino acid sequences selected from the group consisting of SEQ ID NOs: 1, 23, 45, 67, 89, 111, 133, 155, 177, 199, 12, 34, 56, 78, 100, 122, 144, 166, 188, and 210. In some embodiments, the composition further comprises a CD19 binding motif.

DETAILED DESCRIPTION OF THE DISCLOSURE

The present disclosure relates to novel polypeptides comprising novel antigen binding molecules and polynucleotides encoding the same. Some aspects of the disclosure relate to a polynucleotide encoding a chimeric antigen receptor (CAR) comprising at least one of the heavy chain and light chains disclosed herein (or CDRs thereof). The present disclosure also provides vectors (e.g., viral vectors) comprising such polynucleotides and compositions comprising such vectors. The present disclosure further provides polynucleotides encoding such CARs or TCRs and compositions comprising such polynucleotides. The present disclosure additionally provides engineered cells (e.g., T cells) comprising such polynucleotides and/or transduced with such viral vectors and compositions comprising such engineered cells. The present disclosure provides compositions (e.g., pharmaceutical compositions) including a plurality of engineered T cells. The present disclosure provides methods for manufacturing such engineered T cells and compositions and uses (e.g., in treating a melanoma) of such engineered T cells and compositions. And, the present disclosure provides a method of inducing an immunity against a tumor comprising administering to a subject an effective amount of a cell comprising a polynucleotide, a vector, or a polypeptide of the present disclosure. Other aspects of the disclosure relate to cells comprising the CAR and their use in a T cell therapy for the treatment of a patient suffering from a cancer.

Any aspect or embodiment described herein may be combined with any other aspect or embodiment as disclosed herein. While the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims. The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, dictionaries, documents, manuscripts and scientific literature cited herein are hereby incorporated by reference. Other features and advantages of the disclosure will be apparent from the following Detailed Description, comprising the Examples, and the claims.

Definitions

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2$^{nd}$ ed., (2001), CRC Press; "The Dictionary of Cell & Molecular Biology", 5$^{th}$ ed., (2013), Academic Press; and "The Oxford Dictionary Of Biochemistry And Molecular Biology", Cammack et al. eds., 2$^{nd}$ ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system. In general, human antibodies are approximately 150 kD tetrameric agents composed of two identical heavy (H) chain polypeptides (about 50 kD each) and two identical light (L) chain polypeptides (about 25 kD each) that associate with each other into what is commonly referred to as a "Y-shaped" structure. The heavy and light chains are linked or connected to one another by a single disulfide bond; two other disulfide bonds connect the heavy chain hinge regions to one another, so that the dimers are connected to one another and the tetramer is formed. Naturally-produced antibodies are also glycosylated, e.g., on the CH2 domain.

The term "human antibody" is intended to comprise antibodies having variable and constant domain sequences generated, assembled, or derived from human immunoglobulin sequences, or sequences indistinguishable there-from. In some embodiments, antibodies (or antibody components) may be considered to be "human" even though their amino acid sequences comprise residues or elements not encoded by human germline immunoglobulin sequences (e.g., variations introduced by in vitro random or site-specific mutagenesis or introduced by in vivo somatic mutation). The term "humanized" is intended to comprise antibodies having a variable domain with a sequence derived from a variable domain of a non-human species (e.g., a mouse), modified to be more similar to a human germline encoded sequence. In some embodiments, a "humanized" antibody comprises one or more framework domains having substantially the amino acid sequence of a human framework domain, and one or more complementary determining regions having substantially the amino acid sequence as that of a non-human antibody. In some embodiments, a humanized antibody comprises at least a portion of an immunoglobulin constant region (Fc), generally that of a human immunoglobulin constant domain. In some embodiments, a humanized antibodies may comprise a $C_H1$, hinge, $C_H2$, $C_H3$, and, optionally, a $C_H4$ region of a human heavy chain constant domain.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen binding fragments of any of the above. In certain embodiments, antibodies described herein refer to polyclonal antibody populations. Antibodies may also comprise, for example, Fab' fragments, Fd' fragments, Fd fragments, isolated CDRs, single chain Fvs, polypeptide-Fc fusions, single domain antibodies (e.g., shark single domain antibodies such as IgNAR or fragments thereof), camelid antibodies, single chain or Tandem diabodies (TandAb®), Anticalins®, Nanobodies® minibodies, BiTE®s, ankyrin repeat proteins or DARPINS®, Avimers®, DARTs, TCR-like antibodies, Adnectins®, Affilins®, Transbodies®, Affibodies®, TrimerX®, MicroProteins, Fynomers®, Centyrins®, and KALBITOR®s.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen binding fragment or an antigen-binding portion of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments, the antigen binding molecule binds to BCMA, CLL-1, or FLT3. In certain embodiments, the antigen binding molecule binds to CD19, CD20, or both. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

In some instances, a CDR is substantially identical to one found in a reference antibody (e.g., an antibody of the present disclosure) and/or the sequence of a CDR provided in the present disclosure. In some embodiments, a CDR is substantially identical to a reference CDR (e.g., a CDR provided in the present disclosure) in that it is either identical in sequence or contains between 1, 2, 3, 4, or 5 (e.g. 1-5) amino acid substitutions as compared with the reference CDR. In some embodiments a CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR (e.g., 85-90%, 85-95%, 85-100%, 90-95%, 90-100%, or 95-100%). In some embodiments a CDR is substantially identical to a reference CDR in that it shows at least 96%, 96%, 97%, 98%, 99%, or 100% sequence identity with the reference CDR. In some embodiments a CDR is substantially identical to a reference CDR in that one amino acid within the CDR is deleted, added, or substituted as compared with the reference CDR while the CDR has an amino acid sequence that is otherwise identical with that of the reference CDR. In some embodiments a CDR is substantially identical to a reference CDR in that 2, 3, 4, or 5 (e.g. 2-5) amino acids within the CDR are deleted, added, or substituted as compared with the reference CDR while the CDR has an amino acid sequence that is otherwise identical to the reference CDR. In various embodiments, an antigen binding fragment binds a same antigen as a reference antibody.

An antigen binding fragment may be produced by any means. For example, in some embodiments, an antigen binding fragment may be enzymatically or chemically produced by fragmentation of an intact antibody. In some embodiments, an antigen binding fragment may be recombinantly produced (i.e., by expression of an engineered nucleic acid sequence). In some embodiments, an antigen binding fragment may be wholly or partially synthetically produced. In some embodiments, an antigen binding fragment may have a length of at least about 50, 60, 70, 80, 90, 100, 110, 120, 130, 140, 150, 160, 170, 180, 190 amino acids or more; in some embodiments at least about 200 amino acids (e.g., 50-100, 50-150, 50-200, or 100-200 amino acids).

The term "variable region" or "variable domain" is used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

| CDR Numbering | | | | |
|---|---|---|---|---|
| Loop | Kabat | AbM | Chothia | Contact |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32 . . . 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190:382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196:901-917; Al-Lazikani B et al., (1997) J Mol Biol 273:927-948; Chothia C et al., (1992) J Mol Biol 227:799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

The terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

The term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

The term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIA-CORE® or KinExA.

A "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain. In general, two sequences are generally considered to be "substantially similar" if they contain a conservative amino acid substitution in corresponding positions. For example, certain amino acids are generally classified as "hydrophobic" or "hydrophilic" amino acids, and/or as having "polar" or "non-polar" side chains. Substitution of one amino acid for another of the same type may be considered a conservative substitution. Exemplary amino acid categorizations are summarized in Tables 2 and 3 below:

TABLE 2

| Amino Acid | 3-Letter | 1-Letter | Property | Property | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

US 12,583,923 B2

21

TABLE 3

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

The term "heterologous" means from any source other than naturally occurring sequences. For example, a heterologous sequence included as a part of a costimulatory protein having the amino acid sequence of SEQ ID NO: 232, e.g., the corresponding human costimulatory protein, is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

An "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189:1-23; Chayen NE (1997) Structure 5:1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter CW; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270:1388-1394 and Cunningham B C & Wells J A (1989) Science 244:1081-1085 for a description of mutagenesis techniques, including alanine scanning mutagenesis techniques.

An antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

The term "binding" generally refers to a non-covalent association between or among two or more entities. Direct binding involves physical contact between entities or moieties. "Indirect" binding involves physical interaction by way of physical contact with one or more intermediate entities. Binding between two or more entities may be assessed in any of a variety of contexts, e.g., where interacting entities or moieties are studied in isolation or in the context of more complex systems (e.g., while covalently or otherwise associated with a carrier entity and/or in a biological system such as a cell).

The terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen. Binding may comprise preferential association of a binding motif, antibody, or antigen binding system with a target of the binding motif, antibody, or antigen binding system as compared to association of the binding motif, antibody, or antigen binding system with an entity that is not the target (i.e. non-target). In some embodiments, a binding motif, antibody, or antigen binding system selectively binds a target if binding between the binding motif, antibody, or antigen binding system and the target is greater than 2-fold, greater than 5-fold, greater than 10-fold, 20-fold, 30-fold, 40-fold, 50-fold, 60-fold, 70-fold, 80-fold, 90-fold, or greater than 100-fold as compared with binding of the binding motif, antibody, or antigen binding system and a non-target. In some embodiments, a binding motif, antibody, or antigen binding system selectively binds a target if the binding affinity is less than about $10^{-5}$ M, less than about $10^{-6}$ M, less than about $10^{-7}$ M, less than about $10^{-8}$ M, or less than about $10^{-9}$ M.

In another embodiment, molecules that specifically bind to an antigen bind with a dissociation constant ($K_d$) of about $1 \times 10^{-7}$M. In some embodiments, the antigen binding molecule specifically binds an antigen with "high affinity" when the $K_d$ is about $1 \times 10^{-9}$ M to about $5 \times 10^{-9}$ M. In some embodiments, the antigen binding molecule specifically binds an antigen with "very high affinity" when the $K_d$ is $1 \times 10^{-10}$ M to about $5 \times 10^{-10}$ M. In one embodiment, the antigen binding molecule has a $K_d$ of $10^{-9}$ M. In one embodiment, the off-rate is less than about $1 \times 10^{-5}$. In other embodiments, the antigen binding molecule binds human BCMA with a $K_d$ of between about $1 \times 10^{-7}$ M and about $1 \times 10^{-13}$ M. In yet another embodiment, the antigen binding molecule binds human BCMA with a $K_d$ of about $1 \times 10^{-10}$ M to about $5 \times 10^{-10}$ M. In some embodiments, the antigen binding molecule binds human CD19, CD20, or both with a $K_d$ of between about $1 \times 10^{-7}$ M and about $1 \times 10^{-13}$ M. In yet another embodiment, the antigen binding molecule binds human CD19, CD20, or both with a $K_d$ of about $1 \times 10^{-10}$ M to about $5 \times 10^{-10}$ M.

In a specific embodiment, provided herein is an antibody or an antigen binding molecule thereof that binds to a target human antigen, e.g., human BCMA or human CLL-1, with higher affinity than to another species of the target antigen, e.g., a non-human BCMA or a non-human CLL-1. In some embodiments, provided herein is an antibody or an antigen binding molecule thereof that binds to human CD19, human CD20, or both, with higher affinity than to another species of one or both target antigens, e.g., a non-human CD19, non-human CD20, or both. In certain embodiments, provided herein is an antibody or an antigen binding molecule t thereof that binds to the target human antigen, e.g., human BCMA or human CLL-1, with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In certain embodiments, provided herein is an antibody or an antigen binding molecule thereof that binds to human CD19, human CD20, or both, with a 5%, 10%, 15%, 20%, 25%, 30%, 35%, 40%, 45%, 50%, 55%, 60%, 65%, 70% or higher affinity than to another species of one or both target antigens as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

"Chimeric antigen receptor" or "CAR" refers to a molecule engineered to comprise a binding motif and a means of activating immune cells (for example T cells such as naive T cells, central memory T cells, effector memory T cells or combination thereof) upon antigen binding. CARs are also known as artificial T cell receptors, chimeric T cell receptors or chimeric immunoreceptors. In some embodiments, a CAR comprises a binding motif, an extracellular domain, a transmembrane domain, one or more co-stimulatory domains, and an intracellular signaling domain. A T cell that has been genetically engineered to express a chimeric antigen receptor may be referred to as a CAR T cell. "Extracellular domain" (or "ECD") refers to a portion of a polypeptide that, when the polypeptide is present in a cell membrane, is understood to reside outside of the cell membrane, in the extracellular space.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is all or a fragment of CD19 or CD20. A "target" is any molecule bound by a binding motif, antigen binding system, or binding agent, e.g., an antibody. In some embodiments, a target is an antigen or epitope of the present disclosure.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

"Transformation" refers to any process by which exogenous DNA is introduced into a host cell. Transformation may occur under natural or artificial conditions using various methods. Transformation may be achieved using any known method for the insertion of foreign nucleic acid sequences into a prokaryotic or eukaryotic host cell. In some embodiments, some transformation methodology is selected based on the host cell being transformed and/or the nucleic acid to be inserted. Methods of transformation may comprise, yet are not limited to, viral infection, electroporation, and lipofection. In some embodiments, a "transformed" cell is stably transformed in that the inserted DNA is capable of replication either as an autonomously replicating plasmid or as part of the host chromosome. In some embodiments, a transformed cell may express introduced nucleic acid.

Term "vector" refers to a recipient nucleic acid molecule modified to comprise or incorporate a provided nucleic acid sequence. One type of vector is a "plasmid," which refers to a circular double stranded DNA molecule into which additional DNA may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors comprise sequences that direct expression of inserted genes to which they are operatively linked. Such vectors may be referred to herein as "expression vectors." Standard techniques may be used for engineering of vectors, e.g., as found in Sambrook et al., Molecular Cloning: A Laboratory Manual (2d ed., Cold Spring Harbor Laboratory Press, Cold Spring Harbor, N.Y. (1989)), which is incorporated herein by reference for any purpose.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present disclosure include, but are not limited to, cancers of the immune system including lymphoma, leukemia, myeloma, and other leukocyte malignancies. In some embodiments, the methods of the present disclosure can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be Arefractory. A refractory cancer refers to a cancer that is not amendable to surgical intervention and the cancer is either initially unresponsive to chemo- or radiation therapy or the cancer becomes unresponsive over time. Cancer further includes relapsed or refractory large B-cell lymphoma after two or more lines of systemic therapy, including diffuse large B-cell lymphoma (DLBCL) not otherwise specified, primary mediastinal large B-cell lymphoma after two or more lines of systemic therapy, high grade B-cell lymphoma, and DLBCL arising from follicular lymphoma.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-la, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1α), MIP-1β (MIP-1b), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2RB, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

"Linker" (L) or "linker domain" or "linker region" refers to an oligo- or polypeptide region from about 1 to 100 amino acids in length, which links together any of the domains/regions of the CAR of the invention. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL sequences of porcine teschovirus (P2A), virus (T2A) or combinations, variants and functional equivalents thereof. In other embodiments, the linker sequences may comprise Asp-Val/Ile-Glu-X-Asn-Pro-Gly.$^{(2A)}$-Pro.$^{(2B)}$ motif (SEQ ID NO: 314), which results in cleavage between the 2A glycine and the 2B proline. Other linkers will be apparent to those of skill in the art and may be used in connection with alternate embodiments of the invention. By way of example, in some examples, a linker may be used to connect or link different antigen binding systems such as two CARs of a bicistronic CAR. A linker may be a portion of a multi-element agent that connects different elements to one another. For example, a polypeptide comprises two or more functional or structural domains may comprise a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. A linker may connect or link together any of the domains/regions of a CAR of the present disclosure. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length (e.g., 1 to 10, 1 to 20, 1 to 30, 1 to 40, 1 to 50, 1 to 60, 1 to 70, 1 to 80, 1 to 90, 1 to 100, 10 to 20, 10 to 30, 10 to 40, 10 to 50, 10 to 60, 10 to 70, 10 to 80, 10 to 90, or 10 to 100 amino acids in length). In some embodiments, a linker is characterized in that it tends not to adopt a rigid three-dimensional structure, and instead provides flexibility to the polypeptide.

"Single chain variable fragment", "single-chain antibody variable fragments" or "scFv" antibodies refer to forms of antibodies comprising the variable regions of only the heavy and light chains, connected by a linker peptide.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome. Engineering generally comprises manipulation by the hand of man. For example, a polynucleotide is considered to be "engineered" when two or more sequences, that are not linked or connected together in that order in nature, are manipulated by the hand of man to be directly linked or connected to one another in the engineered polynucleotide. In the context of manipulation of cells by techniques of molecular biology, a cell or organism is considered to be "engineered" if it has been manipulated so that its genetic information is altered (e.g., new genetic material not previously present has been introduced, for example by transformation, somatic hybridization, transfection, transduction, or other mechanism, or previously present genetic material is altered or removed, for example by substitution or deletion mutation, or by other protocols). In some embodiments, a binding agent is a modified lymphocyte, e.g., a T cell, may be obtained from a patient or a donor. An engineered cell may be modified to express an exogenous construct, such as, e.g., a chimeric antigen receptor (CAR) or a T cell receptor (TCR), which is incorporated into the cell's genome. Progeny of an engineered polynucleotide or binding agent are generally referred to as "engineered" even though the actual manipulation was performed on a prior entity. In some embodiments, "engineered" refers to an entity that has been designed and produced. The term "designed" refers to an agent (i) whose structure is or was selected by the hand of man; (ii) that is produced by a process requiring the hand of man; and/or (iii) that is distinct from natural substances and other known agents. A "T cell receptor" or "TCR" refers to antigen-recognition molecules present on the surface of T-cells. During normal T-cell development, each of the four TCR genes, α, β, γ, and δ, may rearrange leading to highly diverse TCR proteins.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from a naturally-occurring costimulatory domain, e.g., having the amino acid sequence of SEQ ID NO: 232, or a variant thereof, e.g., a variant having a truncated hinge domain ("THD"), and the activating domain can be derived from, e.g., CD3-zeta. In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708, and these references are incorporated by reference in their entirety. "Adoptive cell therapy" or "ACT" involves transfer of immune cells with anti-tumor activity into a subject, e.g., a cancer patient. In some embodiments, ACT is a treatment approach that involves the use of lymphocytes (e.g., engineered lymphocytes) with anti-tumor activity.

A "patient" includes any human who is afflicted with a cancer (e.g., a lymphoma or a leukemia). The terms "subject" and "patient" are used interchangeably herein.

The term "in vitro" refers to events occurring in an artificial environment, e.g., in a test tube, reaction vessel, cell culture, etc., rather than within a multi-cellular organism. The term "in vitro cell" refers to any cell which is cultured ex vivo. In particular, an in vitro cell can include a T cell. The term "in vivo" refers to events that occur within a multi-cellular organism, such as a human or a non-human animal.

"Antigen-specific targeting region" (ASTR) refers to the region of the CAR which targets specific antigens. The CARs of the invention comprise at least two targeting regions which target at least two different antigens. In an embodiment, CARs comprise three or more targeting regions which target at least three or more different antigens. The targeting regions on the CAR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of the invention. In fact, almost any molecule that binds a given antigen with high affinity can be used as an antigen-specific targeting region, as will be appreciated by those of skill in the art.

"Antigen presenting cell" or "APC" refers to cells that process and present antigens to T-cells. Exemplary APCs comprise dendritic cells, macrophages, B cells, certain activated epithelial cells, and other cell types capable of TCR stimulation and appropriate T cell costimulation.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand" as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CDl-la, CDl-lb, CDl-lc, CDl-ld, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGBl, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CDl la/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

The terms "improve," "increase," "inhibit," and "reduce" indicate values that are relative to a baseline or other reference measurement. In some embodiments, an appropriate reference measurement may comprise a measurement in certain system (e.g., in a single individual) under otherwise comparable conditions absent presence of (e.g., prior to and/or after) an agent or treatment, or in presence of an appropriate comparable reference agent. In some embodiments, an appropriate reference measurement may comprise a measurement in comparable system known or expected to respond in a comparable way, in presence of the relevant agent or treatment.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission. In some embodiments, treatment may be of a subject who does not exhibit signs of the relevant disease, disorder and/or condition and/or of a subject who exhibits only early signs of the disease, disorder, and/or condition. In some embodiments, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "agent" may refer to a molecule or entity of any class comprising, or a plurality of molecules or entities, any of which may be, for example, a polypeptide, nucleic acid, saccharide, lipid, small molecule, metal, cell, or organism (for example, a fraction or extract thereof) or component thereof. In some embodiments, an agent may be utilized in isolated or pure form. In some embodiments, an agent may be utilized in a crude or impure form. In some embodiments, an agent may be provided as a population, collection, or library, for example that may be screened to identify or characterize members present therein.

Two events or entities are "associated" with one another if the presence, level, and/or form of one is correlated with that of the other. For example, an entity (e.g., polypeptide, genetic signature, metabolite, microbe, etc.) is considered to be associated with a disease, disorder, or condition, if its presence, level, and/or form correlates with incidence of and/or susceptibility to the disease, disorder, or condition (e.g., across a relevant population). For example, two or more entities are physically "associated" with one another if they interact, directly or indirectly, so that they are and/or remain in physical proximity with one another (e.g., bind). In additional examples, two or more entities that are physically associated with one another are covalently linked or connected to one another, or non-covalently associated, for example by means of hydrogen bonds, van der Waals interaction, hydrophobic interactions, magnetism, and combinations thereof.

Term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known. Calculation of the percent identity of two nucleic acid or polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-100%).

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm. Other algorithms are also available for comparison of amino acid or nucleic acid sequences, comprising those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215 (3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. Sequences with substantial sequence similarity may be homologs of one another.

"Combination therapy" refers to those situations in which a subject is simultaneously exposed to two or more therapeutic regimens (e.g., two or more therapeutic moieties). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality (ies) to a subject receiving the other agent(s) or modality (ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

"Corresponding to" may be used to designate the position/identity of a structural element in a molecule or composition through comparison with an appropriate reference molecule or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, for purposes of simplicity, residues in a polypeptide may be designated using a canonical numbering system based on a reference related polypeptide, so that an amino acid "corresponding to" a residue at position 100, for example, need not actually be the 100th amino acid in an amino acid chain provided it corresponds to the residue found at position 100 in the reference polypeptide. Various sequence alignment strategies are available, comprising software programs such as, for example, BLAST, CS-BLAST, CUDASW++, DIA-MOND, FASTA, GGSEARCH/GLSEARCH, Genoogle, HMMER, HHpred/HHsearch, IDF, Infernal, KLAST, USE-ARCH, parasail, PSI-BLAST, PSI-Search, ScalaBLAST, Sequilab, SAM, SSEARCH, SWAPHI, SWAPHI-LS, SWIMM, or SWIPE that may be utilized, for example, to identify "corresponding" residues in polypeptides and/or nucleic acids in accordance with the present disclosure.

The term "domain" refers to a portion of an entity. In some embodiments, a "domain" is associated with a structural and/or functional feature of the entity, e.g., so that, when the domain is physically separated from the rest of its parent entity, it substantially or entirely retains the structural and/or functional feature. In some embodiments, a domain may comprise a portion of an entity that, when separated from that (parent) entity and linked or connected with a different (recipient) entity, substantially retains and/or imparts on the recipient entity one or more structural and/or functional features, e.g., that characterized it in the parent entity. In some embodiments, a domain is a portion of a molecule (e.g., a small molecule, carbohydrate, lipid, nucleic acid, or polypeptide). In some embodiments, a domain is a section of a polypeptide; in some such embodiments, a domain is characterized by a structural element (e.g., an amino acid sequence or sequence motif, α-helix character, β-sheet character, coiled-coil character, random coil character, etc.), and/or by a functional feature (e.g., binding activity, enzymatic activity, folding activity, signaling activity, etc.).

The term "dosage form" may be used to refer to a physically discrete unit of an active agent (e.g., an antigen binding system or antibody) for administration to a subject. Generally, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population. The total amount of a therapeutic composition or agent administered to a subject is determined by one or more medical practitioners and may involve administration of more than one dosage forms.

The term "dosing regimen" may be used to refer to a set of one or more unit doses that are administered individually to a subject. In some embodiments, a given therapeutic agent has a recommended dosing regimen, which may involve one or more doses. In some embodiments, a dosing regimen comprises a plurality of doses each of which is separated in time from other doses. In some embodiments, a dosing regimen comprises a plurality of doses and consecutive doses are separated from one another by time periods of equal length; in some embodiments, a dosing regimen comprises a plurality of doses and consecutive doses are separated from one another by time periods of at least two different lengths. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen is periodically adjusted to achieve a desired or beneficial outcome.

"Effector function" refers to a biological result of interaction of an antibody Fc region with an Fc receptor or ligand. Effector functions comprise, without limitation, antibody-dependent cell-mediated cytotoxicity (ADCC), antibody-dependent cell-mediated phagocytosis (ADCP), and complement-mediated cytotoxicity (CMC). An effector function may be antigen binding dependent, antigen binding independent, or both. ADCC refers to lysis of antibody-bound target cells by immune effector cells. Without wishing to be bound by any theory, ADCC is generally understood to involve Fc receptor (FcR)-bearing effector cells recognizing and subsequently killing antibody-coated target cells (e.g., cells that express on their surface antigens to which an antibody is bound). Effector cells that mediate ADCC may comprise immune cells, comprising yet not limited to, one or more of natural killer (NK) cells, macrophages, neutrophils, eosinophils.

"Effector cell" refers to a cell of the immune system that expresses one or more Fc receptors and mediates one or more effector functions. In some embodiments, effector cells may comprise, without limitation, one or more of monocytes, macrophages, neutrophils, dendritic cells, eosinophils, mast cells, platelets, large granular lymphocytes, Langerhans' cells, natural killer (NK) cells, T-lymphocytes, and B-lymphocytes. Effector cells may be of any organism comprising, without limitation, humans, mice, rats, rabbits, and monkeys.

The term "excipient" refers to an agent that may be comprised in a composition, for example to provide or contribute to a desired consistency or stabilizing effect. In some embodiments, a suitable excipient may comprise, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

A "fragment" or "portion" of a material or entity as described herein has a structure that comprises a discrete portion of the whole, e.g., of a physical entity or abstract entity. In some embodiments, a fragment lacks one or more moieties found in the whole. In some embodiments, a fragment consists of or comprises a characteristic structural element, domain or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer (e.g., 85-90%, 85-95%, 85-100%, 90-95%, 90-100%, or 95-100%). The whole material or entity may in some embodiments be referred to as the "parent" of the fragment.

The term "fusion polypeptide" or "fusion protein" generally refers to a polypeptide comprising at least two segments. Generally, a polypeptide containing at least two such segments is considered to be a fusion polypeptide if the two segments are moieties that (1) are not comprised in nature in the same peptide, and/or (2) have not previously been linked or connected to one another in a single polypeptide, and/or (3) have been linked or connected to one another through action of the hand of man.

The term "gene product" or "expression product" generally refers to an RNA transcribed from the gene (pre- and/or post-processing) or a polypeptide (pre- and/or post-modification) encoded by an RNA transcribed from the gene.

The term "isolated" refers to a substance that (1) has been separated from at least some components with which it was associated at an earlier time or with which the substance would otherwise be associated, and/or (2) is present in a composition that comprises a limited or defined amount or concentration of one or more known or unknown contaminants. An isolated substance, in some embodiments, may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% (e.g., 85-90%, 85-95%, 85-100%, 90-95%, 90-100%, or 95-100%) of other non-substance components with which the substance was associated at an earlier time, e.g., other components or contaminants with which the substance was previously or otherwise would be associated. In certain instances, a substance is isolated if it is present in a composition that comprises a limited or reduced amount or concentration of molecules of a same or similar type. For instance, in certain instances, a nucleic acid, DNA, or RNA substance is isolated if it is present in a composition that comprises a limited or reduced amount or concentration of non-substance nucleic acid, DNA, or RNA molecules. For instance, in certain instances, a polypeptide substance is isolated if it is present in a composition that comprises a limited or reduced amount or concentration of non-substance polypeptide molecules. In certain embodiments, an amount may be, e.g., an amount measured relative to the amount of a desired substance present in a composition. In certain embodiments, a limited amount may be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition (e.g., 85-90%, 85-95%, 85-100%, 90-95%, 90-100%, or 95-100%). In certain instances, a composition is pure or substantially pure with respect to a selected substance. In some embodiments, an isolated substance is about 80%, about 85%, about 90%, about 91%, about 92%, about 93%, about 94%, about 95%, about 96%, about 97%, about 98%, about 99%, or more than about 99% pure (e.g., 85-90%, 85-95%, 85-100%, 90-95%, 90-100%, or 95-100%). A substance is "pure" if it is substantially free of other components or of contaminants. In some embodiments, a substance may still be considered "isolated" or even "pure," after having been combined with certain other components such as, for example, one or more carriers or excipients (e.g., buffer, solvent, water, etc.); in such embodiments, percent isolation or purity of the substance is calculated without comprising such carriers or excipients.

"Nucleic acid" refers to any polymeric chain of nucleotides. A nucleic acid may be DNA, RNA, or a combination thereof. In some embodiments, a nucleic acid comprises one or more natural nucleic acid residues. In some embodiments, a nucleic acid comprises of one or more nucleic acid analogs. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long (e.g., 20 to 100, 20 to 500, 20 to 1000, 20 to 2000, or 20 to 5000 or more residues). In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide.

"Operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element.

The term "pharmaceutically acceptable" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or any deleterious effect must be outweighed by a benefit to the recipient. The term "pharmaceutically acceptable carrier" means a pharmaceutically-acceptable material, composition or vehicle, such as a liquid or solid filler, diluent, excipient, or solvent encapsulating material, involved in carrying or transporting an agent from one portion of the body to another (e.g., from one organ to another). Each carrier present in a pharmaceutical composition must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutical composition" refers to a composition in which an active agent is formulated together with one or more pharmaceutically acceptable carriers. In some embodiments, the active agent is present in a unit dose amount appropriate for administration in a therapeutic regimen that shows a statistically significant probability of achieving a predetermined therapeutic effect when administered to a relevant subject or population. In some embodiments, a pharmaceutical composition may be formulated for administration in solid or liquid form, comprising, without limitation, a form adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The term "reference" describes a standard or control relative to which a comparison is performed. For example, in some embodiments, an agent, animal, individual, population, sample, sequence, or value of interest is compared with a reference or control that is an agent, animal, individual, population, sample, sequence, or value. In some embodiments, a reference or control is tested, measured, and/or determined substantially simultaneously with the testing, measuring, or determination of interest. In some embodiments, a reference or control is a historical reference or control, optionally embodied in a tangible medium. Generally, a reference or control is determined or characterized under comparable conditions or circumstances to those under assessment. When sufficient similarities are present to justify reliance on and/or comparison to a selected reference or control.

"Regulatory T cells" ("Treg", "Treg cells", or "Tregs") refer to a lineage of CD4+ T lymphocytes that participate in controlling certain immune activities, e.g., autoimmunity, allergy, and response to infection. Regulatory T cells may regulate the activities of T cell populations, and may also influence certain innate immune system cell types. Tregs may be identified by the expression of the biomarkers CD4, CD25 and Foxp3, and low expression of CD127. Naturally occurring Treg cells normally constitute about 5-10% of the peripheral CD4+T lymphocytes. However, Treg cells within a tumor microenvironment (i.e. tumor-infiltrating Treg cells), Treg cells may make up as much as 20-30% of the total CD4+ T lymphocyte population.

The term "sample" generally refers to an aliquot of material obtained or derived from a source of interest. In some embodiments, a source of interest is a biological or environmental source. In some embodiments, a source of interest may comprise a cell or an organism, such as a cell population, tissue, or animal (e.g., a human). In some embodiments, a source of interest comprises biological tissue or fluid. In some embodiments, a biological tissue or fluid may comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may comprise an intracellular fluid, an extracellular fluid, an intravascular fluid (blood plasma), an interstitial fluid, a lymphatic fluid, and/or a transcellular fluid. In some embodiments, a biological fluid may comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., broncheoalveolar, ductal, nasal, ocular, oral, uterine, vaginal, or other washing or lavage). In some embodiments, a biological sample comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

The term "stage of cancer" refers to a qualitative or quantitative assessment of the level of advancement of a cancer. In some embodiments, criteria used to determine the stage of a cancer may comprise, without limitation, one or more of where the cancer is located in a body, tumor size, whether the cancer has spread to lymph nodes, whether the cancer has spread to one or more different parts of the body, etc. In some embodiments, cancer may be staged using the so-called TNM System, according to which T refers to the size and extent of the main tumor, usually called the primary tumor; N refers to the number of nearby lymph nodes that have cancer; and M refers to whether the cancer has metastasized. In some embodiments, a cancer may be referred to as Stage 0 (abnormal cells are present without having spread to nearby tissue, also called carcinoma in situ, or CIS; CIS is not cancer, though could become cancer), Stage I-III (cancer is present; the higher the number, the larger the tumor and the more it has spread into nearby tissues), or Stage IV (the cancer has spread to distant parts of the body). In some embodiments, a cancer may be assigned to a stage selected from the group consisting of: in situ; localized (cancer is limited to the place where it started, with no sign that it has spread); regional (cancer has spread to nearby lymph nodes, tissues, or organs): distant (cancer has spread to distant parts of the body); and unknown (there is not enough information to determine the stage).

The phrase "therapeutic agent" may refer to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms or human subjects. In some embodiments, an appropriate population may be defined by various criteria, such as a certain age group, gender, genetic background, preexisting clinical conditions, in accordance with presence or absence of a biomarker, etc. In some embodiments, a therapeutic agent is a substance that may be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is an agent that has been or is required to be approved by a government agency before it may be marketed for administration to humans. In some embodiments, a therapeutic agent is an agent for which a medical prescription is required for administration to humans.

Various aspects of the disclosure are described in further detail in the following subsections. The present disclosure provides antigen binding systems and binding agents comprising at least an anti-CD20 binding motif. Among other things, the present disclosure provides methods and compositions useful for treatment of cancer and/or for initiating or modulating immune responses. In certain embodiments, the present disclosure comprises antigen binding systems and binding agents that are dual-targeted in that they comprise an anti-CD20 binding motif and a second binding motif against a second antigen or epitope. In some instances, the second binding motif selectively binds CD19. In various embodiments, one or more binding motifs is an scFv. Exemplary binding motif amino acid sequences, and nucleic acid sequences encoding the same, are provided herein. In some embodiments, an antigen binding system of the present disclosure is a chimeric antigen receptor. In some embodiments, an antigen binding system of the present disclosure is a bispecific or bicistronic chimeric antigen receptor. In some embodiments, a binding agent of the present disclosure is an engineered T cell receptor.

Various embodiments of the present disclosure provide a vector encoding a binding motif or antigen binding system provided herein, e.g., a vector encoding an anti-CD20/anti-CD19 antigen binding system, such as a bispecific or bicistronic anti-CD20/anti-CD19 chimeric antigen receptor. Various embodiments of the present disclosure provide binding agent that is a cell encoding or expressing an antigen binding system or binding motif provided herein, e.g., a T cell engineered to encode or express an anti-CD20/anti-CD19 chimeric antigen receptor, such as a bispecific or bicistronic anti-CD20/anti-CD19 chimeric antigen receptor. The present disclosure provides binding agents, e.g., comprising binding agents that are immune cells genetically modified with an integrated gene, e.g., a nucleotide sequence of interest (e.g., a constitutive expression construct and/or an inducible expression construct that comprises such nucleotide sequence). In some embodiments, the present disclosure provides methods of treating a subject having a tumor, comprising administering to the subject a binding agent therapy described herein and/or a protein therapeutic described herein. In some embodiments, methods further comprise administration of one or more additional therapies (e.g., a second binding agent (e.g., CAR-T cell, CAR-NK cell, TCR-T cell, TIL cell, allogeneic NK cell, and autologous NK cell), an antibody-drug conjugate, an antibody, a bispecific antibody, a T cell-engaging bispecific antibody, an engineered antibody, and/or a polypeptide described herein).

Other features, objects, and advantages of the present disclosure are apparent in the detailed description that follows. It should be understood, however, that the detailed description, while indicating embodiments of the present disclosure, is given by way of illustration only, not limitation.

An anti-CD20 binding motif of the present disclosure may comprise antigen-binding sequences as found in an antibody described herein. In some instances, an anti-CD20 binding motif of the present disclosure comprises an antigen binding fragment described herein. Unless otherwise indicated, it is to be appreciated the references to CD20 in the present disclosure relate to human CD20. In various embodiments, an anti-CD20 binding motif of the present disclosure comprises at least one heavy chain CDR (HCDR) provided herein, e.g., at least one HCDR disclosed in any one of Tables 4-13. In various embodiments, an anti-CD20 binding motif of the present disclosure comprises two HCDRs provided herein, e.g., at least two HCDRs disclosed in any one of Tables 4-13. In various embodiments, an anti-CD20 binding motif of the present disclosure comprises three HCDRs provided herein, e.g., three HCDRs disclosed in any one of Tables 4-13. In various embodiments, an anti-CD20 binding motif of the present disclosure comprises at least one light chain CDR (LCDR) provided herein, e.g., at least one LCDR disclosed in any one of Tables 4-13. In various embodiments, an anti-CD20 binding motif of the present disclosure comprises two LCDRs provided herein, e.g., at least two LCDRs disclosed in any one of Tables 4-13. In various embodiments, an anti-CD20 binding motif of the present disclosure comprises three LCDRs provided herein, e.g., three LCDRs disclosed in any one of Tables 4-13.

In various embodiments, an anti-CD20 binding motif of the present disclosure comprises at least one HCDR provided herein, e.g., at least one HCDR disclosed in any one of Tables 4-13, and at least one LCDR provided herein, e.g., at least one LCDR disclosed in any one of Tables 4-13. In various embodiments, an anti-CD20 binding motif of the present disclosure comprises one HCDR provided herein, e.g., at least one HCDR disclosed in any one of Tables 4-13, and one LCDR provided herein, e.g., derived from the same Table of Tables 4-13 as the HCDR(s). In various embodiments, an anti-CD20 binding motif of the present disclosure comprises two HCDRs provided herein, e.g., at least two HCDRs disclosed in any one of Tables 4-13, and two LCDRs provided herein, e.g., at least two LCDRs disclosed in any one of Tables 4-13. In various embodiments, an anti-CD20 binding motif of the present disclosure comprises two HCDRs provided herein, e.g., at least two HCDRs disclosed in any one of Tables 4-13, and two LCDRs provided herein, e.g., derived from the same Table of Tables 4-13 as the HCDR(s). In various embodiments, an anti-CD20 binding motif of the present disclosure comprises three HCDRs provided herein, e.g., three HCDRs disclosed in any one of Tables 4-13, and three LCDRs provided herein, e.g., three LCDRs disclosed in any one of Tables 4-13. In various embodiments, an anti-CD20 binding motif of the present disclosure comprises three HCDRs provided herein, e.g., three HCDRs disclosed in any one of Tables 4-13, and three LCDRs derived from the same Table of Tables 4-13 as the HCDR(s).

In various embodiments, an anti-CD20 binding motif of the present disclosure comprises at least one heavy chain framework region (heavy chain FR) of a heavy chain variable domain disclosed herein, e.g., at least one heavy chain FR of a heavy chain variable domain disclosed in any one of Tables 4-13. In various embodiments, an anti-CD20 binding motif of the present disclosure comprises two heavy chain FRs of a heavy chain variable domain disclosed herein, e.g., at least two heavy chain FRs of a heavy chain variable domain disclosed in any one of Tables 4-13. In various embodiments, an anti-CD20 binding motif of the present disclosure comprises three heavy chain FRs of a heavy chain variable domain disclosed herein, e.g., three heavy chain FRs of a heavy chain variable domain disclosed in any one of Tables 4-13.

In various embodiments, an anti-CD20 binding motif of the present disclosure comprises at least one light chain FR of a light chain variable domain disclosed herein, e.g., at least one light chain FR of a light chain variable domain disclosed in any one of Tables 4-13. In various embodiments, an anti-CD20 binding motif of the present disclosure comprises two light chain FRs of a light chain variable domain disclosed herein, e.g., at least two light chain FRs of a light chain variable domain disclosed in any one of Tables 4-13. In various embodiments, an anti-CD20 binding motif of the present disclosure comprises three light chain FRs of a light chain variable domain disclosed herein, e.g., three light chain FRs of a light chain variable domain disclosed in any one of Tables 4-13.

In various embodiments, an anti-CD20 binding motif of the present disclosure comprises at least one heavy chain FR of a heavy chain variable domain disclosed herein, e.g., at least one heavy chain FR of a heavy chain variable domain disclosed in any one of Tables 4-13, and at least one light chain FR of a light chain variable domain disclosed herein, e.g., at least one light chain FR of a light chain variable domain disclosed in any one of Tables 4-13. In various embodiments, an anti-CD20 binding motif of the present disclosure comprises one heavy chain FR of a heavy chain variable domain disclosed herein, e.g., at least one heavy chain FR of a heavy chain variable domain disclosed in any one of Tables 4-13, and one light chain FR of a light chain variable domain disclosed herein, e.g., derived from the same Table of Tables 4-13 as the heavy chain FR(s). In various embodiments, an anti-CD20 binding motif of the present disclosure comprises two heavy chain FRs of a heavy chain variable domain disclosed herein, e.g., at least two heavy chain FRs of a heavy chain variable domain disclosed in any one of Tables 4-13, and two light chain FRs of a light chain variable domain disclosed herein, e.g., at least two light chain FRs of a light chain variable domain disclosed in any one of Tables 4-13. In various embodiments, an anti-CD20 binding motif of the present disclosure comprises two heavy chain FRs of a heavy chain variable domain disclosed herein, e.g., at least two heavy chain FRs of a heavy chain variable domain disclosed in any one of Tables 4-13, and two light chain FRs of a light chain variable domain disclosed herein, e.g., derived from the same Table of Tables 4-13 as the heavy chain FR(s). In various embodiments, an anti-CD20 binding motif of the present disclosure comprises three heavy chain FRs of a heavy chain variable domain disclosed herein, e.g., three heavy chain FRs of a heavy chain variable domain disclosed in any one of Tables 4-13, and three light chain FRs of a light chain variable domain disclosed herein, e.g., three light chain FRs of a light chain variable domain disclosed in any one of Tables 4-13. In various embodiments, an anti-CD20 binding motif of the present disclosure comprises three heavy chain FRs of a heavy chain variable domain disclosed herein, e.g., three light chain FRs of a light chain variable domain disclosed in any one of Tables 4-13, and three light chain FRs derived from the same Table of Tables 4-13 as the heavy chain FR(s).

Exemplary antibody sequences provided in Tables 4-13 are suitable for use in any antibody format, comprising, e.g., a tetrameric antibody, a monospecific antibody, a bispecific antibody, an antigen binding fragment, or a binding motif. Heavy chain variable domains and light chain variable domains and portions thereof provided in Tables 4-13 may be comprised in a binding motif.

In various embodiments, an anti-CD20 binding motif of the present disclosure comprises one, two, or three FRs that together or each individually have at least 75% identity (e.g., at least 75%, at least 80%, at least 90%, at least 95%, or 100%, e.g., 85-90%, 85-95%, 85-100%, 90-95%, 90-100%, or 95-100%) to corresponding FR(s) of a heavy chain variable domain of a heavy chain variable domain disclosed in in any one of Tables 4-13. In various embodiments, an anti-CD20 binding motif of the present disclosure comprises one, two, or three FRs that together or each individually have at least 75% identity (e.g., at least 75%, at least 80%, at least 90%, at least 95%, or 100%) to corresponding FR(s) of a light chain variable domain of a light chain variable domain disclosed in any one of Tables 4-13.

In various embodiments, an anti-CD20 binding motif of the present disclosure comprises at least one heavy chain variable domain having at least 75% sequence identity to a heavy chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD20 binding motif of the present disclosure comprises two heavy chain variable domains each having at least 75% sequence identity to a heavy chain variable domain disclosed in Tables 4-13 (e.g., at least 75%, at least 80%, at least 90%, at least 95%, or 100% identity; e.g., 85-90%, 85-95%, 85-100%, 90-95%, 90-100%, or 95-100%), which heavy chain variable domains may be same or different.

In various embodiments, an anti-CD20 binding motif of the present disclosure comprises at least one light chain variable domain having at least 75% sequence identity to a light chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD20 binding motif of the present disclosure comprises two light chain variable domains each having at least 75% sequence identity to a light chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%), which light chain variable domains may be same or different.

In various embodiments, an anti-CD20 binding motif of the present disclosure comprises at least one heavy chain variable domain having at least 75% sequence identity to a heavy chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%) and at least one light chain variable domain having at least 75% sequence identity to a light chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD20 binding motif of the present disclosure comprises one heavy chain variable domain having at least 75% sequence identity to a heavy chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%) and one light chain variable domain having at least 75% sequence identity to a light chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%), where the heavy chain variable domain and light chain variable domain are optionally derived from the same Table of Tables 4-13.

In various embodiments, an anti-CD20 binding motif of the present disclosure comprises two heavy chain variable domains each having at least 75% sequence identity to a heavy chain variable domain disclosed in Tables 4-13 (e.g., at least 75%, at least 80%, at least 90%, at least 95%, or 100% identity; e.g., 85-90%, 85-95%, 85-100%, 90-95%, 90-100%, or 95-100%) and two light chain variable domains each having at least 75% sequence identity to a light chain variable domain disclosed in Tables 4-13 (e.g., at least 75%, at least 80%, at least 90%, at least 95%, or 100% identity; e.g., 85-90%, 85-95%, 85-100%, 90-95%, 90-100%, or 95-100%), where, in various embodiments, (i) each of the heavy chain variable domains may be same or different; (ii) each of the light chain variable domains may be same or different; (iii) at least one heavy chain variable domain and at least one light chain variable domain may be derived from the same Table of Tables 4-13; or (iv) the two heavy chain variable domains and the two light chain variable domains are all derived from the same Table of Tables 4-13. Each of Tables 4-13 represents the heavy chain variable domain and light chain variable domain sequences of an exemplary antibody, comprising (i) the heavy chain variable domain of the exemplary antibody; (ii) a DNA sequence encoding the heavy chain variable domain (iii) three heavy chain variable domain CDRs of the heavy chain variable domain, according to IMGT, Kabat, and Chothia numbering; (iv) the light chain variable domain of the exemplary antibody; (v) a DNA sequence encoding the light chain variable domain; and (vi) three light chain variable domain CDRs of the light chain variable domain, according to IMGT, Kabat, and Chothia numbering. Information provided in each table provides framework amino acid sequences, as well as nucleotide sequences encoding each CDR amino acid sequence and nucleotide sequences encoding corresponding FR amino acid sequence.

In various embodiments a binding motif may comprise a heavy chain variable domain of the present disclosure (e.g., having at least 75% sequence identity to a heavy chain variable domain of any one of Tables 4-13, e.g., at least 80%, 85%, 90%, 95%, or 100% identity; e.g., 85-90%, 85-95%, 85-100%, 90-95%, 90-100%, or 95-100%), a light chain variable domain of the present disclosure (e.g., having at least 75% sequence identity to a light chain variable domain of any one of Tables 4-13, e.g., at least 80%, 85%, 90%, 95%, or 100% identity; e.g., 85-90%, 85-95%, 85-100%, 90-95%, 90-100%, or 95-100%), and a linker (e.g., a linker according to SEQ ID NO: 247 and/or a linker according to any one of SEQ ID NOs: 307-313; see, e.g., Whitlow et al. Protein Eng. 1993 November; 6(8):989-95.). In various embodiments a binding motif may comprise a leader sequence, a heavy chain variable domain of the present disclosure (e.g., having at least 75% sequence identity to a heavy chain variable domain of any one of Tables 4-13, e.g., at least 80%, 85%, 90%, 95%, or 100% identity; e.g., 85-90%, 85-95%, 85-100%, 90-95%, 90-100%, or 95-100%), a light chain variable domain of the present disclosure (e.g., having at least 75% sequence identity to a light chain variable domain of any one of Tables 4-13, e.g., at least 80%, 85%, 90%, 95%, or 100% identity; e.g., 85-90%, 85-95%, 85-100%, 90-95%, 90-100%, or 95-100%), and a linker. If provided with an amino acid or nucleotide sequence of a binding motif comprising a heavy chain variable domain of the present disclosure and a light chain variable domain of the present disclosure, the linker joining the two variable domains will be apparent from the sequence in view of the present disclosure. If provided with an amino acid or nucleotide sequence of a binding motif comprising a heavy chain variable domain of the present disclosure and a light chain variable domain of the present disclosure, the leader sequence will be apparent in view of the present disclosure. For the avoidance of doubt, a heavy chain variable domain and a light chain variable domain of the present disclosure may be present in any orientation, e.g., an orientation in which the heavy chain variable domain is C terminal of the light chain variable domain or in which the heavy chain variable domain is N terminal of the light chain variable domain. In various embodiments a binding motif may comprise a linker according to SEQ ID NO: 247 and/or a linker according to any one of SEQ ID NOs: 307-313 adjacent to one or more additional linkers.

In certain embodiments, an anti-CD20 binding motif of the present disclosure comprises a binding motif that comprises a heavy chain variable domain of the present disclosure, a light chain variable domain of the present disclosure, and a linker having at least 75% sequence identity to SEQ ID NO: 247 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD20 binding motif of the present disclosure comprises a binding motif that comprises a linker according to SEQ ID NO: 247 and/or a linker according to any one of SEQ ID NOs: 307-313. In certain embodiments, an anti-CD20 binding motif of the present disclosure comprises a binding motif that comprises a heavy chain variable domain of the present disclosure, a light chain variable domain of the present disclosure, and a leader sequence having at least 75% sequence identity to SEQ ID NO: 245 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD20 binding motif of the present disclosure comprises a binding motif that comprises a CSF2RA leader sequence according to SEQ ID NO: 245. In certain embodiments, an anti-CD20 binding motif of the present disclosure comprises a binding motif that comprises a heavy chain variable domain of the present disclosure, a light chain variable domain of the present disclosure, a linker of the present disclosure, and a leader sequence of the present disclosure. Exemplary nucleotide sequences encoding an anti-CD19 binding motif and components thereof are found in SEQ ID NOs: 246, and 248. In various embodiments, a binding motif of the present disclosure has a sequence according to any one of the sequences of Table 53 (SEQ ID NOs: 251-260).

A binding agent of the present disclosure that is based on an exemplary antibody provided herein, such as for example Ab1, may be provided in any fragment or format, comprising a heavy chain variable domain according to the indicated exemplary antibody and a light chain variable domain according to the indicated exemplary antibody.

TABLE 4

| Exemplary Antibody Sequences 1 (Ab1) | | |
|---|---|---|
| SEQ ID NO: | Description | Sequence |
| 1 | Heavy Chain Variable Domain | QVQLQQWGAGLLKPSETLSLTCAVYGGSFSGYY WSWIRQPPGKGLEWIGEIDHSGSTNYNPSLKSR VTISVDTSKNQFSLKLSSVTAADTAVYYCARGG GSWYSNWFDPWGQGTMVTVSS |
| 2 | VH (DNA) | CAGGTGCAGCTACAGCAGTGGGGCGCAGGACTG TTGAAGCCTTCGGAGACCCTGTCCCTCACCTGC GCTGTCTATGGTGGGTCCTTCAGTGGTTACTAC TGGAGCTGGATCCGCCAGCCCCCAGGGAAGGGG CTGGAGTGGATTGGGGAAATCGACCATAGTGGA AGCACCAACTACAACCCGTCCCTCAAGAGTCGA GTCACCATATCAGTAGACACGTCCAAGAACCAG TTCTCCCTGAAGCTGAGCTCTGTGACCGCCGCG GACACGGCGGTGTACTACTGCGCCAGAGGTGGA GGAAGTTGGTACAGCAACTGGTTCGACCCATGG GGACAGGGTACAATGGTCACCGTCTCCTCA |
| 3 | CDRH1 IMGT (Prot) | GGSFSGYY |
| 4 | CDRH1 Kabat (Prot) | GYYWS |
| 5 | CDRH1 Chothia (Prot) | GGSFSG |
| 6 | CDRH2 IMGT (Prot) | IDHSGST |
| 7 | CDRH2 Kabat (Prot) | EIDHSGSTNYNPSLKS |
| 8 | CDRH2 Chothia (Prot) | DHSGS |

TABLE 4-continued

Exemplary Antibody Sequences 1 (Ab1)

| SEQ ID NO: | Description | Sequence |
|---|---|---|
| 9 | CDRH3 IMGT (Prot) | ARGGGSWYSNWFDP |
| 10 | CDRH3 Kabat (Prot) | GGGSWYSNWFDP |
| 11 | CDRH3 Chothia (Prot) | GGGSWYSNWFDP |
| 12 | Light Chain Variable Domain | DIQMTQSPSTLSASVGDRVTITCRASQSISSWL AWYQQKPGKAPKLLIYDASSLESGVPSRFSGSG SGTEFTLTISSLQPDDFATYYCQQDRSLPPTFG GGTKVEIK |
| 13 | VL (DNA) | GACATCCAGATGACCCAGTCTCCTTCCACCCTG TCTGCATCTGTAGGAGACAGAGTCACCATCACT TGCCGGGCCAGTCAGAGTATTAGTAGCTGGTTG GCCTGGTATCAGCAGAAACCAGGGAAAGCCCCT AAGCTCCTGATCTATGATGCCTCCAGTTTGGAA AGTGGGGTCCCATCAAGGTTCAGCGGCAGTGGA TCTGGGACAGAATTCACTCTCACCATCAGCAGC CTGCAGCCTGATGATTTTGCAACTTATTACTGC CAGCAGGACCGAAGTCTCCCTCCTACTTTTGGC GGAGGGACCAAGGTTGAGATCAAA |
| 14 | CDRL1 IMGT (Prot) | RASQSISSWLA |
| 15 | CDRL1 Kabat (Prot) | RASQSISSWLA |
| 16 | CDRL1 Chothia (Prot) | RASQSISSWLA |
| 17 | CDRL2 IMGT (Prot) | DASSLES |
| 18 | CDRL2 Kabat (Prot) | DASSLES |
| 19 | CDRL2 Chothia (Prot) | DASSLES |
| 20 | CDRL3 IMGT (Prot) | QQDRSLPPT |
| 21 | CDRL3 Kabat (Prot) | QQDRSLPPT |
| 22 | CDRL3 Chothia (Prot) | QQDRSLPPT |

TABLE 5

Exemplary Antibody Sequences 2 (Ab2)

| SEQ ID NO: | Description | Sequence |
|---|---|---|
| 23 | Heavy Chain Variable Domain | QVQLQQWGAGLLKPSETLSLTCAVYGGSFSGIH WNWIRQPPGKGLEWIGDIDTSGSTNYNPSLKSR VTISVDTSKNQFSLKLSSVTAADTAVYYCARLG QESATYLGMDVWGQGTTVTVSS |
| 24 | VH (DNA) | CAGGTGCAGCTACAGCAGTGGGGCGCAGGACTG TTGAAGCCTTCGGAGACCCTGTCCCTCACCTGC |

TABLE 5-continued

Exemplary Antibody Sequences 2 (Ab2)

| SEQ ID NO: | Description | Sequence |
|---|---|---|
| | | GCTGTCTATGGTGGGTCCTTCAGTGGTATCCAC TGGAACTGGATCCGCCAGCCCCCAGGGAAGGGG CTGGAGTGGATTGGGGACATCGACACAAGTGGA AGCACCAACTACAACCCGTCCCTCAAGAGTCGA GTCACCATATCCGTAGACACGTCCAAGAACCAG TTCTCCCTGAAGCTGAGTTCTGTGACCGCCGCA GACACGGCGGTGTACTACTGCGCCAGATTGGGA CAGGAGTCAGCCACCTATCTCGGAATGGACGTA TGGGGCCAGGGAACAACTGTCACCGTCTCCTCA |
| 25 | CDRH1 IMGT (Prot) | GGSFSGIH |
| 26 | CDRH1 Kabat (Prot) | GIHWN |
| 27 | CDRH1 Chothia (Prot) | GGSFSG |
| 28 | CDRH2 IMGT (Prot) | IDTSGST |
| 29 | CDRH2 Kabat (Prot) | DIDTSGSTNYNPSLKS |
| 30 | CDRH2 Chothia (Prot) | DTSGS |
| 31 | CDRH3 IMGT (Prot) | ARLGQESATYLGMDV |
| 32 | CDRH3 Kabat (Prot) | LGQESATYLGMDV |
| 33 | CDRH3 Chothia (Prot) | LGQESATYLGMDV |
| 34 | Light Chain Variable Domain | DIVMTQSPDSLAVSLGERATINCKSSQSVLYSS NNKNYLAWYQQKPGQPPKLLIYWASTRESGVPD RFSGSGSGTDFTLTISSLQAEDVAVYYCQQLYT YPFTFGGGTKVEIK |
| 35 | VL (DNA) | GACATCGTGATGACCCAGTCTCCAGACTCCCTG GCTGTGTCTCTGGGCGAGAGGGCCACCATCAAC TGCAAGTCCAGCCAGAGTGTTTTATACAGCTCC AACAATAAGAACTACTTAGCTTGGTACCAGCAG AAACCAGGACAGCCTCCTAAGCTGCTCATTTAC TGGGCATCTACCCGGGAATCCGGGGTCCCTGAC CGATTCAGTGGCAGCGGGTCTGGGACAGATTTC ACTCTCACCATCAGCAGCCTGCAGGCTGAAGAT GTGGCAGTTTATTACTGTCAGCAGCTCTACACC TACCCTTTCACTTTTGGCGGAGGGACCAAGGTT GAGATCAAA |
| 36 | CDRL1 IMGT (Prot) | KSSQSVLYSSNNKNYLA |
| 37 | CDRL1 Kabat (Prot) | KSSQSVLYSSNNKNYLA |
| 38 | CDRL1 Chothia (Prot) | KSSQSVLYSSNNKNYLA |
| 39 | CDRL2 IMGT (Prot) | WASTRES |
| 40 | CDRL2 Kabat (Prot) | WASTRES |

TABLE 5-continued

Exemplary Antibody Sequences 2 (Ab2)

| SEQ ID NO: | Description | Sequence |
|---|---|---|
| 41 | CDRL2 Chothia (Prot) | WASTRES |
| 42 | CDRL3 IMGT (Prot) | QQLYTYPFT |
| 43 | CDRL3 Kabat (Prot) | QQLYTYPFT |
| 44 | CDRL3 Chothia (Prot) | QQLYTYPFT |

TABLE 6

Exemplary Antibody Sequences 3 (Ab3)

| SEQ ID NO: | Description | Sequence |
|---|---|---|
| 45 | Heavy Chain Variable Domain | QLQLQESGPGLVKPSETLSLTCTVSGGSISSSS YYWGWIRQPPGKGLEWIGSIYYSGSTYYNPSLK SRVTISVDTSKNQFSLKLSSVTAADTAVYYCAR ETDYSSGMGYGMDVWGQGTTVTVSS |
| 46 | VH (DNA) | CAGCTGCAGCTGCAGGAGTCGGGCCCAGGACTG GTGAAGCCTTCGGAGACCCTGTCCCTCACCTGC ACTGTCTCTGGTGGCTCCATCAGCAGTAGTAGT TACTACTGGGGCTGGATCCGCCAGCCCCCAGGG AAGGGGCTGGAGTGGATTGGGAGTATCTATTAT AGTGGGAGCACCTACTACAACCCGTCCCTCAAG AGTCGAGTCACCATATCCGTAGACACGTCCAAG AACCAGTTCTCCCTGAAGCTGAGTTCTGTGACC GCCGCAGACACGGCGGTGTACTACTGCGCCAGA GAGACTGACTACAGCAGCGGAATGGGATACGGA ATGGACGTATGGGGCCAGGGAACAACTGTCACC GTCTCCTCA |
| 47 | CDRH1 IMGT (Prot) | GGSISSSSYY |
| 48 | CDRH1 Kabat (Prot) | SSSYYWG |
| 49 | CDRH1 Chothia (Prot) | GGSISSSS |
| 50 | CDRH2 IMGT (Prot) | IYYSGST |
| 51 | CDRH2 Kabat (Prot) | SIYYSGSTYYNPSLKS |
| 52 | CDRH2 Chothia (Prot) | YYSGS |
| 53 | CDRH3 IMGT (Prot) | ARETDYSSGMGYGMDV |
| 54 | CDRH3 Kabat (Prot) | ETDYSSGMGYGMDV |
| 55 | CDRH3 Chothia (Prot) | ETDYSSGMGYGMDV |

TABLE 6-continued

Exemplary Antibody Sequences 3 (Ab3)

| SEQ ID NO: | Description | Sequence |
|---|---|---|
| 56 | Light Chain Variable Domain | DIQMTQSPSSLSASVGDRVTITCRASQSINSYL NWYQQKPGKAPKLLIYAASSLQSGVPSRFSGSG SGTDFTLTISSLQPEDFATYYCQQSLADPFTFG GGTKVEIK |
| 57 | VL (DNA) | GACATCCAGATGACCCAGTCTCCATCCTCCCTG TCTGCATCTGTAGGAGACAGAGTCACCATCACT TGCCGGCAAGTCAGAGCATTAACAGCTATTTAA ATTGGTATCAGCAGAAACCAGGGAAAGCCCCTA AGCTCCTGATCTATGCTGCATCCAGTTTGCAAA GTGGGGTCCCATCAAGGTTCAGTGGCAGTGGAT CTGGGACAGATTTCACTCTCACCATCAGCAGTC TGCAACCTGAAGATTTTGCAACTTACTACTGCC AGCAAAGCCTCGCCGACCCTTTCACTTTTGGCG GAGGGACCAAGGTTGAGATCAAA |
| 58 | CDRL1 IMGT (Prot) | RASQSINSYLN |
| 59 | CDRL1 Kabat (Prot) | RASQSINSYLN |
| 60 | CDRL1 Chothia (Prot) | RASQSINSYLN |
| 61 | CDRL2 IMGT (Prot) | AASSLQS |
| 62 | CDRL2 Kabat (Prot) | AASSLQS |
| 63 | CDRL2 Chothia (Prot) | AASSLQS |
| 64 | CDRL3 IMGT (Prot) | QQSLADPFT |
| 65 | CDRL3 Kabat (Prot) | QQSLADPFT |
| 66 | CDRL3 Chothia (Prot) | QQSLADPFT |

TABLE 7

Exemplary Antibody Sequences 4 (Ab4)

| SEQ ID NO: | Description | Sequence |
|---|---|---|
| 67 | Heavy Chain Variable Domain | QVQLVQSGAEVKKPGASVKVSCKASGYTFKEYG ISWVRQAPGQGLEWMGWISAYSGHTYYAQKLQG RVTMTTDTSTSTAYMELRSLRSDDTAVYYCARG PHYDDWSGFIIWFDPWGQGTLVTVSS |
| 68 | VH (DNA) | CAGGTTCAGCTGGTGCAGTCTGGAGCTGAGGTG AAGAAGCCTGGGGCCTCAGTGAAGGTCTCCTGC AAGGCTTCTGGTTACACCTTTAAAGAATATGGT ATCAGCTGGGTGCGACAGGCCCCTGGACAAGGG CTTGAGTGGATGGGATGGATCAGCGCTTACAGT GGTCACACATACTATGCACAGAAGCTCCAGGGC AGAGTCACCATGACCACAGACACATCCACGAGC ACAGCCTACATGGAGCTGAGGAGCCTGAGATCT GACGACACGGCGGTGTACTACTGCGCCAGAGGG CCTCACTACGACGACTGGAGCGGATTTATCATA TGGTTCGACCCATGGGGACAGGGTACATTGGTC ACCGTCTCCTCA |

TABLE 7-continued

Exemplary Antibody Sequences 4 (Ab4)

| SEQ ID NO: | Description | Sequence |
|---|---|---|
| 69 | CDRH1 IMGT (Prot) | GYTFKEYG |
| 70 | CDRH1 Kabat (Prot) | EYGIS |
| 71 | CDRH1 Chothia (Prot) | GYTFKE |
| 72 | CDRH2 IMGT (Prot) | ISAYSGHT |
| 73 | CDRH2 Kabat (Prot) | WISAYSGHTYYAQKLQ |
| 74 | CDRH2 Chothia (Prot) | SAYSG |
| 75 | CDRH3 IMGT (Prot) | ARGPHYDDWSGFIIWFDP |
| 76 | CDRH3 Kabat (Prot) | GPHYDDWSGFIIWFDP |
| 77 | CDRH3 Chothia (Prot) | GPHYDDWSGFIIWFDP |
| 78 | Light Chain Variable Domain | DIQMTQSPSSLSASVGDRVTITCRASQSISSYL NWYQQKPGKAPKLLIYAASSLQSGVPSRFSGSG SGTDFTLTISSLQPEDFATYYCQQSYRFPPTFG QGTKVEIK |
| 79 | VL (DNA) | GACATCCAGATGACCCAGTCTCCATCCTCCCTG TCTGCATCTGTAGGAGACAGAGTCACCATCACT TGCCGGGCAAGTCAGAGCATTAGCAGCTATTTA AATTGGTATCAGCAGAAACCAGGGAAAGCCCCT AAGCTCCTGATCTATGCTGCATCCAGTTTGCAA AGTGGGGTCCCTTCAAGGTTCAGTGGCAGTGGA TCTGGGACAGATTTCACTCTCACCATCAGCAGT CTGCAACCTGAAGATTTTGCAACTTACTACTGT CAACAGAGTTACAGGTTTCCTCCTACCTTTGGC CAAGGGACCAAGGTTGAGATCAAA |
| 80 | CDRL1 IMGT (Prot) | RASQSISSYLN |
| 81 | CDRL1 Kabat (Prot) | RASQSISSYLN |
| 82 | CDRL1 Chothia (Prot) | RASQSISSYLN |
| 83 | CDRL2 IMGT (Prot) | AASSLQS |
| 84 | CDRL2 Kabat (Prot) | AASSLQS |
| 85 | CDRL2 Chothia (Prot) | AASSLQS |
| 86 | CDRL3 IMGT (Prot) | QQSYRFPPT |
| 87 | CDRL3 Kabat (Prot) | QQSYRFPPT |

TABLE 7-continued

Exemplary Antibody Sequences 4 (Ab4)

| SEQ ID NO: | Description | Sequence |
|---|---|---|
| 88 | CDRL3 Chothia (Prot) | QQSYRFPPT |

TABLE 8

Exemplary Antibody Sequences 5 (Ab5)

| SEQ ID NO: | Description | Sequence |
|---|---|---|
| 89 | Heavy Chain Variable Domain | QVQLQESGPGLVKPSETLSLTCTVSGGSISS PDHYWGWIRQPPGKGLEWIGSIYASGSTFYN PSLKSRVTISVDTSKNQFSLKLSSVTAADTA VYYCARETDYSSGMGYGMDVWGQGTTVTVSS |
| 90 | VH (DNA) | CAGGTGCAGCTGCAGGAGTCGGGCCCAGGAC TGGTGAAGCCTTCGGAGACCCTGTCCCTCAC CTGCACTGTCTCTGGTGGCTCCATCAGCAGT CCCGACCACTACTGGGGCTGGATCCGCCAGC CCCCAGGGAAGGGGCTGGAGTGGATTGGGTC CATCTACGCCAGTGGGAGCACCTTCTACAAC CCGTCCCTCAAGAGTCGAGTCACCATATCCG TAGACACGTCCAAGAACCAGTTCTCCCTGAA GCTGAGCTCTGTGACCGCCGCGGACACGGCG GTGTACTACTGCGCCAGAGAGACTGACTACA GCAGCGGAATGGGATACGGAATGGACGTATG GGGCCAGGGAACAACTGTCACCGTCTCCTCA |
| 91 | CDRH1 IMGT (Prot) | GGSISSPDHY |
| 92 | CDRH1 Kabat (Prot) | SPDHYWG |
| 93 | CDRH1 Chothia (Prot) | GGSISSPD |
| 94 | CDRH2 IMGT (Prot) | IYASGST |
| 95 | CDRH2 Kabat (Prot) | SIYASGSTFYNPSLKS |
| 96 | CDRH2 Chothia (Prot) | YASGS |
| 97 | CDRH3 IMGT (Prot) | ARETDYSSGMGYGMDV |
| 98 | CDRH3 Kabat (Prot) | ETDYSSGMGYGMDV |
| 99 | CDRH3 Chothia (Prot) | ETDYSSGMGYGMDV |
| 100 | Light Chain Variable Domain | DIQMTQSPSSLSASVGDRVTITCRASQSINS YLNWYQQKPGKAPKLLIYAASSLQSGVPSRF SGSGSGTDFTLTISSLQPEDFATYYCQQSLA DPFTFGGGTKVEIK |
| 101 | VL (DNA) | GACATCCAGATGACCCAGTCTCCATCCTCCC TGTCTGCATCTGTAGGAGACAGAGTCACCAT CACTTGCCGGGCAAGTCAGAGCATTAACAGC TATTTAAATTGGTATCAGCAGAAACCAGGGA AAGCCCCTAAGCTCCTGATCTATGCTGCATC |

TABLE 8-continued

| | | Exemplary Antibody Sequences 5 (Ab5) |
|---|---|---|
| SEQ ID NO: | Description | Sequence |
| | | CAGTTTGCAAAGTGGGGTCCCATCAAGGTTC AGTGGCAGTGGATCTGGGACAGATTTCACTC TCACCATCAGCAGTCTGCAACCTGAAGATTT TGCAACTTACTACTGCCAGCAAAGCCTCGCC GACCCTTTCACTTTTGGCGGAGGGACCAAGG TTGAGATCAAA |
| 102 | CDRL1 IMGT (Prot) | RASQSINSYLN |
| 103 | CDRL1 Kabat (Prot) | RASQSINSYLN |
| 104 | CDRL1 Chothia (Prot) | RASQSINSYLN |
| 105 | CDRL2 IMGT (Prot) | AASSLQS |
| 106 | CDRL2 Kabat (Prot) | AASSLQS |
| 107 | CDRL2 Chothia (Prot) | AASSLQS |
| 108 | CDRL3 IMGT (Prot) | QQSLADPFT |
| 109 | CDRL3 Kabat (Prot) | QQSLADPFT |
| 110 | CDRL3 Chothia (Prot) | QQSLADPFT |

TABLE 9

| | | Exemplary Antibody Sequences 6 (Ab6) |
|---|---|---|
| SEQ ID NO: | Description | Sequence |
| 111 | Heavy Chain Variable Domain | QITLKESGPTLVKPTQTLTLTCTFSGFSLDT EGVGVGWIRQPPGKALEWLALIYFNDQKRYS PSLKSRLTITKDTSKNQVVLTMTNMDPVDTA VYYCARDTGYSRWYYGMDVWGQGTTVTVSS |
| 112 | VH (DNA) | CAGATCACCTTGAAGGAGTCTGGTCCTACGC TGGTGAAACCCACACAGACCCTCACGCTGAC CTGCACCTTCTCTGGGTTCTCACTCGACACT GAAGGAGTGGGTGTGGGCTGGATCCGTCAGC CCCCAGGAAAGGCCCTGGAGTGGCTTGCACT CATTTATTTCAATGATCAAAAGCGCTACAGC CCATCTCTGAAGAGCAGGCTCACCATCACCA AGGACACCTCCAAAAACCAGGTGGTCCTTAC AATGACCAACATGGACCCTGTGGACACGGCG GTGTACTACTGCGCCAGAGACACGGGATACA GCCGATGGTACTACGGCATGGATGTATGGGG CCAGGGAACAACTGTCACCGTCTCCTCA |
| 113 | CDRH1 IMGT (Prot) | GFSLDTEGVG |
| 114 | CDRH1 Kabat (Prot) | TEGVGVG |

TABLE 9-continued

| | | Exemplary Antibody Sequences 6 (Ab6) |
|---|---|---|
| SEQ ID NO: | Description | Sequence |
| 115 | CDRH1 Chothia (Prot) | GFSLDTEG |
| 116 | CDRH2 IMGT (Prot) | IYFNDQK |
| 117 | CDRH2 Kabat (Prot) | LIYFNDQKRYSPSLKS |
| 118 | CDRH2 Chothia (Prot) | YFNDQ |
| 119 | CDRH3 IMGT (Prot) | ARDTGYSRWYYGMDV |
| 120 | CDRH3 Kabat (Prot) | DTGYSRWYYGMDV |
| 121 | CDRH3 Chothia (Prot) | DTGYSRWYYGMDV |
| 122 | Light Chain Variable Domain | DIQMTQSPSSVSASVGDRVTITCRASQGISS WLAWYQQKPGKAPKLLIYAASSLQSGVPSRF SGSGSGTDFTLTISSLQPEDFATYYCQQAYA YPITFGGGTKVEIK |
| 123 | VL (DNA) | GACATCCAGATGACCCAGTCTCCATCTTCCG TGTCTGCATCTGTAGGAGACAGAGTCACCAT CACTTGTCGGGCGAGTCAGGGTATTAGCAGC TGGTTAGCCTGGTATCAGCAGAAACCAGGGA AAGCCCCTAAGCTCCTGATCTATGCTGCATC CAGTTTGCAAAGTGGGGTCCCATCAAGGTTC AGCGGCAGTGGATCTGGGACAGATTTCACTC TCACCATCAGCAGCCTGCAGCCTGAAGATTT TGCAACTTATTACTGTCAGCAGGCATACGCC TACCCTATCACTTTTGGCGGAGGGACCAAGG TTGAGATCAAA |
| 124 | CDRL1 IMGT (Prot) | RASQGISSWLA |
| 125 | CDRL1 Kabat (Prot) | RASQGISSWLA |
| 126 | CDRL1 Chothia (Prot) | RASQGISSWLA |
| 127 | CDRL2 IMGT (Prot) | AASSLQS |
| 128 | CDRL2 Kabat (Prot) | AASSLQS |
| 129 | CDRL2 Chothia (Prot) | AASSLQS |
| 130 | CDRL3 IMGT (Prot) | QQAYAYPIT |
| 131 | CDRL3 Kabat (Prot) | QQAYAYPIT |
| 132 | CDRL3 Chothia (Prot) | QQAYAYPIT |

TABLE 10

| | | |
|---|---|---|
| | Exemplary Antibody Sequences 7 (Ab7) | |
| SEQ ID NO: | Description | Sequence |
| 133 | Heavy Chain Variable Domain | QVQLQQWGAGLLKPSETLSLTCAVYGGSFEK YYWSWIRQPPGKGLEWIGEIYHSGLTNYNPS LKSRVTISVDTSKNQFSLKLSSVTAADTAVY YCARVRYDSSDSYYYSYDYGMDVWGQGTTVT VSS |
| 134 | VH (DNA) | CAGGTGCAGCTACAGCAGTGGGGCGCAGGAC TGTTGAAGCCTTCGGAGACCCTGTCCCTCAC CTGCGCTGTCTATGGTGGGTCCTTCGAAAAA TACTACTGGAGCTGGATCCGCCAGCCCCCAG GGAAGGGGCTGGAGTGGATTGGGGAAATCTA CCATAGTGGACTCACCAACTACAACCCGTCC CTCAAGAGTCGAGTCACCATATCAGTAGACA CGTCCAAGAACCAGTTCTCCCTGAAGCTGAG CTCTGTGACCGCCGCGGACACGGCGGTGTAC TACTGCGCCAGGGTCAGATACGACAGCAGCG ACTCCTACTACTATAGCTACGATTATGGAAT GGACGTATGGGGCCAGGGAACAACTGTCACC GTCTCCTCA |
| 135 | CDRH1 IMGT (Prot) | GGSFEKYY |
| 136 | CDRH1 Kabat (Prot) | KYYWS |
| 137 | CDRH1 Chothia (Prot) | GGSFEK |
| 138 | CDRH2 IMGT (Prot) | IYHSGLT |
| 139 | CDRH2 Kabat (Prot) | EIYHSGLTNYNPSLKS |
| 140 | CDRH2 Chothia (Prot) | YHSGL |
| 141 | CDRH3 IMGT (Prot) | ARVRYDSSDSYYYSYDYGMDV |
| 142 | CDRH3 Kabat (Prot) | VRYDSSDSYYYSYDYGMDV |
| 143 | CDRH3 Chothia (Prot) | VRYDSSDSYYYSYDYGMDV |

TABLE 10-continued

| | | |
|---|---|---|
| | Exemplary Antibody Sequences 7 (Ab7) | |
| SEQ ID NO: | Description | Sequence |
| 144 | Light Chain Variable Domain | DIVLTQSPDSLAVSLGERATINCKSSQSVLY SSNNKNYLAWYQQKPGQPPKLLIYWASSRES GVPDRFSGSGSGTDFTLTISSLQAEDVAVYY CQQSYSFPWTFGGGTKVEIK |
| 145 | VL (DNA) | GACATCGTGCTGACCCAGTCTCCAGACTCCC TGGCTGTGTCTCTGGGCGAGAGGGCCACCAT CAACTGCAAGTCCAGCCAGAGTGTTTTATAC AGCTCCAACAATAAGAACTACTTAGCTTGGT ACCAGCAGAAACCAGGACAGCCTCCTAAGCT GCTCATTTACTGGGCATCTAGCCGGGAATCC GGGGTCCCTGACCGATTCAGTGGCAGCGGGT CTGGGACAGATTTCACTCTCACCATCAGCAG CCTGCAGGCTGAAGATGTGGCAGTTTATTAC TGTCAGCAGTCCTACTCCTTCCCTTGGACTT TTGGCGGAGGGACCAAGGTTGAGATCAAA |
| 146 | CDRL1 IMGT (Prot) | KSSQSVLYSSNNKNYLA |
| 147 | CDRL1 Kabat (Prot) | KSSQSVLYSSNNKNYLA |
| 148 | CDRL1 Chothia (Prot) | KSSQSVLYSSNNKNYLA |
| 149 | CDRL2 IMGT (Prot) | WASSRES |
| 150 | CDRL2 Kabat (Prot) | WASSRES |
| 151 | CDRL2 Chothia (Prot) | WASSRES |
| 152 | CDRL3 IMGT (Prot) | QQSYSFPWT |
| 153 | CDRL3 Kabat (Prot) | QQSYSFPWT |
| 154 | CDRL3 Chothia (Prot) | QQSYSFPWT |

TABLE 11

| | | |
|---|---|---|
| | Exemplary Antibody Sequences 8 (Ab8) | |
| SEQ ID NO: | Description | Sequence |
| 155 | Heavy Chain Variable Domain | QVQLQQWGAGLLKPSETLSLTCAVYGGSFSRYVWSWIR QPPGKGLEWIGEIDSSGKTNYNPSLKSRVTISVDTSKNQF SLKLSSVTAADTAVYYCARVRYDSSDSYYYSYDYGMD VWGQGTTVTVSS |
| 156 | VH (DNA) | CAGGTGCAGCTACAGCAGTGGGGCGCAGGACTGTTG AAGCCTTCGGAGACCCTGTCCCTCACCTGCGCTGTCT ATGGTGGGTCCTTCAGTCGATACGTATGGAGCTGGAT CCGCCAGCCCCCAGGGAAGGGGCTGGAGTGGATTGG GGAAATCGACTCCAGTGGAAAAACCAACTACAACCC GTCCCTCAAGAGTCGAGTCACCATATCAGTAGACACG TCCAAGAACCAGTTCTCCCTGAAGCTGAGCTCTGTGA CCGCCGCGGACACGGCGGTGTACTACTGCGCCAGGGT CAGATACGACAGCAGCGACTCCTACTACTATAGCTAC GATTATGGAATGGACGTATGGGGCCAGGGAACAACT GTCACCGTCTCCTCA |

TABLE 11-continued

| | Exemplary Antibody Sequences 8 (Ab8) | |
|---|---|---|
| SEQ ID NO: | Description | Sequence |
| 157 | CDRH1 IMGT (Prot) | GGSFSRYV |
| 158 | CDRH1 Kabat (Prot) | RYVWS |
| 159 | CDRH1 Chothia (Prot) | GGSFSR |
| 160 | CDRH2 IMGT (Prot) | IDSSGKT |
| 161 | CDRH2 Kabat (Prot) | EIDSSGKTNYNPSLKS |
| 162 | CDRH2 Chothia (Prot) | DSSGK |
| 163 | CDRH3 IMGT (Prot) | ARVRYDSSDSYYYSYDYGMDV |
| 164 | CDRH3 Kabat (Prot) | VRYDSSDSYYYSYDYGMDV |
| 165 | CDRH3 Chothia (Prot) | VRYDSSDSYYYSYDYGMDV |
| 166 | Light Chain Variable Domain | DIVLTQSPDSLAVSLGERATINCKSSQSVLYSSNNKNYL AWYQQKPGQPPKLLIYWASSRESGVPDRFSGSGSGTDF TLTISSLQAEDVAVYYCQQSYSFPWTFGGGTKVEIK |
| 167 | VL (DNA) | GACATCGTGCTGACCCAGTCTCCAGACTCCCTGGCTG TGTCTCTGGGCGAGAGGGCCACCATCAACTGCAAGTC CAGCCAGAGTGTTTTATACAGCTCCAACAATAAGAAC TACTTAGCTTGGTACCAGCAGAAACCAGGACAGCCTC CTAAGCTGCTCATTTACTGGGCATCTAGCCGGGAATC CGGGGTCCCTGACCGATTCAGTGGCAGCGGGTCTGGG ACAGATTTCACTCTCACCATCAGCAGCCTGCAGGCTG AAGATGTGGCAGTTTATTACTGTCAGCAGTCCTACTC CTTCCCTTGGACTTTTGGCGGAGGGACCAAGGTTGAG ATCAAA |
| 168 | CDRL1 IMGT (Prot) | KSSQSVLYSSNNKNYLA |
| 169 | CDRL1 Kabat (Prot) | KSSQSVLYSSNNKNYLA |
| 170 | CDRL1 Chothia (Prot) | KSSQSVLYSSNNKNYLA |
| 171 | CDRL2 IMGT (Prot) | WASSRES |
| 172 | CDRL2 Kabat (Prot) | WASSRES |
| 173 | CDRL2 Chothia (Prot) | WASSRES |
| 174 | CDRL3 IMGT (Prot) | QQSYSFPWT |
| 175 | CDRL3 Kabat (Prot) | QQSYSFPWT |
| 176 | CDRL3 Chothia (Prot) | QQSYSFPWT |

TABLE 12

| | Exemplary Antibody Sequences 9 (Ab9) | |
|---|---|---|
| SEQ ID NO: | Description | Sequence |
| 177 | Heavy Chain Variable Domain | QVQLQQWGAGLLKPSETLSLTCAVYGGSFSGYAWSWI RQPPGKGLEWIGEIDHRGFTNYNPSLKSRVTISVDTSKN QFSLKLSSVTAADTAVYYCARVRYDSSDSYYYSYDYG MDVWGQGTTVTVSS |
| 178 | VH (DNA) | CAGGTGCAGCTACAGCAGTGGGGCGCAGGACTGTTG AAGCCTTCGGAGACCCTGTCCCTCACCTGCGCTGTCT ATGGTGGGTCCTTCTCCGGTTACGCATGGAGCTGGAT CCGCCAGCCCCCAGGGAAGGGGCTGGAGTGGATTGG GGAAATCGACCATCGAGGATTCACCAACTACAACCC GTCCCTCAAGAGTCGAGTCACCATATCAGTAGACACG TCCAAGAACCAGTTCTCCCTGAAGCTGAGCTCTGTGA CCGCCGCGGACACGGCGGTGTACTACTGCGCCAGGGT CAGATACGACAGCAGCGACTCCTACTACTATAGCTAC |

TABLE 12-continued

| Exemplary Antibody Sequences 9 (Ab9) | | |
| --- | --- | --- |
| SEQ ID NO: | Description | Sequence |
| | | GATTATGGAATGGACGTATGGGGCCAGGGAACAACT GTCACCGTCTCCTCA |
| 179 | CDRH1 IMGT (Prot) | GGSFSGYA |
| 180 | CDRH1 Kabat (Prot) | GYAWS |
| 181 | CDRH1 Chothia (Prot) | GGSFSG |
| 182 | CDRH2 IMGT (Prot) | IDHRGFT |
| 183 | CDRH2 Kabat (Prot) | EIDHRGFTNYNPSLKS |
| 184 | CDRH2 Chothia (Prot) | DHRGF |
| 185 | CDRH3 IMGT (Prot) | ARVRYDSSDSYYYSYDYGMDV |
| 186 | CDRH3 Kabat (Prot) | VRYDSSDSYYYSYDYGMDV |
| 187 | CDRH3 Chothia (Prot) | VRYDSSDSYYYSYDYGMDV |
| 188 | Light Chain Variable Domain | DIVLTQSPDSLAVSLGERATINCKSSQSVLYSSNNKNYL AWYQQKPGQPPKLLIYWASSRESGVPDRFSGSGSGTDF TLTISSLQAEDVAVYYCQQSYSFPWTFGGGTKVEIK |
| 189 | VL (DNA) | GACATCGTGCTGACCCAGTCTCCAGACTCCCTGGCTG TGTCTCTGGGCGAGAGGGCCACCATCAACTGCAAGTC CAGCCAGAGTGTTTTATACAGCTCCAACAATAAGAAC TACTTAGCTTGGTACCAGCAGAAACCAGGACAGCCTC CTAAGCTGCTCATTTACTGGGCATCTAGCCGGGAATC CGGGGTCCCTGACCGATTCAGTGGCAGCGGGTCTGGG ACAGATTTCACTCTCACCATCAGCAGCCTGCAGGCTG AAGATGTGGCAGTTTATTACTGTCAGCAGTCCTACTC CTTCCCTTGGACTTTTGGCGGAGGGACCAAGGTTGAG ATCAAA |
| 190 | CDRL1 IMGT (Prot) | KSSQSVLYSSNNKNYLA |
| 191 | CDRL1 Kabat (Prot) | KSSQSVLYSSNNKNYLA |
| 192 | CDRL1 Chothia (Prot) | KSSQSVLYSSNNKNYLA |
| 193 | CDRL2 IMGT (Prot) | WASSRES |
| 194 | CDRL2 Kabat (Prot) | WASSRES |
| 195 | CDRL2 Chothia (Prot) | WASSRES |
| 196 | CDRL3 IMGT (Prot) | QQSYSFPWT |
| 197 | CDRL3 Kabat (Prot) | QQSYSFPWT |
| 198 | CDRL3 Chothia (Prot) | QQSYSFPWT |

TABLE 13

| Exemplary Antibody Sequences 10 (Ab10) | | |
| --- | --- | --- |
| SEQ ID NO: | Description | Sequence |
| 199 | Heavy Chain Variable Domain | QVQLQQWGAGLLKPSETLSLTCAVYGGSFQKYYWSWI RQPPGKGLEWIGEIDTSGFTNYNPSLKSRVTISVDTSKNQ FSLKLSSVTAADTAVYYCARVGRYSYGYYITAFDIWGQ GTTVTVSS |
| 200 | VH (DNA) | CAGGTGCAGCTACAGCAGTGGGGCGCAGGACTGTTG AAGCCTTCGGAGACCCTGTCCCTCACCTGCGCTGTCT ATGGTGGGTCCTTCCAAAAATACTACTGGAGCTGGAT CCGCCAGCCCCCAGGGAAGGGGCTGGAGTGGATTGG GGAAATCGACACCAGTGGATTCACCAACTACAACCC GTCCCTCAAGAGTCGAGTCACCATATCAGTAGACACG TCCAAGAACCAGTTCTCCCTGAAGCTGAGCTCTGTGA CCGCCGCGGACACGGCGGTGTACTACTGCGCCAGAGT |

TABLE 13-continued

| Exemplary Antibody Sequences 10 (Ab10) | | |
| --- | --- | --- |
| SEQ ID NO: | Description | Sequence |
| | | GGGAAGGTACAGCTACGGATACTATATCACCGCATTC GACATATGGGGTCAGGGTACAACTGTCACCGTCTCCT CA |
| 201 | CDRH1 IMGT (Prot) | GGSFQKYY |
| 202 | CDRH1 Kabat (Prot) | KYYWS |
| 203 | CDRH1 Chothia (Prot) | GGSFQK |
| 204 | CDRH2 IMGT (Prot) | IDTSGFT |
| 205 | CDRH2 Kabat (Prot) | EIDTSGFTNYNPSLKS |
| 206 | CDRH2 Chothia (Prot) | DTSGF |
| 207 | CDRH3 IMGT (Prot) | ARVGRYSYGYYITAFDI |
| 208 | CDRH3 Kabat (Prot) | VGRYSYGYYITAFDI |
| 209 | CDRH3 Chothia (Prot) | VGRYSYGYYITAFDI |
| 210 | Light Chain Variable Domain | DIVMTQSPDSLAVSLGERATINCKSSQSVLYSSNNKNYL AWYQQKPGQPPKLLIYWASTRESGVPDRFSGSGSGTDF TLTISSLQAEDVAVYYCQQHYSFPFTFGGGTKVEIK |
| 211 | VL (DNA) | GACATCGTGATGACCCAGTCTCCAGACTCCCTGGCTG TGTCTCTGGGCGAGAGGGCCACCATCAACTGCAAGTC CAGCCAGAGTGTTTTATACAGCTCCAACAATAAGAAC TACTTAGCTTGGTACCAGCAGAAACCAGGACAGCCTC CTAAGCTGCTCATTTACTGGGCATCTACCCGGGAATC CGGGGTCCCTGACCGATTCAGTGGCAGCGGGTCTGGG ACAGATTTCACTCTCACCATCAGCAGCCTGCAGGCTG AAGATGTGGCAGTTTATTACTGTCAGCAGCACTACTC CTTCCCTTTCACTTTTGGCGGAGGGACCAAGGTTGAG ATCAAA |
| 212 | CDRL1 IMGT (Prot) | KSSQSVLYSSNNKNYLA |
| 213 | CDRL1 Kabat (Prot) | KSSQSVLYSSNNKNYLA |
| 214 | CDRL1 Chothia (Prot) | KSSQSVLYSSNNKNYLA |
| 215 | CDRL2 IMGT (Prot) | WASTRES |
| 216 | CDRL2 Kabat (Prot) | WASTRES |
| 217 | CDRL2 Chothia (Prot) | WASTRES |
| 218 | CDRL3 IMGT (Prot) | QQHYSFPFT |
| 219 | CDRL3 Kabat (Prot) | QQHYSFPFT |
| 220 | CDRL3 Chothia (Prot) | QQHYSFPFT |

The present disclosure comprises antibodies and antigen binding systems that comprise an anti-CD20 binding motif and a second binding motif that binds a second target antigen or epitope, e.g., an antigen that is not CD20 (e.g., CD19). Dual-targeted antigen binding systems comprise bispecific CARs and bicistronic CARs. Many antigen binding motifs are known. In various embodiments, the second target antigen is CD19. The present specification comprises a variety of second target antigens, comprising, without limitation, a second antigen that is 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRVIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 enve-lope glycoprotein gpl20, IL-llRalpha, kappa chain, lambda chain, melanoma-associated antigen, mesothelin, MUC-1, mutated p53, mutated ras, prostate-specific antigen, ROR1, VEGFR2, or a combination thereof. Accordingly in various embodiments, an antigen binding system or antibody of the present disclosure may comprise a first binding motif that is an anti-CD20 binding motif and a second binding motif that binds a second antigen that is 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gpl20, IL-llRalpha, kappa chain, lambda chain, melanoma-associated antigen, mesothelin, MUC-1, mutated p53, mutated ras, prostate-specific antigen, ROR1, VEGFR2, EphA3 (EPH receptor A3), BAFFR (B-cell activating factor receptor), or a combination thereof. In some embodiments, a second antigen is an antigen that is characteristic of B-cells or of a subset thereof, optionally wherein the second antigen is not CD19 or CD20. Examples of binding motifs that target these second antigens are known and/or provided herein.

In some instances, in an antigen binding system such as a bispecific CAR that comprises an anti-CD20 binding motif (e.g., comprising a heavy chain variable domain and/or a light chain variable domain of the present disclosure) and an anti-CD19 binding motif (e.g., comprising a heavy chain variable domain and/or a light chain variable domain of the present disclosure), the anti-CD20 binding motif (or a heavy chain variable domain and/or a light chain variable domain thereof) is closer to the C-terminus of the chimeric antigen receptor than the anti-CD19 binding motif (or than a heavy chain variable domain and/or a light chain variable domain thereof). In some instances, in an antigen binding system such as a bispecific CAR comprising an anti-CD20 binding motif (e.g., comprising a heavy chain variable domain and/or a light chain variable domain of the present disclosure) and an anti-CD19 binding motif (e.g., comprising a heavy chain variable domain and/or a light chain variable domain of the present disclosure), the anti-CD20 binding motif (or a heavy chain variable domain and/or a light chain variable domain thereof) is closer to the N-terminus of the agent than the anti-CD19 binding motif (or than a heavy chain variable domain and/or a light chain variable domain thereof).

CD19 (also known as Cluster of Differentiation 19, B-lymphocyte antigen CD19, B-lymphocyte surface antigen B4, B4, CVID3, Differentiation antigen CD19) is a protein that is encoded by the CD19 gene in humans. Unless otherwise indicated, it is to be appreciated the references to CD19 in the present disclosure relate to human CD19. It is found on the surface of B cells. Since CD19 expression is a hallmark of B cells, it may be useful as an antigen, e.g., in recognizing B cells and cancer cells that arise from B cells, e.g., B-cell lymphomas. Anti-CD19 antibodies may bind CD19 expressed on, e.g., B lymphocytes in peripheral blood and spleen, B cell chronic lymphocytic leukemia (B-CLL) cells, pro lymphocytic leukemia (PLL) cells, hairy cell leukemia (HCL) cells, common acute lymphoblastic leukemia (CALL) cells, pre-B acute lymphoblastic leukemia (pre-B-ALL) cells, and NULL-acute lymphoblastic leukemia (NULL-ALL) cells, to provide a few non limiting examples. An exemplary pharmaceutical product that comprises an antigen binding system that comprises an anti-CD19 binding motif is the pharmaceutical product YES-CARTA®. YESCARTA® is a CD19-directed genetically modified autologous T cell immunotherapy indicated for the treatment of adult patients with relapsed or refractory large B-cell lymphoma after two or more lines of systemic therapy, comprising diffuse large B-cell lymphoma (DLBCL) not otherwise specified, primary mediastinal large B-cell lymphoma, high grade B-cell lymphoma, and DLBCL arising from follicular lymphoma (See YES-CARTA® FDA-approved package insert, the entirety of which is incorporated herein by reference with respect to methods and compositions relating to immunotherapy). Another exemplary pharmaceutical product that comprises an antigen binding system that comprises an anti-CD19 binding motif is the pharmaceutical product KYMRIAH®.

KYMRIAH® is a CD19-directed genetically modified autologous T-cell immunotherapy indicated for the treatment of: (1) Patients up to 25 years of age with B-cell precursor acute lymphoblastic leukemia (ALL) that is refractory or in second or later relapse; and (2) Adult patients with relapsed or refractory (r/r) large B-cell lymphoma after two or more lines of systemic therapy comprising diffuse large B-cell lymphoma (DLBCL) not otherwise specified, high grade B-cell lymphoma and DLBCL arising from follicular lymphoma (See KYMRIAH® FDA-approved package insert, the entirety of which is incorporated herein by reference with respect to methods and compositions relating to immunotherapy).

Both YESCARTA® and KYMRIAH® comprise antibody binding domains derived from an anti-human CD19 antibody. Many anti-CD19 antibodies are thought to bind an epitope of CD19 encoded in exon 4 of the CD19 gene. Other anti-CD19 binding motifs may recognize different epitopes of CD19, or the same epitope with differential affinities. Antigen binding systems may comprise antigen binding domains derived, for example, from SJ25C1. The CD19 antibody, clone SJ25C1 was derived from hybridization of Sp2/0 mouse myeloma cells with spleen cells isolated from BALB/c mice immunized with NALM1 and NALM16 cells. SJ25C1 antigen binding domains were used in other investigational CD19-targeting chimeric antigen receptor (CAR) T-cell therapy.

An anti-CD19 binding motif of the present disclosure may comprise antigen-binding sequences as found in an antibody described herein. In some embodiments, an anti-CD19 binding motif of the present disclosure comprises an antigen binding fragment provided herein.

In various embodiments, an anti-CD19 binding motif of the present disclosure comprises at least one HCDR provided herein, e.g., at least one HCDR disclosed in Table 14. In various embodiments, an anti-CD19 binding motif of the present disclosure comprises two HCDRs provided herein, e.g., at least two HCDRs disclosed in Table 14. In various embodiments, an anti-CD19 binding motif of the present disclosure comprises three HCDRs provided herein, e.g., three HCDRs disclosed in Table 14.

In various embodiments, an anti-CD19 binding motif of the present disclosure comprises at least one LCDR provided herein, e.g., at least one LCDR disclosed in Table 14. In various embodiments, an anti-CD19 binding motif of the present disclosure comprises two LCDRs provided herein, e.g., at least two LCDRs disclosed in Table 14. In various embodiments, an anti-CD19 binding motif of the present disclosure comprises three LCDRs provided herein, e.g., three LCDRs disclosed in Table 14.

In various embodiments, an anti-CD19 binding motif of the present disclosure comprises at least one HCDR provided herein, e.g., at least one HCDR disclosed in Table 14, and at least one LCDR provided herein, e.g., at least one LCDR disclosed in Table 14. In various embodiments, an anti-CD19 binding motif of the present disclosure comprises two HCDRs provided herein, e.g., at least two HCDRs disclosed in Table 14, and two LCDRs provided herein, e.g., at least two LCDRs disclosed in Table 14. In various embodiments, an anti-CD19 binding motif of the present disclosure comprises three HCDRs provided herein, e.g., three HCDRs disclosed in Table 14, and three LCDRs provided herein, e.g., three LCDRs disclosed in Table 14.

In various embodiments, an anti-CD19 binding motif of the present disclosure comprises at least one heavy chain framework region (heavy chain FR) of a heavy chain variable domain disclosed herein, e.g., at least one heavy chain FR of a heavy chain variable domain disclosed in Table 14. In various embodiments, an anti-CD19 binding motif of the present disclosure comprises two heavy chain FRs of a heavy chain variable domain disclosed herein, e.g., at least two heavy chain FRs of a heavy chain variable domain disclosed in Table 14. In various embodiments, an anti-CD19 binding motif of the present disclosure comprises three heavy chain FRs of a heavy chain variable domain disclosed herein, e.g., three heavy chain FRs of a heavy chain variable domain disclosed in Table 14.

In various embodiments, an anti-CD19 binding motif of the present disclosure comprises at least one light chain FR of a light chain variable domain disclosed herein, e.g., at least one light chain FR of a light chain variable domain disclosed in Table 14. In various embodiments, an anti-CD19 binding motif of the present disclosure comprises two light chain FRs of a light chain variable domain disclosed herein, e.g., at least two light chain FRs of a light chain variable domain disclosed in Table 14. In various embodiments, an anti-CD19 binding motif of the present disclosure comprises three light chain FRs of a light chain variable domain disclosed herein, e.g., three light chain FRs of a light chain variable domain disclosed in Table 14.

In various embodiments, an anti-CD19 binding motif of the present disclosure comprises at least one heavy chain FR of a heavy chain variable domain disclosed herein, e.g., at least one heavy chain FR of a heavy chain variable domain disclosed in Table 14, and at least one light chain FR of a light chain variable domain disclosed herein, e.g., at least one light chain FR of a light chain variable domain disclosed in Table 14. In various embodiments, an anti-CD19 binding motif of the present disclosure comprises two heavy chain FRs of a heavy chain variable domain disclosed herein, e.g., at least two heavy chain FRs of a heavy chain variable domain disclosed in Table 14, and two light chain FRs of a light chain variable domain disclosed herein, e.g., at least two light chain FRs of a light chain variable domain disclosed in Table 14. In various embodiments, an anti-CD19 binding motif of the present disclosure comprises three heavy chain FRs of a heavy chain variable domain disclosed herein, e.g., three heavy chain FRs of a heavy chain variable domain disclosed in Table 14, and three light chain FRs of a light chain variable domain disclosed herein, e.g., three light chain FRs of a light chain variable domain disclosed in Table 14.

In various embodiments, an anti-CD19 binding motif of the present disclosure comprises one, two, or three FRs that together or each individually have at least 75% identity (e.g., at least 75%, at least 80%, at least 90%, at least 95%, or 100% identity; e.g., 85-90%, 85-95%, 85-100%, 90-95%, 90-100%, or 95-100%) to corresponding FR(s) of a heavy chain variable domain of a heavy chain variable domain disclosed in in Table 14. In various embodiments, an anti-CD19 binding motif of the present disclosure comprises one, two, or three FRs that together or each individually have at least 75% identity (e.g., at least 75%, at least 80%, at least 90%, at least 95%, or 100% identity; e.g., 85-90%, 85-95%, 85-100%, 90-95%, 90-100%, or 95-100%) to corresponding FR(s) of a light chain variable domain of a light chain variable domain disclosed in Table 14.

In various embodiments, an anti-CD19 binding motif of the present disclosure comprises at least one heavy chain variable domain having at least 75% sequence identity to a heavy chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%). In various embodiments, an anti- CD19 binding motif of the present disclosure comprises two heavy chain variable domains each having at least 75% sequence identity to a heavy chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%), which heavy chain variable domains may be same or different.

In various embodiments, an anti-CD19 binding motif of the present disclosure comprises at least one light chain variable domain having at least 75% sequence identity to a light chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD19 binding motif of the present disclosure comprises two light chain variable domains each having at least 75% sequence identity to a light chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%), which light chain variable domains may be same or different.

In various embodiments, an anti-CD19 binding motif of the present disclosure comprises at least one heavy chain variable domain having at least 75% sequence identity to a heavy chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%) and at least one light chain variable domain having at least 75% sequence identity to a light chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%).

In various embodiments, an anti-CD19 binding motif of the present disclosure comprises two heavy chain variable domains each having at least 75% sequence identity to a heavy chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%) and two light chain variable domains each having at least 75% sequence identity to a light chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%), where, in various embodiments, (i) each of the heavy chain variable domains may be same or different; or (ii) each of the light chain variable domains may be same or different.

In certain embodiments, an anti-CD19 binding motif of the present disclosure comprises a binding motif that comprises a heavy chain variable domain of the present disclosure, a light chain variable domain of the present disclosure, and a linker having at least 75% sequence identity to SEQ ID NO: 247 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD19 binding motif of the present disclosure comprises a binding motif that comprises a linker according to SEQ ID NO: 247 and/or a linker according to any one of SEQ ID NOs: 307-313. In certain embodiments, an anti-CD19 binding motif of the present disclosure comprises a binding motif that comprises a heavy chain variable domain of the present disclosure, a light chain variable domain of the present disclosure, and a leader sequence having at least 75% sequence identity to SEQ ID NO: 245 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD19 binding motif of the present disclosure comprises a binding motif that comprises a CSF2RA leader sequence according to SEQ ID NO: 245. In certain embodiments, an anti-CD19 binding motif of the present disclosure comprises a binding motif that comprises a heavy chain variable domain of the present disclosure, a light chain variable domain of the present disclosure, a linker of the present disclosure, and a leader sequence of the present disclosure.

In certain embodiments a binding motif has the sequence set forth in SEQ ID NO: 243. Exemplary nucleotide sequences encoding an anti-CD19 binding motif and components thereof are found in SEQ ID NOs: 244, 246, and 248. In various embodiments a binding motif may comprise a linker according to SEQ ID NO: 247 and/or a linker according to any one of SEQ ID NOs: 307-313 adjacent to one or more additional linkers.

TABLE 14

| Exemplary anti-CD19 Antibody Sequences (Ab11) | | |
|---|---|---|
| SEQ ID NO: | Description | Sequence |
| 221 | Heavy Chain Variable Domain | EVKLQESGPGLVAPSQSLSVTCTVSGVSLPDYGVSWIRQ PPRKGLEWLGVIWGSETTYYNSALKSRLTIIKDNSKSQV FLKMNSLQTDDTAIYYCAKHYYYGGSYAMDYWGQGT SVTVSS |
| 222 | VH (DNA) | GAGGTGAAACTGCAGGAGTCAGGACCTGGCCTGGTG GCGCCCTCACAGAGCCTGTCCGTCACATGCACTGTCT CAGGGGTCTCATTACCCGACTATGGTGTAAGCTGGAT TCGCCAGCCTCCACGAAAGGGTCTGGAGTGGCTGGG AGTAATATGGGGTAGTGAAACCACATACTATAATTCA GCTCTCAAATCCAGACTGACCATCATCAAGGACAACT CCAAGAGCCAAGTTTTCTTAAAAATGAACAGTCTGCA AACTGATGACACAGCCATTTACTACTGTGCCAAACAT TATTACTACGGTGGTAGCTATGCTATGGACTACTGGG GTCAAGGAACCTCAGTCACCGTCTCCTCA |
| 223 | CDRH1 IMGT (Prot) | GVSLPDYG |
| 224 | CDRH1 Kabat (Prot) | DYGVS |
| 225 | CDRH1 Chothia (Prot) | GVSLPDY |
| 226 | CDRH2 IMGT (Prot) | IWGSETT |
| 227 | CDRH2 Kabat (Prot) | VIWGSETTYYNSALKS |
| 228 | CDRH2 Chothia (Prot) | WGSET |
| 229 | CDRH3 IMGT (Prot) | AKHYYYGGSYAMDY |
| 230 | CDRH3 Kabat (Prot) | HYYYGGSYAMDY |
| 231 | CDRH3 Chothia (Prot) | HYYYGGSYAMDY |
| 232 | Light Chain Variable Domain | DIQMTQTTSSLSASLGDRVTISCRASQDISKYLNWYQQK PDGTVKLLIYHTSRLHSGVPSRFSGSGSGTDYSLTISNLE QEDIATYFCQQGNTLPYTFGGGTKLEIT |
| 233 | VL (DNA) | GACATCCAGATGACACAGACTACATCCTCCCTGTCTG CCTCTCTGGGAGACAGAGTCACCATCAGTTGCAGGGC AAGTCAGGACATTAGTAAATATTTAAATTGGTATCAG CAGAAACCAGATGGAACTGTTAAACTCCTGATCTACC ATACATCAAGATTACACTCAGGAGTCCCATCAAGGTT CAGTGGCAGTGGGTCTGGAACAGATTATTCTCTCACC ATTAGCAACCTGGAGCAAGAAGATATTGCCACTTACT TTTGCCAACAGGGTAATACGCTTCCGTACACGTTCGG AGGGGGGACTAAGTTGGAAATAACA |
| 234 | CDRL1 IMGT (Prot) | RASQDISKYLN |
| 235 | CDRL1 Kabat (Prot) | RASQDISKYLN |

TABLE 14-continued

| | Exemplary anti-CD19 Antibody Sequences (Ab11) | |
|---|---|---|
| SEQ ID NO: | Description | Sequence |
| 236 | CDRL1 Chothia (Prot) | RASQDISKYLN |
| 237 | CDRL2 IMGT (Prot) | HTSRLHS |
| 238 | CDRL2 Kabat (Prot) | HTSRLHS |
| 239 | CDRL2 Chothia (Prot) | HTSRLHS |
| 240 | CDRL3 IMGT (Prot) | QQGNTLPYT |
| 241 | CDRL3 Kabat (Prot) | QQGNTLPYT |
| 242 | CDRL3 Chothia (Prot) | QQGNTLPYT |
| 243 | binding motif (Prot) | DIQMTQTTSSLSASLGDRVTISCRASQDISKYLNWYQQK PDGTVKLLIYHTSRLHSGVPSRFSGSGSGTDYSLTISNLE QEDIATYFCQQGNTLPYTFGGGTKLEITGSTSGSGKPGS GEGSTKGEVKLQESGPGLVAPSQSLSVTCTVSGVSLPDY GVSWIRQPPRKGLEWLGVIWGSETTYYNSALKSRLTIIK DNSKSQVFLKMNSLQTDDTAIYYCAKHYYYGGSYAMD YWGQGTSVTVSS |
| 244 | binding motif (DNA) | gacatccagatgacacagactacatcctccctgtctgcctctctgggagacagagtcacc atcagttgcagggcaagtcaggacattagtaaatatttaaattggtatcagcagaaaccag atggaactgttaaactcctgatctaccatacatcaagattacactcaggagtcccatcaag gttcagtggcagtgggtctggaacagattattctctcaccattagcaacctggagcaaga agatattgccacttacttttgccaacagggtaatacgcttccgtacacgttcggagggggg actaagttggaaataacaggctccacctctggatccggcaagcccggatctggcgagg gatccaccaagggcgaggtgaaactgcaggagtcaggacctggcctggtggcgccct cacagagcctgtccgtcacatgcactgtctcaggggtctcattacccgactatggtgtaa gctggattcgccagcctccacgaaagggtctggagtggctgggagtaatatggggtagt gaaaccacatactataattcagctctcaaatccagactgaccatcatcaaggacaactcca agagccaagttncttaaaaatgaacagtctgcaaactgatgacacagccatttactactgt gccaaacattattactacggtggtagctatgctatggactactggggtcaaggaacctca gtcaccgtctcctca |
| 245 | Leader (CSF2RA) (Prot) | MLLLVTSLLLCELPHPAFLLIP |
| 246 | Leader (CSF2RA) (DNA) | atgcttctcctggtgacaagccttctgctctgtgagttaccacacccagcattcctcctgat ccca |
| 247 | Linker (Prot) | GSTSGSGKPGSGEGSTKG |
| 248 | Linker (DNA) | ggctccacctctggatccggcaagcccggatctggcgagggatccaccaagggc |

Antigen binding systems comprise, as examples, bispecific and bicistronic chimeric antigen receptors (CARs). The present disclosure provides, among other things, antigen binding systems that target both CD20 and a second target antigen, e.g., CD19. In some embodiments, an antigen binding system of the present disclosure comprises a bispecific antigen binding system. In some embodiments, an antigen binding system of the present disclosure comprises a bicistronic antigen binding system (e.g., a system comprising a first CAR and a second CAR, which first and second CARs are expressed in the same cell). Bicistronic CARs can comprise two CARs that bind different targets and are encoded by a single vector. Bicistronic CARs may comprise a first CAR comprising an anti-CD19 binding motif and a second CAR comprising an anti-CD20 binding motif. The binding motif associated with various CAR frameworks is interchangeable, and combinations of features provided in the present Example are exemplary, not limiting. In some embodiments, a first CAR and a second CAR of a bicistronic CAR (e.g., an anti-CD20 CAR and an anti-CD19 CAR) are encoded by separate genes and/or expressed as separate mRNA molecules. In some embodiments, a first CAR and a second CAR of a bicistronic CAR (e.g., an anti-CD20 CAR and an anti-CD19 CAR) are encoded by a single gene and/or expressed together in a single mRNA molecule, where a protein expressed comprises the first CAR, a cleavable linker domain, and a second CAR. First and second CARs of a bicistronic CAR are generally to be expressed together in immune cells, e.g., in CAR-T cells, so that individual CAR-T cells expressed CARs targeting each of the target antigens (e.g., each of CD20 and CD19).

In various embodiments, a bicistronic CAR vector utilizes a ribosomal skip sequence or internal ribosomal entry sites. A single vector encoding two independent CAR molecules separated by a ribosomal skip sequence may express a bicistronic CAR. In various embodiments, a bicistronic CAR comprises a first CAR and a second CAR where the sequence of the first CAR and the second CAR differ only with respect to the binding motif. In various embodiments, a bicistronic CAR comprises a first CAR and a second CAR where the sequence of the first CAR and the second CAR differ only with respect to a heavy chain variable domain sequence and/or a light chain variable domain sequence. Thus, in some embodiments, a first CAR and a second CAR of a bicistronic CAR may have same or different sequences for any or all of one or more components thereof, e.g., same or different costimulatory domains. For example, one or both of a first CAR and a second CAR of a bicistronic CAR may comprise a costimulatory domain provided herein, such as a CD28, 41BB, OX40, or ICOS costimulatory domain.

A CAR of a bicistronic CAR may comprise a binding motif, a hinge, a transmembrane domain, and an intracellular domain comprising a costimulatory domain and an activation domain. The binding motif may be an anti-CD19 or an anti-CD20 binding motif of the present disclosure. A hinge and transmembrane domain may be a 28T (CD28) domain or a CD8K domain that comprises a hinge domain and a transmembrane domain. A costimulatory domain may be a CD28 or 41BB costimulatory domain. An activation domain may be a CD3z activation domain.

In some embodiments, a first binding motif and a second binding motif (e.g., distinct anti-CD20 and anti-CD19 binding motifs) are both comprised in single bispecific CAR. In such bispecific CARs, a CAR molecule itself may be engineered to recognize more than one antigen. In tandem bispecific CARs, the first and second binding motifs are extracellular and may be characterized as a membrane-proximal binding motif and a membrane-distal binding motif. In some embodiments, an anti-CD20 binding motif is membrane-proximal and an anti-CD19 binding motif is membrane-distal. In other embodiments, an anti-CD19 binding motif is membrane-distal and an anti-CD20 binding motif is membrane proximal.

Chimeric antigen receptors (CARs) are engineered receptors that may direct or redirect T cells (e.g., patient or donor T cells) to target a selected antigen. A CAR may be engineered to recognize an antigen and, when bound to that antigen, activate the immune cell to attack and destroy the cell bearing that antigen. When these antigens exist on tumor cells, an immune cell that expresses the CAR may target and kill the tumor cell. CARs generally comprise an extracellular binding motif that mediates antigen binding (e.g., an anti-CD20 and/or an anti-CD19 binding motif), a transmembrane domain that spans, or is understood to span, the cell membrane when the antigen binding system is present at a cell surface or cell membrane, and an intracellular (or cytoplasmic) signaling domain.

According to at least one non-limiting view, there have been at least three "generations" of CAR compositions. In a first generation of CARs, a binding motif (e.g., a single chain fragment variable, binding motif) is linked or connected to a signaling domain (e.g., CD3ζ) via a transmembrane domain, optionally comprising a hinge domain and one or more spacers. In a second generation of CARs, a costimulatory domain (CM1, such as CD28, 4-1BB, or OX-40) is introduced with the signaling domain (e.g., CD3ζ). In a third generation of CARs, a second costimulatory domain (CM2) is comprised.

TCRs are heterodimers composed of an α-chain and a β-chain. TCR signaling requires recruitment of signaling proteins that generate an immune synapse. In addition, TCR localization at the plasma membrane depends on CD3 complex, which is expressed in T cells. Engineered single chain TCRs may be generated, e.g., using transmembrane and signaling domains of CAR constructs, methods and constructs for which are known (e.g., sTCR and TCR-CAR molecules, e.g., fusion of a TCRβ chain with CD28 TM and CD28 and CD3ζ signaling modules). An anti-CD20 and/or anti-CD19 Antigen binding system of the present disclosure may comprise one or more antigen binding motifs that bind CD20 and/or CD19. In some embodiments, an antigen binding system further comprises a costimulatory domain, and/or an extracellular domain (e.g., a "hinge" or "spacer" region), and/or a transmembrane domain, and/or an intracellular (signaling) domain, and/or a CD3-zeta or CD3-epsilon activation domain. In some embodiments, an -CD20 and/or anti-CD19 Antigen binding system of the present disclosure comprises at least a binding motif that binds human CD20, a costimulatory domain, an extracellular domain, a transmembrane domain, and a CD3-zeta or CD3-epsilon activating domain.

In some embodiments, an antigen binding system of the present disclosure may comprise an antigen binding system that comprises one or more, or all, of a leader peptide (P), a binding motif (B), a costimulatory protein's extracellular domain (E), a transmembrane domain (T), a costimulatory domain (C), a second costimulatory domain (C'), and an activation domain (A). In some instances, an antigen binding system is configured according to the following: B E T A. In some instances, an antigen binding system is configured according to the following: P B E T A. In some instances, an antigen binding system is configured according to the following: B E T C A. In some instances, an antigen binding system is configured according to the following: P B E T C A. In some instances, an antigen binding system is configured according to the following: B E T C C'A. In some instances, an antigen binding system is configured according to the following: P B E T C C' A. In some embodiments, the antigen binding system comprises a VH and a VL, optionally wherein the CAR is configured according to the following: P-VH-VL-E-T-C-A or P-VL-VH-E-T-C-A. In some embodiments, the VH and the VL are connected by a linker (L), optionally wherein the CAR is configured according to the following, from N-terminus to C-terminus: P-VH-L-VL-E-T-C-A or P-VH-L-VL-E-T-C-A.

One or more antigen binding motifs determine the target (s) of an antigen binding system. A binding motif of an antigen binding system may comprise any binding motif, e.g., an antibody provided by the present disclosure, e.g., a binding motif of the present disclosure. In some embodiments, a binding motif may comprise an anti-CD20 binding motif and/or anti-CD19 binding motif. In some embodiments, a binding motif may comprise an anti-CD20 binding motif and/or anti-CD19 binding motif.

Binding motifs are used in chimeric antigen receptors at least in part because they may be engineered to be expressed as part of a single chain along with the other CAR components. See, for example, U.S. Pat. Nos. 7,741,465, and 6,319,494 as well as Eshhar et al., Cancer Immunol Immunotherapy (1997) 45:131-136, Krause et al., J. Exp. Med., Volume 188, No. 4, 1998 (619-626); Finney et al., Journal of Immunology, 1998, 161:2791-2797, each of which is incorporated herein by reference with respect to binding motif domains in CARs. A binding motif, or scFv, is a single chain antigen binding fragment comprising a heavy chain variable domain and a light chain variable domain, which heavy chain variable domain and light chain variable domain are linked or connected together. See, for example, U.S. Pat. Nos. 7,741,465, and 6,319,494 as well as Eshhar et al., Cancer Immunol Immunotherapy (1997) 45:131-136, each of which is incorporated herein by reference with respect to binding motif domains. When derived from a parent antibody, a binding motif may retain some of, retain all of, or essentially retain the parent antibody's binding of a target antigen.

A hinge may be an extracellular domain of an antigen binding system positioned between the binding motif and the transmembrane domain. A hinge may also be referred to as an extracellular domain or as a "spacer." A hinge may contribute to receptor expression, activity, and/or stability. In some embodiments, a hinge domain is positioned between a binding motif and a transmembrane domain. A hinge may also provide flexibility to access the targeted antigen. Hinges comprise immunoglobulin-like hinge domains.

In some embodiments, an Antigen binding system of the present disclosure may comprise a hinge that is, is from, or is derived from (e.g., comprises all or a fragment of) an immunoglobulin-like hinge domain. In some embodiments, a hinge domain is from or derived from an immunoglobulin. In some embodiments, a hinge domain is selected from the hinge of IgG1, IgG2, IgG3, IgG4, IgA, IgD, IgE, or IgM, or a fragment thereof.

A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8.alpha., CD8.beta., CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TN-FRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof. In certain embodiments, a CAR does not comprise a CD28 hinge.

In some embodiments, an antigen binding system of the present disclosure may comprise a hinge that is, is from, or is derived from (e.g., comprises all or a fragment of) a hinge of CD8 alpha. In some embodiments a hinge is, is from, or is derived from a hinge of CD28. In some embodiments, a hinge is, is from, or is derived from a fragment of a hinge of CD8 alpha or a fragment of a hinge of CD28, wherein the fragment is anything less than the whole. In some embodiments, a fragment of a CD8 alpha hinge or a fragment of a CD28 hinge comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of a CD8 alpha hinge, or of a CD28 hinge. Exemplary hinge sequences comprise those provided in Table 54 (SEQ ID NOs: 261-269).

Polynucleotide and polypeptide sequences of these hinge domains are known. In some embodiments, the polynucleotide encoding a hinge domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a hinge domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

In general, a "transmembrane domain" (e.g., of an antigen binding system) refers to a domain having an attribute of being present in the membrane when present in a molecule at a cell surface or cell membrane (e.g., spanning a portion or all of a cellular membrane). A costimulatory domain for an antigen binding system of the present disclosure may further comprise a transmembrane domain and/or an intracellular signaling domain. It is not required that every amino acid in a transmembrane domain be present in the membrane. For example, in some embodiments, a transmembrane domain is characterized in that a designated stretch or portion of a protein is substantially located in the membrane. Amino acid or nucleic acid sequences may be analyzed using a variety of algorithms to predict protein subcellular localization (e.g., transmembrane localization). The programs psort (PSORT.org) and Prosite (prosite.expasy.org) are exemplary of such programs.

The type of transmembrane domain comprised in an antigen binding system described herein is not limited to any type. In some embodiments, a transmembrane domain is selected that is naturally associated with a binding motif and/or intracellular domain. In some instances, a transmembrane domain comprises a modification of one or more amino acids (e.g., deletion, insertion, and/or substitution), e.g., to avoid binding of such domains to a transmembrane domain of the same or different surface membrane proteins to minimize interactions with other members of the receptor complex.

A transmembrane domain may be derived either from a natural or from a synthetic source. Where the source is natural, a domain may be derived from any membrane-bound or transmembrane protein. Exemplary transmembrane domains may be derived from (e.g., may comprise at least a transmembrane domain of) an alpha, beta or zeta chain of a T-cell receptor, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CDS, CEACAM1, CRTAM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet.

Polynucleotide and polypeptide sequences of transmembrane domains provided herein are known. In some embodiments, the polynucleotide encoding a transmembrane domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a transmembrane domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a polypeptide sequence known. Optionally, short spacers may form linkages between any or some of the extracellular, transmembrane, and intracellular domains of the CAR.

The intracellular domain (or cytoplasmic domain) comprises one or more signaling domains that, upon binding of target antigen to the binding motif, cause and/or mediate an intracellular signal, e.g., that activates one or more immune cell effector functions (e.g., native immune cell effector functions). In some embodiments, signaling domains of an intracellular domain mediate activation at least one of the normal effector functions of the immune cell. Effector function of a T cell, for example, may be cytolytic activity or helper activity comprising the secretion of cytokines. In some embodiments, signaling domains of an intracellular domain mediate T cell activation, proliferation, survival, and/or other T cell function. An intracellular domain may comprise a signaling domain that is an activating domain. An intracellular domain may comprise a signaling domain that is a costimulatory signaling domain.

Intracellular signaling domains that may transduce a signal upon binding of an antigen to an immune cell are known, any of which may be comprised in an antigen binding system of the present disclosure. For example, cytoplasmic sequences of a T cell receptor (TCR) are known to initiate signal transduction following TCR binding to an antigen (see, e.g., Brownlie et al., Nature Rev. Immunol. 13:257-269 (2013)).

In some embodiments, a signaling domain and/or activation domain comprises an immunoreceptor tyrosine-based activation motif (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2: a002485 (2010); Smith-Garvin et al., Annu. Rev. Immunol. 27:591-619 (2009)).

In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

A CAR may comprise a costimulatory signaling domain, e.g., to increase signaling potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). Signals generated through a TCR alone may be insufficient for full activation of a T cell and a secondary or co-stimulatory signal may increase activation. Thus, in some embodiments, a signaling domain further comprises one or more additional signaling domains (e.g., costimulatory signaling domains) that activate one or more immune cell effector functions (e.g., a native immune cell effector function described herein). In some embodiments, a portion of such costimulatory signaling domains may be used, as long as the portion transduces the effector function signal. In some embodiments, a cytoplasmic domain described herein comprises one or more cytoplasmic sequences of a T cell co-receptor (or fragment thereof). Non-limiting examples of such T cell co-receptors comprise CD27, CD28, 4-1BB (CD137), OX40, CD30, CD40, PD-1, ICOS, lymphocyte function-associated antigen-1 (LFA-1), MYD88, CD2, CD7, LIGHT, NKG2C, B7-H3, and a ligand that binds with CD83. An exemplary costimulatory protein has the amino acid sequence of a costimulatory protein found naturally on T cells, the complete native amino acid sequence of which costimulatory protein is described in NCBI Reference Sequence: NP_006130.1. In certain instances, a CAR comprises a 41BB costimulatory domain encoded by the sequence according to SEQ ID NO: 270, as shown below:

```
                                SEQ ID NO: 270
AGATTCAGCGTTGTGAAGAGAGGCCGGAAGAAGCTGCTGTACATCTTCA

AGCAGCCCTTCATGAGACCTGTGCAGACCACACAGGAGGAAGACGGCTG

CAGCTGTAGATTCCCCGAGGAAGAGGAGGGCGGCTGTGAGCTGAGAGTT

AAGTTCAGCAGGAGCGCCGACGCCCCTGCCTACCAGCAAGGACAGAATC

AACTGTACAACGAGCTGAACCTGGGCAGACGGGAGGAATACGATGTGCT

GGACAAGAGGAGAGGCAGAGACCCCGAGATGGGCGGCAAACCTAGAAGA

AAGAACCCCCAGGAGGGCCTGTATAACGAGCTCCAGAAGGACAAGATGG

CCGAGGCCTACAGCGAGATCGGCATGAAGGGCGAAAGAAGAAGAGGCAA

GGGCCACGACGGCCTCTACCAGGGCTTAAGCACAGCTACAAAGGACACC

TACGACGCCCTGCACATGCAGGCCCTGCCCCCTAGATGATTAATTAAat cgat
```

The polynucleotide and polypeptide sequences of signaling domains provided herein are known. In some embodiments, the polynucleotide encoding a signaling domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known nucleotide sequence. In some embodiments, the polypeptide sequence of a signaling domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

In various embodiments, a mechanism of modulating (e.g., decreasing) antigen binding system activity is desired, e.g., to minimize or curtail adverse events resulting from antigen binding system activity. It may also be desired to comprise an inducible "on" or "accelerator" switch in immune cells. Suitable techniques comprise use of inducible caspase-9 (U.S. Appl. 2011/0286980) or a thymidine kinase, before, after, or at the same time, as the cells are transduced with the CAR construct of the present disclosure. Additional methods for introducing suicide genes and/or "on" switches comprise TALENS, zinc fingers, RNAi, siRNA, shRNA, antisense technology, and other techniques.

In accordance with the present disclosure, on-off or other types of control switch techniques may be incorporated herein. These techniques may comprise use of dimerization domains and optional activators of such domain dimerization, e.g., as disclosed by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of each of which is also incorporated by reference herein with respect to dimerization technology. Additional dimerization pairs may comprise cyclosporine-A/cyclophilin, receptor, estrogen/estrogen receptor (optionally using tamoxifen, 4-hydroxytamoxifen, or endoxifen), glucocorticoids/glucocorticoid receptor, tetracycline/tetracycline receptor, and/or vitamin D/vitamin D receptor. Further examples of dimerization technology may be found in e.g., WO 2014/127261, WO 2015/090229, US 2014/0286987, US 2015/0266973, US 2016/0046700, U.S. Pat. No. 8,486,693, US 2014/0171649, and US 2012/0130076, the contents of which are further incorporated by reference herein in their entirety.

In some embodiments, an antigen binding system of the present disclosure comprises a leader peptide (also referred to herein as a "signal peptide" or "leader sequence"). In certain embodiments, a leader peptide comprises an amino acid sequence that is at least about 75%, at least about 80%, at least about 85%, at least about 90%, at least about 95%, at least about 96%, at least about 97%, at least about 98%, at least about 99%, or 100% (e.g., 85-90%, 85-95%, 85-100%, 90-95%, 90-100%, or 95-100%) identical to the amino acid sequence MEWTWVFLFLLSVTAGVHS (SEQ ID NO: 249), MALPVTALLLPLALLLHAARP (SEQ ID NO: 250), or MLLLVTSLLLCELPHPAFLLIP (SEQ ID NO: 295).

Components of a CAR may be exchanged or "swapped" using routine techniques of biotechnology for equivalent components. To provide just a few non-limiting and partial examples, a CAR of the present disclosure may comprise a binding motif as provided herein in combination with a hinge provided herein and a costimulatory domain provided herein. In certain examples, a CAR of the present disclosure may comprise a leader sequence as provided herein together with a binding motif as provided herein in combination with a hinge provided herein and s costimulatory domain provided herein. In various embodiments, the present disclosure provides a binding motif according to any one of SEQ ID NOs: 251-260 in combination with (e.g., adjacently fused to) a hinge according to any one of SEQ ID NOs: 261-269, optionally in further combination with (e.g., adjacently fused to) a 41BB costimulatory domain according to SEQ ID NO: 270. A few, non-limiting examples thereof are provided in SEQ ID NOs: 271-290.

A bicistronic CAR may comprise a first CAR sequence and a second CAR sequence expressed as a single polypeptide comprising a cleavable linker between the first and second CARs. An exemplary cleavable linker is Furin-GSG-T2A (see, e.g., Chng et al. MAbs. 2015 March-April; 7 (2): 403-412, which is herein incorporated by reference with respect to cleavable linkers; see also Guedan et al. Mol Ther Methods Clin Dev. 2019 Mar. 15; 12:145-156, which is incorporated herein by reference with respect to bicistronic CAR design). To provide just one non-limiting example of a bicistronic CAR structure, a bicistronic CAR may comprise (a) a first CAR comprising (i) a signal peptide (e.g., a CSF2RA signal peptide); (ii) an anti-CD19 light chain variable domain; (iii) a linker (e.g., a G4S linker or plurality thereof); (iv) an anti-CD19 heavy chain variable domain; (v) a spacer or hinge (e.g., a CD28T spacer); (vi) a transmembrane domain (e.g., a CD28 transmembrane domain); (vii) a costimulatory domain (e.g., a CD28 costimulatory domain); (viii) a stimulatory domain (e.g., a CD3z stimulatory domain); (b) a cleavable linker (e.g., a Furin GSG-T2A linker); and (c) a second CAR comprising (i) a signal peptide (e.g., a CD8a signal peptide); (ii) an anti-CD20 heavy chain variable domain of the present disclosure; (iii) a linker (e.g., a linker according to SEQ ID NO: 247 and/or a linker according to any one of SEQ ID NOs: 307-313); (iv) an anti-CD20 light chain variable domain of the present disclosure; (v) a spacer or hinge (e.g., a CD8a spacer); (vi) a transmembrane domain (e.g., a CD8 transmembrane domain); (vii) a costimulatory domain (e.g., a 41bb costimulatory domain); and (viii) a stimulatory domain (e.g., a CD3z stimulatory domain). Thus, without limitation, an exemplary anti-CD20/anti-CD19 bicistronic CAR may have or comprise the nucleotide and amino acid sequences set forth in SEQ ID NOs: 291 and 292.

A bispecific CAR may be a single polypeptide that comprises a first binding motif of the present disclosure and a second binding motif that is an anti-CD19 binding motif. In a non-limiting exemplary embodiment, a bispecific CAR may comprise (i) a leader (e.g., a CSF2RA signal peptide), (ii) an anti-CD20 light chain variable domain of the present disclosure; (iii) a linker (iv) an anti-CD20 heavy chain variable domain; (v) a linker (e.g., a truncated linker); (vi) an anti-CD19 light chain variable domain; (vii) a linker; (viii) an anti-CD19 heavy chain variable domain; (ix) an extracellular domain (e.g., a CD28T hinge or IgG4 hinge); (x) a transmembrane domain (e.g., a CD28 transmembrane domain); (xi) an intracellular region (e.g., a CD28 intracellular costimulatory domain and/or 41bb costimulatory domain); and a stimulatory domain (e.g., a CD3z stimulatory domain). Thus, without limitation, an exemplary anti-CD20/anti-CD19 bispecific CAR may have or comprise the nucleotide and amino acid sequences set forth in SEQ ID NOs: 293-306.

Various CAR sequences, components, and/or frameworks are known, comprising without limitation sequences of hinges, spacers, transmembrane domains, costimulatory domains, stimulatory domains, binding motifs, and variants of each, and a CAR with desired binding and components or architecture can be readily constructed if, e.g., a heavy chain variable domain sequence or CDR sequences and a light chain variable domain sequence or CDR sequences are provided.

The present disclosure provides, among other things, bispecific antibodies that bind CD20 and a second target antigen, e.g., CD19. Bispecific antibodies comprise antibodies having a first binding motif that binds a first target antigen and a second binding motif that binds a second target antigen. In some embodiments, a bispecific antibody comprises an anti-CD20 binding motif of the present and an anti-CD19 binding motif of the present disclosure. In some embodiments, a bispecific antibody comprises an anti-CD20 binding motif that comprises an anti-CD20 heavy chain variable domain of the present disclosure and an anti-CD20 light chain variable domain of the present disclosure, as well as an anti-CD19 binding motif that comprises an anti-CD19 heavy chain variable domain and an anti-CD19 light chain variable domain.

The present disclosure comprises conjugates in which an antibody of the present disclosure is associated with a therapeutic agent or a detectable moiety. In various embodiments, the therapeutic agent is an anti-cancer agent as provided herein. In certain embodiments, provided conjugate comprises one or more detectable moieties, i.e., is "labeled" with one or more such moieties. In some such embodiments, a conjugate of the present disclosure is useful in diagnostic or imaging applications, e.g., diagnosing or imaging cancer. Any of a wide variety of detectable moieties may be used in labeled antibody conjugates described herein. Suitable detectable moieties comprise, without limitation: various ligands, radionuclides; fluorescent dyes; chemiluminescent agents (such as, for example, acridinium esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; digoxigenin; haptens; and proteins for which antisera or monoclonal antibodies are available.

The present disclosure comprises nucleic acids encoding anti-CD20 binding motifs and/or anti-CD19 binding motifs provided herein. The present disclosure comprises nucleic acids encoding antibodies of the provided herein, comprising, without limitation, nucleic acids encoding binding motifs (e.g., anti-CD20 binding motifs and anti-CD19 binding motifs). The present disclosure comprises nucleic acids encoding antigen binding systems provided herein, comprising without limitation nucleic acids encoding bicistronic and bispecific chimeric antigen receptors (e.g., bicistronic and bispecific chimeric antigen receptors that bind CD20 and CD19). The nucleic acid sequence of SEQ ID NO: 2 comprises and provides exemplary nucleic acid sequences corresponding to and encoding each of SEQ ID NOs: 1 and 3-11. The nucleic acid sequence of SEQ ID NO: 13 comprises and provides exemplary nucleic acid sequences corresponding to and encoding each of SEQ ID NOs: 12 and 14-22. The nucleic acid sequence of SEQ ID NO: 24 comprises and provides exemplary nucleic acid sequences corresponding to and encoding each of SEQ ID NOs: 23 and 25-33. The nucleic acid sequence of SEQ ID NO: 35 comprises and provides exemplary nucleic acid sequences corresponding to and encoding each of SEQ ID NOs: 34 and 36-44. The nucleic acid sequence of SEQ ID NO: 46 comprises and provides exemplary nucleic acid sequences corresponding to and encoding each of SEQ ID NOs: 45 and 47-55. The nucleic acid sequence of SEQ ID NO: 57 comprises and provides exemplary nucleic acid sequences corresponding to and encoding each of SEQ ID NOs: 56 and 58-66. The nucleic acid sequence of SEQ ID NO: 68 comprises and provides exemplary nucleic acid sequences corresponding to and encoding each of SEQ ID NOs: 67 and 69-77. The nucleic acid sequence of SEQ ID NO: 79 comprises and provides exemplary nucleic acid sequences corresponding to and encoding each of SEQ ID NOs: 78 and 80-88. The nucleic acid sequence of SEQ ID NO: 90 comprises and provides exemplary nucleic acid sequences corresponding to and encoding each of SEQ ID NOs: 89 and 91-99. The nucleic acid sequence of SEQ ID NO: 101 comprises and provides exemplary nucleic acid sequences corresponding to and encoding each of SEQ ID NOs: 100 and 102-110. The nucleic acid sequence of SEQ ID NO: 112 comprises and provides exemplary nucleic acid sequences corresponding to and encoding each of SEQ ID NOs: 111 and 113-121. The nucleic acid sequence of SEQ ID NO: 123 comprises and provides exemplary nucleic acid sequences corresponding to and encoding each of SEQ ID NOs: 122 and 124-132. The nucleic acid sequence of SEQ ID NO: 134 comprises and provides exemplary nucleic acid sequences corresponding to and encoding each of SEQ ID NOs: 133 and 135-143. The nucleic acid sequence of SEQ ID NO: 145 comprises and provides exemplary nucleic acid sequences corresponding to and encoding each of SEQ ID NOs: 144 and 146-154. The nucleic acid sequence of SEQ ID NO: 156 comprises and provides exemplary nucleic acid sequences corresponding to and encoding each of SEQ ID NOs: 155 and 157-165. The nucleic acid sequence of SEQ ID NO: 167 comprises and provides exemplary nucleic acid sequences corresponding to and encoding each of SEQ ID NOs: 166 and 168-176. The nucleic acid sequence of SEQ ID NO: 178 comprises and provides exemplary nucleic acid sequences corresponding to and encoding each of SEQ ID NOs: 177 and 179-187. The nucleic acid sequence of SEQ ID NO: 189 comprises and provides exemplary nucleic acid sequences corresponding to and encoding each of SEQ ID NOs: 188 and 190-198. The nucleic acid sequence of SEQ ID NO: 200 comprises and provides exemplary nucleic acid sequences corresponding to and encoding each of SEQ ID NOs: 199 and 201-209. The nucleic acid sequence of SEQ ID NO: 211 comprises and provides exemplary nucleic acid sequences corresponding to and encoding each of SEQ ID NOs: 210 and 212-220. The present disclosure comprises nucleic acids encoding anti-CD19 binding motifs provided herein. The nucleic acid sequence of SEQ ID NO: 222 comprises and provides exemplary nucleic acid sequences corresponding to and encoding each of SEQ ID NOs: 221 and 223-231. The nucleic acid sequence of SEQ ID NO: 233 comprises and provides exemplary nucleic acid sequences corresponding to and encoding each of SEQ ID NOs: 232 and 234-242.

The present disclosure comprises vectors that comprise nucleic acids of the present disclosure and/or that encode polypeptides of the present disclosure. In various embodiments, the present disclosure comprises a vector that comprises a nucleic acid encoding an anti-CD20 binding motif and/or an anti-CD19 binding motif provided herein. In various embodiments, the present disclosure comprises a vector that comprises a nucleic acid encoding an antibody provided herein, comprising, without limitation, a nucleic acid encoding a binding motif molecule (e.g., an anti-CD20 binding motif or an anti-CD19 binding motif). In various embodiments, the present disclosure comprises a vector that comprises a nucleic acid encoding one or more antigen binding systems provided herein, comprising without limitation nucleic acids encoding a bicistronic or bispecific chimeric antigen receptor (e.g., a bicistronic and bispecific chimeric antigen receptor that bind CD20 and CD19).

Any vector may be suitable for the present disclosure. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof. Suitable exemplary vectors include e.g., pGAR, pBABE-puro, pBABE-neo largeTcDNA, pBABE-hygro-hTERT, pMKO.1 GFP, MSCV-IRES-GFP, pMSCV PIG (Puro IRES GFP empty plasmid), pMSCV-loxp-dsRed-loxp-eGFP-Puro-WPRE, MSCV IRES Luciferase, pMIG, MDH1-PGK-GFP_2.0, TtRMPVIR, pMSCV-IRES-mCherry FP, pRetroX GFP T2A Cre, pRXTN, pLncEXP, and pLXIN-Luc.

A recombinant expression vector may be any suitable recombinant expression vector. Suitable vectors comprise those designed for propagation and expansion or for expression or both, such as plasmids and viruses. For example, a vector may be selected from the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also may be used. Examples of plant expression vectors useful in the context of the disclosure comprise pBI01, pBI101.2, pBI101.3, pBI121 and pBIN19 (Clontech). Examples of animal expression vectors useful in the context of the disclosure comprise pcDNA, pEUK-Cl, pMAM, and pMAMneo (Clontech). In some embodiments, a bicistronic IRES vector (e.g., from Clontech) is used to comprise both a nucleic acid encoding an antigen binding system and an inducible expression construct described herein.

In some embodiments, a recombinant expression vector is a viral vector. Suitable viral vectors comprise, without limitation, retroviral vectors, alphaviral, vaccinial, adenoviral, adeno-associated viral, herpes viral, and fowl pox viral vectors, and preferably have a native or engineered capacity to transform an immune cell (e.g., T cell).

Recombinant expression vectors may be prepared using standard recombinant DNA techniques described in, for example, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994. Constructs of expression vectors, which are circular or linear, may be prepared to contain a replication system functional in a prokaryotic or eukaryotic host cell. Replication systems may be derived, e.g., from ColE1, 2μ plasmid, λ, SV40, bovine papilloma virus, and the like.

A recombinant expression vector may comprise one or more marker genes, which allow for selection of transformed or transfected hosts. Marker genes comprise biocide resistance, e.g., resistance to antibiotics, heavy metals, etc., complementation in an auxotrophic host to provide prototrophy, and the like. Suitable marker genes for the recombinant expression vectors comprise, for instance, neomycin/G418 resistance genes, puromycin resistance genes, hygromycin resistance genes, histidinol resistance genes, tetracycline resistance genes, and ampicillin resistance genes.

Vectors useful in the context of the disclosure may be "naked" nucleic acid vectors (i.e., vectors having little or no proteins, sugars, and/or lipids encapsulating them), or vectors complexed with other molecules. Other molecules that may be suitably combined with the vectors comprise without limitation viral coats, cationic lipids, liposomes, polyamines, gold particles, and targeting moieties such as ligands, receptors, or antibodies that target cellular molecules.

Vector DNA may be introduced into a cell, e.g., an immune cell, via conventional transformation, transfection, or transduction techniques. The terms "transformation" and "transfection" encompass a variety of art-recognized techniques for introducing foreign nucleic acid (e.g., DNA) into a cell, such as calcium phosphate or calcium chloride co-precipitation, DEAE-dextran-mediated transfection, lipofection, gene gun, nanoparticle-mediated delivery, or electroporation. Transduction comprises viral delivery of a vector to a cell, e.g., by a vector disclosed herein, comprising without limitation retrovirus, lentivirus, and AAV.

The present disclosure comprises cells that comprise, express, or are engineered (e.g., transformed or transduced) to comprise or express, at least one vector or nucleic acid of the present disclosure. In some embodiments, a method comprises transducing a cell with a vector that comprises a polynucleotide encoding at least one antigen binding system. The present disclosure comprises cells that comprise, or are transformed to comprise, at least one vector that encodes one or more polypeptides of the present disclosure. The present disclosure comprises cells that comprise, or are transformed to comprise, at least one vector that encodes an anti-CD20 binding motif and/or an anti-CD19 binding motif provided herein. The present disclosure comprises cells that comprise, or are transformed to comprise, at least one vector that encodes an antibody provided herein, comprising, without limitation, a binding motif molecule (e.g., an anti-CD20 binding motif or an anti-CD19 binding motif). The present disclosure comprises cells that comprise, or are transformed to comprise, at least one vector that encodes one or more antigen binding systems provided herein, comprising without limitation a bicistronic or bispecific chimeric antigen receptor (e.g., a bicistronic or bispecific chimeric antigen receptor that bind CD20 and CD19). In some embodiments, cells are co-transfected or co-transduced with two vectors, each vector encoding a different CAR, which two different CARs together are a bicistronic CAR. Transfection or transduction of cells with two different vectors encoding two different CARs that together are a bicistronic CAR may be performed simultaneously on a single population of cells, simultaneously on two different populations of cells with each population transduced with only one of the two vectors, or independently on two different populations of cells each transduced with only one of the two vectors.

The present disclosure comprises cells that comprise one or more polypeptides of the present disclosure. The present disclosure comprises cells that comprise (e.g., express) an anti-CD20 binding motif and/or an anti-CD19 binding motif provided herein. The present disclosure comprises cells that comprise (e.g., express) an antibody provided herein, comprising, without limitation, a binding motif (e.g., an anti-CD20 binding motif or an anti-CD19 binding motif). The present disclosure comprises cells that comprise (e.g., express) one or more antigen binding systems provided herein, comprising without limitation a bicistronic or bispecific chimeric antigen receptor (e.g., a bicistronic and bispecific chimeric antigen receptor that bind CD20 and CD19).

In other aspects, provided herein are cells comprising a polynucleotide or a vector of the present disclosure. In some embodiments, the present disclosure is directed to cells, e.g., in vitro cells, comprising a polynucleotide encoding a CAR or a TCR comprising one or two of the scfv disclosed herein. In other embodiments, the present disclosure is directed to cells, e.g., in vitro cells, comprising a polypeptide encoded by a CAR or a TCR comprising one or two of the scfv disclosed herein. In some embodiments, the polypeptide comprise the amino acid sequence set forth below, or any combination thereof.

SEQ ID NO: 232 (anti-CD19 scFv light chain):
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIT

SEQ ID NO: 221 (anti-CD19 scFv heavy chain):
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS

SEQ ID NO: 56 (anti-CD20 light chain):
DIQMTQSPSSLSASVGDRVTITCRASQSINSYLNWYQQKPGKAPKLLIYA

ASSLQSGVPSRFSGSGSGTDFTLTISSLQPEDFATYYCQQSLADPFTFGG

GTKVEIK

SEQ ID NO: 45 (anti-CD20 heavy chain):
QLQLQESGPGLVKPSETLSLTCTVSGGSISSSSYYWGWIRQPPGKGLEWI

GSIYYSGSTYYNPSLKSRVTISVDTSKNQFSLKLSSVTAADTAVYYCARE

TDYSSGMGYGMDVWGQGTTVTVSS

SEQ ID NO: 56 (anti-CD20 scFv 2 light chain):
DIQMTQSPSSLSASVGDRVTITCRASQSINSYLNWYQQKPGKAPKLLIYA

ASSLQSGVPSRFSGSGSGTDFTLTISSLQPEDFATYYCQQSLADPFTFGG

GTKVEIK

SEQ ID NO: 155 (anti-CD20 scFv 2 heavy chain):
QVQLQQWGAGLLKPSETLSLTCAVYGGSFSRYVWSWIRQPPGKGLEWIGE

IDSSGKTNYNPSLKSRVTISVDTSKNQFSLKLSSVTAADTAVYYCARVRY

DSSDSYYYSYDYGMDVWGQGTTVTVSS

SEQ ID NO: 144 (anti-CD20 scFv 3 light chain):
DIVLTQSPDSLAVSLGERATINCKSSQSVLYSSNNKNYLAWYQQKPGQPP

KLLIYWASSRESGVPDRFSGSGSGTDFTLTISSLQAEDVAVYYCQQSYSF

PWTFGGGTKVEIK

SEQ ID NO: 177 (anti-CD20 scFv 3 heavy chain):
QVQLQQWGAGLLKPSETLSLTCAVYGGSFSGYAWSWIRQPPGKGLEWIGE

IDHRGFTNYNPSLKSRVTISVDTSKNQFSLKLSSVTAADTAVYYCARVRY

DSSDSYYYSYDYGMDVWGQGTTVTVSS

SEQ ID NO: 78 (anti-CD20 scFv 4 light chain):
DIQMTQSPSSLSASVGDRVTITCRASQSISSYLNWYQQKPGKAPKLLIYA

ASSLQSGVPSRFSGSGSGTDFTLTISSLQPEDFATYYCQQSYRFPPTFGQ

GTKVEIK

SEQ ID NO: 67 (anti-CD20 scFv 4 heavy chain):
QVQLVQSGAEVKKPGASVKVSCKASGYTFKEYGISWVRQAPGQGLEWMGW

ISAYSGHTYYAQKLQGRVTMTTDTSTSTAYMELRSLRSDDTAVYYCARGP

HYDDWSGFIIWFDPWGQGTLVTVSS

Any cell may be used as a host cell for the polynucleotides, the vectors, or the polypeptides of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof.

Chimeric antigen receptors (CARs or CAR-Ts) and engineered T cell receptors (TCRs) may be readily inserted into and expressed by immune cells, e.g., T cells, producing binding agents. In certain embodiments, cells (e.g., immune cells such as T cells) are obtained from a donor subject. In some embodiments, the donor subject is human patient afflicted with a cancer or a tumor. In other embodiments, the donor subject is a human patient not afflicted with a cancer or a tumor. In some embodiments, an engineered cell is autologous to a subject. In some embodiments, an engineered cell is allogeneic to a subject.

The cell of the present disclosure may be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In certain embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semiautomated flowthrough centrifuge, e.g., the Cobe™ 2991 cell processor, the Baxter CytoMate™, or the like. In some embodiments, the washed cells are resuspended in one or more biocompatible buffers, or other saline solution with or without buffer. In certain embodiments, the undesired components of the apheresis sample are removed. Additional methods of isolating T cells for a T cell therapy are disclosed in U.S. Patent Publication No. 2013/0287748, which is herein incorporated by references in its entirety.

In certain embodiments, T cells are isolated from PBMCs by lysing the red blood cells and depleting the monocytes, e.g., by using centrifugation through a PERCOLL™ gradient. In some embodiments, a specific subpopulation of T cells, such as CD4$^+$, CD8$^+$, CD28$^+$, CD45RA$^+$, and CD45RO$^+$ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for CD4$^+$ cells by negative selection, a monoclonal antibody cocktail typically includes antibodies to CD8, CD11b, CD14, CD16, CD20, and HLA-DR. In certain embodiments, flow cytometry and cell sorting are used to isolate cell populations of interest for use in the present disclosure.

In some embodiments, PBMCs are used directly for genetic modification with the immune cells (such as CARs or TCRs) using methods as described herein. In certain embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, CD8$^+$ cells are further sorted into naive, central memory, and effector cells by identifying cell surface antigens that are associated with each of these types of CD8$^+$ cells. In some embodiments, the expression of phenotypic markers of central memory T cells includes CCR7, CD3, CD28, CD45RO, CD62L, and CD127 and are negative for granzyme B. In some embodiments, central memory T cells are CD8$^+$, CD45RO$^+$, and CD62L$^+$ T cells. In some embodiments, effector T cells are negative for CCR7, CD28, CD62L, and CD127 and positive for granzyme B and perforin. In certain embodiments, CD4$^+$ T cells are further sorted into subpopulations. For example, CD4$^+$ T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In various aspects of the present disclosure, a cell that comprises, expresses, encodes, or is transformed to encode a vector or polypeptide of the present disclosure (e.g., an anti-CD20 binding motif of the present disclosure and/or an anti-CD20/anti-CD19 antigen binding system) is a binding agent. A binding agent, or population of binding agents, can be used as a (e.g., as the active agent of) a binding agent (a composition that comprises cells useful as a treatment, e.g., for a cancer).

The present disclosure further comprises methods and process for producing antibody agents as disclosed herein, e.g., by transformation (e.g., transduction) of a cell with a vector or nucleic acid of the present disclosure. In some embodiments, a method or process for producing antibody agents as disclosed herein comprises transforming (e.g., transducing) a cell with a nucleic acid (e.g., a nucleic acid present in a vector) encoding at least one antigen binding system provided herein. In general, antibody agents described herein may be produced from an immune cell, e.g., a cell useful in or capable of use in adoptive cell therapy. In some embodiments, a binding agent is produced from a cell type selected from a group consisting of TILs, T-cells, CD8$^+$ cells, CD4$^+$ cells, NK-cells, gamma-delta T-cells, regulatory T-cells or peripheral blood mononuclear cells. "Tumor-infiltrating lymphocytes" or TILs refer to white blood cells that have left the bloodstream and migrated into a tumor. Lymphocytes may be divided into three groups comprising B cells, T cells and natural killer cells. "T-cells" refers to CD3$^+$ cells, comprising CD4$^+$ helper cells, CD8$^+$ cytotoxic T-cells and gamma-delta T cells.

In certain embodiments a binding agent is produced by genetically modifying (e.g., transforming) a cell, e.g., an immune cell, with a nucleic acid encoding an antigen binding system and/or an expression construct described herein (e.g., (i) a first recombinant expression vector that comprises a nucleic acid encoding an antigen binding system and a second recombinant expression vector that comprises an inducible expression construct, (ii) a single recombinant expression vector that comprises both a nucleic acid encoding an antigen binding system and an inducible expression construct; or (iii) a recombinant expression vector that comprises a constitutive expression construct). The recombinant expression vector may comprise any type of nucleotides, comprising, without limitation, DNA and RNA, which may be single-stranded or double-stranded, synthesized or obtained in part from natural sources, and which may contain natural, non-natural or altered nucleotides. A recombinant expression vector may comprise naturally-occurring or non-naturally-occurring internucleotide linkages, or both types of linkages.

In some embodiments, a method comprises transducing a cell with a polynucleotide encoding an antigen binding system, as disclosed herein. In some embodiments, a method comprises transducing a cell with a vector comprising the polynucleotide encoding an antigen binding system.

In some embodiments, the donor T cells for use in the T cell therapy are obtained from the patient (e.g., for an autologous T cell therapy). In other embodiments, the donor T cells for use in the T cell therapy are obtained from a subject that is not the patient. In an exemplary aspect, subjects may undergo leukapheresis, wherein leukocytes are collected, enriched, or depleted ex vivo to select and/or isolate the cells of interest, e.g., T cells. These T cell isolates may be expanded by methods and treated such that one or more CAR constructs of the disclosure may be introduced, thereby creating a CAR T cell of the disclosure.

In some embodiments, an immune cell is obtained from a subject and is transformed, e.g., transduced, with inducible expression construct or a constitutive expression construct described herein, e.g., an expression vector comprising an inducible expression construct or a constitutive expression construct described herein, to obtain a binding agent. Thus, in some embodiments, a binding agent comprises an autologous cell that is administered into the same subject from which an immune cell was obtained. In some embodiments, an immune cell is obtained from a subject and is transformed, e.g., transduced, with an inducible expression construct or a constitutive expression construct described herein, e.g., an expression vector comprising an inducible expression construct or a constitutive expression construct described herein, to obtain a binding agent that is allogeneically transferred into another subject.

In certain embodiments, the T cells are obtained from a donor subject. In some embodiments, the donor subject is human patient afflicted with a cancer or a tumor. In other embodiments, the donor subject is a human patient not afflicted with a cancer or a tumor.

Various compositions of the present disclosure comprise populations of engineered cells, which may be produced by any means. In some embodiments, the present disclosure provides populations of human cells engineered to express an antigen binding system as described herein. In some embodiments, such a population comprises binding agents. In some embodiments, such a population comprises a cultured population. In some embodiments, such a population is a cultured population of cells from a single human source who may, in some embodiments, receive administration of the cultured population. As disclosed herein, a binding agent may comprise any single cell or population of cells, e.g. population of engineered cells, as provided herein.

Other aspects of the present disclosure are directed to compositions comprising a polynucleotide described herein, a vector described herein, a polypeptide described herein, or an in vitro cell described herein. In some embodiments, the composition comprises a pharmaceutically acceptable carrier, diluent, solubilizer, emulsifier, preservative and/or adjuvant. In some embodiments, the composition comprises an excipient. In one embodiment, the composition comprises a polynucleotide encoding a CAR or a TCR comprising antigen binding molecules described herein. In another embodiment, the composition comprises a CAR or a TCR comprising a TCD encoded by a polynucleotide of the present disclosure. In another embodiment, the composition comprises a T cell comprising a CAR or a TCR comprising one or two of the scfv disclosed herein.

In other embodiments, the composition is selected for parenteral delivery, for inhalation, or for delivery through the digestive tract, such as orally. The preparation of such pharmaceutically acceptable compositions is within the ability of one skilled in the art. In certain embodiments, buffers are used to maintain the composition at physiological pH or at a slightly lower pH, typically within a pH range of from about 5 to about 8. In certain embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In certain embodiments, the vehicle for parenteral injection is sterile distilled water in which composition described herein, with or without at least one additional therapeutic agent, is formulated as a sterile, isotonic solution, properly preserved. In certain embodiments, the preparation involves the formulation of the desired molecule with polymeric compounds (such as polylactic acid or polyglycolic acid), beads or liposomes, that provide for the controlled or sustained release of the product, which are then be delivered via a depot injection. In certain embodiments, implantable drug delivery devices are used to introduce the desired molecule.

In some embodiments, the present disclosure provides pharmaceutical compositions that comprise and/or deliver one or more of the present disclosure, e.g., an antigen binding systems of the present disclosure, nucleic acids that encode them, and/or cell(s) or populations thereof that comprise and/or express them.

In some embodiments, the present disclosure provides pharmaceutical compositions that comprise and or deliver one or more cells as provided herein, e.g., a binding agent that encodes or expresses a polypeptide provided herein, e.g., an anti-CD20/anti-CD19 CAR (i.e., a "binding agent pharmaceutical compositions"). A binding agent pharmaceutical composition may comprise one or a plurality of cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Binding agent pharmaceutical composition of the present disclosure may be formulated for administration according to any embodiment set forth herein, at least one non-limiting example of which is intravenous administration. A composition may be formulated for intravenous, intratumoral, intraarterial, intramuscular, intraperitoneal, intrathecal, epidural, and/or subcutaneous administration routes. Preferably, the composition is formulated for a parenteral route of administration. A composition suitable for parenteral administration may be an aqueous or nonaqueous, isotonic sterile injection solution, which may contain antioxidants, buffers, bacteriostats, and solutes, for example, that render the composition isotonic with the blood of the intended recipient. An aqueous or nonaqueous sterile suspension may contain one or more suspending agents, solubilizers, thickening agents, stabilizers, and preservatives. Binding agent pharmaceutical compositions of the present disclosure may be administered in a manner appropriate to the disease to be treated (or prevented).

The sterile composition for injection may be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Non-limiting examples of oily liquid comprise sesame oil and soybean oil, and it may be combined with benzyl benzoate or benzyl alcohol as a solubilizing agent. Other items that may be comprised are a buffer such as a phosphate buffer, or sodium acetate buffer, a soothing agent such as procaine hydrochloride, a stabilizer such as benzyl alcohol or phenol, and an antioxidant. The formulated injection may be packaged in a suitable ampule.

In one embodiment, a binding agent pharmaceutical composition is substantially free of detectable levels of a contaminant, e.g., of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans,*

*Escherichia coli, Haemophilus influenzae, Neisseria meningitides, Pseudomonas aeruginosa, Staphylococcus aureus, Streptococcus pneumonia,* and/or *Streptococcus pyogenes* group A.

In various embodiments, cells provided herein (e.g., binding agents, e.g., engineered T cells or engineered NK cells) may be activated and/or expanded from, and/or to produce, a binding agent pharmaceutical composition. In some embodiments, additional steps may be performed prior to administration to a subject. For instance, a binding agent may be expanded in vitro after contacting (e.g., transducing or transfecting) an immune cell with an inducible expression construct or a constitutive expression construct described herein (e.g., an expression vector comprising an inducible expression construct or a constitutive expression construct), prior to the administration to a subject. In vitro expansion may proceed for 1 day or more, e.g., 2 days or more, 3 days or more, 4 days or more, 6 days or more, or 8 days or more, prior to the administration to a subject. In some embodiments, in vitro expansion may proceed for 21 days or less, e.g., 18 days or less, 16 days or less, 14 days or less, 10 days or less, 7 days or less, or 5 days or less, prior to administration to a subject. For example, in vitro expansion may proceed for 1-7 days, 2-10 days, 3-5 days, or 8-14 days prior to the administration to a subject. A binding agent pharmaceutical composition comprising, e.g., binding agents (e.g., engineered T cells or engineered NK cells), may be formulated for administration at a desired dosage, e.g., a dosage of $10^4$ to $10^9$ cells/kg body weight (e.g., $10^5$ to $10^6$ cells/kg body weight). Certain embodiments of the disclosure comprise methods of administering to a subject a pharmaceutical composition as described herein, such as, for example, a binding agent described (e.g., a population of engineered cells of the present disclosure) herein, a protein therapeutic described herein, a composition comprising a binding agent, and/or a composition comprising a protein therapeutic, e.g., in an amount effective to treat a subject, when administered in an appropriate dosing regimen.

In some embodiments, a binding agent is autologous to a subject, and the subject may be immunologically naive, immunized, diseased, or in another condition prior to isolation of an immune cell from the subject. In some embodiments, during in vitro expansion, a binding agent may be stimulated with an antigen (e.g., a TCR antigen). Antigen-stimulated expansion optionally may be supplemented with expansion under conditions that non-specifically stimulate lymphocyte proliferation such as, for example, anti-CD3 antibody, anti-Tac antibody, anti-CD28 antibody, or phytohemagglutinin (PHA). The expanded binding agent may be directly administered into a subject or may be frozen for future use, i.e., for subsequent administrations to a subject.

In some embodiments, a binding agent is treated ex vivo with interleukin-2 (IL-2) prior to infusion into a cancer patient, and the cancer patient is treated with IL-2 after infusion. Furthermore, in some embodiments, a cancer patient may undergo preparative lymphodepletion—the temporary ablation of the immune system—prior to administration of a binding agent. A combination of IL-2 treatment and preparative lymphodepletion may enhance persistence of a binding agent. In some embodiments, a binding agent is transduced or transfected with a nucleic acid encoding a cytokine, which nucleic acid may be engineered to provide for constitutive, regulatable, or temporally-controlled expression of the cytokine. Suitable cytokines comprise, for example, cytokines which act to enhance the survival of T lymphocytes during the contraction phase, which may facilitate the formation and survival of memory T lymphocytes.

In certain embodiments, a binding agent is administered prior to, substantially simultaneously with, or after the administration of another therapeutic agent, such as a cancer therapeutic agent. The cancer therapeutic agent may be, e.g., a chemotherapeutic agent, a biological agent, or radiation treatment. In some embodiments, a subject receiving a binding agent is not administered a treatment which is sufficient to cause a depletion of immune cells, such as lymphodepleting chemotherapy or radiation therapy.

Dosage administered to a subject in some embodiments, may vary with the embodiment, the composition employed, the method of administration, and the site and subject being treated. However, a dose should be sufficient to provide a therapeutic response. A clinician may determine the therapeutically effective amount of a composition to be administered to a human or other subject in order to treat or prevent a medical condition. The precise amount of the composition required to be therapeutically effective may depend upon numerous factors, e.g., such as the activity of the binding agent, and the route of administration.

A suitable number binding agent cells may be administered to a subject. While a single binding agent cell described herein is capable of expanding and providing a therapeutic benefit, in some embodiments, $10^2$ or more, e.g., $10^3$ or more, $10^4$ or more, $10^5$ or more, or $10^8$ or more, binding agent cells are administered. In some embodiments, $10^{12}$ or less, e.g., $10^{11}$ or less, $10^9$ or less, $10^7$ or less, or $10^5$ or less, binding agent cells described herein are administered to a subject. In some embodiments, $10^2$-$10^5$, $10^4$-$10^7$, $10^3$-$10^9$, or $10^5$-$10^{10}$ binding agent cells described herein are administered. A binding agent pharmaceutical composition may be administered, e.g., a dosage of $10^4$ to $10^9$ cells/kg body weight (e.g., $10^5$ to $10^6$ cells/kg body weight). A binding agent pharmaceutical composition may be administered at a dosage of, e.g., about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

A dose of a binding agent described herein may be administered to a mammal at one time or in a series of subdoses administered over a suitable period of time, e.g., on a daily, semi-weekly, weekly, bi-weekly, semi-monthly, bi-monthly, semi-annual, or annual basis, as needed. A dosage unit comprising an effective amount of a binding agent may be administered in a single daily dose, or the total daily dosage may be administered in two, three, four, or more divided doses administered daily, as needed.

A suitable means of administration may be selected by a medical practitioner. Route of administration may be parenteral, for example, administration by injection, transnasal administration, transpulmonary administration, or transcutaneous administration. Administration may be systemic or local by intravenous injection, intramuscular injection, intraperitoneal injection, subcutaneous injection. In some embodiments, a composition is selected for parenteral delivery, for inhalation, or for delivery through the digestive tract, such as orally. Dose and method of administration may vary depending on the weight, age, condition, and the like of the subject, and may be suitably selected.

In various embodiments, a binding agent described herein may be incorporated into a pharmaceutical composition. Pharmaceutical compositions comprising a binding agent of the present disclosure may be formulated by known methods (such as described in Remington's Pharmaceutical Sciences, 17th edition, ed. Alfonso R. Gennaro, Mack Publishing Company, Easton, Pa. (1985)). In various instances, a pharmaceutical composition comprising a binding agent of the present disclosure may be formulated to comprise a pharmaceutically acceptable carrier or excipient. Examples of pharmaceutically acceptable carriers comprise, without limitation, any and all solvents, dispersion media, coatings, antibacterial and antifungal agents, isotonic and absorption delaying agents, and the like that are physiologically compatible. Compositions comprising a binding agent of the present disclosure may comprise a pharmaceutically acceptable salt, e.g., an acid addition salt or a base addition salt.

In various embodiments, a composition comprising a binding agent as described herein, e.g., a sterile formulation for injection, may be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like. As disclosed herein, a pharmaceutical composition comprising a binding agent may be in any form. Such forms comprise, e.g., liquid, semi-solid and solid dosage forms, such as liquid solutions (e.g., injectable and infusible solutions), dispersions or suspensions, tablets, pills, powders, liposomes and suppositories.

Selection or use of any form may depend, in part, on the intended mode of administration and therapeutic application. For example, a composition comprising a binding agent of the present disclosure intended for systemic or local delivery may be in the form of injectable or infusible solutions. Accordingly, the compositions comprising a binding agent of the present disclosure may be formulated for administration by a parenteral mode (e.g., intravenous, subcutaneous, intraperitoneal, or intramuscular injection). Parenteral administration refers to modes of administration other than enteral and topical administration, usually by injection, and comprise, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

Route of administration may be parenteral, for example, administration by injection, transnasal administration, transpulmonary administration, or transcutaneous administration. Administration may be systemic or local by intravenous injection, intramuscular injection, intraperitoneal injection, subcutaneous injection.

In various embodiments, a pharmaceutical composition comprising a binding agent of the present disclosure may be formulated as a solution, microemulsion, dispersion, liposome, or other ordered structure suitable for stable storage at high concentration. Sterile injectable solutions may be prepared by incorporating a composition comprising a binding agent of the present disclosure in the required amount in an appropriate solvent with one or a combination of ingredients enumerated above, as required, followed by filter sterilization. Generally, dispersions are prepared by incorporating a composition comprising a binding agent of the present disclosure into a sterile vehicle that contains a basic dispersion medium and the required other ingredients from those enumerated above. In the case of sterile powders for the preparation of sterile injectable solutions, methods for preparation comprise vacuum drying and freeze-drying that yield a powder of a composition comprising a binding agent of the present disclosure plus any additional desired ingredient (see below) from a previously sterile-filtered solution thereof. The proper fluidity of a solution may be maintained, for example, by the use of a coating such as lecithin, by the maintenance of the required particle size in the case of dispersion and by the use of surfactants. Prolonged absorption of injectable compositions comprising a binding agent of the present disclosure may be brought about by comprising in the composition comprising a binding agent of the present disclosure a reagent that delays absorption, for example, monostearate salts, and gelatin.

A pharmaceutical composition comprising a binding agent of the present disclosure may be administered parenterally in the form of an injectable formulation comprising a sterile solution or suspension in water or another pharmaceutically acceptable liquid. For example, the pharmaceutical composition comprising a binding agent of the present disclosure may be formulated by suitably combining the therapeutic molecule with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient comprised in the pharmaceutical preparations is such that a suitable dose within the designated range is provided. Nonlimiting examples of oily liquid comprise sesame oil and soybean oil, and it may be combined with benzyl benzoate or benzyl alcohol as a solubilizing agent. Other items that may be comprised are a buffer such as a phosphate buffer, or sodium acetate buffer, a soothing agent such as procaine hydrochloride, a stabilizer such as benzyl alcohol or phenol, and an antioxidant. The formulated injection may be packaged in a suitable ampule.

In some embodiments, a composition comprising a binding agent of the present disclosure may be formulated for storage at a temperature below 0° C. (e.g., –20° C. or –80° C.). In some embodiments, the composition comprising a binding agent of the present disclosure may be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions comprising a binding agent of the present disclosure are stable in storage for at least 1 year at 2-8° C. (e.g., 4° C.).

In some instances, a pharmaceutical composition comprising a binding agent of the present disclosure may be formulated as a solution. In some embodiments, a composition comprising a binding agent of the present disclosure may be formulated, for example, as a buffered solution at a suitable concentration and suitable for storage at 2-8° C. (e.g., 4° C.). Pharmaceutical compositions comprising a binding agent as described herein may be formulated in immunoliposome compositions. Liposomes with enhanced circulation time are disclosed in, e.g., U.S. Pat. No. 5,013,556.

In certain embodiments, compositions comprising a binding agent of the present disclosure may be formulated with a carrier that will protect the composition against rapid release, such as a controlled release formulation, comprising implants and microencapsulated delivery systems. Biodegradable, biocompatible polymers may be used, such as ethylene vinyl acetate, polyanhydrides, polyglycolic acid, collagen, polyorthoesters, and polylactic acid. Many methods for the preparation of such formulations are known. See, e.g., J. R. Robinson (1978) "Sustained and Controlled Release Drug Delivery Systems," Marcel Dekker, Inc., New York.

In some embodiments, compositions comprising a binding agent of the present disclosure may be formulated in a composition suitable for intrapulmonary administration (e.g., for administration via an inhaler or nebulizer) to a mammal such as a human. Methods for formulating such compositions are known. Dry powder inhaler formulations and suitable systems for administration of the formulations are also known. Pulmonary administration may be oral and/or nasal. Examples of pharmaceutical devices for pulmonary delivery comprise metered dose inhalers, dry powder inhalers (DPIs), and nebulizers. For example, a composition comprising a binding agent of the present disclosure may be administered to the lungs of a subject by way of a dry powder inhaler. These inhalers are propellant-free devices that deliver dispersible and stable dry powder formulations to the lungs. Dry powder inhalers are known and comprise, without limitation: the TURBOHALER® (AstraZeneca; London, England) the AIR® inhaler (ALKERMES®; Cambridge, Mass.); ROTAHALER® (GlaxoSmithKline; London, England); and ECLIPSE™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, a composition comprising a binding agent of the present disclosure may be intrapulmonarily administered by way of a metered dose inhaler. These inhalers rely on a propellant to deliver a discrete dose of a molecule to the lungs. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, compositions comprising a binding agent of the present disclosure may be formulated for delivery to the eye, e.g., in the form of a pharmaceutically acceptable solution, suspension or ointment. A preparation for use in treating an eye may be in the form of a sterile aqueous solution containing, e.g., additional ingredients such as, without limitation, preservatives, buffers, tonicity agents, antioxidants and stabilizers, nonionic wetting or clarifying agents, and viscosity-increasing agents. A preparation as described herein may be administered topically to the eye of the subject in need of treatment (e.g., a subject afflicted with AMD) by conventional methods, e.g., in the form of drops, or by bathing the eye in a therapeutic solution, containing one or more compositions.

A variety of devices for introducing drugs into the vitreal cavity of the eye may be appropriate, in certain embodiments, for administration of a composition comprising a binding agent of the present disclosure. For example, U.S. Publication No. 2002/0026176 describes a pharmaceutical-containing plug that may be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. U.S. Pat. Nos. 5,773,019 and 6,001,386 each disclose an implantable drug delivery device attachable to the scleral surface of an eye. Additional methods and devices (e.g., a transscleral patch and delivery via contact lenses) for delivery of a therapeutic agent to the eye are described in, e.g., Ambati and Adamis (2002) Prog Retin Eye Res 21(2): 145-151; Ranta and Urtti (2006) Adv Drug Delivery Rev 58(11): 1164-1181; Barocas and Balachandran (2008) Expert Opin Drug Delivery 5(1):1-10(10); Gulsen and Chauhan (2004) Invest Opthalmol Vis Sci 45:2342-2347; Kim et al. (2007) Ophthalmic Res 39:244-254; and PCT publication no. WO 04/073551, the disclosures of which are incorporated herein by reference in their entirety.

In various embodiments, subcutaneous administration may be accomplished by means of a device, such as a syringe, a prefilled syringe, an auto-injector (e.g., disposable or reusable), a pen injector, a patch injector, a wearable injector, an ambulatory syringe infusion pump with subcutaneous infusion sets, or other device for combining with binding agent drug for subcutaneous injection.

An injection system of the present disclosure may employ a delivery pen as described in U.S. Pat. No. 5,308,341. Pen devices are commonly used for self-delivery of insulin to patients with diabetes. Such devices may comprise at least one injection needle (e.g., a 31 gauge needle of about 5 to 8 mm in length), are generally pre-filled with one or more therapeutic unit doses of a therapeutic solution, and are useful for rapidly delivering solution to a subject with as little pain as possible. One medication delivery pen comprises a vial holder into which a vial of a therapeutic or other medication may be received. The pen may be an entirely mechanical device or it may be combined with electronic circuitry to accurately set and/or indicate the dosage of medication that is injected into the user. See, e.g., U.S. Pat. No. 6,192,891. In some embodiments, the needle of the pen device is disposable and the kits comprise one or more disposable replacement needles. Pen devices suitable for delivery of any one of the presently featured compositions comprising a binding agent of the present disclosure are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, MOLLY™, manufactured by Scandinavian Health Ltd.

In some embodiments, a composition comprising a binding agent of the present disclosure may be delivered to a subject by way of local administration that does not rely upon transport of the binding agent to its intended target tissue or site via the vascular system. For example, the composition comprising a binding agent of the present disclosure may be delivered by injection or implantation of the composition comprising a binding agent of the present disclosure or by injection or implantation of a device containing the composition comprising a binding agent of the present disclosure. In certain embodiments, following local administration in the vicinity of a target tissue or site, the composition comprising a binding agent of the present disclosure, or one or more components thereof, may diffuse to an intended target tissue or site that is not the site of administration.

In some embodiments, a composition comprising a binding agent of the present disclosure may be locally administered to a joint, e.g., directly to a joint (e.g., into a joint space) or in the vicinity of a joint. Examples of intraarticular joints to which a composition comprising a binding agent of the present disclosure may be locally administered comprise, e.g., the hip, knee, elbow, wrist, sternoclavicular, temporomandibular, carpal, tarsal, ankle, and any other joint subject to arthritic conditions. A composition comprising a binding agent of the present disclosure may also be administered to bursa such as, e.g., acromial, bicipitoradial, cubitoradial, deltoid, infrapatellar, ischial, and any other bursa.

In some embodiments, the compositions comprising a binding agent of the present disclosure provided herein are present in unit dosage form, which unit dosage form may be suitable for self-administration. Such a unit dosage form may be provided within a container, generally, for example, a vial, cartridge, prefilled syringe or disposable pen. A doser such as the doser device described in U.S. Pat. No. 6,302,855, may also be used, for example, with an injection system as described herein.

A pharmaceutical solution may comprise a therapeutically effective amount of a composition comprising a binding agent of the present disclosure. Such effective amounts may be readily determined based, in part, on the effect of the administered composition comprising a binding agent of the present disclosure, or the combinatorial effect of the composition comprising a binding agent of the present disclosure and one or more additional active agents, if more than one agent is used. A therapeutically effective amount of a composition comprising a binding agent of the present disclosure may also vary according to factors such as the disease state, age, sex, and weight of the individual, and the ability of the composition (and one or more additional active agents) to elicit a desired response in the individual, e.g., amelioration of at least one condition parameter, e.g., amelioration of at least one symptom of the complement-mediated disorder. For example, a therapeutically effective amount of a composition comprising a binding agent of the present disclosure may inhibit (lessen the severity of or eliminate the occurrence of) and/or prevent a disorder, and/or any one of the symptoms of the disorder. A therapeutically effective amount is also one in which any toxic or detrimental effects of the composition comprising a binding agent of the present disclosure are outweighed by the therapeutically beneficial effects.

A composition comprising a binding agent of the present disclosure may be administered as a fixed dose, or in a milligram per kilogram (mg/kg) dose. In some embodiments, the dose may also be chosen to reduce or avoid production of antibodies or other host immune responses against one or more of the antigen-binding molecules in the composition comprising a binding agent of the present disclosure. While in no way intended to be limiting, exemplary dosages of a binding agent, such as a composition comprising a binding agent of the present disclosure comprise, e.g., 1-1000 mg/kg, 1-100 mg/kg, 0.5-50 mg/kg, 0.1-100 mg/kg, 0.5-25 mg/kg, 1-20 mg/kg, and 1-10 mg/kg. Exemplary dosages of a composition comprising a binding agent of the present disclosure comprise, without limitation, 0.1 mg/kg, 0.5 mg/kg, 1.0 mg/kg, 2.0 mg/kg, 4 mg/kg, 8 mg/kg, or 20 mg/kg.

Suitable human doses of any of the compositions comprising a binding agent of the present disclosure may further be evaluated in, e.g., Phase I dose escalation studies. See, e.g., van Gurp et al. (2008) Am J Transplantation 8(8):1711-1718; Hanouska et al. (2007) Clin Cancer Res 13(2, part 1):523-531; and Hetherington et al. (2006) Antimicrobial Agents and Chemotherapy 50(10):3499-3500.

In various embodiments, a pharmaceutical composition may comprise a nucleic acid of the present disclosure, e.g., a vector. Methods of formulating pharmaceutical compositions comprising a nucleic acid of the present disclosure are known, e.g., in the books in the series Drugs and the Pharmaceutical Sciences: a Series of Textbooks and Monographs (Dekker, N.Y.). For example, solutions or suspensions used for parenteral, intradermal, or subcutaneous application may comprise the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH may be adjusted with acids or bases, such as hydrochloric acid or sodium hydroxide. Parenteral preparations may be enclosed, e.g., in ampoules, disposable syringes, or more than one dose vials made of glass or plastic.

Pharmaceutical compositions comprising a nucleic acid of the present disclosure suitable for injection may comprise sterile aqueous solutions or dispersions and sterile powders for the extemporaneous preparation of sterile injectable solutions or dispersion. For intravenous administration, suitable carriers may comprise physiological saline, bacteriostatic water, Cremophor EL™ (BASF, Parsippany, N.J.) or phosphate buffered saline (PBS). The carrier may be a solvent or dispersion medium containing, for example, water, ethanol, polyol (for example, glycerol, propylene glycol, and liquid polyethylene glycol, and the like), and suitable mixtures thereof.

Sterility, stability, viscosity and other factors relating to effective therapeutic use may be considered. One method of maintaining fluidity, for example, comprises the use of a coating such as lecithin, the maintenance of required particle size, or the use of surfactants. In some instances, it will be preferable to comprise isotonic agents, for example, sugars, polyalcohols such as mannitol, sorbitol, sodium chloride in the composition. In some instances, prolonged absorption of injectable compositions comprising a nucleic acid of the present disclosure may be brought about by comprising in the composition an agent that delays absorption, for example, aluminum monostearate and gelatin.

Sterile injectable solutions may be prepared by incorporating one or a combination of ingredients such as antibacterial and antifungal agents (for example, parabens, chlorobutanol, phenol, ascorbic acid, thimerosal, and the like), and/or by filtered sterilization. In some instances, dispersions are prepared by incorporating the active molecule into a sterile vehicle, which contains a basic dispersion medium and antibacterial or antifungal agents. In the case of sterile powders for the preparation of sterile injectable solutions, methods of preparation comprise vacuum drying and freeze-drying from a previously sterile-filtered solution thereof.

Oral compositions comprising a nucleic acid of the present disclosure may comprise an inert diluent or an edible carrier. For the purpose of oral therapeutic administration, a nucleic acid of the present disclosure may be incorporated with excipients and used, e.g., in the form of tablets, troches, or capsules, e.g., gelatin capsules. Oral compositions comprising a nucleic acid of the present disclosure may also be prepared using a fluid carrier for use as a mouthwash. Pharmaceutically compatible binding agents, and/or adjuvant materials may be comprised as part of the composition. The tablets, pills, capsules, troches and the like may contain any of the following ingredients, or molecules of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Sterotes®; a glidant such as colloidal silicon dioxide; a sweetening agent such as sucrose or saccharin; or a flavoring agent such as peppermint, methyl salicylate, or orange flavoring.

In some embodiments, nucleic acids may be administered by any method suitable for administration of nucleic acid agents, such as a DNA vaccine. These methods comprise, e.g., gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, e.g., Hamajima et al., (1998) Clin. Immunol. Immunopathol. 88(2), 205-10. Liposomes (e.g., as described in U.S. Pat. No. 6,472,375). In certain instances, microencapsulation may be used. In addition, biodegradable targetable microparticle delivery systems may be used (e.g., as described in U.S. Pat. No. 6,471,996).

Compositions comprising a nucleic acid of the present disclosure may comprise components such as adjuvants, diluents, binders, stabilizers, buffers, salts, lipophilic solvents, preservatives, mixtures thereof, or any component for inclusion in therapeutic compositions comprising a nucleic acid. A nucleic acid composition may comprise, e.g., saline, solvents, dispersion media, coatings, antibacterial and antifungal agents, isotonic and absorption delaying agents, and the like, a phosphate buffered saline solution, water, and emulsions, such as an oil/water or water/oil emulsion, and various types of wetting agents, compatible with pharmaceutical administration. Supplementary active molecules may also be incorporated into compositions comprising a nucleic acid of the present disclosure of the present disclosure. Compositions comprising a nucleic acid of the present disclosure of the present disclosure may comprise stabilizers and preservatives and any of the carriers described herein with the optional additional proviso that they be acceptable for use in vivo. For examples of additional carriers, stabilizers, and adjuvants, see Martin REMINGTON'S PHARM. SCI., 15th Ed. (Mack Publ. Co., Easton (1975) and Williams & Williams, (1995), and in the "PHYSICIAN'S DESK REFERENCE," 52nd ed., Medical Economics, Montvale, N.J. (1998).

Methods described herein comprise the manufacture and use of pharmaceutical compositions comprising a nucleic acid of the present disclosure. Pharmaceutical compositions comprising a nucleic acid of the present disclosure are generally formulated to be compatible with their intended route of administration. Examples of routes of administration comprise parenteral, e.g., intravenous, intracranial, intradermal, subcutaneous, oral (e.g., inhalation), transdermal (topical), transmucosal, and rectal administration.

A nucleic acid composition may comprise a buffer or a pH adjusting agent. A buffer may be a salt prepared from an organic acid or base. Buffers of the present disclosure comprise organic acid salts such as salts of citric acid, ascorbic acid, gluconic acid, carbonic acid, tartaric acid, succinic acid, acetic acid, or phthalic acid, Tris, tromethamine hydrochloride, and phosphate buffers. Additional carriers comprise polymeric excipients or additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as TWEEN 20® and TWEEN 80®), lipids (e.g., phospholipids, fatty acids), steroids (e.g., cholesterol), and chelating agents (e.g., EDTA).

In certain embodiments in which a nucleic acid of the present disclosure is a vector, the present disclosure comprises a composition for gene transduction and/or gene therapy, e.g., a composition comprising viral particles, e.g., AAV particles and/or retroviral particles such as lentiviral particles. The terms "genome particles (gp)," or "genome equivalents," as used in reference to a viral titer, refer to the number of virions containing the recombinant viral genome, e.g., recombinant AAV DNA genome, regardless of infectivity or functionality. The number of genome particles in a vector preparation may be measured. The terms "infection unit (IU)," "infectious particle," or "replication unit," as used in reference to a viral titer, refer to the number of infectious and replication-competent recombinant virus, e.g., of recombinant AAV vector particles, as may be measured by the infectious center assay, also known as replication center assay. The term "transducing unit (TU)" as used in reference to a viral titer, refers to the number of infectious recombinant vector particles, e.g., recombinant AAV vector particles, that result in the production of a functional transgene product.

In some embodiments, a composition comprises, e.g., $2\times10^6$ to $2\times10^{12}$, $2\times10^7$ to $2\times10^{11}$, or $2\times10^8$ to $2\times10^{11}$ DNA-containing viral particles per dose. In certain embodiments, the concentration or titer of vector in a unit dosage form is, e.g., at least: (a) $1\times10^{12}$ particles per mL, $2\times10^{12}$ particles per mL, $3\times10^{12}$ particles per mL, $4\times10^{12}$ particles per mL, $5\times10^{12}$ particles per mL, $6\times10^{12}$ particles per mL, $7\times10^{12}$ particles per mL, $8\times10^{12}$ particles per mL, $9\times10^{12}$ particles per mL, $10\times10^{12}$ particles per mL, $15\times10^{12}$ particles per mL, $20\times10^{12}$ particles per mL, $25\times10^{12}$ particles per mL, or $50\times10^{12}$ particles per mL; (b) $1\times10^9$ TU/mL, $2\times10^9$ TU/mL, $3\times10^9$ TU/mL, $4\times10^9$ TU/mL, $5\times10^9$ TU/mL, $6\times10^9$ TU/mL, $7\times10^9$ TU/mL, $8\times10^9$ TU/mL, $9\times10^9$ TU/mL, $10\times10^9$ TU/mL, $15\times10^9$ TU/mL, $20\times10^9$ TU/mL, 25, or $50\times10^9$ TU/mL; or (c) $1\times10^{10}$ IU/mL, $2\times10^{10}$ IU/mL, $3\times10^{10}$ IU/mL, $4\times10^{10}$ IU/mL, $5\times10^{10}$ IU/mL, $6\times10^{10}$ IU/mL, $7\times10^{10}$ IU/mL, $8\times10^{10}$ IU/mL, $9\times10^{10}$ IU/mL, $10\times10^{10}$ IU/mL, $15\times10^{10}$ IU/mL, $20\times10^{10}$ IU/mL, $25\times10^{10}$ IU/mL, or $50\times10^{10}$ IU/mL. Such embodiments do not limit the unit dosages encompassed by the present disclosure and do not limit the various measures of dosage that may be used in conjunction with various compositions comprising a nucleic acid of the present disclosure of the present disclosure. For instance, a particle dosage, concentration, or amount may be measured and/or expressed in terms of vector genomes per kilogram subject (Vg/Kg) or Vg/dose. The preferred means of measuring and/or expressing particle dosage, concentration, or amount may vary depending upon various factors, e.g., route of administration.

The present disclosure provides technologies for simultaneously targeting CD20 and another antigen, e.g., CD19. In some embodiments, the present disclosure provides technologies for initiating and/or modulating immune responses. In some embodiments, the present disclosure provides technologies for treating cancer (e.g., cancer characterized by cell(s) with surface-expressed CD20).

The present specification comprises use of a binding agent pharmaceutical composition provided herein to treat or prevent cancer. Another aspect of the present disclosure is directed to a method for treating or preventing a malignancy, said method comprising administering to a subject in need thereof an effective amount of a binding agent pharmaceutical composition, e.g., where the cells comprises at least one Antigen binding system provided herein. Methods of the present disclosure comprising administration of an pharmaceutically effective amount of a binding agent pharmaceutical composition of the present disclosure may be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, a method provided herein induces a complete response. In some embodiments, a method provided herein induces a partial response. In certain embodiments the binding agent pharmaceutical composition is, comprises, comprises as the active agent, or comprises as the sole active agent, cells provided herein, e.g., cells that comprise or express at least one CAR of the present disclosure. In some embodiments, the binding agent pharmaceutical composition comprises a bicistronic CAR system comprising an anti-CD20 car and an anti-CD19 CAR, or the binding agent pharmaceutical composition comprises a bispecific anti-C20/anti-CD19 CAR of the present disclosure.

In various embodiments, the present disclosure comprises use of a binding agent pharmaceutical composition provided herein to induce in a subject, or provide a subject with, immunity against a cancer. The present disclosure further comprises a method of preventing cancer in a subject by administering to the subject a binding agent pharmaceutical composition provided herein. The present disclosure further comprises a method of inducing an immune response in a subject by administering to the subject a binding agent pharmaceutical composition provided herein. In certain embodiments the binding agent pharmaceutical composition is, comprises, comprises as the active agent, or comprises as the sole active agent, cells provided herein, e.g., cells that comprise or express at least one CAR of the present disclosure. In some embodiments, the binding agent pharmaceutical composition comprises a bicistronic CAR system comprising an anti-CD20 car and an anti-CD19 CAR, or the binding agent pharmaceutical composition comprises a bispecific anti-C20/anti-CD19 CAR of the present disclosure.

In certain embodiments, a method of treating a cancer in a subject in need thereof comprises administering to the subject a polynucleotide, vector, antibody, or antigen binding system disclosed herein. In one embodiment, the method comprises administering a polynucleotide encoding an antigen binding system or antibody (e.g., an antigen binding system). In another embodiment, the method comprises administering a vector comprising a polynucleotide encoding an antigen binding system or antibody. In another embodiment, the method comprises administering an antigen binding system or antibody to the subject.

Another aspect of the disclosure is directed to a method of making a cell expressing a CAR or a TCR comprising transducing a cell with a polynucleotide disclosed herein under suitable conditions. In some embodiments, the method comprises transducing a cell with a polynucleotide encoding a CAR or a TCR, as disclosed herein. In some embodiments, the method comprises transducing a cell with a vector comprising the polynucleotide encoding a CAR or a TCR. In certain embodiments, the present disclosure provides a T cell therapy in which a binding agent pharmaceutical composition comprises T cells transfected or transduced with a vector comprising a polynucleotide sequence encoding an antigen-binding agent of the present disclosure (e.g., an antigen binding system). In some embodiments, the donor T cells for use in the T cell therapy are obtained from the patient (e.g., for an autologous T cell therapy). In other embodiments, the donor T cells for use in the T cell therapy are obtained from a subject that is not the patient. In one embodiment, the T cell therapy of the present disclosure is an Autologous Cell Therapy (eACT™). According to this embodiment, the method may comprise collecting blood cells from the patient. The isolated blood cells (e.g., T cells) may then be engineered to express an antigen binding system of the present disclosure. In certain embodiments, the binding agents are administered to the patient. In some embodiments, the binding agents treat or are intended to treat or a cancer in the patient. For instance, in one embodiment the binding agents reduce the size of a tumor. In various embodiments, cells of the present disclosure may be cells freshly isolated from a human subject, cells freshly isolated from a cell culture, or cells having been stored, e.g., frozen.

Another aspect of the present disclosure is directed to a method of inducing an immunity against a tumor comprising administering to a subject an effective amount of a cell comprising a polynucleotide described herein, a vector described herein, or a CAR or a TCR described herein. In one embodiment, the method comprises administering to a subject an effective amount of a cell comprising a polynucleotide encoding a CAR or a TCR disclosed herein. In another embodiment, the method comprises administering to a subject an effective amount of a cell comprising a vector comprising a polynucleotide encoding a CAR or a TCR disclosed herein. In another embodiment, the method comprises administering to a subject an effective amount of a cell comprising a CAR or a TCR encoded by a polynucleotide disclosed herein.

Another aspect of the present disclosure is directed to a method of inducing an immune response in a subject comprising administering an effective amount of the engineered immune cells of the present application. In some embodiments, the immune response is a T cell-mediated immune response. In some embodiments, the T cell-mediated immune response is directed against one or more target cells. In some embodiments, the engineered immune cell comprises a CAR or a TCR, wherein the CAR or the TCR comprises a THD described in the present disclosure. In some embodiments, the target cell is a tumor cell.

Another aspect of the present disclosure is directed to a method for treating or preventing a malignancy, said method comprising administering to a subject in need thereof an effective amount of at least one immune cell, wherein the immune cell comprises at least one CAR or TCR, and wherein the CAR or the TCR comprises one or two of the scfv disclosed herein.

Another aspect of the present disclosure is directed to a method of treating a cancer in a subject in need thereof comprising administering to the subject a polynucleotide, a vector, a CAR or a TCR, a cell, or a composition disclosed herein. In one embodiment, the method comprises administering a polynucleotide encoding a CAR or a TCR. In another embodiment, the method comprises administering a vector comprising a polynucleotide encoding a CAR or a TCR. In another embodiment, the method comprises administering a CAR or a TCR encoded by a polynucleotide disclosed herein. In another embodiment, the method comprises administering a cell comprising the polynucleotide, or a vector comprising the polynucleotide, encoding a CAR or a TCR.

In some embodiments, the methods of treating a cancer in a subject in need thereof comprise a T cell therapy. In one embodiment, the T cell therapy of the present disclosure is engineered Autologous Cell Therapy (eACT™). According to this embodiment, the method can include collecting blood cells from the patient. The isolated blood cells (e.g., T cells) can then be engineered to express a CAR or a TCR of the present disclosure. In a particular embodiment, the CAR T cells or the TCR T cells are administered to the patient. In some embodiments, the CAR T cells or the TCR T cells treat a tumor or a cancer in the patient. In one embodiment the CAR T cells or the TCR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient.

The T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In one particular embodiment, the therapeutically effective amount of the CAR T cells or the TCR T cells is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $2 \times 10^7$ cells/kg, about $3 \times 10^7$ cells/kg, about $4 \times 10^7$ cells/kg, about $5 \times 10^7$ cells/kg, about $6 \times 10^7$ cells/kg, about $7 \times 10^7$ cells/kg, about $8 \times 10^7$ cells/kg, or about $9 \times 10^7$ cells/kg.

The methods of the disclosure can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

In certain embodiments, the cancer comprises cells that express CD19, e.g., on the surface of the cell. In certain embodiments the cancer comprises cells that express CD20, e.g., on the surface of the cell. In certain embodiments the cancer comprises cells that each individually express both CD19 and CD20, e.g., on the surface of the cell.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In certain embodiments, the cancer is acute lymphoblastic leukemia (ALL) (including non T cell ALL), acute lymphoid leukemia (ALL), and hemophago-cytic lymphohistiocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myel-ogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syn-drome (Macrophage Activating Syndrome (MAS), Hodg-kin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined sig-nificance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T-cell acute lymphoid leukemia ("TALL"), T-cell lymphoma, transformed follicular lymphoma, Waldenstrom macroglobulinemia, or a combination thereof. In one embodiment, the cancer is a myeloma. In one particular embodiment, the cancer is multiple myeloma. In another embodiment, the cancer is a leukemia. In one embodiment, the cancer is acute myeloid leukemia.

In various instances, a method of using a binding agent pharmaceutical composition provided herein to treat cancer is an autologous cell therapy. In various instances, a method of using a binding agent pharmaceutical composition provided herein to treat cancer is an allogeneic cell therapy.

Certain method using a binding agent pharmaceutical composition provided herein comprise collecting blood cells from the subject. Isolated subject blood cells (e.g., T cells) may then be engineered to express, e.g., an antigen binding system of the present disclosure. In some embodiments, the binding agents are administered to the subject. In some embodiments, the binding agents treat cancer in the subject. In one embodiment the binding agents reduce the size of a tumor.

In various embodiments, a cell therapy provided herein for use in the present disclosure may be administered to a subject in a course of treatment that further comprises administration of one or more additional therapeutic agents or therapies that are not a cell therapy provided herein. In certain embodiments, the present disclosure provides combination therapy for the treatment of cancer, the treatment comprising administering an anti-cancer agent to a subject receiving and/or in need of a binding agent provided herein.

In certain embodiments, administration of a binding agent provided herein may be to a subject having previously received, scheduled to receive, or in the course of a treatment regimen comprising an additional anti-cancer therapy. In various embodiments, an additional agent or therapy administered in combination with a binding agent provided herein as described herein may be administered at the same time as binding agent provided herein, on the same day as binding agent provided herein, or in the same week as binding agent provided herein. In various embodiments, an additional agent or therapy administered in combination with a binding agent provided herein as described herein may be administered such that administration of the binding agent provided herein and the additional agent or therapy are separated by one or more hours before or after, one or more days before or after, one or more weeks before or after, or one or more months before or after administration of binding agent provided herein. In various embodiments, the administration frequency of one or more additional agents may be the same as, similar to, or different from the administration frequency of a binding agent provided herein.

An agent or therapy used in combination with binding agent provided herein may be administered in a single therapeutic composition or dose together with binding agent provided herein, at the same time as binding agent provided herein in the form of a separate composition, or in a manner temporally distinct from the administration of binding agent provided herein. When a binding agent provided herein is to be used in combination with an additional agent, the binding agent provided herein may be co-formulated with the additional agent or the binding agent provided herein may be formulated separately from the additional agent formulation.

In some embodiments, the methods further comprise administering a chemotherapeutic. In certain embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient. In other embodiments, the antigen binding molecule, transduced (or otherwise engineered) cells (such as CARs or TCRs), and the chemotherapeutic agent are administered each in an amount effective to treat the disease or condition in the subject.

In certain embodiments, compositions comprising CAR- and/or TCR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone;

aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4 (5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche). Additional therapeutic agents suitable for use in combination with the disclosure include, but are not limited to, ibrutinib (IMBRUVICA®), ofatumumab (ARZERRA®), rituximab (RITUXAN®), bevacizumab (AVASTIN®) trastuzumab (HERCEPTIN®), trastuzumab emtansine (KADCYLA®), imatinib (GLEEVEC®) cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR- and/or TCR-containing immune are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of propoxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In certain embodiments, the compositions described herein are administered in conjunction with a cytokine. "Cytokine" is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. In various embodiments, a binding agent provided herein for use in the present disclosure may be administered to a subject in a course of treatment that further comprises administration of an anti-inflammatory agent. Anti-inflammatory agents may comprise, without limitation, steroids and glucocorticoids (comprising betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) comprising aspirin, ibuprofen, naproxen, methotrexate, sulfasalazine, leflunomide, anti-TNF medications, cyclophosphamide and mycophenolate. Exemplary NSAIDs comprise ibuprofen, naproxen, naproxen sodium, Cox-2 inhibitors, and sialylates. Exemplary analgesics comprise acetaminophen, oxycodone, tramadol of propoxyphene hydrochloride. Exemplary glucocorticoids comprise cortisone, dexamethasone, hydrocortisone, methylprednisolone, prednisolone, or prednisone. Exemplary biological response modifiers comprise molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers comprise monoclonal antibodies as well as recombinant forms of molecules. Exemplary DMARDs comprise azathioprine, cyclophosphamide, cyclosporine, methotrexate, penicillamine, leflunomide, sulfasalazine, hydroxychloroquine, Gold (oral (auranofin) and intramuscular), and minocycline.

In various embodiments, a binding agent provided herein for use in the present disclosure may be administered to a subject in a course of treatment that further comprises administration of a CHOP. CHOP consists of (C)yclophosphamide, an alkylating agent which damages DNA by binding to it and causing the formation of cross-links; (H)ydroxydaunorubicin (also called doxorubicin or adriamycin), an intercalating agent which damages DNA by inserting itself between DNA bases; (O)ncovin (vincristine), which prevents cells from duplicating by binding to the protein tubulin; and (P)rednisone or (P)rednisolone, which are corticosteroids.

Additional Exemplary Embodiments. The present disclosure comprises, without limitation, the following exemplary embodiments:

Embodiment 1. An isolated polynucleotide encoding a chimeric antigen receptor (CAR) or a T cell receptor (TCR), which comprises (i) an antigen binding molecule, (ii) a costimulatory domain, and (iii) an activating domain, wherein the costimulatory domain comprises an extracellular domain, a transmembrane domain, and an intracellular domain, wherein the extracellular domain comprises an antigen binding molecule consisting essentially of or consisting of (i) an amino acid sequence at least about 80%, at least about 85%, at least about 90%, at least about 95%, at least about 96%, at least about 97%, at least about 98%, at least about 99%, or about 100% identical to the amino acid sequence of any of the constructs described in SEQ ID NO. 232, 221, 56, 45, 155, 144, 177, 78, and 67.

Embodiment 2. The polynucleotide of embodiment 1, wherein the transmembrane domain is a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD33, CD37, CD45, CD64, CD80, CD86, CD134, CD137, CD154, or a zeta chain of a T cell receptor, or any combination thereof.

Embodiment 3. The polynucleotide of embodiment 1 or 2, wherein the intracellular domain comprises a signaling region of 4-1BB/CD137, activating NK cell receptors, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD1 la, CD1 lb, CD1 lc, CD1 ld, CDS, CEACAM1, CRT AM, cytokine receptors, DAP-10, DNAM1 (CD226), Fc gamma receptor, GADS, GITR, HVEM (LIGHTR), IA4, ICAM-1, ICAM-1, Ig alpha (CD79a), IL2R beta, IL2R gamma, IL7R alpha, Immunoglobulin-like proteins, inducible T cell costimulator (ICOS), integrins, ITGA4, ITGA4, ITGA6, ITGAD, ITGAE, ITGAL, ITGAM, ITGAX, ITGB2, ITGB7, ITGBl, KIRDS2, LAT, LFA-1, LFA-1, a ligand that specifically binds with CD83, LIGHT, LIGHT (tumor necrosis factor superfamily member 14; TNFSF14), LTBR, Ly9 (CD229), lymphocyte function-associated antigen-1 (LFA-1 (CD1 la/CD18), MHC class I molecule, NKG2C, NKG2D, NKp30, NKp44, NKp46, NKp80 (KLRF1), OX-40, PAG/ Cbp, programmed death-1 (PD-1), PSGL1, SELPLG (CD162), signaling lymphocytic activation molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, a Toll ligand receptor, TRANCE/RANKL, VLA1, or VLA-6, or a combination thereof.

Embodiment 4. The polynucleotide of embodiments 1 to 3, wherein at least one of the antigen binding molecule specifically binds an antigen selected from the group consisting of 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gpl20, IL-llRalpha, kappa chain, lambda chain, melanoma-associated antigen, mesothelin, MUC-1, mutated p53, mutated ras, prostate-specific antigen, ROR1, or VEGFR2, or a combination thereof.

Embodiment 5. The polynucleotide of any of embodiments 1 to 4, wherein the polynucleotide encodes a polypeptide comprising the amino acid sequence set forth in SEQ ID NOs 232, 221, 56, 45, 155, 144, 177, 78, and 67.

Embodiment 6. A polypeptide encoded by the polynucleotide of any one of embodiments 1 to 5.

Embodiment 7. A polypeptide comprising the amino acid sequence as set forth in SEQ ID NOs. 232, 221, 56, 45, 155, 144, 177, 78, and 67.

Embodiment 8. A vector comprising the polynucleotide of any one of embodiments 1 to 5.

Embodiment 9. The vector of embodiment 7, wherein the vector is an adenoviral vector, an adenovirus-associated vector, a DNA vector, a lentiviral vector, a plasmid, a retroviral vector, or an RNA vector, or any combination thereof.

Embodiment 10. A cell comprising the polynucleotide of any one of embodiments 1 to 5, the polypeptide of claim 6 or 7, the vector of claim 8 or 9, or any combination thereof.

Embodiment 11. A composition comprising the polynucleotide of any one of embodiments 1 to 5, the polypeptide of claim 6 or 7, the vector of claim 8 or 9, the cell of claim 10, or any combination thereof.

Embodiment 12. A method of making a cell comprising the polynucleotide of any one of claims 1 to 5, the polypeptide of embodiment 6 or 7, the vector of claim 8 or 9, or any combination thereof.

Embodiment 13. A method of inducing an immunity against a tumor comprising administering to a subject an effective amount the polynucleotide of any one of claims 1 to 5, the polypeptide of embodiment 6 or 7, the vector of embodiment 8 or 9, the cell of embodiment 10, the composition of embodiment 11 or any combination thereof.

Embodiment 14. Use of the polynucleotide of any one of embodiments 1 to 5, the polypeptide of embodiment 6 or 7, the vector of embodiment 8 or 9, the cell of embodiment 11, or the composition of embodiment 12 for the manufacture of a medicament for treating a cancer in a subject in need thereof.

Embodiment 15. The use of embodiment 15, wherein the cancer is acute lymphoblastic leukemia (ALL) (including non T cell ALL), acute myeloid leukemia, B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome, non-Hodgkin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (including plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T-cell acute lymphoid leukemia ("TALL"), T-cell lymphoma, transformed follicular lymphoma, or Waldenstrom macroglobulinemia, or a combination thereof.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present disclosure. To the extent that any of the definitions or terms provided in the references incorporated by reference differ from the terms and discussion provided herein, the present terms and definitions control. The contents of all references cited throughout this application are expressly incorporated herein by reference.

EXAMPLES

Example 1

The present Example provides exemplary produced anti-CD20 heavy chain variable domains and light chain variable domains, and combinations thereof. CDR sequences of exemplary anti-CD20 heavy chain variable domains and anti-CD20 light chain variable domains, and thereby exemplary combinations of HCDRs and LCDRs, are also provided in below Tables 4-13. Tables 4-13 comprise exemplary nucleic acid sequences encoding exemplary variable domains (and thus also provides exemplary nucleic acid sequences encoding the identified CDRs of the exemplary variable domains).

To determine cell binding by exemplary heavy chain variable domains and light chain variable domains of the present disclosure, purified IgGs were characterized for cell binding at a concentration of 10 nM by flow cytometry. Antibodies were incubated with CHO-S cells overexpressing CD20, Raji, and Namalwa CD20+ cell lines; and with EoL-1 and CHO-S CD20-cell lines. FITC-LC was used to detect IgGs. The ratio of binding over negative controls was calculated for each antibody. Exemplary cell binding by selected anti-CD20 antibodies is provided in Table 15.

TABLE 15

| Ab | CHO-CD20 Cell Binding FOB (Fold Over Background) | Raji Cell Binding FON (Fold Over Negative) | Namalwa Cell Binding FON (Fold Over Negative) | EOL-1 Cell Binding FON (Fold Over Negative) |
|---|---|---|---|---|
| Ab1 | 813 | 266 | 12 | 1 |
| Ab2 | 2790 | 101 | 3 | 1 |
| Ab3 | 2002 | 316 | 16 | 1 |
| Ab4 | 3617 | 479 | 19 | 1 |
| Ab5 | 2480 | 185 | 17 | 1 |
| Ab6 | 2525 | 13 | 2 | 1 |
| Ab7 | 4083 | 549 | 11 | 1 |
| Ab8 | 3831 | 562 | 10 | 1 |
| Ab9 | 3618 | 562 | 11 | 1 |
| Ab10 | 3159 | 186 | 4 | 1 |

Example 2

The present Example provides bicistronic and bispecific CARs. Bicistronic and bispecific CARs comprise two binding motifs (in two CAR molecules or on a single CAR molecule, respectively). A first binding motif binds CD20 and a second binding motif binds CD19. Antibody sequences that bind CD19, and/or are useful in constructing binding motifs, antibodies, and antigen binding systems that bind CD19 are known. The present Example uses antibody sequences of an anti-CD19 binding agent referred to here as antibody Ab11, which are set forth in Table 14.

Bispecific CARs of the present Example were generated to comprise the following domains: a first binding motif, a second binding motif, a hinge, a transmembrane domain, and an intracellular domain comprising a costimulatory domain and an activation domain. In the present Example, each bispecific CAR comprised a first binding motif comprising a heavy chain variable domain and a light chain variable domain, which heavy chain and light chain variable domains are the heavy chain variable domain and the light chain variable domain from a single set of exemplary antibody sequences of Example 1 (i.e., both are from the same table of Tables 4-13, corresponding to Ab1-Ab10). Thus, binding motifs can be identified by reference to a source antibody or source table, and refer to a binding motif having the heavy chain variable domain and light chain variable domain of the source antibody as set out in the corresponding table. In the present Example, each bispecific CAR comprised a second binding motif comprising a heavy chain variable domain and a light chain variable domain, which heavy chain and light chain variable domains are the heavy chain variable domain and the light chain variable domain of antibody Ab11 (i.e., SEQ ID NOs: 221 and 232). Bispecific CARs of the present Example comprised a 28T (CD28) domain that comprises a hinge domain and a transmembrane domain. Bispecific CARs of the present Example comprised a CD28 costimulatory domain. Bispecific CARs of the present Example comprised a CD3z activation domain.

The present Example comprises four bicistronic CARs, identified as Bic-2, Bic-8, Bic-9, and Bic-14. Each of the four bicistronic CARs comprised a first CAR construct comprising an anti-CD20 binding motif that comprises a heavy chain variable domain and light chain variable domain pair of Example 1, as set forth in Table 16 below, and a second CAR construct comprising an anti-CD19 binding motif.

TABLE 16 anti-CD20 binding motif sequences of bicistronic CARs

| CAR | Binding motif | VH SEQ ID | VL SEQ ID |
|---|---|---|---|
| Bic-2 | Ab3 | 45 | 56 |
| Bic-8 | Ab8 | 155 | 166 |
| Bic-9 | Ab9 | 177 | 188 |
| Bic-14 | Ab4 | 67 | 78 |

Example 3

CD4$^+$ and CD8$^+$ T cells were isolated by positive selection from apheresis material from healthy donors and used to generate anti-CD20 monovalent or anti-CD20/anti-CD19 bicistronic CAR T-cell products. T cells were activated with bound-anti-CD3 and soluble CD28 antibodies and transduced with a lentiviral vector encoding for a CAR construct. As a control, non-transduced (NTD) T cells were generated from the same donor T cells in parallel. On the harvest day (Days 8-10 of manufacture), CAR T-cell products were stained and analyzed by flow cytometry to assess transduction efficiency and used in co-culture assays. Transduction efficiency of T cells with vector encoding monovalent CAR and vector encoding bicistronic CAR were monitored.

To determine the T cell transduction efficiency of vector encoding a monovalent CAR, CAR-T products were stained with a panel of antibodies (anti-CD3, anti-CD4, anti-CD8, and anti-linker antibodies) in the presence of a fixable viability dye and analyzed by flow cytometry to assess the percentage of viable CAR-positive cells (see WO/US2017/ 041534, which is incorporated herein by reference with respect to the anti-linker antibody). The anti-linker antibody is an antibody that binds the linker between the heavy and light chains of the binding motif of the anti-CD20 CAR and is used to measure transduction efficiency. Controls comprised non-transduced cells (NTD), cells transduced with a retrovirus comprising a control anti-CD19 binding agent, and cells transduced with a control anti-CD20 binding agent (Ab12 binding motif).

To determine the T cell transduction efficiency of vector encoding a bicistronic CAR, CAR-T products were stained with a panel of antibodies (comprising anti-CD3, anti-CD4, anti-CD8, anti-idiotypic, and anti-linker antibodies) in the presence of a fixable viability dye and analyzed by flow cytometry to assess the percentage of viable CAR-positive cells. The anti-idiotypic antibody binds the binding motif of the Ab11 anti-CD19 binding motif. Thus, the anti-idiotypic antibody binds the anti-CD19 CAR. It is used to measure the transduction efficiency of the anti-CD19 CAR. The anti-linker antibody is used to measure transduction efficiency of the anti-CD20 CAR. Controls comprised non-transduced cells (NTD), cells transduced with a retrovirus comprising a control anti-CD19 binding agent, and cells transduced with control anti-CD20/anti-CD19 bispecific CARs (Ab13/Ab14 bispecific; Ab11/Ab12 bispecific).

TABLE 17A

Transduction efficiency of anti-CD20 monovalent CARs

| binding motif # | Transduction Efficiency (% CD20 CAR+) |
|---|---|
| Ab3 | 65.6 |
| Ab5 | 60.9 |
| Ab6 | 70.7 |
| Ab10 | 51.1 |
| Ab7 | 52.8 |
| Ab8 | 40.6 |
| Ab9 | 33 |
| Ab1 | 44.4 |
| Ab4 | 62.6 |
| Ab2 | 35.8 |
| NTD | 0.25 |
| Ab11 | 47.8 |
| Ab12 | 60.7 |

TABLE 17B

Transduction Efficiency of anti-CD20/anti-CD19 Bicistronic CARs

| Bic-binding motif # | Anti-CD20 binding motif | Transduction Efficiency (%) | |
|---|---|---|---|
| | | % CD19 CAR+ | % CD20 CAR+ |
| Bic-2 | Ab3 | 52.72 | 46.42 |
| Bic-8 | Ab8 | 50.2 | 45.57 |
| Bic-9 | Ab9 | 44.72 | 41.36 |
| Bic-14 | Ab4 | 40.28 | 37.04 |
| NTD | N/A | 0.56 | 0.09 |
| Ab11 | N/A | 59.52 | 69.3 |
| Ab13/Ab14 bispecific | N/A | 56.77 | 60.99 |
| Ab11/Ab12 bispecific | N/A | 47.54 | 49.33 |

Example 4

The present Example provides, among other things, an exemplary method of co-culturing CAR-T cells with cells expressing CAR-T target antigens. To facilitate tracking of T cells in culture, CAR-T cells were labeled with Cell-Trace™ Violet (CTV) reagent according to the manufacturer's instructions and subsequently washed with R-10% media. To facilitate tracking of cells expressing CAR-T target antigens ("target cells"), target cells were engineered to express luciferase. Luciferase-expressing target cells comprised Nalm6 and Raji, both of which expresses both the CD19 and CD20 antigens. In addition, Nalm6 and Raji cells not expressing CD19 or CD20 (knockout cells, or KO) were prepared. These CD19KO and CD20KO cells were clonally selected from Nalm6 and Raji parental cells and express CD20 but not CD19, or CD19 but not CD20, respectively. The CD19KO and CD20KO strains were generated and used as controls to functionally assess antigen binding of each CAR of cells expressing bicistronic anti-CD20/anti-CD19 CAR.

Luciferase-expressing target cells were plated together with CTV labeled CAR-T cells at various ratios in R-10% media (Day 0 of co-culture). The ratio may be referred to as the ratio of effector (CAR-T) cells to target cells (effector: target or E:T). To plate cells at desired ratios, CAR-T cells were serially diluted 2 to 3-fold while the number of target cells per well was held constant at 25,000 cells. Co-cultures were incubated at 37° C. for either 16 hours (h) or 4 days and functional assessments were performed as described below.

Example 5

In this example, T cells were co-cultured with target cells as described in Example 4. T-cell mediated cytotoxicity was measured as a function of the reduction in target luciferase signal in co-culture wells compared to the signal emitted by target cells plated alone. On Day 4 after co-culture initiation, D-luciferin substrate was added to the co-culture wells at a final concentration of 0.14 mg/mL and plates were incubated at 37° C. in the dark for 10 minutes. Luminescent signal was read immediately after in a VarioSkan™ LUX or VarioSkan® Flash multimode microplate reader. T cell-mediated cytotoxicity was calculated as follows: % Cytotoxicity=[1−luciferase signal of (sample of interest/target alone control)]*100.

Controls comprised non-transduced (NTD) T cells (i.e., T cells not expressing a CAR) as a negative control, cells transduced with a retrovirus comprising a control anti-CD19 binding agent, cells transduced with a control anti-CD20 binding agent, cells transduced with control anti-CD20/anti-CD19 bispecific CARs (Ab13/Ab14 bispecific; Ab15/Ab16 bispecific).

TABLE 18

Percent cytotoxicity of anti-CD20 CAR-T in co-culture after 4 days (Nalm6 wild type cells)

| binding motif # | Ab # | 3 to 1 | | | 1 to 1 | | | 1 to 3 | | |
|---|---|---|---|---|---|---|---|---|---|---|
| 2 | Ab3 | 92 | 91 | 92 | 72 | 73 | 77 | 64 | 62 | 53 |
| 3 | Ab5 | 97 | 96 | 97 | 65 | 74 | 77 | 68 | 67 | 60 |
| 5 | Ab6 | 12 | 21 | 23 | −11 | −10 | −13 | −12 | −20 | −22 |
| 6 | Ab10 | 37 | 46 | 55 | 11 | 4 | 6 | −4 | −8 | −8 |
| 7 | Ab7 | 98 | 98 | 98 | 89 | 91 | 90 | 79 | 76 | 75 |
| 8 | Ab8 | 99 | 99 | 99 | 86 | 91 | 93 | 89 | 86 | 90 |
| 9 | Ab9 | 70 | 68 | 66 | 71 | 72 | 72 | 91 | 90 | 92 |
| 10 | Ab1 | 23 | 23 | 27 | 7 | 4 | 5 | −8 | −6 | −17 |
| 14 | Ab4 | 100 | 100 | 100 | 52 | 70 | 68 | 65 | 70 | 70 |
| 16 | Ab2 | 22 | 20 | 27 | −13 | −7 | −13 | −20 | −23 | −30 |
| NTD | N/A | 17 | 20 | 24 | −7 | 0 | 4 | −4 | −2 | −18 |
| Ab11 | N/A | 100 | 100 | 100 | 93 | 95 | 96 | 96 | 94 | 96 |
| Ab12 | N/A | 100 | 100 | 100 | 82 | 90 | 88 | 83 | 86 | 83 |

| binding motif # | Ab # | 1 to 9 | | | 1 to 27 | | |
|---|---|---|---|---|---|---|---|
| 2 | Ab3 | 19 | 21 | 20 | 13 | 4 | 2 |
| 3 | Ab5 | 21 | 18 | 22 | 21 | 12 | 7 |
| 5 | Ab6 | −8 | −12 | −3 | −9 | −21 | −21 |
| 6 | Ab10 | −7 | −8 | −1 | −2 | −15 | −18 |
| 7 | Ab7 | 32 | 34 | 40 | 28 | 24 | 21 |
| 8 | Ab8 | 66 | 63 | 59 | 63 | 58 | 59 |
| 9 | Ab9 | 88 | 84 | 78 | 99 | 100 | 99 |
| 10 | Ab1 | −16 | −9 | 3 | −8 | 3 | −9 |
| 14 | Ab4 | 36 | 37 | 40 | 65 | 64 | 59 |
| 16 | Ab2 | −9 | −8 | 0 | −18 | −4 | −9 |
| NTD | N/A | 0 | −2 | 1 | −4 | 1 | −3 |
| Ab11 | N/A | 73 | 65 | 68 | 84 | 79 | 76 |
| Ab12 | N/A | 45 | 43 | 41 | 58 | 62 | 56 |

TABLE 19

Percent cytotoxicity of anti-CD20 CAR-T in co-culture after 4 days (Raji wild type cells)

| binding motif # | Ab # | 3 to 1 | | | 1 to 1 | | | 1 to 3 | | |
|---|---|---|---|---|---|---|---|---|---|---|
| 2 | Ab3 | 100 | 100 | 100 | 61 | 75 | 82 | 58 | 53 | 50 |
| 3 | Ab5 | 100 | 100 | 100 | 61 | 55 | 59 | 55 | 60 | 57 |
| 5 | Ab6 | 33 | 40 | 46 | 5 | 2 | 5 | −7 | −9 | −8 |
| 6 | Ab10 | 99 | 99 | 99 | 57 | 62 | 71 | 36 | 34 | 30 |
| 7 | Ab7 | 100 | 100 | 100 | 65 | 70 | 78 | 55 | 44 | 43 |
| 8 | Ab8 | 100 | 100 | 100 | 70 | 68 | 57 | 67 | 62 | 65 |
| 9 | Ab9 | 100 | 100 | 100 | 63 | 60 | 63 | 73 | 72 | 61 |
| 10 | Ab1 | 18 | 17 | 23 | −15 | −28 | −25 | −24 | −12 | −10 |
| 14 | Ab4 | 100 | 100 | 100 | 17 | −1 | 5 | 31 | 36 | 31 |

TABLE 19-continued

Percent cytotoxicity of anti-CD20 CAR-T in co-culture after 4 days (Raji wild type cells)

| 16 | Ab2 | 60 | 63 | 69 | 2 | −6 | −6 | −6 | −2 | −8 |
| NTD | N/A | 29 | 24 | 27 | −8 | 4 | 5 | 11 | 18 | 3 |
| Ab11 | N/A | 100 | 100 | 100 | 47 | 42 | 43 | 61 | 64 | 58 |
| Ab12 | N/A | 100 | 100 | 100 | 40 | 30 | 27 | 47 | 52 | 40 |

| binding motif # | Ab # | | 1 to 9 | | | 1 to 27 | |
|---|---|---|---|---|---|---|---|
| 2 | Ab3 | 15 | 16 | 29 | 10 | 6 | 0 |
| 3 | Ab5 | 12 | 14 | 28 | 10 | 4 | −6 |
| 5 | Ab6 | 2 | 2 | 8 | −16 | −15 | −29 |
| 6 | Ab10 | 9 | 7 | 21 | 2 | −3 | −16 |
| 7 | Ab7 | 9 | 21 | 32 | 6 | 7 | 0 |
| 8 | Ab8 | 40 | 30 | 40 | 39 | 30 | 24 |
| 9 | Ab9 | 33 | 37 | 55 | 37 | 33 | 21 |
| 10 | Ab1 | 0 | −1 | 7 | −13 | −10 | 1 |
| 14 | Ab4 | 6 | 19 | 28 | 24 | 35 | 26 |
| 16 | Ab2 | 15 | 13 | 12 | 11 | 7 | 2 |
| NTD | N/A | 9 | 16 | 13 | 0 | 12 | 7 |
| Ab11 | N/A | 10 | 18 | 29 | 40 | 40 | 31 |
| Ab12 | N/A | 12 | 22 | 29 | 25 | 26 | 15 |

TABLE 20

Percent cytotoxicity of anti-CD20/anti-CD19 bicistronic CAR-T in co-culture after 4 days (Nalm6 wild type cells)

| Bic-binding motif # | Ab # | Nalm6 WT Cells at Various E:T Ratios | | | | | |
|---|---|---|---|---|---|---|---|
| | | 3 to 1 | | 1 to 1 | | 1 to 3 | |
| Bic-2 | Ab3 | 100.11 | 100.05 | 100.08 | 100.02 | 99.54 | 98.84 |
| Bic-8 | Ab8 | 100.2 | 100.18 | 100.19 | 100.13 | 100.06 | 99.54 |
| Bic-9 | Ab9 | 100.21 | 100.19 | 100.19 | 100.17 | 99.45 | 96.37 |
| Bic-14 | Ab4 | 100.21 | 100.18 | 100.17 | 100.13 | 99.86 | 99.69 |
| NTD | N/A | 8.92 | −12.24 | −17.23 | −29.28 | −17.13 | −30.68 |
| Ab11 | N/A | 100.21 | 100.17 | 100.19 | 100.16 | 99.79 | 99.01 |
| Ab13/Ab14 bispecific | N/A | 100.17 | 100.06 | 99.91 | 99.48 | 93.02 | 83.24 |
| Ab15/Ab16 bispecific | N/A | 100.05 | 100.06 | 99.89 | 99.89 | 98.89 | 96.03 |

| Bic-binding motif # | Ab # | 1 to 9 | | 1 to 27 | | 1 to 81 | |
|---|---|---|---|---|---|---|---|
| Bic-2 | Ab3 | 77.98 | 72.64 | 46.65 | 33.58 | 20.07 | 9.87 |
| Bic-8 | Ab8 | 97.6 | 87.64 | 67.03 | 51.79 | 28.36 | 12.92 |
| Bic-9 | Ab9 | 91.03 | 77.15 | 53.63 | 32.1 | 21.94 | 2.87 |
| Bic-14 | Ab4 | 99.5 | 99.49 | 84.68 | 76.42 | 48.83 | 38.37 |
| NTD | N/A | −10.7 | −19.68 | −3.76 | −11.49 | 0.02 | −8.9 |
| Ab11 | N/A | 89.83 | 87.75 | 55.83 | 43.85 | 22.23 | 0.48 |
| Ab13/Ab14 bispecific | N/A | 77.28 | 50.19 | 22.73 | 11.85 | 11.58 | −2.9 |
| Ab15/Ab16 bispecific | N/A | 66.63 | 40.98 | 25.75 | 10.27 | 5.66 | −9.98 |

TABLE 21

Percent cytotoxicity of anti-CD20/anti-CD19 bicistronic CAR-T in co-culture after 4 days (Raji wild type cells)

| Bic-binding motif # | Ab # | Raji WT Cells at Various E:T Ratios | | | | | |
|---|---|---|---|---|---|---|---|
| | | 3 to 1 | | 1 to 1 | | 1 to 3 | |
| Bic-2 | Ab3 | 99.96 | 100.01 | 88.29 | 85.71 | 53.5 | 42.14 |
| Bic-8 | Ab8 | 100.02 | 100.05 | 70.5 | 74.72 | 53.41 | 56.52 |
| Bic-9 | Ab9 | 100.06 | 100.06 | 77.3 | 64.45 | 27.42 | 43.62 |
| Bic-14 | Ab4 | 100.09 | 100.11 | 99.58 | 99.47 | 78.71 | 90.26 |
| NTD | N/A | | 14.29 | | 7.61 | | −20.48 |
| Ab11 | N/A | 100.1 | 100.11 | 96.49 | 98.25 | 71.1 | 70.95 |
| Ab13/Ab14 bispecific | N/A | 99.96 | 100.07 | 96.49 | 97.86 | 33.42 | 34.31 |
| Ab15/Ab16 bispecific | N/A | 99.6 | 99.08 | 85.33 | 89.26 | 29.88 | 32.49 |

TABLE 21-continued

Percent cytotoxicity of anti-CD20/anti-CD19 bicistronic CAR-T in co-culture
after 4 days (Raji wild type cells)

| Bic-binding motif # | Ab # | 1 to 9 | | 1 to 27 | | 1 to 81 | |
|---|---|---|---|---|---|---|---|
| Bic-2 | Ab3 | 24.84 | 34.73 | −14.98 | −2.59 | −25.65 | 3.89 |
| Bic-8 | Ab8 | 20.34 | 8.78 | −1.02 | 4.33 | −0.83 | 7.66 |
| Bic-9 | Ab9 | 18.64 | 18.79 | −6.64 | 1.03 | −11.66 | −5.01 |
| Bic-14 | Ab4 | 40.22 | 30.49 | 14.88 | 15.82 | −0.97 | 4.59 |
| NTD | N/A | | −6.05 | | −4.56 | | −8.23 |
| Ab11 | N/A | 23.88 | 14.55 | 11.65 | 5.89 | −8.43 | −0.33 |
| Ab13/Ab14 bispecific | N/A | 10.08 | 30.72 | 12.69 | 10.41 | −7.6 | −7.03 |
| Ab15/Ab16 bispecific | N/A | 5.83 | 9.17 | −8.37 | 8.85 | −18.35 | −7.06 |

TABLE 22

Percent cytotoxicity of anti-CD20/anti-CD19 bicistronic CAR-T in co-culture
after 4 days (Nalm6 CD19KO cells)

| Bic-binding motif # | Ab # | Nalm6 CD19KO Cells at Various E:T Ratios | | | | | |
|---|---|---|---|---|---|---|---|
| | | 3 to 1 | | 1 to 1 | | 1 to 3 | |
| Bic-2 | Ab3 | 41.94 | 47.16 | 22.68 | 21.26 | −16.73 | −4.21 |
| Bic-8 | Ab8 | 43.75 | 40.8 | 16.79 | 1.89 | −22.77 | −11.37 |
| Bic-9 | Ab9 | 43.71 | 39.92 | 0.98 | −4.54 | −17.33 | −20.52 |
| Bic-14 | Ab4 | 75.1 | 74.88 | 39.07 | 26.69 | 10.6 | 31.47 |
| NTD | N/A | −16.73 | −5.35 | −31.94 | −30.48 | −23.75 | −36.72 |
| Ab11 | N/A | 31.93 | 36.32 | −8.57 | −7.77 | −26.58 | −23.61 |
| Ab13/Ab14 bispecific | N/A | 81.71 | 85.04 | 72.06 | 51.9 | 39.52 | 38.16 |
| Ab15/Ab16 bispecific | N/A | 67.95 | 73.67 | 47.26 | 54.21 | 20 | 32.61 |

| Bic-binding motif # | Ab # | 1 to 9 | | 1 to 27 | | 1 to 81 | |
|---|---|---|---|---|---|---|---|
| Bic-2 | Ab3 | −22.58 | −8.65 | −26.2 | −22.17 | −11.82 | −18.02 |
| Bic-8 | Ab8 | −28.81 | −21.81 | −34.06 | −28.68 | −29.45 | −20.23 |
| Bic-9 | Ab9 | −26.39 | −22.98 | −41.15 | −32.2 | −34.02 | −29.96 |
| Bic-14 | Ab4 | 2.6 | 4.87 | −12.92 | −12.22 | −26.69 | −10.49 |
| NTD | N/A | −27.18 | −14.79 | −15.71 | −22.76 | −15.37 | −17.73 |
| Ab11 | N/A | −30.02 | −24.23 | −37.34 | −25.77 | −28.09 | −15.96 |
| Ab13/Ab14 bispecific | N/A | 7.05 | 7.22 | −16.35 | −23.2 | −25.86 | −25.63 |
| Ab15/Ab16 bispecific | N/A | 9.13 | −6.85 | −22.84 | −15.85 | −33.56 | −18.83 |

TABLE 23

Percent cytotoxicity of anti-CD20/anti-CD19 bicistronic CAR-T in co-culture
after 4 days (Nalm6 CD20KO cells)

| Bic-binding motif # | Ab # | Nalm6 CD20KO Cells at Various E:T Ratios | | | | | |
|---|---|---|---|---|---|---|---|
| | | 3 to 1 | | 1 to 1 | | 1 to 3 | |
| Bic-2 | Ab3 | 100.01 | 100.06 | 100.02 | 100.05 | 97.34 | 97.11 |
| Bic-8 | Ab8 | 100.14 | 100.17 | 100 | 100.12 | 95.96 | 94.9 |
| Bic-9 | Ab9 | 100.15 | 100.19 | 100.13 | 100.13 | 84.99 | 81.09 |
| Bic-14 | Ab4 | 100.15 | 100.2 | 100.11 | 100.13 | 99.31 | 99.01 |
| NTD | N/A | 13.47 | 20.49 | −5.54 | 4.54 | −11.02 | −3.62 |
| Ab11 | N/A | 100.14 | 100.15 | 100.11 | 100.16 | 89.94 | 90.48 |
| Ab13/Ab14 bispecific | N/A | 100.13 | 100.12 | 99.25 | 99.19 | 72.92 | 79.13 |
| Ab15/Ab16 bispecific | N/A | 100.01 | 100.06 | 99.54 | 99.63 | 90.53 | 87.4 |

| Bic-binding motif # | Ab # | 1 to 9 | | 1 to 27 | | 1 to 81 | |
|---|---|---|---|---|---|---|---|
| Bic-2 | Ab3 | 75.37 | 74.98 | 30.97 | 14.79 | 3.49 | 19.71 |
| Bic-8 | Ab8 | 59.25 | 71.18 | 16.46 | 24.12 | 3.67 | 9.64 |
| Bic-9 | Ab9 | 43.28 | 48.23 | 11.87 | 13.08 | −0.46 | 5.06 |
| Bic-14 | Ab4 | 96.4 | 96.13 | 58.68 | 58.6 | 17.97 | 20.79 |
| NTD | N/A | −6.55 | 2.96 | −3.3 | 2.3 | 8.61 | 11 |
| Ab11 | N/A | 82.02 | 74.55 | 12.37 | 7.52 | −8.48 | −1.93 |
| Ab13/Ab14 bispecific | N/A | 38.53 | 30.15 | −5.74 | 1.34 | −18.63 | −18.22 |
| Ab15/Ab16 bispecific | N/A | 34.92 | 32.63 | 0.2 | 9.2 | −5.64 | 1.78 |

TABLE 24

Percent cytotoxicity of anti-CD20/anti-CD19 bicistronic CAR-T in co-culture after 4 days (Raji CD19KO cells)

| Bic-binding motif # | Ab # | Raji CD19KO Cells at Various E:T Ratios | | | | | |
|---|---|---|---|---|---|---|---|
| | | 3 to 1 | | 1 to 1 | | 1 to 3 | |
| Bic-2 | Ab3 | 100.02 | 100.1 | 91.85 | 89.69 | 55.92 | 52.39 |
| Bic-8 | Ab8 | 100.14 | 100.16 | 68.63 | 67.49 | 57.76 | 55.82 |
| Bic-9 | Ab9 | 100.09 | 100.16 | 91.11 | 83.72 | 33.32 | 45.71 |
| Bic-14 | Ab4 | 100.03 | 100.05 | 97.97 | 97.47 | 64.86 | 69.55 |
| NTD | N/A | | 40.71 | | 15.06 | | 3.97 |
| Ab11 | N/A | 33.35 | 27.24 | 12.88 | 16.32 | −8.36 | 3.73 |
| Ab13/Ab14 bispecific | N/A | 100.03 | 100.01 | 76.44 | 82.17 | 56.77 | 55.08 |
| Ab15/Ab16 bispecific | N/A | 99.84 | 99.92 | 92.45 | 90.15 | 42.9 | 52.01 |

| Bic-binding motif # | Ab # | 1 to 9 | | 1 to 27 | | 1 to 81 | |
|---|---|---|---|---|---|---|---|
| Bic-2 | Ab3 | 24.24 | 44.1 | −3.13 | 21.88 | −7.78 | 15.73 |
| Bic-8 | Ab8 | 30.49 | 32.83 | 23.56 | 33.43 | 6.7 | 19.54 |
| Bic-9 | Ab9 | 20.8 | 32.03 | 12.07 | 17.72 | −4.15 | 14.19 |
| Bic-14 | Ab4 | 47.46 | 54.56 | 33.42 | 36.33 | 9.45 | 22.34 |
| NTD | N/A | | 6.28 | | −1.56 | | −2.01 |
| Ab11 | N/A | −15.98 | 0.93 | −6.53 | −6.94 | −3.47 | −2.64 |
| Ab13/Ab14 bispecific | N/A | 26.72 | 35.95 | 11.49 | 25.38 | 20.53 | 19.5 |
| Ab15/Ab16 bispecific | N/A | 33.11 | 35.35 | 12.34 | 22.23 | −0.75 | 5.69 |

TABLE 25

Percent cytotoxicity of anti-CD20/anti-CD19 bicistronic CAR-T in co-culture after 4 days (Raji CD20KO cells)

| Bic-binding motif # | Ab # | Raji CD20KO Cells at Various E:T Ratios | | | | | |
|---|---|---|---|---|---|---|---|
| | | 3 to 1 | | 1 to 1 | | 1 to 3 | |
| Bic-2 | Ab3 | 100.04 | 100.1 | 95 | 90.48 | 67.63 | 74.09 |
| Bic-8 | Ab8 | 100.15 | 100.18 | 84.19 | 84.25 | 81.09 | 80.16 |
| Bic-9 | Ab9 | 100.19 | 100.18 | 97.38 | 93.04 | 63.87 | 58.26 |
| Bic-14 | Ab4 | 100.18 | 100.19 | 98.61 | 97.05 | 85.53 | 82.29 |
| NTD | N/A | | 56.92 | | 28.9 | | 16.55 |
| Ab11 | N/A | 100.19 | 100.16 | 99.93 | 99.39 | 81.15 | 76.78 |
| Ab13/Ab14 bispecific | N/A | 99.24 | 99.36 | 86.31 | 86.76 | 77.15 | 75.46 |
| Ab15/Ab16 bispecific | N/A | 99.16 | 99.74 | 87.16 | 79.93 | 67.07 | 67.48 |

| Bic-binding motif # | Ab # | 1 to 9 | | 1 to 27 | | 1 to 81 | |
|---|---|---|---|---|---|---|---|
| Bic-2 | Ab3 | 60.58 | 60.16 | 31.83 | 46.37 | 0.15 | 39.97 |
| Bic-8 | Ab8 | 65.44 | 64.02 | 48.52 | 51.56 | 23.53 | 35.21 |
| Bic-9 | Ab9 | 49.76 | 54.83 | 25.93 | 30.53 | 20.54 | 23.32 |
| Bic-14 | Ab4 | 73.45 | 74 | 55.92 | 57.01 | 31.8 | 36.38 |
| NTD | N/A | | 8.06 | | −2.8 | | −5.43 |
| Ab11 | N/A | 60.19 | 62.53 | 47.63 | 39.67 | 10.91 | 15.16 |
| Ab13/Ab14 bispecific | N/A | 58.77 | 52.6 | 32.16 | 39.92 | 15.56 | 20.28 |
| Ab15/Ab16 bispecific | N/A | 49.49 | 54.48 | 18.17 | 19.02 | −3.47 | −3.58 |

Example 6

In this example, T cells were co-cultured with target cells as described in Example 4. After 16h in co-culture, supernatants were collected and analyzed for cytokine levels using the Meso Scale Discovery V-PLEX Proinflammatory Panel 1 human kit according to the manufacturer's instructions. Supernatants from the co-cultures of T-cell products plated at the 1:1 E:T ratio with antigen-expressing target cells were analyzed for levels of interferon gamma (IFN-γ), IL-2, tumor necrosis factor alpha (TNF-α), and IL-10 secretion mediated by antigen engagement. All samples were diluted to be within the range of detection. The level of each cytokine is reported as pg/mL and the lower limit of quantitation and upper limit of quantitation of each assay is reported.

Controls comprised non-transduced (NTD) T cells (i.e., T cells not expressing a CAR) as a negative control, cells transduced with a retrovirus comprising a control anti-CD19 binding agent, cells transduced with a control anti-CD20 binding agent, cells transduced with a control bispecific antigen binding system (Ab13/Ab14 bispecific), and cells transduced with a bispecific antigen binding system (Ab15/Ab16 bispecific).

TABLE 26

Cytokine production (pg/mL) in 16 h co-culture of anti-CD20 CAR-T with Nalm6 wild type cells

| binding motif # | Ab # | Cytokines (pg/mL) Upon Co-culture with Nalm6 WT | | | | | |
|---|---|---|---|---|---|---|---|
| | | IL-10 | | | IL-2 | | |
| 2 | Ab3 | 2.886 | 2.251 | 3.438 | 110.474 | 86.758 | 70.6158 |
| 3 | Ab5 | 4.305 | 4.194 | 3.125 | 163.198 | 174.192 | 167.524 |
| 5 | Ab6 | 0.277 | 0.147 | 0.327 | 1.39082 | 1.08314 | 2.446 |
| 6 | Ab10 | 0.769 | 0.772 | 0.832 | 2.70375 | 6.86764 | 4.13888 |
| 7 | Ab7 | 3.170 | 4.423 | 6.179 | 209.604 | 272.439 | 233.01 |
| 8 | Ab8 | 5.736 | 4.562 | 5.283 | 314.496 | 273.505 | 259.131 |
| 9 | Ab9 | 7.970 | 8.754 | 6.446 | 455.254 | 445.985 | 408.829 |
| 10 | Ab1 | 0.321 | 0.573 | 0.296 | 1.25038 | 2.8819 | 0.3113 |
| 14 | Ab4 | 5.948 | 5.325 | 3.942 | 383.166 | 351.627 | 364.473 |
| 16 | Ab2 | 0.276 | 0.312 | 0.191 | 1.52526 | 1.84837 | 0.5235 |
| NTD | N/A | 0.157 | 0.348 | 0.451 | 4.83766 | 2.43654 | 5.10316 |
| Ab11 | N/A | 19.959 | 13.241 | 16.798 | 860.093 | 843.101 | 690.879 |
| Ab12 | N/A | 7.613 | 6.145 | 5.710 | 750.441 | 802.013 | 704.947 |
| | LLOQ | | 1.360 | | | 1.78 | |
| | ULOQ | | 466.000 | | | 1876 | |

| binding motif # | Ab # | TNF-a | | | IFN-g | | |
|---|---|---|---|---|---|---|---|
| 2 | Ab3 | 87.1829 | 70.8648 | 71.7046 | 5669.7 | 4265.89 | 4974.73 |
| 3 | Ab5 | 154.755 | 143.572 | 142.014 | 9479.79 | 8824.55 | 9192.87 |
| 5 | Ab6 | 1.1906 | 1.2789 | 1.53004 | 67.7508 | 61.6543 | 75.6417 |
| 6 | Ab10 | 5.08074 | 6.14829 | 5.80572 | 172.603 | 188.02 | 229.674 |
| 7 | Ab7 | 112.546 | 143.963 | 137.234 | 5556.7 | 7514.95 | 6939.41 |
| 8 | Ab8 | 249.849 | 201.326 | 194.1 | 12452.8 | 12117.7 | 10956.6 |
| 9 | Ab9 | 263.572 | 286.889 | 267.453 | 12689.3 | 12716.4 | 10847.6 |
| 10 | Ab1 | 2.51653 | 2.46732 | 1.80637 | 134.553 | 103.288 | 90.2425 |
| 14 | Ab4 | 314.402 | 240.486 | 251.363 | 17113.1 | 14123.9 | 13754.6 |
| 16 | Ab2 | 2.05431 | 2.63529 | 2.19805 | 107.334 | 136.239 | 100.073 |
| NTD | N/A | 1.72614 | 1.68826 | 1.3141 | 83.4983 | 106.559 | 77.1905 |
| Ab11 | N/A | 392.426 | 395.229 | 347.665 | 38674.9 | 37969.3 | 32962.3 |
| Ab12 | N/A | 381.969 | 387.54 | 307.418 | 20023.6 | 18118.9 | 15659.7 |
| | LLOQ | | 1.38 | | | 149.4 | |
| | ULOQ | | 496 | | | 18760 | |

TABLE 27

Cytokine production (pg/mL) in 16 h co-culture of anti-CD20 CAR-T with Raji wild type cells

| binding motif # | Ab # | Cytokines (pg/mL) Upon Co-culture with Raji WT | | | | | |
|---|---|---|---|---|---|---|---|
| | | IL-10 | | | IL-2 | | |
| 2 | Ab3 | 4.22791 | 4.06553 | 4.09989 | 1470.48 | 1168.14 | 1572.25 |
| 3 | Ab5 | 4.71127 | 4.54175 | 5.42819 | 1098.24 | 959.202 | 1242.67 |
| 5 | Ab6 | 2.94802 | 3.02925 | 3.27569 | 48.5778 | 46.0853 | 36.4492 |
| 6 | Ab10 | 4.12995 | 6.20356 | 4.34137 | 532.235 | 638.548 | 477.869 |
| 7 | Ab7 | 6.22517 | 4.41875 | 5.68705 | 1632.41 | 1256.81 | 1629.67 |
| 8 | Ab8 | 6.82197 | 5.50928 | 5.61023 | 1406.26 | 1167.16 | 1552.86 |
| 9 | Ab9 | 8.0439 | 6.16812 | 8.28169 | 1493.89 | 1541.38 | 1341.7 |
| 10 | Ab1 | 2.57139 | 2.58163 | 2.76773 | 1.61246 | 1.07776 | 2.95043 |
| 14 | Ab4 | 3.83274 | 4.91531 | 4.91929 | 559.513 | 846.005 | 1004.86 |
| 16 | Ab2 | 4.33862 | 4.97592 | 5.1657 | 44.1423 | 63.8978 | 75.554 |
| NTD | N/A | 3.54859 | 3.26674 | 3.67311 | 4.17588 | 5.40813 | 2.67597 |
| Ab11 | N/A | 8.76434 | 7.89571 | 10.5552 | 562.35 | 531.706 | 574.047 |
| Ab12 | N/A | 5.66881 | 4.89856 | 4.90972 | 1309.6 | 1156.2 | 1335.23 |
| | LLOQ | | 0.600 | | | 17.8 | |
| | ULOQ | | 466.000 | | | 18760 | |

| binding motif # | Ab # | TNF-a | | | IFN-g | | |
|---|---|---|---|---|---|---|---|
| 2 | Ab3 | 355.825 | 330.247 | 415.31 | 34934.1 | 27937.3 | 40433.3 |
| 3 | Ab5 | 299.426 | 287.003 | 372.212 | 35868.4 | 29774.6 | 42922.3 |
| 5 | Ab6 | 49.2653 | 47.2393 | 44.2108 | 1325.8 | 2259.4 | 1672.66 |
| 6 | Ab10 | 230.666 | 295.155 | 213.26 | 17114.2 | 24139.8 | 18852.1 |
| 7 | Ab7 | 385.919 | 272.502 | 371.498 | 30569.3 | 21404.7 | 30464.6 |
| 8 | Ab8 | 400.397 | 322.357 | 409.831 | 30576.4 | 23842.2 | 38718.6 |
| 9 | Ab9 | 379.925 | 424.475 | 338.892 | 34630.1 | 39572.9 | 35143.5 |
| 10 | Abl | 10.2538 | 11.2538 | 10.461 | 64.3593 | 84.505 | 87.5275 |

TABLE 27-continued

Cytokine production (pg/mL) in 16 h co-culture of anti-CD20 CAR-T with Raji wild type cells

| | | | | | | | |
|---|---|---|---|---|---|---|---|
| 14 | Ab4 | 189.652 | 276.922 | 313.618 | 15464.9 | 22870.4 | 26823.3 |
| 16 | Ab2 | 76.1237 | 81.5253 | 92.838 | 1755.37 | 2782.59 | 3461.08 |
| NTD | N/A | 8.11105 | 6.99595 | 7.40474 | 52.2049 | 42.1524 | 51.0898 |
| Ab11 | N/A | 216.851 | 209.783 | 211.514 | 35496.6 | 33980.6 | 32858.6 |
| Ab12 | N/A | 354.528 | 350.431 | 328.904 | 30852.3 | 26033 | 28850.7 |
| | LLOQ | 13.8 | | | 352 | | |
| | ULOQ | 4960 | | | 187600 | | |

TABLE 28

Cytokine production (pg/mL) in 16 h co-culture of anti-CD20/anti-CD19 bicistronic CAR-T with Nalm6 wild type cells

| Bic-binding motif # | Ab # | Nalm6 WT | | | |
|---|---|---|---|---|---|
| | | IL-10 | | IL-2 | |
| Bic-2 | Ab3 | 319.96 | 148.07 | 3841.67 | 997.02 |
| Bic-8 | Ab8 | 340.60 | 198.04 | 4787.34 | 2351.16 |
| Bic-9 | Ab9 | 339.47 | 228.56 | 4472.49 | 3070.04 |
| Bic-14 | Ab4 | 310.71 | 306.43 | 3456.34 | 2075.77 |
| NTD | N/A | 22.11 | 26.07 | 47.13 | 57.14 |
| Ab11 | N/A | 156.72 | 129.75 | 5898.60 | 5164.57 |
| Ab13/Ab14 bispecific | N/A | 175.34 | 137.17 | 466.18 | 462.89 |
| Ab15/Ab16 bispecific | N/A | 220.27 | 184.11 | 914.97 | 609.44 |
| | LLOQ | 13.60 | | 17.80 | |
| | ULOQ | 4660.00 | | 18760.00 | |

| Bic-binding motif # | Ab # | TNF-a | | IFN-g | |
|---|---|---|---|---|---|
| Bic-2 | Ab3 | 1162.13 | 547.11 | 31344.55 | 17704.04 |
| Bic-8 | Ab8 | 1326.76 | 943.35 | 41201.40 | 26645.47 |
| Bic-9 | Ab9 | 1297.88 | 1123.15 | 44205.89 | 30919.65 |
| Bic-14 | Ab4 | 1314.55 | 1092.37 | 41473.90 | 32712.72 |
| NTD | N/A | 15.38 | 17.73 | 127.03 | 310.15 |
| Ab11 | N/A | 1765.65 | 1481.87 | 50877.54 | 46996.98 |
| Ab13/Ab14 bispecific | N/A | 716.26 | 700.12 | 33318.42 | 26294.09 |
| Ab15/Ab16 bispecific | N/A | 845.64 | 801.45 | 44585.96 | 36507.97 |
| | LLOQ | 13.80 | | 1494.00 | |
| | ULOQ | 4960.00 | | 187600.00 | |

TABLE 29

Cytokine production (pg/mL) in 16 h co-culture of anti-CD20/anti-CD19 bicistronic CAR-T with Raji wild type cells

| Bic-binding motif # | Ab # | Raji WT | | | |
|---|---|---|---|---|---|
| | | IL-10 | | IL-2 | |
| Bic-2 | Ab3 | 249.61 | 302.79 | 5716.65 | 6324.53 |
| Bic-8 | Ab8 | 286.93 | 375.44 | 5657.78 | 6398.44 |
| Bic-9 | Ab9 | 199.97 | 364.30 | 5311.75 | 6221.35 |
| Bic-14 | Ab4 | 289.02 | 441.49 | 4524.40 | 5178.06 |
| NTD | N/A | 20.08 | 31.64 | 52.78 | 68.18 |
| Ab11 | N/A | 158.93 | 168.48 | 6913.98 | 6266.77 |
| Ab13/Ab14 bispecific | N/A | 104.07 | 120.62 | 7388.26 | 7908.03 |
| Ab15/Ab16 bispecific | N/A | 152.99 | 196.19 | 6620.35 | 7598.18 |
| | LLOQ | 13.60 | | 17.80 | |
| | ULOQ | 4660.00 | | 18760.00 | |

| Bic-binding motif # | Ab # | TNF-a | | IFN-g | |
|---|---|---|---|---|---|
| Bic-2 | Ab3 | 1276.98 | 1348.49 | 46275.13 | 39485.80 |
| Bic-8 | Ab8 | 1248.22 | 1538.31 | 44611.85 | 52535.86 |

TABLE 29-continued

Cytokine production (pg/mL) in 16 h co-culture of anti-CD20/anti-CD19 bicistronic CAR-T with Raji wild type cells

| | | | | | |
|---|---|---|---|---|---|
| Bic-9 | Ab9 | 1329.21 | 1649.67 | 37559.20 | 49128.37 |
| Bic-14 | Ab4 | 1500.30 | 1815.74 | 50827.49 | 65974.91 |
| NTD | N/A | 24.85 | 31.77 | 132.97 | 290.37 |
| Ab11 | N/A | 1833.09 | 1748.65 | 43391.37 | 47478.31 |
| Ab13/Ab14 bispecific | N/A | 2599.76 | 2726.70 | 84185.42 | 118333.60 |
| Ab15/Ab16 bispecific | N/A | 2270.58 | 2434.51 | 62974.89 | 85048.84 |
| | LLOQ | 13.80 | | 1494.00 | |
| | ULOQ | 4960.00 | | 187600.00 | |

TABLE 30

Cytokine production (pg/mL) in 16 h co-culture of anti-CD20/anti-CD19 bicistonic CAR-T with Nalm6 CD19KO cells

| Bic-binding motif # | Ab # | Nalm6 CD19KO | | | |
|---|---|---|---|---|---|
| | | IL-10 | | IL-2 | |
| Bic-2 | Ab3 | 20.85 | 21.32 | 415.03 | 397.66 |
| Bic-8 | Ab8 | 25.07 | 23.96 | 371.09 | 419.08 |
| Bic-9 | Ab9 | 17.46 | 16.68 | 315.63 | 308.79 |
| Bic-14 | Ab4 | 27.34 | 37.57 | 239.42 | 263.16 |
| NTD | N/A | 12.07 | 12.33 | 13.90 | 5.93 |
| Ab11 | N/A | 11.94 | 10.61 | 7.24 | 8.06 |
| Ab13/Ab14 bispecific | N/A | 22.57 | 25.85 | 1373.50 | 1344.97 |
| Ab11/Ab12 bispecific | N/A | 19.22 | 27.92 | 758.03 | 769.46 |
| | LLOQ | 3.4 | | 4.45 | |
| | ULOQ | 1165 | | 4690 | |

| Bic-binding motif # | Ab # | TNF-a | | IFN-g | |
|---|---|---|---|---|---|
| Bic-2 | Ab3 | 317.89 | 371.73 | 33687.05 | 41534.70 |
| Bic-8 | Ab8 | 414.53 | 293.49 | 33669.96 | 46572.37 |
| Bic-9 | Ab9 | 386.27 | 293.61 | 41476.85 | 32400.90 |
| Bic-14 | Ab4 | 418.64 | 307.18 | 44847.72 | 41189.26 |
| NTD | N/A | 21.43 | 30.02 | 2183.86 | 1360.11 |
| Ab11 | N/A | 33.88 | 28.23 | 1707.39 | 2083.68 |
| Ab13/Ab14 bispecific | N/A | 836.78 | 842.73 | 113383.20 | 130673.40 |
| Ab11/Ab12 bispecific | N/A | 720.37 | 614.86 | 98809.63 | 79846.05 |
| | LLOQ | 17.25 | | 933.75 | |
| | ULOQ | 13700 | | 117250 | |

TABLE 31

Cytokine production (pg/mL) in 16 h co-culture of anti-CD20/anti-CD19 bicistronic CAR-T with Nalm6 CD20KO cells

| Bic-binding | | Nalm6 CD20KO | | | |
|---|---|---|---|---|---|
| motif # | Ab # | IL-10 | | IL-2 | |
| Bic-2 | Ab3 | 12.82183 | 8.967694 | 300.3656 | 255.746 |
| Bic-8 | Ab8 | 3.530049 | 4.734808 | 158.655 | 112.5326 |
| Bic-9 | Ab9 | 13.69715 | 12.26638 | 464.8549 | 435.2715 |
| Bic-14 | Ab4 | 27.21842 | 23.67642 | 238.8009 | 202.8983 |
| NTD | N/A | 3.795072 | 3.924667 | 5.336147 | 10.97881 |
| Ab11 | N/A | 13.97866 | 10.62249 | 170.2153 | 136.2659 |
| Ab13/Ab14 bispecific | N/A | 5.964617 | 6.354307 | 192.2036 | 214.7087 |
| Ab15/Ab16 bispecific | N/A | | 25.07804 | | 389.0046 |
| | LLOQ | 1.36 | | 1.78 | |
| | ULOQ | 466 | | 1876 | |

| Bic-binding motif # | Ab # | TNF-a | | IFN-g | |
|---|---|---|---|---|---|
| Bic-2 | Ab3 | 208.4781 | 184.026 | 25169.65 | 20518.19 |
| Bic-8 | Ab8 | 173.3662 | 143.7201 | 17698.8 | 14222.19 |
| Bic-9 | Ab9 | 302.2407 | 268.2183 | 174.1232 | 143.1469 |
| Bic-14 | Ab4 | 295.3972 | 261.3406 | 46810.13 | 41911.35 |
| NTD | N/A | 7.415782 | 7.415782 | 108.3741 | 3143.67 |
| Ab11 | N/A | 448.6204 | 337.0853 | 81984.54 | 65671.96 |
| Ab13/Ab14 bispecific | N/A | 182.4278 | 144.6086 | 23278.19 | 20362.21 |
| Ab15/Ab16 bispecific | N/A | | 419.7012 | | 81159.51 |
| | LLOQ | 13.8 | | 1494 | |
| | ULOQ | 4960 | | 87600 | |

Example 7

T cells were co-cultured with target cells as described in Example 4. After 16h co-culture, T-cell products plated at the specified E:T ratio with antigen-positive target cells were harvested, stained with a panel of antibody-fluorophores to identify T cells (CD3, CD4, CD8) and 4-1BB, an activation marker, and analyzed by flow cytometry. A fixable viability dye allowed analysis of viable cells. Events were systematically gated on live cells (viability dye-negative), lymphocytes (using forward scatter [FSC]-area by side scatter [SSC]-area plot), single cells (using FSC-area by FSC-height plot), and then T cells (CD3+). T cells were then analyzed for level of activation (ie, percentage of 4-1BB$^+$ cells); the 4-1BB gating threshold was set based on the level expressed by the NTD control T cells.

Controls comprised non-transduced (NTD) T cells (i.e., T cells not expressing a CAR) as a negative control, cells transduced with a retrovirus comprising a control anti-CD19 binding agent, cells transduced with a control anti-CD20 binding agent, cells transduced with a control bispecific antigen binding system (Ab13/Ab14 bispecific), and cells transduced with a bispecific antigen binding system.

TABLE 32

Activation of anti-CD20 CAR-T cells in 16 h co-culture with Nalm6 wild type and Raji wild type cells

| binding | | % 4-1BB Upon 16 h Co-culture with Target Cells | |
|---|---|---|---|
| motif # | Ab # | Nalm6 | Raji |
| 2 | Ab3 | 32.54 | 36.85 |
| 3 | Ab5 | 35.72 | 38.89 |
| 5 | Ab6 | 8.99 | 16.81 |
| 6 | Ab10 | 14.62 | 33.19 |
| 7 | Ab7 | 36.28 | 35.65 |
| 8 | Ab8 | 46.66 | 58.46 |
| 9 | Ab9 | 56.88 | 61.44 |
| 10 | Ab1 | 6.48 | 8.66 |
| 14 | Ab4 | 39.49 | 36.66 |
| 16 | Ab2 | 8.29 | 32.31 |
| NTD | N/A | 5.6 | 6.08 |
| Ab11 | N/A | 57.68 | 45.09 |
| Ab12 | N/A | 50.26 | 40.1 |

TABLE 33

Activation of anti-CD20/anti-CD19 bicistronic CAR-T cells in 16 h co-culture with Nalm6 wild type, Nalm6 CD20KO, and Nalm6 CD19KO cells

| Bic-binding motif # | Ab # | % 4-1BB Upon 16 h Co-culture with Target Cells | | | | | |
|---|---|---|---|---|---|---|---|
| | | Nalm6 WT | | Nalm6 CD19KO | | Nalm6 CD20KO | |
| Bic-2 | Ab3 | 31.93 | 33.75 | 42.84 | 31.46 | 28.57 | 22.82 |
| Bic-8 | Ab8 | 25.23 | 27.71 | 39.2 | 40.04 | 25.57 | 27.1 |
| Bic-9 | Ab9 | 24.35 | 32.54 | 25.95 | 26.99 | 18.87 | 21.66 |

TABLE 33-continued

Activation of anti-CD20/anti-CD19 bicistronic CAR-T cells in 16 h co-culture with
Nalm6 wild type, Nalm6 CD20KO, and Nalm6 CD19KO cells

| | | % 4-1BB Upon 16 h Co-culture with Target Cells | | | | | |
|---|---|---|---|---|---|---|---|
| Bic-binding motif # | Ab # | Nalm6 WT | | Nalm6 CD19KO | | Nalm6 CD20KO | |
| Bic-14 | Ab4 | 28.33 | 27.05 | 27.81 | 28.21 | 18.65 | 22.4 |
| NTD | N/A | 1.31 | 1.51 | 5.01 | 6.1 | 2.66 | 2.23 |
| Ab11 | N/A | 23.63 | 20.6 | 5.39 | 5.58 | 24.33 | 19.05 |
| Ab13/Ab14 bispecific | N/A | 17.56 | 19.25 | 18.85 | 19.06 | 15.22 | 13.31 |
| Ab11/Ab12 bispecific | N/A | 25.89 | 22.71 | 22.24 | 22.93 | 19.82 | 15.46 |

Example 8

T cells were co-cultured with target cells as described in Example 4. The proliferative capacity of the T-cell products was determined by flow cytometric analysis of the cell division-driven dilution of CTV dye compared with NTD control T cells in response to antigen-expressing target cells. On Day 4 after co-culture initiation, T-cell products plated at the 3:1 ET ratio with antigen-expressing target cells were harvested, stained with a panel of antibody-fluorophores (CD3, CD4, CD8) in the presence of a fixable viability dye to identify viable T cells and analyzed by flow cytometry. The percentage of proliferating cells as well as the mean fluorescence intensity (MFI) of CTV signal is reported. The decrease in MFI of CTV is proportional to the number of rounds of cell division the product has undergone (i.e., the lower the CTV MFI, the more proliferation the cell has undergone).

Controls comprised non-transduced (NTD) T cells (i.e., T cells not expressing a CAR) as a negative control, cells transduced with a retrovirus comprising a control anti-CD19 binding agent, cells transduced with a control anti-CD20 binding agent, cells transduced with a control bispecific antigen binding system (Ab13/Ab14 bispecific), and cells transduced with a Ab11/Ab12 bispecific antigen binding system.

TABLE 34

Fluorescence of anti-CD20 CAR-T cells in four day co-culture with Nalm6 wild type and Raji wild type cells

| binding motif # | Ab # | Nalm6 WT CTV MFI | Raji WT CTV MFI |
|---|---|---|---|
| 2 | Ab3 | 4902.56 | 3100.8 |
| 3 | Ab5 | 3426.83 | 2640.14 |
| 5 | Ab6 | 6396.87 | 3041.46 |
| 6 | Ab10 | 5645.62 | 2177.05 |
| 7 | Ab7 | 4698.94 | 2483.31 |
| 8 | Ab8 | 4905.7 | 2068.97 |
| 9 | Ab9 | 5039.64 | 2033.59 |
| 10 | Ab1 | 10316.89 | 5653.56 |
| 14 | Ab4 | 4640.49 | 2200.1 |
| 16 | Ab2 | 9129.9 | 3097.49 |
| NTD | N/A | 7739.37 | 4816.32 |
| Ab11 | N/A | 3548.72 | 2113.72 |
| Ab12 | N/A | 2909.96 | 2498.54 |

TABLE 34

Percent proliferation of anti-CD20 CAR-T cells in four day co-culture with Nalm6 wild type and Raji wild type cells

| binding motif # | Ab # | Nalm6 WT % Proliferation | Raji WT % Proliferation |
|---|---|---|---|
| 2 | Ab3 | 68.77 | 74.95 |
| 3 | Ab5 | 81.21 | 78.35 |
| 5 | Ab6 | 40.43 | 78.68 |
| 6 | Ab10 | 52.31 | 87.53 |
| 7 | Ab7 | 76.23 | 78.48 |
| 8 | Ab8 | 76.6 | 84.79 |
| 9 | Ab9 | 75.91 | 87.42 |
| 10 | Ab1 | 33.94 | 53.61 |
| 14 | Ab4 | 76.1 | 80.6 |
| 16 | Ab2 | 38.16 | 85.05 |
| NTD | N/A | 37.38 | 48.15 |
| Ab11 | N/A | 74.96 | 86.98 |
| Ab12 | N/A | 86.32 | 72.9 |

TABLE 35

Fluorescence of anti-CD20/anti-CD19 bicistronic CAR-T cells in four day co-culture with Nalm6 wild type, Nalm6 CD19KO, Raji wild type, and Raji CD19KO cells

| Bic-binding motif # | Ab # | CellTrace Violet (MFI) | | | |
|---|---|---|---|---|---|
| | | Nalm6 WT | | Nalm6 CD19KO | |
| Bic-2 | Ab3 | 1196.99 | 1191.69 | 1433.19 | 1433.24 |
| Bic-8 | Ab8 | 1266.27 | 1297.78 | 1503.07 | 1486.28 |
| Bic-9 | Ab9 | 1533.09 | 1503.48 | 1747.27 | 1815.87 |
| Bic-14 | Ab4 | 1242.68 | 1241.04 | 1421.57 | 1405.64 |
| NTD | N/A | 2823.57 | 2775.76 | 2269.11 | 2500.3 |
| Ab11 | N/A | 1307.52 | 1273.51 | 2392.63 | 2350.37 |
| Ab13/Ab14 bispecific | N/A | 1434.19 | 1406.81 | 1409.42 | 1614.71 |
| Ab11/Ab12 bispecific | N/A | 1207.67 | 1358.15 | 1319.45 | 1448.75 |

| Bic-binding motif # | Ab # | Raji WT | | Raji CD19KO | |
|---|---|---|---|---|---|
| Bic-2 | Ab3 | 1166.68 | 1277.03 | 1227.25 | 1249.14 |
| Bic-8 | Ab8 | 1286.29 | 1426.14 | 1285.56 | 1271.65 |
| Bic-9 | Ab9 | 1613.51 | 1474.92 | 1453.13 | 1456.33 |
| Bic-14 | Ab4 | 1767.75 | 1820.79 | 1115.55 | 1113.95 |
| NTD | N/A | 2150.62 | 2065.69 | 2050.38 | 2016.25 |
| Ab11 | N/A | 1575.17 | 1438.12 | 2011.85 | 1793.87 |
| Ab13/Ab14 bispecific | N/A | 1330.39 | 1708.95 | 1407.7 | 1628.62 |
| Ab11/Ab12 bispecific | N/A | 1636.56 | 1773.56 | 1347.75 | 1426.61 |

TABLE 36

Percent proliferation of anti-CD20/anti-CD19 bicistronic
CAR-T cells in four day co-culture with Nalm6 wild type,
Nalm6 CD19KO, Raji wild type, and Raji CD19KO cells

| Bic-binding motif # | Ab # | % Proliferation | | | |
|---|---|---|---|---|---|
| | | Nalm6 WT | | Nalm6 CD19KO | |
| Bic-2 | Ab3 | 91.59 | 92.65 | 87.03 | 87.51 |
| Bic-8 | Ab8 | 90.61 | 90.43 | 81.44 | 81.91 |
| Bic-9 | Ab9 | 86.97 | 86.6 | 78.09 | 79.86 |
| Bic-14 | Ab4 | 90.56 | 88.55 | 84.14 | 83.74 |
| NTD | N/A | 32.78 | 35.81 | 55.57 | 50.62 |
| Ab11 | N/A | 90.4 | 90.37 | 43.6 | 46.56 |
| Ab13/Ab14 bispecific | N/A | 87.37 | 86.42 | 89.06 | 80.19 |
| Ab11/Ab12 bispecific | N/A | 91.92 | 89.53 | 89.29 | 86.6 |

| Bic-binding motif # | Ab # | Raji WT | | Raji CD19KO | |
|---|---|---|---|---|---|
| Bic-2 | Ab3 | 92.78 | 89.58 | 92.52 | 92.77 |
| Bic-8 | Ab8 | 84.65 | 87.63 | 88.89 | 90.11 |
| Bic-9 | Ab9 | 85.06 | 77.69 | 87.2 | 87.81 |
| Bic-14 | Ab4 | 83.43 | 88.9 | 91.96 | 91.38 |
| NTD | N/A | 64.5 | 65.09 | 61.81 | 60.57 |
| Ab11 | N/A | 92.01 | 88.46 | 57.51 | 56.55 |
| Ab13/Ab14 bispecific | N/A | 92.56 | 77.42 | 90.38 | 81.8 |
| Ab11/Ab12 bispecific | N/A | 89.16 | 87.23 | 91.48 | 88.6 |

Example 9

The present Example provides data relating to hinges for use in anti-CD20 antigen binding systems. CAR T cells of the present Example comprise a monovalent anti-CD20 CAR. The present Example tests CAR-T constructs against a disseminated luciferase-expressing Raji human B-Cell lymphoma model in NSG mice. Weekly blood samples were monitored for CAR-T persistence. Response was evaluated based on bioluminescence imaging (BLI) and survival endpoints. Whole blood was drawn for analysis at days 7, 13, 20, 27, 34, and 41. BLI was performed on days 5, 12, 19, 26, 33, and 47. Study was terminated on day 55.

CAR-T cells of this study are shown in Table 37 below, each of which CAR-T cell types of Table 37 was administered to six mice. Table 37 provides the experimental conditions or groups referred to in subsequent tables of this Example. All CAR-T cells were administered intravenously (QD×1) at a dose of 2E+07 cells/mL. All mice also received a human IL-2 dosage of 36 μg ((Q12H×2)QD×3). Human IL-2 promotes CAR-T persistence and survival. Constructs of CAR T cells identified as groups 4, 5, and 7-10 of Table 37 comprised a 41BB costimulatory domain. CAR T cells identified as group 6 of Table 37 comprised a CD28 costimulatory domain.

TABLE 37

| 1 | PBS control |
|---|---|
| 2 | Mock CAR-T cells control (non-transduced T cells) |
| 3 | CAR-T cells comprising anti-CD19 control CAR |
| 4 | CAR-T cells comprising anti-CD20 CAR with CD8 hinge (8k) and an anti-CD19 CAR (bicistronic CAR) |
| 5 | CAR-T cells comprising anti-CD20 CAR with IgG4 hinge and an anti-CD19 CAR (bicistronic CAR) |
| 6 | CAR-T cells comprising anti-CD20 CAR with 28T (CD28) hinge and an anti-CD19 CAR (bicistronic CAR) |
| 7 | CAR-T cells comprising anti-CD20 CAR with 28T (CD28) hinge and an anti-CD19 CAR (bicistronic CAR) |
| 8 | CAR-T cells comprising anti-CD20 CAR with G4sx1 linker and an anti-CD19 CAR (bicistronic CAR) |
| 9 | CAR-T cells comprising anti-CD20 CAR with G4sx2 linker and an anti-CD19 CAR (bicistronic CAR) |
| 10 | CAR-T cells comprising anti-CD20 CAR with G4sx3 linker and an anti-CD19 CAR (bicistronic CAR) |

All CAR-T cell treatments were well tolerated by study mice. Within each group, a number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan. Results are shown in Table 38 below, noting that data reflect monitoring through termination of the experiment at day 55.

TABLE 38

| Group # | Treatment Related Weight Change (%) | Treatment Related Deaths (%) | Median Tumor Growth Delay (Days) | Median % T/C (Day 12) | % PR | % CR | % TFS | Increased Life Span % |
|---|---|---|---|---|---|---|---|---|
| 1 | −6.5 | 0 | 0 | 100 | 0 | 0 | 0 | 0.0 |
| 2 | −15.9 | 0 | 0.4 | 73.8 | 0 | 0 | 0 | 0.1 |
| 3 | 5.6 | 0 | >37.3 | 2.5 | 0 | 83 | 83 | >345.5 |
| 4 | −6 | 0 | >37.3 | 2.1 | 0 | 100 | 100 | >345.5 |
| 5 | 5.5 | 0 | >37.3 | 2.4 | 0 | 100 | 83 | >345.5 |
| 6 | −2.7 | 0 | 15.5 | 4.6 | 0 | 0 | 0 | 131.8 |
| 7 | 4 | 0 | >37.3 | 2.4 | 0 | 100 | 33 | >345.5 |
| 8 | 1.3 | 0 | 35.6 | 3.8 | 0 | 33 | 0 | 331.8 |
| 9 | 3 | 0 | 23.3 | 2.3 | 0 | 100 | 0 | 186.4 |
| 10 | −3.1 | 0 | 18.3 | 2.8 | 0 | 67 | 17 | 200.0 |

Example 10

The present Example provides data relating to the antitumor efficacy of CAR-T cells comprising bicistronic CARs comprising an anti-CD19 CAR and an anti-CD20 CAR, the anti-CD20 CARS comprising various anti-CD20 binding motifs and/or hinges.

Bicistronic anti-CD20/anti-CD19 CAR-T cells were tested against disseminated luciferase-expressing Raji CD19KO B cell lymphoma tumors in NSG mice. Weekly blood samples were monitored for CAR-T persistence. Response was evaluated based on bioluminescence imaging (BLI) and survival endpoints. Whole blood was drawn for analysis at days 7, 13, 20, 27, 34, and 41. BLI was performed on days 5, 12, 19, 26, 33, 40, and 48. Study was terminated on day 55. CAR-T cells of this study as shown in rows 5-14 of Table 39 below are bicistronic CAR-T cells comprising an anti-CD20 CAR as indicated in Table 39 and an anti-CD19 CAR (Ab11 CAR comprising a 28T (CD28) hinge and a CD28 costimulatory domain). Table 39 provides the experimental conditions or groups referred to in subsequent tables of this Example. CAR-T cells were administered to six mice (except that four mice received non-transduced T cells (row 2 of Table 39)). All CAR-T cells were administered intravenously (QD×1) at a dose of 1E+07 cells/mL (rows 2-7, 9, 11, and 13) or 4E+06 (rows 8, 10, 12, and 14). All mice also received a human IL-2 dosage of 36 μg ((Q12H×2) QD×3).

TABLE 39

| 1 | PBS control |
| 2 | Mock CAR-T cells control (non-transduced T cells) |

TABLE 39-continued

| 14 | CAR-T cells comprising anti-CD20 CAR comprising binding motif #14 (CD8 hinge (8k), 41BB costimulatory domain) and an anti-CD19 CAR (bicistronic CAR) |

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 40 below, noting that data reflect monitoring through termination of the experiment at day 55.

All CAR-T cell treatments were well tolerated by study mice. All CAR-T cell treatments tested elicited an anti-tumor response. All treatment regimens resulted in median tumor growth delays of >30.2 days and increase in life spans (ILS) of >226.7%. All treatment regimens resulted in median % T/C on Day 19 of 0%, except treatment with non-transduced (NTD) cells (24%).

TABLE 40

| Group # | Treatment Related Weight Change (%) | Treatment Related Deaths (%) | Median Tumor Growth Delay (Days) | Median % T/C (Day 19) | % PR | % CR | % TFS | Increased Life Span (ILS) % |
|---|---|---|---|---|---|---|---|---|
| 1 | −18.0 | 0.0 | 0.0 | 100.0 | 0.0 | 0.0 | 0.0 | 0.0 |
| 2 | −2.1 | 0.0 | >30.2 | 23.8 | 0.0 | 0.0 | 0.0 | >226.7 |
| 3 | −5.2 | 0.0 | >30.2 | 0.0 | 0.0 | 100.0 | 100.0 | >226.7 |
| 4 | 1.1 | 16.7 | >30.2 | 0.0 | 0.0 | 100.0 | 100.0 | >226.7 |
| 5 | −1.0 | 0.0 | >30.2 | 0.0 | 16.7 | 66.7 | 66.7 | >226.7 |
| 6 | 2.0 | 0.0 | >30.2 | 0.0 | 50.0 | 50.0 | 16.7 | >226.7 |
| 7 | −4.4 | 0.0 | >30.2 | 0.0 | 0.0 | 66.7 | 66.7 | >226.7 |
| 8 | −2.4 | 0.0 | >30.2 | 0.0 | 0.0 | 100.0 | 33.3 | >226.7 |
| 9 | −3.0 | 0.0 | >30.2 | 0.0 | 33.3 | 66.7 | 50.0 | >226.7 |
| 10 | 2.5 | 0.0 | >30.2 | 0.0 | 0.0 | 83.3 | 33.0 | >226.7 |
| 11 | −2.7 | 0.0 | >30.2 | 0.0 | 0.0 | 100.0 | 50.0 | >226.7 |
| 12 | 4.6 | 0.0 | >30.2 | 0.0 | 0.0 | 66.7 | 33.3 | >226.7 |
| 13 | 4.0 | 0.0 | >30.2 | 0.0 | 16.7 | 83.3 | 66.7 | >226.7 |
| 14 | 5.4 | 0.0 | >30.2 | 0.0 | 0.0 | 100.0 | 66.7 | >226.7 |

TABLE 39-continued

| 3 | CAR-T cells comprising anti-CD20 control CAR (CD8 hinge (8k), 41BB costimulatory domain) |
| 4 | CAR-T cells comprising anti-CD20 control CAR |
| 5 | CAR-T cells comprising anti-CD20 control CAR (CD8 hinge (8k), 41BB costimulatory domain) and an anti-CD19 CAR |
| 6 | CAR-T cells comprising anti-CD20 CAR comprising binding motif #9 (CD28 hinge, 41BB costimulatory domain) and an anti-CD19 CAR (bicistronic CAR) |
| 7 | CAR-T cells comprising anti-CD20 CAR comprising binding motif #2 (CD8 hinge (8k), 41BB costimulatory domain) and an anti-CD19 CAR (bicistronic CAR) |
| 8 | CAR-T cells comprising anti-CD20 CAR comprising binding motif #2 (CD8 hinge (8k), 41BB costimulatory domain) and an anti-CD19 CAR (bicistronic CAR) |
| 9 | CAR-T cells comprising anti-CD20 CAR comprising binding motif #8 (CD8 hinge (8k), 41BB costimulatory domain) and an anti-CD19 CAR (bicistronic CAR) |
| 10 | CAR-T cells comprising anti-CD20 CAR comprising binding motif #8 (CD8 hinge (8k), 41BB costimulatory domain) and an anti-CD19 CAR (bicistronic CAR) |
| 11 | CAR-T cells comprising anti-CD20 CAR comprising binding motif #9 (CD8 hinge (8k), 41BB costimulatory domain) and an anti-CD19 CAR (bicistronic CAR) |
| 12 | CAR-T cells comprising anti-CD20 CAR comprising binding motif #9 (CD8 hinge (8k), 41BB costimulatory domain) and an anti-CD19 CAR (bicistronic CAR) |
| 13 | CAR-T cells comprising anti-CD20 CAR comprising binding motif #14 (CD8 hinge (8k), 41BB costimulatory domain) and an anti-CD19 CAR (bicistronic CAR) |

Example 11

The present Example provides data relating to the anti-tumor efficacy of CAR-T cells comprising bispecific CARs comprising an anti-CD19 binding motif and an anti-CD20 binding motif. Bispecific anti-CD20/anti-CD19 CAR-T cells were tested against disseminated luciferase-expressing Raji B cell lymphoma tumors in NSG mice. Weekly blood samples were monitored for CAR-T persistence. Response was evaluated based on bioluminescence imaging (BLI) and survival endpoints. Whole blood was drawn for analysis at days 7, 13, 20, 27, 32, and 41. BLI was performed on days 5, 12, 19, 26, 33, 40, and 47. The study was terminated on day 54.

CAR-T cells of this study as shown in rows 4-8 of Table 41 below are bispecific CAR-T cells comprising an anti-CD19 binding motif and an anti-CD20 binding motif, where the anti-CD19 binding motif is Ab11. Table 41 provides the experimental conditions or groups referred to in subsequent tables of this Example. CAR-T cells were administered at a dose, and to a number of mice, shown in Table 41. All CAR-T cells were administered intravenously (QD×1). All mice also received a human IL-2 dosage of 36 μg ((Q12H×2) QD×3).

133

134

TABLE 41

| 1 | PBS control (6 mice) |
|---|---|
| 2 | Mock CAR-T cells control (non-transduced T cells) (1.5E+07 cells; 6 mice) |
| 3 | CAR-T cells comprising anti-CD19 control CAR (1.2E+07 cells; 6 mice) |
| 4 | Monospecific ant-CD19 CAR (1.5E+07 cells; 6 mice) |
| 5 | CAR-T cells comprising anti-CD20/anti-CD19 bispecific CAR comprising an anti-CD20 binding motif #2 (1.5E+07 cells; 5 mice) |
| 6 | CAR-T cells comprising anti-CD20/anti-CD19 bispecific CAR comprising an anti-CD20 binding motif #2 (1.0E+07 cells; 4 mice) |
| 7 | CAR-T cells comprising anti-CD20/anti-CD19 bispecific CAR comprising an anti-CD20 binding motif #8 (7.0E+06 cells; 6 mice) |
| 8 | CAR-T cells comprising anti-CD20/anti-CD19 bispecific CAR comprising an anti-CD20 binding motif #8 (1.5E+07 cells; 6 mice) |

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 42 below. Anti-tumor efficacy was observed.

TABLE 42

| Group # | Treatment Related Weight Change (%) | Treatment Related Deaths (%) | Median Tumor Growth Delay (Days) | Median % T/C (Day 12) | % PR | % CR | % TFS | Increased Life Span (ILS) % |
|---|---|---|---|---|---|---|---|---|
| 1 | -10.2 | 0.0 | 0.0 | 100.0 | 0.0 | 0.0 | 0.0 | 0.0 |
| 2 | -15.7 | 0.0 | 1.3 | 58.7 | 0.0 | 0.0 | 0.0 | 21.7 |
| 3 | -4.1 | 0.0 | 25.5 | 6.0 | 0.0 | 83.3 | 0.0 | 295.7 |
| 4 | -8.8 | 0.0 | 7.2 | 13.2 | 0.0 | 0.0 | 0.0 | 73.9 |
| 5 | -3.5 | 0.0 | 11.7 | 12.2 | 0.0 | 0.0 | 0.0 | 113.0 |
| 6 | 0.2 | 0.0 | 10.4 | 9.6 | 0.0 | 0.0 | 0.0 | 160.9 |
| 7 | 1.9 | 50.0 | >25.5 | 5.4 | 0.0 | 100.0 | 0.0 | 195.7 |
| 8 | 1.9 | 17.0 | 15.0 | 7.1 | 0.0 | 0.0 | 0.0 | 126.1 |

Example 12

The present Example provides data relating to anti-tumor efficacy of (i) CAR-T cells comprising bicistronic CARs comprising an anti-CD19 CAR and an anti-CD20 CAR; and (ii) bispecific CARs comprising an anti-CD19 binding motif and an anti-CD20 binding motif. Bicistronic and bispecific anti-CD20/anti-CD19 CAR-T cells were tested against disseminated luciferase-expressing Raji B cell lymphoma tumors in NSG mice. Weekly blood samples were monitored for CAR-T persistence. Response was evaluated based on bioluminescence imaging (BLI) and survival endpoints. Whole blood was drawn for analysis at days 7, 13, 20, 27, 34, and 40. BLI was performed on days 5, 12, 19, 26, 33, and 40. Study was terminated on day 48.

CAR-T cells of this study as shown in Table 43 below are bicistronic or bispecific CAR-T cells comprising an anti-CD20 binding motif an anti-CD19 binding motif (Ab11). Table 43 provides the experimental conditions or groups referred to in subsequent tables of this Example. CAR-T cells were administered at a dose of 6.0E+06, each of which CAR-T cell types was administered to six mice. All CAR-T cells were administered intravenously (QD×1). All mice also received a human IL-2 dosage of 36 μg ((Q12H×2) QD×3) intraperitoneally.

TABLE 43

| 1 | PBS control |
|---|---|
| 2 | Mock CAR-T cells control (non-transduced T cells) (60.0E+06 cells) |
| 3 | CAR-T cells comprising anti-CD19 control CAR (2.6E+06 cells) |
| 4 | CAR-T cells comprising an anti-CD19 CAR with a linker according to SEQ ID NO: 247 |
| 5 | CAR-T cells comprising an anti-CD19 CAR with a G4S linker |
| 6 | CAR-T cells comprising a bicistronic CAR comprising binding motif #2 |
| 7 | CAR-T cells comprising a bicistronic CAR comprising binding motif #9 |
| 8 | CAR-T cells comprising a bicistronic CAR comprising binding motif #14 |
| 9 | CAR-T cells comprising a bispecific CAR comprising binding motif #2 |
| 10 | CAR-T cells comprising a bispecific CAR comprising binding motif #9 |
| 11 | CAR-T cells comprising a bispecific CAR comprising binding motif #14 |
| 12 | CAR-T cells comprising a control bispecific anti-CD20/anti-CD19 CAR |

TABLE 43-continued

| 13 | CAR-T cells comprising a control bispecific anti-CD20/anti-CD19 CAR |
|---|---|

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 44 below, noting that data reflect monitoring through termination of the experiment at day 48.

All treatments were tolerated. All treatment regimens, excluding non-transduced cells and LG cells, resulted in median tumor growth delays of at least 21 days, increase in life span (ILS) of >223%, median % T/C on Day 12 of approximately 0%, and many resulted partial and/or complete tumor regressions.

TABLE 44

| Group # | Treatment Related Weight Change (%) | Treatment Related Deaths (%) | Median Tumor Growth Delay (Days) | Median % T/C (Day 12) | % PR | % CR | % TFS | Increased Life Span (ILS) % |
|---|---|---|---|---|---|---|---|---|
| 1 | −21.8 | 0.0 | 0.0 | 100.0 | 0.0 | 0.0 | 0.0 | 0.0 |
| 2 | −22.2 | 0.0 | 0.1 | 108.3 | 0.0 | 0.0 | 0.0 | 0.0 |
| 3 | −7 | 0.0 | >28.5 | 0.1 | 50.0 | 33.3 | 0.0 | >223.1 |
| 4 | −6.8 | 0.0 | >28.5 | 0.2 | 33.3 | 66.6 | 50.0 | >223.1 |
| 5 | −4.8 | 0.0 | >28.5 | 0.3 | 67.0 | 33.3 | 0.0 | >223.1 |
| 6 | −5.8 | 0.0 | >28.5 | 0.4 | 16.6 | 66.6 | 0.0 | >223.1 |
| 7 | −5.4 | 0.0 | >28.5 | 0.8 | 50.0 | 16.6 | 0.0 | >223.1 |
| 8 | −3.3 | 0.0 | >28.5 | 0.1 | 33.3 | 66.6 | 0.0 | >223.1 |
| 9 | −5.1 | 0.0 | >28.5 | 0.7 | 16.6 | 0.0 | 0.0 | >223.1 |
| 10 | −4.6 | 0.0 | 25.2 | 0.5 | 0.0 | 0.0 | 0.0 | >223.1 |
| 11 | −4.4 | 0.0 | >28.5 | 0.2 | 16.6 | 33.3 | 0.0 | >223.1 |
| 12 | −6.6 | 0.0 | 3.8 | 26.7 | 0.0 | 0.0 | 0.0 | 61.5 |
| 13 | −3.3 | 0.0 | 20.8 | 3.2 | 16.6 | 0.0 | 0.0 | >223.1 |

Example 13

The present Example provides data relating to the anti-tumor efficacy of CAR-T cells comprising monovalent anti-CD20 CARs. Anti-CD20 CAR-T cells were tested against disseminated luciferase-expressing Raji B cell lymphoma tumors (CD19 WT) in NSG mice. Weekly blood samples were monitored for CAR-T persistence. Response was evaluated based on bioluminescence imaging (BLI) and survival endpoints. BLI was performed on days 5, 12, 21, 28, 33, 40, and 47. Study was terminated on day 55. CAR-T cells of this study as shown in Table 45 below, administered at the dosage and number of mice shown in Table 45. Table 45 provides the experimental conditions or groups referred to in subsequent tables of this Example. All CAR-T cells were administered intravenously (QD×1). All mice received a human IL-2 dosage of 36 µg ((Q12H×2) QD×3).

TABLE 45

1 PBS control (6 mice)
2 Mock CAR-T cells control (non-transduced T cells) (1.5E+07 cells) (6 mice)
3 CAR-T cells comprising anti-CD19 CAR (6.58E+06 cells) + non-transduced T cells (8.39E+06 cells) (5 mice)
4 CAR-T cells comprising anti-CD19 CAR (1.32E+06 cells) + non-transduced T cells (1.37E+07 cells) (6 mice)
5 CAR-T cells comprising anti-CD20 CAR (1.1E+07 cells) + non-transduced T cells (4.1E+06 cells) (5 mice)
6 CAR-T cells comprising anti-CD20 CAR (2.2E+06 cells) + non-transduced T cells (1.3E+07 cells) (5 mice)
7 CAR-T cells comprising anti-CD20 CAR comprising binding motif #8 (1.5E+07 cells) (5 mice)
8 CAR-T cells comprising anti-CD20 CAR comprising binding motif #8 (3.0E+06 cells) (5 mice)
9 CAR-T cells comprising anti-CD20 CAR comprising binding motif #9 (1.1E+07 cells) (5 mice)
10 CAR-T cells comprising anti-CD20 CAR comprising binding motif #9 (1.3E+06 cells) (4 mice)
11 CAR-T cells comprising anti-CD20 CAR comprising binding motif #14 (1.1E+07 cells) + non-transduced T cells (4.0E+06 cells) (6 mice)
12 CAR-T cells comprising anti-CD20 CAR comprising binding motif #14 (2.2E+06 cells) + non-transduced T cells (1.3E+07 cells) (5 mice)

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 46 below.

TABLE 46

| Group # | Treatment Related Weight Change (%) | Increased Life Span (%) | Median % T/C Day 12 | Tumor Growth Delay (days) | % CR | % PR | % TFS |
|---|---|---|---|---|---|---|---|
| 1 | −17.1 | 0.0 | 100.0 | 0.0 | 0.0 | 0.0 | 0.0 |
| 2 | −23.6 | 27.3 | 61.7 | 0.9 | 0.0 | 0.0 | 0.0 |
| 3 | −4.9 | 218.2 | 3.7 | 20.5 | 0.0 | 0.0 | 0.0 |
| 4 | −9.4 | 118.2 | 26.6 | 4.1 | 0.0 | 0.0 | 0.0 |
| 5 | −8.4 | >290.9 | 36.3 | >35.9 | 60.0 | 0.0 | 0.0 |
| 6 | −10.3 | >290.9 | 59.2 | 29.5 | 0.0 | 0.0 | 0.0 |
| 7 | −8.7 | >290.9 | 4.6 | >35.9 | 0.0 | 0.0 | 0.0 |
| 8 | −6.1 | >290.9 | 42.7 | 5.7 | 0.0 | 0.0 | 0.0 |
| 9 | −10.2 | >290.9 | 3.3 | >35.9 | 40.0 | 0.0 | 40.0 |
| 10 | −11.2 | 263.6 | 58.0 | 4.4 | 0.0 | 0.0 | 0.0 |
| 11 | −5.9 | 227.3 | 24.0 | 18.7 | 0.0 | 0.0 | 0.0 |
| 12 | −10.0 | 254.5 | 50.7 | 2.9 | 0.0 | 0.0 | 0.0 |

Example 14

The present Example provides data relating to the anti-tumor efficacy of CAR-T cells comprising bicistronic CARs comprising an anti-CD19 CAR and an anti-CD20 CAR, and to the anti-tumor efficacy of CAR-T cells comprising monovalent anti-CD20 CARs. CAR-T cells were tested against disseminated luciferase-expressing Raji B cell lymphoma tumors in NSG mice. Weekly blood samples were monitored for CAR-T persistence. Response was evaluated based on bioluminescence imaging (BLI) and survival endpoints. BLI was performed on days 5, 12, 19, 26, 33, and 40.

CAR-T cells of this this study are shown in Table 47 below. Table 47 provides the experimental conditions or groups referred to in subsequent tables of this Example. Groups 1-10 comprise only controls and monospecific CAR-T cells, while groups 11-16 comprise bicistronic CAR-T cells. Bicistronic CAR-T cells comprise an anti-CD20 CAR as indicated in Table 39 and an anti-CD19 CAR (Ab11 CAR). Each condition shown in Table 47 comprised 6 mice. All CAR-T cells were administered intravenously (QD×1) at the indicated dose. All mice also received intraperitoneal human IL-2 at a dosage of 36 µg ((Q12H×2) QD×3).

TABLE 47

1 PBS control
2 Mock CAR-T cells control (non-transduced T cells) (9.0E+06 cells)

TABLE 47-continued

| | |
|---|---|
| 3 | Mock CAR-T cells control (non-transduced T cells) (1.4E+07 cells) |
| 4 | CAR-T cells comprising anti-CD19 control CAR comprising an Ab11 binding motif (1.40E+07 cells) |
| 5 | CAR-T cells comprising anti-CD19 control CAR comprising an Ab11 binding motif (7.0E+06 cells) + Non-transduced T cells (2.00E+06 cells) |
| 6 | CAR-T cells comprising anti-CD19 control CAR comprising an Ab11 binding motif (1.40E+06 cells) + Non-transduced T cells (7.60E+06 cells) |
| 7 | CAR-T cells comprising anti-CD20 CAR comprising binding motif #14 (6.80E+06 cells) + Non-transduced T cells (2.20E+06 cells) |
| 8 | CAR-T cells comprising anti-CD20 CAR comprising binding motif #14 (1.40E+06 cells) + Non-transduced T cells (7.60E+06 cells) |
| 9 | CAR-T cells comprising control anti-CD20 CAR (7.0E+06 cells) + Non-transduced T cells (2.00E+06 cells) |
| 10 | CAR-T cells comprising control anti-CD20 CAR (1.40E+06 cells) + Non-transduced T cells (7.60E+06 cells) |
| 11 | CAR-T cells comprising anti-CD20 CAR comprising binding motif #14 and an anti-CD19 CAR (bicistronic CAR) (7.50E+06 cells) + Non-transduced T cells (1.40E+06 cells) |
| 12 | CAR-T cells comprising anti-CD20 CAR comprising binding motif #14 and an anti-CD19 CAR (bicistronic CAR) (1.50E+06 cells) + Non-transduced T cells (7.50E+06 cells) |
| 13 | CAR-T cells comprising anti-CD20 CAR control and an anti-CD19 CAR (bicistronic CAR) (8.0E+06 cells) + Non-transduced T cells (9.50E+06 cells) |
| 14 | CAR-T cells comprising anti-CD20 CAR control and an anti-CD19 CAR (bicistronic CAR) (1.60E+06 cells) + Non-transduced T cells (7.40E+06 cells) |
| 15 | CAR-T cells comprising anti-CD20 CAR comprising binding motif #14 and an anti-CD19 CAR (bicistronic CAR) (9.0E+06 cells) |
| 16 | CAR-T cells comprising anti-CD20 CAR comprising binding motif #14 and an anti-CD19 CAR (bicistronic CAR) (1.80E+06 cells) + Non-transduced T cells (7.20E+06 cells) |

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 48 below. All CAR-T cell treatments were well tolerated by study mice.

TABLE 48

| Group # | Treatment Related Weight Change (%) | Treatment Related Death (%) | Increased Life Span (%) | Median ΔT/ΔC Day 12 (%) | Tumor Growth Delay (days) | % CR | % PR | % TFS |
|---|---|---|---|---|---|---|---|---|
| 1 | −16.5 | 0.0 | 0.0 | 100.0 | 0.0 | 0.0 | 0.0 | 0.0 |
| 2 | −23.9 | 0.0 | 28.0 | 67.3 | 0.9 | 0.0 | 0.0 | 0.0 |
| 3 | −23.0 | 0.0 | 28.0 | 84.8 | 0.3 | 0.0 | 0.0 | 0.0 |
| 4 | −10.8 | 0.0 | >188.0 | 4.6 | >28.3 | 33.3 | 0.0 | 0.0 |
| 5 | −2.6 | 0.0 | >188.0 | 5.6 | >28.3 | 0.0 | 0.0 | 0.0 |
| 6 | −4.2 | 0.0 | 164.0 | 6.9 | 20.4 | 0.0 | 0.0 | 0.0 |
| 7 | −9.0 | 0.0 | >188.0 | 4.9 | >28.3 | 16.6 | 0.0 | 16.6 |
| 8 | −4.4 | 0.0 | >188.0 | 9.0 | >28.3 | 0.0 | 0.0 | 0.0 |
| 9 | −9.1 | 0.0 | >188.0 | 4.5 | >28.3 | 0.0 | 0.0 | 0.0 |
| 10 | −0.5 | 0.0 | 188.0 | 9.0 | 24.5 | 0.0 | 0.0 | 0.0 |
| 11 | −7.3 | 0.0 | >188.0 | 4.8 | >28.3 | 0.0 | 0.0 | 0.0 |
| 12 | −2.9 | 0.0 | >188.0 | 7.6 | 24.5 | 0.0 | 0.0 | 0.0 |
| 13 | −4.6 | 0.0 | >188.0 | 4.4 | >28.3 | 0.0 | 0.0 | 0.0 |
| 14 | −0.8 | 0.0 | >188.0 | 7.2 | >28.3 | 0.0 | 0.0 | 0.0 |
| 15 | −6.2 | 0.0 | >188.0 | 5.0 | >28.3 | 0.0 | 0.0 | 0.0 |
| 16 | −4.9 | 0.0 | >188.0 | 5.0 | >28.3 | 0.0 | 0.0 | 0.0 |

Example 15

The present Example provides data relating to the anti-tumor efficacy of CAR-T cells comprising bicistronic CARs comprising an anti-CD19 CAR and an anti-CD20 CAR, and to the anti-tumor efficacy of CAR-T cells comprising monovalent anti-CD20 CARs. CAR-T cells were tested against a luciferase-expressing NALM6 human acute lymphoblastic leukemia model in NSG mice. Blood samples were monitored for CAR-T persistence. Response was evaluated based on bioluminescence imaging (BLI) and survival endpoints. Whole blood was drawn for analysis at days 4, 11, 20, 25, 32, and 39. BLI was performed on days 3, 10, 18, 24, 31, 38, and 45. The study was terminated on day 48.

CAR-T cells of this this study are shown in Table 49 below. Table 49 provides the experimental conditions or groups referred to in subsequent tables of this Example. Groups 1-8 comprise only controls and monospecific CAR-T cells, while groups 9-12 comprise bicistronic CAR-T cells. Bicistronic CAR-T cells comprise an anti-CD20 CAR as indicated in Table 49 and an anti-CD19 CAR (Ab11 CAR). Each condition shown in Table 49 comprised 6 mice. All CAR-T cells were administered intravenously (QD×1) at the indicated dose.

TABLE 49

| | |
|---|---|
| 1 | PBS control |
| 2 | Mock CAR-T cells control (non-transduced T cells) (1.1E+07 cells) |
| 3 | CAR-T cells comprising anti-CD19 control CAR comprising an Ab11 binding motif (9.70E+06 cells) + Non-transduced T cells (8.90E+05 cells) |
| 4 | CAR-T cells comprising anti-CD19 control CAR comprising an Ab11 binding motif (1.90E+06 cells) + Non-transduced T cells (8.70E+06 cells) |
| 5 | CAR-T cells comprising anti-CD20 CAR comprising binding motif #14 (6.50E+06 cells) + Non-transduced T cells (4.10E+06 cells) |
| 6 | CAR-T cells comprising anti-CD20 CAR comprising binding motif #14 (1.30E+06 cells) + Non-transduced T cells (9.30E+06 cells) |
| 7 | CAR-T cells comprising control anti-CD20 CAR (7.00E+06 cells) + Non-transduced T cells (3.60E+06 cells) |

TABLE 49-continued

8 CAR-T cells comprising control anti-CD20 CAR (1.40E+06 cells) +
    Non-transduced T cells (9.20E+06 cells)
9 CAR-T cells comprising anti-CD20 CAR comprising binding
    motif #14 and an anti-CD19 CAR (bicistronic CAR) (1.10E+07 cells)
10 CAR-T cells comprising anti-CD20 CAR comprising binding
    motif #14 and an anti-CD19 CAR (bicistronic CAR)
    (2.10E+06 cells) + Non-transduced T cells (8.50E+06 cells)
11 CAR-T cells comprising anti-CD20 CAR control and an anti-CD19
    CAR (bicistronic CAR) (8.4E+06 cells) + Non-transduced T cells
    (2.30E+06 cells)
12 CAR-T cells comprising anti-CD20 CAR control and an anti-CD19
    CAR (bicistronic CAR) (1.70E+06 cells) + Non-transduced T cells
    (9.00E+06 cells)

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 50 below. All CAR-T cell treatments were tolerated by study mice.

TABLE 50

| Group # | Treatment Related Weight Change (%) | Treatment Related Deaths (%) | Increased Life Span (ILS) (%) | Median Tumor Growth Delay (Days) | Median % T/C (Day 18) | % PR | % CR | % TFS |
|---|---|---|---|---|---|---|---|---|
| 1 | 2.8 | 0.0 | 0.0 | 0.0 | 100.0 | 0.0 | 0.0 | 0.0 |
| 2 | 3.8 | 0.0 | 0.0 | 0.0 | 121.6 | 0.0 | 0.0 | 0.0 |
| 3 | −2.2 | 0.0 | >150.0 | 27.0 | 0.0 | 50.0 | 50.0 | 16.6 |
| 4 | 3.9 | 0.0 | 72.2 | 13.0 | 0.2 | 33.3 | 0.0 | 0.0 |
| 5 | −8.7 | 0.0 | >150.0 | 27.0 | 0.0 | 66.6 | 0.0 | 0.0 |
| 6 | −2.2 | 0.0 | 86.1 | 15.5 | 13.5 | 0.0 | 0.0 | 0.0 |
| 7 | −5.4 | 0.0 | 106.6 | 19.0 | 1.25 | 0 | 0.0 | 0.0 |
| 8 | −2.4 | 0.0 | 97.2 | 17.5 | 39.4 | 0.0 | 0.0 | 0.0 |
| 9 | −2.2 | 0.0 | >150.0 | 27.0 | 0.0 | 83.3 | 16.6 | 16.6 |
| 10 | −2.2 | 0.0 | >150.0 | 27.0 | 0.1 | 100.0 | 0.0 | 0.0 |
| 11 | 6.5 | 0.0 | >150.0 | 27.0 | 0.0 | 100.0 | 0.0 | 0.0 |
| 12 | 10.3 | 0.0 | 111.1 | 20.0 | 0.2 | 16.6 | 0.0 | 0.0 |

Example 16

The present Example provides data relating to sequences for use as components of CARs. Four anti-CD20 binding motifs are tested in combination with 4 hinges (CD8 hinge (8k), truncated CD28 hinge (28T), truncated CD28 hinge with a G4S linker; and IgG4 hinge (14)). All bispecific and bicistronic CARs comprise an Ab11 anti-CD19 binding motif. $CD4^+$ and $CD8^+$ T cells were isolated by positive selection from apheresis material from healthy donors and used to generate anti-CD20 monovalent or anti-CD20/anti-CD19 bicistronic CAR T-cell products. T cells were activated with bound-anti-CD3 and soluble CD28 antibodies and transduced with a lentiviral vector encoding for a CAR construct. As a control, non-transduced (NTD) T cells were generated from the same donor T cells in parallel. On the harvest day (Days 8-10 of manufacture), CAR T-cell products were stained and analyzed by flow cytometry to assess transduction efficiency and used in co-culture assays. Transduction efficiency of T cells with vector encoding monovalent CAR and vector encoding bicistronic CAR were monitored.

To determine the T cell transduction efficiency of vector encoding a monovalent CAR, CAR-T products were stained with a panel of antibodies (anti-CD3, anti-CD4, anti-CD8, and anti-linker) in the presence of a fixable viability dye and analyzed by flow cytometry to assess the percentage of viable CAR-positive cells. The anti-linker antibody is an antibody that binds the linker between the heavy and light chains of the binding motif of the anti-CD20 CAR and is used to measure transduction efficiency. Controls comprised non-transduced cells (NTD), cells transduced with a retrovirus comprising a control anti-CD19 binding agent, and cells transduced with a control anti-CD20 binding agent (Ab12 binding motif).

To determine the T cell transduction efficiency of vector encoding a bicistronic CAR, CAR-T products were stained with a panel of antibodies (comprising anti-CD3, anti-CD4, anti-CD8, anti-idiotypic, and anti-linker) in the presence of a fixable viability dye and analyzed by flow cytometry to assess the percentage of viable CAR-positive cells. The anti-idiotypic antibody binds the binding motif of the Ab11 anti-CD19 binding motif. Thus, the anti-idiotypic antibody binds the anti-CD19 CAR. It is used to measure the transduction efficiency of the anti-CD19 CAR. The anti-linker antibody is used to measure transduction efficiency of the anti-CD20 CAR. Controls comprised non-transduced cells (NTD), cells transduced with a retrovirus comprising a control anti-CD19 binding agent, and cells transduced with control anti-CD20/anti-CD19 bispecific CARs (Ab13/Ab14 bispecific; Ab11/Ab12 bispecific).

To facilitate tracking of T cells in culture, CAR-T cells were labeled with CellTrace™ Violet (CTV) reagent according to the manufacturer's instructions and subsequently washed with R-10% media. To facilitate tracking of cells expressing CAR-T target antigens ("target cells"), target cells were engineered to express luciferase. Luciferase-expressing target cells comprised Nalm6 and Raji, both of which expresses both the CD19 and CD20 antigens. In addition, Nalm6 and Raji cells not expressing CD19 or CD20 (knockout cells, or KO) were prepared. These CD19KO and CD20KO cells were clonally selected from Nalm6 and Raji parental cells and express CD20 but not CD19, or CD19 but not CD20, respectively. The CD19KO and CD20KO strains were generated and used as controls to functionally assess antigen binding of each CAR of cells expressing bicistronic anti-CD20/anti-CD19 CAR.

Luciferase-expressing target cells were plated together with CTV labeled CAR-T cells at various ratios in R-10% media (Day 0 of co-culture). The ratio may be referred to as the ratio of effector (CAR-T) cells to target cells (effector: target or E:T). To plate cells at desired ratios, CAR-T cells were serially diluted 2 to 3-fold while the number of target cells per well was held constant at 25,000 cells. Co-cultures were incubated at 37° C. for either 16 hours (h) or 4 days and functional assessments were performed as described below.

T-cell mediated cytotoxicity was measured as a function of the reduction in target luciferase signal in co-culture wells compared to the signal emitted by target cells plated alone. On Day 4 after co-culture initiation, D-luciferin substrate was added to the co-culture wells at a final concentration of 0.14 mg/mL and plates were incubated at 37° C. in the dark for 10 minutes. Luminescent signal was read immediately after in a VarioSkan™ LUX or VarioSkan® Flash multi-mode microplate reader. T cell-mediated cytotoxicity was calculated as follows: % Cytotoxicity=[1−luciferase signal of (sample of interest/target alone control)]*100.

Cytokine production was measured after 16h in co-culture, at which time supernatants were collected and analyzed for cytokine levels using the Meso Scale Discovery V-PLEX Proinflammatory Panel 1 human kit according to the manufacturer's instructions. Supernatants from the co-cultures of T-cell products plated at the 1:1 E:T ratio with antigen-expressing target cells were analyzed for levels of interferon gamma (IFN-γ), IL-2, tumor necrosis factor alpha (TNF-α), and IL-10 secretion mediated by antigen engagement. All samples were diluted to be within the range of detection. The level of each cytokine is reported as pg/mL and the lower limit of quantitation and upper limit of quantitation of each assay is reported.

To determine T cell activation after 16h co-culture, T-cell products were plated at the specified E:T ratio with antigen-positive target cells were harvested, stained with a panel of antibody-fluorophores to identify T cells (CD3, CD4, CD8) and 4-1BB, an activation marker, and analyzed by flow cytometry. A fixable viability dye allowed analysis of viable cells. Events were systematically gated on live cells (viability dye-negative), lymphocytes (using forward scatter [FSC]-area by side scatter [SSC]-area plot), single cells (using FSC-area by FSC-height plot), and then T cells (CD3$^+$). T cells were then analyzed for level of activation (ie, percentage of 4-1BB$^+$ cells); the 4-1BB gating threshold was set based on the level expressed by the NTD control T cells.

The proliferative capacity of the T-cell products was determined by flow cytometric analysis of the cell division-driven dilution of CTV dye compared with NTD control T cells in response to antigen-expressing target cells. On Day 4 after co-culture initiation, T-cell products plated at the 3:1 E:T ratio with antigen-expressing target cells were harvested, stained with a panel of antibody-fluorophores (CD3, CD4, CD8) in the presence of a fixable viability dye to identify viable T cells and analyzed by flow cytometry. The percentage of proliferating cells as well as the mean fluorescence intensity (MFI) of CTV signal is reported. The decrease in MFI of CTV is proportional to the number of rounds of cell division the product has undergone.

CAR-T cells used in this Example comprised the CARs identified in Table 51 below. Table 51 provides the experimental conditions or groups referred to in subsequent tables of this Example. Transduction efficiency is shown in Table 52. Day 4 cytotoxicity in Nalm6 (CD19+; CD20low), Nalm6CD19KO (CD19−; CD20+), Raji (CD19+, CD20+) and Raji CD19KO (CD19−,CD20+) is shown in Tables 53A-53D. Cytokine production at 14h post-co-culture at a 1:3 E:T ratio in Nalm6 CD19KO target cells is shown in Tables 54A-54D, as measured in pg/mL (2 replicates per condition). T cell activation as measured by upregulation of 41BB (percent 41BB+ live T cells) at 16h post co-culture is shown in Tables 55A-D (2 replicates per condition). Proliferation of T cells at 4d post co-culture is shown in Table 56 (percent proliferating CD3+, two replicates per condition).

TABLE 51

| | Type (e.g., Bicistronic v. Bispecific) |
|---|---|
| 1 | Non-transduced control |
| 2 | Monospecific anti-CD19 CAR comprising G4S linker |
| 3 | Monospecific anti-CD19 CAR comprising G4S linker |
| 4 | Monospecific anti-CD19 CAR comprising G4S linker |
| 5 | Monospecific anti-CD20 CAR comprising CD8 hinge (8k) |
| 6 | Bicistronic anti-CD20/anti-CD19 CAR, the anti-CD20 CAR comprising CD8 hinge (8k) |
| 7 | Bicistronic anti-CD20/anti-CD19 CAR, the anti-CD20 CAR comprising IgG4 hinge |
| 8 | Bicistronic anti-CD20/anti-CD19 CAR |
| 9 | Bicistronic anti-CD20/anti-CD19 CAR, the anti-CD20 CAR comprising binding motif #2 and a CD8 hinge (8k) |
| 10 | Bicistronic anti-CD20/anti-CD19 CAR, the anti-CD20 CAR comprising binding motif #8 and a CD8 hinge (8k) |
| 11 | Bicistronic anti-CD20/anti-CD19 CAR, the anti-CD20 CAR comprising binding motif #9 and a CD8 hinge (8k) |
| 12 | Bicistronic anti-CD20/anti-CD19 CAR, the anti-CD20 CAR comprising binding motif #14 and a CD8 hinge (8k) |
| 13 | Bicistronic anti-CD20/anti-CD19 CAR, the anti-CD20 CAR comprising binding motif #2 and an CD28 hinge |
| 14 | Bicistronic anti-CD20/anti-CD19 CAR, the anti-CD20 CAR comprising binding motif #8 and an CD28 hinge |
| 15 | Bicistronic anti-CD20/anti-CD19 CAR, the anti-CD20 CAR comprising binding motif #9 and an CD28 hinge |
| 16 | Bicistronic anti-CD20/anti-CD19 CAR, the anti-CD20 CAR comprising binding motif #14 and an CD28 hinge |
| 17 | Bicistronic anti-CD20/anti-CD19 CAR, the anti-CD20 CAR comprising binding motif #2 and an CD28 hinge with a G4S linker |
| 18 | Bicistronic anti-CD20/anti-CD19 CAR, the anti-CD20 CAR comprising binding motif #8 and an CD28 hinge |
| 19 | Bicistronic anti-CD20/anti-CD19 CAR, the anti-CD20 CAR comprising binding motif #9 and an CD28 hinge with a G4S linker |
| 20 | Bicistronic anti-CD20/anti-CD19 CAR, the anti-CD20 CAR comprising binding motif #14 and an CD28 hinge with a G4S linker |
| 21 | Bicistronic anti-CD20/anti-CD19 CAR, the anti-CD20 CAR comprising binding motif #2 and an IgG4 hinge |
| 22 | Bicistronic anti-CD20/anti-CD19 CAR, the anti-CD20 CAR comprising binding motif #8 and an IgG4 hinge |
| 23 | Bicistronic anti-CD20/anti-CD19 CAR, the anti-CD20 CAR comprising binding motif #9 and an IgG4 hinge |
| 24 | Bicistronic anti-CD20/anti-CD19 CAR, the anti-CD20 CAR comprising binding motif #14 and an IgG4 hinge |

TABLE 52

| | Group | | | | | |
|---|---|---|---|---|---|---|
| | 1 | 2 | 5 | 6 | 7 | 8 |
| % CD19 CAR + Live T Cells | 0.56 | 59.52 | 2.35 | 47.54 | 29.05 | 56.77 |
| % CD20 CAR + Live T Cells | 0.09 | 69.3 | 75.76 | 49.33 | 40.13 | 60.99 |

| | Group | | | | | |
|---|---|---|---|---|---|---|
| | 9 | 10 | 11 | 12 | 13 | 14 |
| % CD19 CAR + Live T Cells | 52.72 | 50.2 | 44.72 | 40.28 | 38.99 | 34.12 |
| % CD20 CAR + Live T Cells | 46.42 | 45.57 | 41.36 | 37.04 | 37.15 | 34.7 |

| | Group | | | | | |
|---|---|---|---|---|---|---|
| | 15 | 16 | 17 | 18 | 19 | 20 |
| % CD19 CAR + Live T Cells | 34.87 | 51.32 | 28.89 | 41.69 | 41.34 | 36.22 |
| % CD20 CAR + Live T Cells | 33.78 | 47.97 | 28.87 | 41.82 | 41.95 | 35.14 |

| | Group | | | |
|---|---|---|---|---|
| | 21 | 22 | 23 | 24 |
| % CD19 CAR + Live T Cells | 37.07 | 30.62 | 32.18 | 39.93 |
| % CD20 CAR + Live T Cells | 38.69 | 41 | 41.23 | 46.43 |

TABLE 53A

Nalm6 WT

| | Group | | | | | | | |
|---|---|---|---|---|---|---|---|---|
| E:T Ratio | 1 | | 2 | | 3 | | 4 | |
| 1 to 243 | 30.2 | 21.9 | -22.9 | -11.5 | -0.5 | -12.1 | -13.8 | -11.7 |
| 1 to 81 | -0.8 | -7.5 | -20.9 | -16.4 | -8.1 | -10.2 | -27.6 | -11.9 |
| 1 to 27 | -19.5 | -37.2 | -5.7 | -17.2 | -13.3 | -15.9 | -2.1 | -13.2 |
| 1 to 9 | -13.6 | -20.2 | 14.9 | -1.5 | 8.7 | -5.9 | 13.4 | 1.2 |
| 1 to 3 | -7.1 | -28.9 | 100 | 100 | 100.1 | 100.1 | 100.1 | 100.1 |
| 3 to 1 | 16 | 4.6 | 100.4 | 100.1 | 100.5 | 100.1 | 100.5 | 100.1 |

| E:T Ratio | 5 | | 6 | | 7 | | 8 | |
|---|---|---|---|---|---|---|---|---|
| 1 to 243 | -14.6 | -12.6 | -4 | -10.2 | -7.3 | -11.6 | -9.8 | -9.9 |
| 1 to 81 | 5.2 | -20.1 | -6.2 | -20.5 | -5.7 | -15 | -2.2 | -7 |
| 1 to 27 | -8 | -21.2 | 3.2 | -10.9 | 6 | -5.5 | -8.1 | -8.9 |
| 1 to 9 | -1.8 | 0.6 | 19.4 | 16.1 | 19 | 1.7 | 18.7 | 11 |
| 1 to 3 | 100.1 | 99.9 | 100.1 | 100.1 | 100.1 | 100.1 | 100 | 99.9 |
| 3 to 1 | 100.5 | 100.1 | 100.5 | 100.1 | 100.5 | 100.1 | 100.4 | 100 |

| E:T Ratio | 9 | | 10 | | 11 | | 12 | |
|---|---|---|---|---|---|---|---|---|
| 1 to 243 | 43.6 | 48.1 | -16 | 0.7 | -8.3 | -14.3 | -3.1 | -19.9 |
| 1 to 81 | 9.5 | 20.1 | -7.5 | -2.4 | -10.7 | -22.4 | -10.2 | -14.2 |
| 1 to 27 | -8.2 | 0.9 | -8.9 | -1.6 | -12.8 | -9.7 | 3 | -13 |
| 1 to 9 | 6.5 | 10.3 | 0.3 | 5 | -2.3 | -10.9 | -0.4 | -16.9 |
| 1 to 3 | 100 | 100.1 | 100.1 | 100.1 | 100.1 | 100.1 | 100.1 | 100.1 |
| 3 to 1 | 100.1 | 100.1 | 100.1 | 100.1 | 100.1 | 100.1 | 100.1 | 100.1 |

| E:T Ratio | 13 | | 14 | | 15 | | 16 | |
|---|---|---|---|---|---|---|---|---|
| 1 to 243 | -11.6 | -21.9 | -13.8 | -21.2 | -9 | -16.6 | -2.9 | -12.6 |
| 1 to 81 | -11 | -31.6 | -20.8 | -25 | -15.7 | -20.6 | -6.3 | -8 |
| 1 to 27 | -13.6 | -10.1 | -22.3 | -4.6 | -15.4 | -11.1 | 0.9 | 3.2 |
| 1 to 9 | -6.5 | -20.4 | -7.1 | -7.5 | -13.3 | -17.6 | 14.1 | 17.3 |

TABLE 53A-continued

Nalm6 WT

| | | | | | | | | |
|---|---|---|---|---|---|---|---|---|
| 1 to 3 | 100.1 | 100.1 | 100.1 | 100.1 | 100.1 | 100.1 | 100 | 99.9 |
| 3 to 1 | 100.1 | 100.1 | 100.1 | 100.1 | 100.1 | 100.1 | 100 | 100 |

| E:T Ratio | 17 | | 18 | | 19 | | 20 | |
|---|---|---|---|---|---|---|---|---|
| 1 to 243 | 30.4 | 32.6 | -1.9 | -6.4 | -2.2 | -16 | -18.5 | -13 |
| 1 to 81 | 8.7 | 9.1 | -8.1 | -5.6 | -20.8 | -19.4 | -31.6 | -26.6 |
| 1 to 27 | 1.5 | -3.7 | -0.9 | -6 | 41 | -7 | -15.6 | -10.9 |
| 1 to 9 | 6.5 | 0 | -4.7 | -1.4 | -0.6 | 11.7 | -22 | -4.2 |
| 1 to 3 | 100.1 | 100 | 100.1 | 100.1 | 100.1 | 100.1 | 100.1 | 100 |
| 3 to 1 | 100.1 | 100.5 | 100.1 | 100.5 | 100.1 | 100.5 | 100.1 | 100.5 |

| E:T Ratio | 21 | | 22 | | 23 | | 24 | |
|---|---|---|---|---|---|---|---|---|
| 1 to 243 | -11.2 | -12.1 | -9.4 | -32.5 | -10.9 | -29.1 | -17.9 | -19.8 |
| 1 to 81 | -22.6 | -17.9 | -20.9 | -26.9 | -17.6 | -24.6 | -17.4 | -19.2 |
| 1 to 27 | -5.1 | -8.3 | 6.1 | -7.6 | -2.2 | -9.4 | 3.6 | -2.6 |
| 1 to 9 | -8.6 | -2.4 | 0.4 | 14.4 | 22.5 | -3.5 | 19.5 | 5.3 |
| 1 to 3 | 100.1 | 100.1 | 100.1 | 100.1 | 100.1 | 100.1 | 100 | 99.9 |
| 3 to 1 | 100.1 | 100.5 | 100.1 | 100.5 | 100.1 | 100.5 | 100 | 100.4 |

TABLE 53B

Nalm6 CD19KO

| | Group | | | | | | | |
|---|---|---|---|---|---|---|---|---|
| E:T Ratio | 1 | | 2 | | 3 | | 4 | |
| 1 to 243 | -10.2 | -10.7 | -14.4 | -14.8 | -7.3 | -11.3 | -15.8 | -14.1 |
| 1 to 81 | -8.7 | -21.5 | -5 | -14.6 | -5.8 | -16.6 | -7.8 | -12.2 |
| 1 to 27 | 3.8 | -18.2 | -2.3 | -13.6 | -4.7 | -21.8 | -1 | -18.8 |
| 1 to 9 | -0.2 | -11.2 | -3.5 | -10.3 | -3.8 | -13.7 | -4.8 | -3.6 |
| 1 to 3 | 39.2 | 30.5 | 33.6 | 19.8 | 33.2 | 24.5 | 33.9 | 26.7 |
| 3 to 1 | 56.2 | 41.9 | 39.4 | 32.6 | 43.8 | 40.7 | 38 | 32.9 |

| E:T Ratio | 5 | | 6 | | 7 | | 8 | |
|---|---|---|---|---|---|---|---|---|
| 1 to 243 | -9 | -15.4 | -8.2 | -13.9 | -12.9 | -11.9 | -11.1 | -9.2 |
| 1 to 81 | 6.3 | -4.5 | -1.9 | -9.9 | -3.6 | -13.4 | 5.3 | 5.3 |
| 1 to 27 | 13.6 | 16.5 | 18.8 | 5.5 | 10 | -0.6 | 23.1 | 19.3 |
| 1 to 9 | 40.5 | 33.2 | 45.3 | 44.7 | 35.7 | 20.2 | 59.2 | 46.4 |
| 1 to 3 | 100.1 | 99.9 | 100.3 | 100.1 | 99.8 | 99.7 | 100.1 | 99.8 |
| 3 to 1 | 100.9 | 101.1 | 101.1 | 101.2 | 101.1 | 101.2 | 101 | 101 |

| E:T Ratio | 9 | | 10 | | 11 | | 12 | |
|---|---|---|---|---|---|---|---|---|
| 1 to 243 | -6 | -8 | -6 | -11.4 | -8.2 | -7.6 | -7.8 | -4.3 |
| 1 to 81 | 4.4 | 10.8 | -1.5 | -0.1 | 2.3 | 0.3 | 8.5 | 10.4 |
| 1 to 27 | -2.7 | 6.1 | 12 | -5.9 | 4.5 | 21.5 | 38.2 | 21.7 |
| 1 to 9 | 32.2 | 34.6 | 17.6 | 14.1 | 17.3 | 11.4 | 30.8 | 22.7 |
| 1 to 3 | 100.2 | 100.8 | 100.1 | 100.9 | 100.2 | 100.8 | 100.1 | 100.8 |
| 3 to 1 | 101 | 101.4 | 101 | 101.4 | 101 | 101.5 | 101 | 101.4 |

| E:T Ratio | 13 | | 14 | | 15 | | 16 | |
|---|---|---|---|---|---|---|---|---|
| 1 to 243 | -5.3 | -7.2 | -8.6 | 5.8 | -5.3 | 18.7 | -7.4 | 8.1 |
| 1 to 81 | 5 | 0.5 | -2.5 | 9.6 | -1.7 | 5.8 | 7.1 | 13 |
| 1 to 27 | 13.6 | 18.6 | 10.4 | 40.6 | 11.9 | 27.8 | 27.8 | 28.2 |
| 1 to 9 | 8.4 | 3.1 | 31.3 | 20.3 | 2.2 | 7.9 | 32.3 | 42.4 |
| 1 to 3 | 98.2 | 99.8 | 100.2 | 100.8 | 100.1 | 100.8 | 100 | 100.6 |
| 3 to 1 | 99.6 | 100.1 | 101.1 | 101.4 | 101.1 | 101.3 | 101 | 101.3 |

| E:T Ratio | 17 | | 18 | | 19 | | 20 | |
|---|---|---|---|---|---|---|---|---|
| 1 to 243 | -1.9 | -5 | -8.5 | -12.4 | -9 | -7.7 | -12.7 | -14.3 |
| 1 to 81 | -5.9 | -10.3 | -10.6 | -10.5 | -4.8 | -11 | -11.2 | -15.9 |
| 1 to 27 | -5.6 | -2.8 | 1.4 | -0.4 | 16.1 | 14.8 | -0.7 | 2.4 |
| 1 to 9 | 21.5 | 4.9 | 8.9 | 3.7 | 20.6 | 35.4 | 1.3 | 7 |
| 1 to 3 | 97 | 94.4 | 100.2 | 100 | 100.3 | 100.1 | 100.2 | 99.3 |
| 3 to 1 | 99.6 | 101.3 | 100.2 | 101.9 | 100.2 | 101.9 | 100.2 | 101.9 |

TABLE 53B-continued

Nalm6 CD19KO

| E:T Ratio | 21 | | 22 | | 23 | | 24 | |
|---|---|---|---|---|---|---|---|---|
| 1 to 243 | −5.8 | 0.2 | −4.2 | −9.4 | 7 | −12.5 | −2 | −10.2 |
| 1 to 81 | −0.5 | −5.4 | 8.3 | −4.3 | 4.1 | −10.1 | 6.2 | 2.1 |
| 1 to 27 | 32.9 | 13.9 | 41.7 | 27.8 | 34.2 | 14.4 | 35.6 | 26.8 |
| 1 to 9 | 22.9 | 32.9 | 38.3 | 46 | 44.5 | 19.7 | 43.5 | 25.5 |
| 1 to 3 | 100.3 | 100.1 | 100.3 | 100.1 | 100.2 | 100 | 100.2 | 100 |
| 3 to 1 | 100.2 | 101.9 | 100.2 | 101.8 | 100.1 | 101.7 | 100 | 101.7 |

TABLE 53C

Raji WT

Group

| E:T Ratio | 1 | | 2 | | 3 | | 4 | |
|---|---|---|---|---|---|---|---|---|
| 1 to 243 | 2.2 | −33.8 | −12.6 | −23 | −19.4 | −30.3 | −8.1 | −22.8 |
| 1 to 81 | 16.3 | −29.4 | −2.5 | −15 | −2.8 | −16.3 | −6.4 | −17.7 |
| 1 to 27 | −9.2 | −48.8 | 1.6 | −33.1 | −2 | −29.4 | 2.7 | −25.3 |
| 1 to 9 | −6.5 | −35.9 | 13.5 | −9.7 | 14 | −10.5 | 11.6 | −5.5 |
| 1 to 3 | 8.9 | −17.9 | 99.8 | 99.9 | 99.9 | 99.9 | 100.1 | 100 |
| 3 to 1 | 19.5 | 5.9 | 103.8 | 100.1 | 103.9 | 100.2 | 103.9 | 100.2 |

| E:T Ratio | 5 | | 6 | | 7 | | 8 | |
|---|---|---|---|---|---|---|---|---|
| 1 to 243 | −11 | −21.7 | −7.9 | −25.1 | −6.5 | −18.8 | −5.1 | −14.7 |
| 1 to 81 | −4.6 | −14.9 | −0.5 | −19.2 | 0.4 | −2 | −0.1 | −0.1 |
| 1 to 27 | −0.1 | −14.1 | 8.6 | −20.6 | 7.9 | −6.6 | 10.4 | −8.8 |
| 1 to 9 | 13.6 | −2.6 | 16.5 | 5.1 | 22.2 | −3.3 | 23.8 | −0.5 |
| 1 to 3 | 100.2 | 99.9 | 100.1 | 100.1 | 100.1 | 100 | 99.9 | 99.8 |
| 3 to 1 | 104 | 100.2 | 103.9 | 100.2 | 103.9 | 100.1 | 103.8 | 100 |

| E:T Ratio | 9 | | 10 | | 11 | | 12 | |
|---|---|---|---|---|---|---|---|---|
| 1 to 243 | −30.8 | −24.1 | −30.9 | −12.5 | −17.6 | −14.4 | −23.9 | −6.8 |
| 1 to 81 | −26.7 | −15.7 | −9.8 | −14.6 | −6.9 | −6 | −6.5 | −13.2 |
| 1 to 27 | −20.6 | −22.8 | −6.5 | −3.3 | −4.1 | −4 | 0.3 | 2.3 |
| 1 to 9 | −7.4 | −15.1 | −1.5 | −14.6 | −2.5 | −12.8 | 9.3 | −3.7 |
| 1 to 3 | 104.4 | 104.6 | 104.4 | 104.6 | 104.4 | 104.5 | 104.5 | 104.5 |
| 3 to 1 | 108 | 105.9 | 108.1 | 105.9 | 108.1 | 105.8 | 108.1 | 105.9 |

| E:T Ratio | 13 | | 14 | | 15 | | 16 | |
|---|---|---|---|---|---|---|---|---|
| 1 to 243 | −28.5 | −8.4 | −17.4 | −11.5 | −11.1 | −11 | −9.9 | −5.6 |
| 1 to 81 | −11.4 | −7.2 | −16.4 | −13.8 | −9.9 | −10.4 | 4.7 | 1.7 |
| 1 to 27 | 1 | 0.7 | −1.6 | 5.2 | 6.9 | −3.3 | 10.2 | 13.5 |
| 1 to 9 | 3.3 | −12 | 7.7 | −11 | 4 | −2.3 | 14.4 | 9.9 |
| 1 to 3 | 104.4 | 104.6 | 104.4 | 104.5 | 104.4 | 104.5 | 104.3 | 104.4 |
| 3 to 1 | 108.1 | 105.9 | 108 | 105.9 | 108 | 105.8 | 107.8 | 105.7 |

| E:T Ratio | 17 | | 18 | | 19 | | 20 | |
|---|---|---|---|---|---|---|---|---|
| 1 to 243 | −28.3 | −21 | −22.1 | −16.4 | −11.4 | −11.8 | −10.6 | −11.1 |
| 1 to 81 | −18.5 | −22.7 | −14.6 | −26.2 | −11.4 | −34.7 | −12.6 | −28.9 |
| 1 to 27 | −23 | −21.7 | −14.5 | −26.5 | 8.2 | −5.9 | −5.3 | −14.9 |
| 1 to 9 | −9.5 | −34.2 | −11.2 | −39.6 | −6.9 | −15.5 | −17.8 | −27.7 |
| 1 to 3 | 100 | 100.2 | 100 | 100.2 | 100.1 | 100.2 | 100.1 | 100.2 |
| 3 to 1 | 101.2 | 120.1 | 101.2 | 120.1 | 101.2 | 120.1 | 101.2 | 120.1 |

| E:T Ratio | 21 | | 22 | | 23 | | 24 | |
|---|---|---|---|---|---|---|---|---|
| 1 to 243 | −7 | −4.1 | −9.6 | −6.3 | −8.1 | −11.1 | −7.5 | −1.1 |
| 1 to 81 | −5.8 | −14.4 | −2.6 | −19.2 | 9 | −19.9 | 19.2 | −4.6 |
| 1 to 27 | 5.3 | −6.3 | −5.1 | 2.4 | 4.9 | 0.7 | 13.3 | 5.4 |
| 1 to 9 | −6.7 | −14.2 | −7.4 | −6.1 | 9.6 | −16.6 | 15.3 | −9 |
| 1 to 3 | 100.1 | 100.2 | 100.1 | 100.2 | 100.1 | 100.2 | 99.9 | 100.1 |
| 3 to 1 | 101.2 | 120.1 | 101.2 | 120.1 | 101.2 | 120.1 | 101 | 119.9 |

TABLE 53D

Raji CD19KO

| E:T Ratio | Group | | | | | | | |
|---|---|---|---|---|---|---|---|---|
| | 1 | | 2 | | 3 | | 4 | |
| 1 to 243 | 51 | 55 | 36.7 | 26.2 | −18.2 | 12.5 | −44.9 | 0 |
| 1 to 81 | −0.4 | 33.7 | −85.1 | 3.4 | −143.7 | 3 | −190.3 | 9.3 |
| 1 to 27 | 15.3 | −0.9 | 4.5 | 6.3 | −0.5 | 2.7 | 4 | 1.1 |
| 1 to 9 | −1.9 | 3.3 | 2.9 | 2 | 8.4 | 6.5 | 1.5 | 15.2 |
| 1 to 3 | 34.5 | 20.9 | 37.3 | 20.8 | 16.3 | 16 | 5.5 | 11.7 |
| 3 to 1 | 41.3 | 14.2 | 14.6 | 2.1 | 11.2 | 19.7 | 4.6 | 3.8 |

| E:T Ratio | 5 | | 6 | | 7 | | 8 | |
|---|---|---|---|---|---|---|---|---|
| 1 to 243 | −15.1 | −3.2 | 22.8 | −1.4 | −5.5 | 0.2 | −85.7 | −2.4 |
| 1 to 81 | −217.9 | 3.3 | −201.5 | −2.2 | −227.2 | −0.9 | −210.3 | 2.5 |
| 1 to 27 | −0.6 | 7 | 11.8 | 3.4 | 1.9 | −1.6 | 1.4 | 9.5 |
| 1 to 9 | 8.5 | 17 | 22.1 | 21.5 | 13.5 | 12.6 | 30.9 | 21 |
| 1 to 3 | 98.8 | 99.8 | 99.4 | 100.6 | 91.9 | 93.5 | 98.8 | 99.6 |
| 3 to 1 | 99.6 | 99.7 | 99.8 | 100.1 | 99.1 | 99.6 | 99.7 | 99.9 |

| E:T Ratio | 9 | | 10 | | 11 | | 12 | |
|---|---|---|---|---|---|---|---|---|
| 1 to 243 | 9 | 11.5 | −2.9 | 10.2 | −0.6 | 2.2 | −2.4 | 17.6 |
| 1 to 81 | 10.3 | 17.5 | 6.6 | 9.6 | 8.1 | 8.5 | −2.6 | 3.2 |
| 1 to 27 | 15.7 | 21.5 | 16 | 21.2 | 20.2 | 32 | 16.2 | 22 |
| 1 to 9 | 25.6 | 35 | 38.1 | 32.2 | 32.9 | 27.9 | 23.7 | 28.8 |
| 1 to 3 | 99.7 | 100.2 | 99.7 | 100 | 99.9 | 100 | 99.8 | 100.1 |
| 3 to 1 | 99.9 | 100.9 | 99.8 | 100.9 | 100 | 101 | 99.9 | 101 |

| E:T Ratio | 13 | | 14 | | 15 | | 16 | |
|---|---|---|---|---|---|---|---|---|
| 1 to 243 | −1.8 | 9.8 | −3 | 2.6 | 5.6 | 1.9 | −7.7 | 14.5 |
| 1 to 81 | −2.8 | 0.5 | −0.4 | −2.7 | −6.3 | −11.5 | −3.3 | −2.5 |
| 1 to 27 | 10.5 | 19.6 | −0.8 | 11.7 | −4.4 | 8.6 | 8.7 | 16.7 |
| 1 to 9 | 14.7 | 15.7 | 24.3 | 22.5 | 7.3 | 10.8 | 15 | 12.3 |
| 1 to 3 | 96.1 | 98.5 | 97.2 | 99.7 | 95.3 | 97 | 92.3 | 97.7 |
| 3 to 1 | 96.2 | 96.2 | 98.4 | 98.7 | 97.5 | 97.5 | 96.1 | 95.7 |

| E:T Ratio | 17 | | 18 | | 19 | | 20 | |
|---|---|---|---|---|---|---|---|---|
| 1 to 243 | 7.6 | 20.4 | 5.1 | 6.1 | −0.1 | 8.8 | 4.6 | 11.8 |
| 1 to 81 | 9.7 | 13.2 | 11.1 | 11.8 | 8.9 | 13.2 | 3 | 6.8 |
| 1 to 27 | 18.1 | 10.1 | 29.9 | 18.7 | 24.4 | 21.3 | 13.8 | 15.8 |
| 1 to 9 | 44.9 | 19.3 | 37 | 26.8 | 33.6 | 32.3 | 24.1 | 16 |
| 1 to 3 | 87.9 | 84.7 | 99.7 | 99.1 | 98.7 | 97.5 | 93.8 | 92.5 |
| 3 to 1 | 95 | 96.5 | 99.7 | 100 | 99.7 | 99.9 | 96.1 | 95 |

| E:T Ratio | 21 | | 22 | | 23 | | 24 | |
|---|---|---|---|---|---|---|---|---|
| 1 to 243 | −5.9 | 6.6 | 2.9 | −9.9 | 2.7 | −2.6 | −4.3 | −3.4 |
| 1 to 81 | 11.5 | −5.2 | 10.7 | −0.3 | 8 | −3.2 | 7.3 | 0.4 |
| 1 to 27 | 26 | 20.7 | 21.9 | 16.7 | 22.1 | 14.1 | 31.7 | 20.6 |
| 1 to 9 | 18.6 | 28.9 | 21.2 | 25.8 | 32.1 | 9.2 | 28.7 | 19.7 |
| 1 to 3 | 100.4 | 100.2 | 100.4 | 100.1 | 100.4 | 100.2 | 100.2 | 100 |
| 3 to 1 | 100 | 100.1 | 100 | 100.1 | 100 | 100.1 | 99.8 | 100 |

TABLE 54A

| TNFa | | | | | | | |
|---|---|---|---|---|---|---|---|
| Group | | | | | | | |
| 1 | | 2 | | 3 | | 4 | |
| 21.43362 | 30.0185 | 33.8795 | 28.22578 | 23.07486 | 21.60766 | 28.62412 | 32.4843 |
| 5 | | 6 | | 7 | | 8 | |
| 769.5068 | 750.8404 | 720.3671 | 614.8629 | 229.2041 | 233.5543 | 836.7802 | 842.7271 |
| 9 | | 10 | | 11 | | 12 | |
| 317.8869 | 371.7266 | 414.5337 | 293.488 | 386.2704 | 293.6139 | 418.6442 | 307.1845 |
| 13 | | 14 | | 15 | | 16 | |
| 252.4179 | 152.0566 | 185.1981 | 253.8267 | 180.7021 | 249.8017 | 208.5401 | 327.4072 |
| 17 | | 18 | | 19 | | 20 | |
| 203.6143 | 217.2118 | 405.7839 | 345.8976 | 467.5809 | 425.1003 | 269.5771 | 258.1286 |
| 21 | | 22 | | 23 | | 24 | |
| 472.2237 | 421.9478 | 446.7417 | 402.7078 | 430.8759 | 441.7219 | 432.4396 | 494.9866 |

TABLE 54B

| IL10 | | | | | | | |
|---|---|---|---|---|---|---|---|
| Group | | | | | | | |
| 1 | | 2 | | 3 | | 4 | |
| 12.06837 | 12.32633 | 11.93813 | 10.60854 | 11.04015 | 12.18301 | 9.930545 | 14.15293 |
| 5 | | 6 | | 7 | | 8 | |
| 17.26261 | 17.49864 | 19.22346 | 27.91504 | 28.00769 | 25.40533 | 22.57109 | 25.85191 |
| 9 | | 10 | | 11 | | 12 | |
| 20.85123 | 21.31715 | 25.06719 | 23.96362 | 17.45668 | 16.68065 | 27.34339 | 37.56894 |
| 13 | | 14 | | 15 | | 16 | |
| 15.01034 | 17.85805 | 21.4962 | 15.99171 | 17.25999 | 16.67803 | 29.79311 | 30.33925 |
| 17 | | 18 | | 19 | | 20 | |
| 20.35921 | 24.0903 | 22.76352 | 23.08782 | 15.64091 | 19.16565 | 25.07248 | 18.56677 |
| 21 | | 22 | | 23 | | 24 | |
| 16.28242 | 12.91556 | 15.43415 | 18.99226 | 16.57846 | 14.00925 | 22.48675 | 23.85015 |

TABLE 54C

| IL-2 | | | | | | | |
|---|---|---|---|---|---|---|---|
| Group | | | | | | | |
| 1 | | 2 | | 3 | | 4 | |
| 13.90412 | 5.925647 | 7.239758 | 8.057854 | 3.416301 | 10.05507 | 5.481665 | 4.24322 |
| 5 | | 6 | | 7 | | 8 | |
| 1979.747 | 1880.755 | 758.0331 | 769.4632 | 136.3706 | 143.4531 | 1373.496 | 1344.97 |

TABLE 54C-continued

| IL-2 | | | | | | | |
|---|---|---|---|---|---|---|---|
| 9 | | 10 | | 11 | | 12 | |
| 415.0335 | 397.6617 | 371.0906 | 419.0813 | 315.6276 | 308.785 | 239.4187 | 263.1596 |
| 13 | | 14 | | 15 | | 16 | |
| 81.99199 | 101.7831 | 191.2544 | 191.099 | 258.0696 | 200.4818 | 149.9144 | 150.8354 |
| 17 | | 18 | | 19 | | 20 | |
| 83.13918 | 96.59951 | 234.2623 | 273.2762 | 400.7794 | 439.0895 | 132.4347 | 146.6177 |
| 21 | | 22 | | 23 | | 24 | |
| 324.6525 | 284.3169 | 312.9986 | 304.5192 | 284.8684 | 245.4556 | 171.9664 | 220.1387 |

TABLE 54D

| IFNg | | | | | | | |
|---|---|---|---|---|---|---|---|
| Group | | | | | | | |
| 1 | | 2 | | 3 | | 4 | |
| 2183.862 | 1360.111 | 1707.394 | 2083.675 | 1077.22 | 1338.666 | 1977.427 | 1416.691 |
| 5 | | 6 | | 7 | | 8 | |
| 82883.42 | 90801.34 | 98809.63 | 79846.05 | 25763.3 | 22756.31 | 113383.2 | 130673.4 |
| 9 | | 10 | | 11 | | 12 | |
| 33687.05 | 41534.7 | 33669.96 | 46572.37 | 41476.85 | 32400.9 | 44847.72 | 41189.26 |
| 13 | | 14 | | 15 | | 16 | |
| 18695.39 | 13259.19 | 22300.69 | 18887.22 | 19159.02 | 26725.05 | 27437.53 | 38194.28 |
| 17 | | 18 | | 19 | | 20 | |
| 19441.39 | 19547.47 | 36846.64 | 34373.3 | 30178.64 | 49566.75 | 27345.52 | 24419.34 |
| 21 | | 22 | | 23 | | 24 | |
| 42811.57 | 31839.23 | 44792.28 | 37959.75 | 40016.19 | 41814.98 | 56819.12 | 56847.75 |

45

TABLE 55A

| Raji CD19KO | | | | | | | |
|---|---|---|---|---|---|---|---|
| Group | | | | | | | |
| 1 | | 2 | | 3 | | 4 | |
| 5.09 | 4.2 | 3.34 | 4.04 | 3.54 | 3.98 | 4.31 | 3.94 |
| 5 | | 6 | | 7 | | 8 | |
| 21.8 | 17.92 | 18.12 | 18.53 | 15.05 | 12.81 | 18.42 | 15.43 |
| 9 | | 10 | | 11 | | 12 | |
| 17.44 | 21.84 | 18.46 | 14.89 | 17.75 | 16.01 | 20.06 | 16.96 |
| 13 | | 14 | | 15 | | 16 | |
| 9.52 | 9.53 | 10.54 | 11.11 | 12 | 11.99 | 16.69 | 16.19 |

TABLE 55A-continued

| Raji CD19KO | | | | | | | |
|---|---|---|---|---|---|---|---|
| 17 | | 18 | | 19 | | 20 | |
| 8.38 | 7.48 | 16.6 | 14.92 | 15.64 | 11.99 | 13.78 | 14.05 |
| 21 | | 22 | | 23 | | 24 | |
| 18.7 | 18.72 | 13.26 | 14.9 | 16.55 | 18.4 | 17.12 | 17.54 |

TABLE 55B

| Raji parental | | | | | | | |
|---|---|---|---|---|---|---|---|
| Group | | | | | | | |
| 1 | | 2 | | 3 | | 4 | |
| 24.53 | 4.51 | 22.54 | 23.61 | 17.08 | 18.23 | 23.65 | 24.2 |
| 5 | | 6 | | 7 | | 8 | |

TABLE 55B-continued

| Raji parental | | | | | | | |
|---|---|---|---|---|---|---|---|
| 21.84 | 23.46 | 25.65 | 19.57 | 20.96 | 20.04 | 17.69 | 17.27 |

| 9 | | 10 | | 11 | | 12 | |
|---|---|---|---|---|---|---|---|
| 25.04 | 24.38 | 22.53 | 25.75 | 25.69 | 21.61 | 23.93 | 27.4 |

| 13 | | 14 | | 15 | | 16 | |
|---|---|---|---|---|---|---|---|
| 21.25 | 23.01 | 19.43 | 21.15 | 18.99 | 21.92 | 27.95 | 30.26 |

| 17 | | 18 | | 19 | | 20 | |
|---|---|---|---|---|---|---|---|
| 15.13 | 15.72 | 26.86 | 28 | 27.46 | 25.72 | 24.49 | 23.03 |

| 21 | | 22 | | 23 | | 24 | |
|---|---|---|---|---|---|---|---|
| 25.59 | 25.04 | 20.98 | 19.29 | 23.01 | 20.78 | 22.14 | 21.49 |

TABLE 55C

| Nalm6 CD19KO | | | | | | | |
|---|---|---|---|---|---|---|---|
| Group | | | | | | | |

| 1 | | 2 | | 3 | | 4 | |
|---|---|---|---|---|---|---|---|
| 5.12 | 5.19 | 3.6 | 3.55 | 5.1 | 4.64 | 5.12 | 5.07 |

| 5 | | 6 | | 7 | | 8 | |
|---|---|---|---|---|---|---|---|
| 14.47 | 20.84 | 18.69 | 19.81 | 13.33 | 17.17 | 18.12 | 17.87 |

| 9 | | 10 | | 11 | | 12 | |
|---|---|---|---|---|---|---|---|
| 22.37 | 23.08 | 19.86 | 19.82 | 19.28 | 18.98 | 19.01 | 23.35 |

| 13 | | 14 | | 15 | | 16 | |
|---|---|---|---|---|---|---|---|
| 8.87 | 10.25 | 10.83 | 12.05 | 13.18 | 14.8 | 17.6 | 17.86 |

| 17 | | 18 | | 19 | | 20 | |
|---|---|---|---|---|---|---|---|
| 9.04 | 8.8 | 19.73 | 18.54 | 18.22 | 16.83 | 16.11 | 14.89 |

| 21 | | 22 | | 23 | | 24 | |
|---|---|---|---|---|---|---|---|
| 19.29 | 18.03 | 18.25 | 15.5 | 18.01 | 15.89 | 15.89 | 16.97 |

TABLE 55D

| Nalm6 parental | | | | | | | |
|---|---|---|---|---|---|---|---|
| Group | | | | | | | |

| 1 | | 2 | | 3 | | 4 | |
|---|---|---|---|---|---|---|---|
| 1.95 | 1.53 | 23.14 | 25.28 | 19.79 | 19.69 | 23.06 | 23.75 |

| 5 | | 6 | | 7 | | 8 | |
|---|---|---|---|---|---|---|---|
| 19.06 | 23.01 | 21.27 | 20.07 | 18.62 | 20.4 | 15.82 | 14.64 |

| 9 | | 10 | | 11 | | 12 | |
|---|---|---|---|---|---|---|---|
| 25.8 | 28.75 | 26.91 | 26.98 | 32.3 | 27.59 | 23.53 | 25.26 |

| 13 | | 14 | | 15 | | 16 | |
|---|---|---|---|---|---|---|---|
| 24.38 | 28.81 | 21.38 | 21.64 | 21.2 | 23.73 | 23.59 | 28.61 |

TABLE 55D-continued

| Nalm6 parental | | | | | | | |
|---|---|---|---|---|---|---|---|
| 17 | | 18 | | 19 | | 20 | |
| 20.24 | 19.63 | 28.58 | 30.28 | 28.35 | 26.96 | 26.32 | 23.5 |

| 21 | | 22 | | 23 | | 24 | |
|---|---|---|---|---|---|---|---|
| 26.96 | 24.02 | 24.71 | 20.78 | 23.5 | 24.06 | 23.58 | 20.73 |

TABLE 56

| Group | Raji parental | | Raji CD19KO | | Nalm6 CD19KO | | Nalm6 parental | |
|---|---|---|---|---|---|---|---|---|
| | replicate 1 | replicate 2 | replicate 1 | replicate 2 | replicate 1 | replicate 2 | replicate 1 | replicate 2 |
| 1 | 64.5 | 65.1 | 61.8 | 60.6 | 55.6 | 50.6 | 32.8 | 35.8 |
| 2 | 92 | 88.5 | 57.5 | 56.6 | 43.6 | 46.6 | 90.4 | 72.1 |
| 3 | 84.1 | 84.6 | 58.3 | 59.8 | 43.4 | 50.3 | 87.1 | 83.9 |
| 4 | 91.8 | 90.4 | 63.5 | 59.9 | 44.3 | 47.6 | 91 | 89.7 |
| 5 | 77 | 69.1 | 78.6 | 78.4 | 64.7 | 70.7 | 90 | 88.7 |
| 6 | 89.2 | 87.2 | 91.5 | 88.6 | 89.3 | 86.6 | 91.9 | 89.5 |
| 7 | 87.2 | 83 | 88.8 | 86.4 | 84 | 82 | 91.7 | 90.2 |
| 8 | 92.6 | 77.4 | 90.4 | 81.8 | 89.1 | 80.2 | 87.4 | 86.4 |
| 9 | 92.8 | 89.6 | 92.5 | 92.8 | 87 | 87.5 | 91.6 | 92.6 |
| 10 | 84.6 | 87.6 | 88.9 | 90.1 | 81.4 | 81.9 | 90.6 | 90.4 |
| 11 | 85.1 | 77.7 | 87.2 | 87.8 | 78.1 | 79.9 | 87 | 86.6 |
| 12 | 83.4 | 88.9 | 92 | 91.4 | 84.1 | 83.7 | 90.6 | 88.5 |
| 13 | 88 | 81.8 | 80.4 | 78.2 | 65.2 | 66.6 | 89.1 | 88.5 |
| 14 | 81 | 74.4 | 81.4 | 80.6 | 77.3 | 76.8 | 88.5 | 89.2 |
| 15 | 74.8 | 72.5 | 81 | 81 | 75.9 | 77.5 | 85.5 | 84.2 |
| 16 | 91.8 | 91.6 | 87.9 | 88.1 | 81.7 | 81.4 | 92.4 | 92.1 |
| 17 | 83.3 | 84.3 | 77.6 | 80.7 | 62.2 | 62.9 | 88.1 | 86.8 |
| 18 | 70.2 | 76.4 | 82 | 83.4 | 74.5 | 78.1 | 85.6 | 108 |
| 19 | 81.8 | 85.6 | 88.9 | 89.6 | 82.4 | 82.7 | 88 | 90.4 |
| 20 | 77.5 | 81.2 | 83.6 | 84.4 | 78.1 | 79.6 | 88.1 | 88.5 |
| 21 | 80.1 | 86.8 | 90.5 | 90.2 | 85.3 | 84.6 | 90.9 | 91.9 |
| 22 | 82.6 | 77.9 | 88.5 | 88.4 | 83.7 | 83.7 | 90.3 | 89.7 |
| 23 | 75.8 | 71.2 | 86.8 | 85.7 | 79.2 | 80.1 | 84.6 | 89.4 |
| 24 | 84.6 | 84.9 | 89.7 | 89.7 | 82.6 | 84.2 | 89.7 | 89.5 |

Example 17

Comparison of hinges was undertaken in anti-CD20 monovalent CARs. Data presented in this Example was obtained using the methods set forth in the Example above. CAR-T cells used in this Example comprised the CARs identified in Table 57 below. Table 57 provides the experimental conditions or groups referred to in subsequent tables of this Example. The Example utilized four anti-CD20 binding motifs, identified in this Example as binding motif A, binding motif B, binding motif C, and binding motif D. Hinges tested comprise a truncated CD28 hinge (28T), a CD8 hinge (8k), and an IgG4 hinge (14).

Transduction efficiency is shown in Table 58. Day 4 cytotoxicity in Raji (CD19+, CD20high), Raji CD20KO (CD19+, CD20−), Namalwa (CD19+, CD20low) and Nalm6 (CD19+, CD20low) is shown in Tables 59 and 60. Cytokine production at 14h post-co-culture at a 1:1 E:T ratio is shown in Tables 61A-D. T cell activation as measured by upregulation of 41BB at 16h post co-culture is shown at E:T 1:1 or 1:4 in Tables 62 and 63 respectively. Proliferation of T cells at 4d post co-culture is shown at E:T 1:1 or 1:4 in Tables 64 and 65, respectively.

TABLE 57

| | Type (e.g., Bicistronic v. Bispecific) |
|---|---|
| 1 | Non-transduced control |
| 2 | Monovalent anti-CD20 CAR comprising scFv#A and a CD28 hinge |
| 3 | Monovalent anti-CD20 CAR comprising binding motif #A and a CD8 hinge |
| 4 | Monovalent anti-CD20 CAR comprising binding motif #A and a IgG4 hinge |
| 5 | Monovalent anti-CD20 CAR comprising binding motif #B and a CD28 hinge |
| 6 | Monovalent anti-CD20 CAR comprising binding motif #B and a CD8 hinge |
| 7 | Monovalent anti-CD20 CAR comprising binding motif #B and a IgG4 hinge |
| 8 | Monovalent anti-CD20 CAR comprising binding motif #C and a CD28 hinge |
| 9 | Monovalent anti-CD20 CAR comprising binding motif #C and a CD8 hinge |
| 10 | Monovalent anti-CD20 CAR comprising binding motif #C and a IgG4 hinge |
| 11 | Monovalent anti-CD20 CAR comprising binding motif #D and a CD28 hinge |
| 12 | Monovalent anti-CD20 CAR comprising binding motif #D and a CD8 hinge |

TABLE 57-continued

| | Type (e.g., Bicistronic v. Bispecific) |
|---|---|
| 13 | Monovalent anti-CD20 CAR comprising binding motif #D and a IgG4 hinge |

TABLE 58

| Group | Transduction efficiency (% CAR+) |
|---|---|
| 1 | 0.15 |
| 2 | 62.3 |
| 3 | 56.3 |
| 4 | 89.2 |
| 5 | 51.6 |
| 6 | 66.5 |
| 7 | 71.6 |
| 8 | 73.9 |
| 9 | 77.0 |
| 10 | 85.4 |
| 11 | 66.8 |
| 12 | 80.8 |
| 13 | 84.8 |

TABLE 59

| Cell Type | Targets Alone | | | 1 | | |
|---|---|---|---|---|---|---|
| Raji | 79202.8 | 70452 | 71294.3 | 59370.9 | 60525.3 | 62135.5 |
| Raji CD20KO | 94864.6 | 93729.3 | 107518 | 80627 | 79824.4 | 59886.5 |
| Namalwa | 38530.1 | 44751.2 | 48600.5 | 33016.5 | 37313.6 | 30919.3 |
| Nalm6 | 90735.3 | 91482.2 | 98863.8 | 59924.4 | 59786.6 | 64853.3 |
| T Cells Alone | | | | 31.3053 | 784287 | 81.2964 |

| Cell Type | 2 | | | 3 | | |
|---|---|---|---|---|---|---|
| Raji | 20933.5 | 16844.6 | 18439.3 | 11943.1 | 11014.1 | 12652.8 |
| Raji CD20KO | 56081.3 | 52181.7 | 57347.3 | 4569.03 | 5957.66 | 3498.72 |
| Namalwa | 4394.22 | 2694.15 | 3891.21 | 519.957 | 3115.59 | 3057.82 |
| Nalm6 | 2658.44 | 3592.39 | 5366.27 | 305.796 | 2897.74 | 3346.3 |
| T Cells Alone | 25.6924 | 18.7526 | 11.3603 | 26.524 | 20.1956 | −1.40636 |

| Cell Type | 4 | | | 5 | | |
|---|---|---|---|---|---|---|
| Raji | 22070.7 | 28253 | 17675.7 | 14077.7 | 14314.2 | 10548.3 |
| Raji CD20KO | 10671 | 12115.3 | 7939.32 | 5497.05 | 4740.32 | 3396.25 |
| Namalwa | 2134.36 | 1335.68 | 1012.9 | 209.453 | 3599.39 | 112.932 |
| Nalm6 | 379.48 | 231.061 | 1459.7 | 386.438 | 393.678 | 259.554 |
| T Cells Alone | 76.2154 | 50.5227 | 19.5781 | 61.926 | 24.5794 | 4.43293 |

| Cell Type | 6 | | | 7 | | |
|---|---|---|---|---|---|---|
| Raji | 18323.8 | 20951.1 | 13738 | 12898.1 | 13121.6 | 11526.1 |
| Raji CD20KO | 16686.9 | 15579.5 | 10419.2 | 17695.6 | 15896.4 | 12334.8 |
| Namalwa | 294.986 | 262.702 | 290.627 | 156.625 | 84.3594 | 212.663 |
| Nalm6 | 274.516 | 183.039 | 319.083 | 185.179 | 188.334 | 200.887 |
| T Cells Alone | 48.7191 | 15.8604 | 32.1614 | 35.2493 | 59.7065 | 25.6558 |

| Cell Type | 8 | | | 9 | | |
|---|---|---|---|---|---|---|
| Raji | 20733.1 | 21458.2 | 17483 | 23005.8 | 20136 | 21075.7 |
| Raji CD20KO | 52536.7 | 49496 | 44758.5 | 9961.2 | 10555.9 | 5704.38 |
| Namalwa | 847.869 | 815.512 | 533.335 | 532.712 | 306.157 | 265.491 |
| Nalm6 | 427.827 | 272.767 | 816.448 | 248.126 | 248.976 | 188.004 |
| T Cells Alone | 31.0058 | 17.5848 | 1.5163 | 34.0876 | 48.9268 | 4.17612 |

| Cell Type | 10 | | | 11 | | |
|---|---|---|---|---|---|---|
| Raji | 15456.7 | 17261 | 13376.7 | 9450.65 | 6450.55 | 3648.15 |
| Raji CD20KO | 1032.2 | 1686.96 | 867.172 | 23411.8 | 46859.6 | 39609.5 |
| Namalwa | 173.011 | 170.523 | 157.236 | 180.832 | 376.613 | 147.429 |
| Nalm6 | 309.551 | 236.001 | 148.273 | 1231.56 | 1128.79 | 1102.86 |
| T Cells Alone | 48.6274 | 28.5599 | 17.4688 | 55.8118 | 16.6736 | 7.52665 |

TABLE 59-continued

| | 12 | | | 13 | | |
|---|---|---|---|---|---|---|
| Raji | 14053.5 | 17263.2 | 11094.7 | 15470.9 | 13763.4 | 10694 |
| Raji CD20KO | 15535.6 | 17771.9 | 13844.9 | 14099.5 | 14913.9 | 8969.65 |
| Namalwa | 326.695 | 492.742 | 221.914 | 487.203 | 504.029 | 297.42 |
| Nalm6 | 718.3 | 704.494 | 680.758 | 925.057 | 960.085 | 641.792 |
| T Cells Alone | 25.8577 | 13.3904 | 24.335 | 47.1967 | 22.3783 | −3.57676 |

TABLE 60

| Cell Type | | Group | | | | | | | | | | | |
|---|---|---|---|---|---|---|---|---|---|---|---|---|---|
| | Targets Alone | | | 1 | | | 2 | | | 3 | | | |
| Raji | 79202.8 | 70452 | 71294.3 | 70496.5 | 65321.5 | 58423.9 | 42813 | 44348.5 | 37624.9 | 39257.9 | 38721.7 | 30611 | |
| Namalwa | 38530.1 | 44751.2 | 48600.5 | 33819.1 | 32454.5 | 41126 | 22632.1 | 19889.3 | 18162 | 22050.6 | 12958.9 | 7359.29 | |
| Nalm6 | 90735.3 | 91482.2 | 98863.8 | 73391.3 | 65922.4 | 72170.8 | 46819.9 | 38689.7 | 34293.5 | 21699.7 | 33426.3 | 9867.04 | |

| | 4 | | | 5 | | | 6 | | | 7 | | | |
|---|---|---|---|---|---|---|---|---|---|---|---|---|---|
| Raji | 44017.5 | 43902.4 | 33164 | 38984.7 | 36843.5 | 36870.2 | 40930.5 | 39351.8 | 36485.6 | 39262.2 | 41832.7 | 34967.1 | |
| Namalwa | 22821.8 | 19476.6 | 18126.5 | 13029.1 | 11967.4 | 9916 | 11781.4 | 9822.72 | 9658.94 | 7294.71 | 7892.54 | 12538.3 | |
| Nalm6 | 44203.2 | 41959.1 | 35773 | 21237.1 | 33388 | 20677.9 | 28267.6 | 23091.1 | 34779.9 | 20386.4 | 18653.5 | 27414.2 | |

| | 8 | | | 9 | | | 10 | | | 11 | | | |
|---|---|---|---|---|---|---|---|---|---|---|---|---|---|
| Raji | 41713 | 45451.7 | 32434 | 39503.7 | 46552.6 | 32453.8 | 39272 | 45873.5 | 27479.8 | 41628.7 | 48931.1 | 30158.6 | |
| Namalwa | 17375.7 | 15523.3 | 16927.4 | 15573.5 | 13148.5 | 10366.2 | 13962.5 | 14478.1 | 7466.35 | 17478.4 | 11443.5 | 2857.6 | |
| Nalm6 | 40265.3 | 34385.2 | 44712.1 | 29146.2 | 33328.6 | 45078.6 | 27153.9 | 24678.3 | 23030.7 | 35739.8 | 25712.2 | 19693.8 | |

| | 12 | | | 13 | | | |
|---|---|---|---|---|---|---|---|
| Raji | 35491 | 40527.2 | 26702.8 | 40345.8 | 43589.9 | 32952.6 | |
| Namalwa | 12422.4 | 9309.45 | 5395.27 | 20039.8 | 18096.3 | 8713.27 | |
| Nalm6 | 32197.1 | 22364.4 | 6859.16 | 21170.7 | 23463 | 18225.7 | |

TABLE 61A

| | | TNFa | | | | | | |
|---|---|---|---|---|---|---|---|---|
| Cell type | Group | | Replicates | | Group | | Replicates | |
| Raji | 1 | 742.7049 | 719.9322 | 860.8748 | 2 | 13789.44 | 1000.926 | 13787.09 |
| | | | | | 3 | 40482.31 | 10509.95 | 22032.99 |
| | | | | | 4 | 29963.57 | 10729.04 | 30770.2 |
| Raji CD20KO | 1 | 141.045 | 123.2006 | 193.527 | 2 | 2335.533 | 136.1735 | 1378.167 |
| | | | | | 3 | 12412.38 | 1591.951 | 6519.058 |
| | | | | | 4 | 19806.9 | 5900.966 | 28857.1 |
| Namalwa | 1 | 51.37436 | 54.13314 | 67.40804 | 2 | 5755.176 | 760.4728 | 4287.225 |
| | | | | | 3 | 13230.78 | 5171.471 | 4564.486 |
| | | | | | 4 | 16464.95 | 1756.426 | 29002.14 |
| Nalm6 | 1 | 85.77411 | 41.52716 | 65.44027 | 2 | 2071.754 | 243.4781 | 1436.396 |
| | | | | | 3 | 5188.394 | 354.1513 | 3276.759 |
| | | | | | 4 | 8136.712 | 3462.309 | 9516.77 |
| T cells alone | 1 | 32.09018 | 27.34532 | 41.75542 | 2 | 60.93963 | | 73.35283 |
| | | | | | 3 | 53.7447 | 132.6905 | 40.34432 |
| | | | | | 4 | 202.1004 | 49.30805 | 404.2379 |
| Raji | 5 | 5234.629 | 29643.24 | 25173.66 | 8 | 11804.04 | 5948.771 | 17987.23 |
| | 6 | 5881.73 | 11238.04 | 12382.32 | 9 | 23295.94 | 32399.1 | 41903.58 |
| | 7 | 14913.76 | 7566.033 | 20158.56 | 10 | 25189.57 | 6263.5 | 30133.63 |
| Raji CD20KO | 5 | 5938.115 | 6402.741 | 5130.22 | 8 | 215.2762 | 905.5388 | 2441.275 |
| | 6 | 13127.4 | 3087.198 | 2251.109 | 9 | 1131.756 | 11010.04 | 17227.01 |
| | 7 | 5314.634 | 3215.46 | 968.1883 | 10 | 1335.315 | 4004.466 | 19501.31 |
| Namalwa | 5 | 10163.08 | 41246.69 | 4330.718 | 8 | 769.9154 | 1797.08 | 12106.37 |
| | 6 | 16230.87 | 15604.86 | 3141.588 | 9 | 1521.87 | 8562.425 | 28414.64 |
| | 7 | 12714.45 | 16044.57 | 5474.505 | 10 | 2997.275 | 2239.813 | 23060.28 |
| Nalm 6 | 5 | 2356.156 | 601.0444 | 4148.512 | 8 | 2480.164 | 547.2608 | 1625.393 |
| | 6 | 4695.265 | 555.9875 | 735.1625 | 9 | 5150.879 | 998.5473 | 7296.929 |
| | 7 | 3560.739 | 2614.049 | 485.996 | 10 | 5296.607 | 666.9747 | 3631.616 |
| T cells alone | 5 | 35.14156 | 55.05909 | 86.07184 | 8 | 60.31223 | 26.13958 | 107.2801 |
| | 6 | 79.07053 | 56.76139 | 11.75329 | 9 | 48.80656 | 33.28641 | 122.8503 |
| | 7 | 94.67347 | 121.4341 | 87.89045 | 10 | 54.93238 | 77.29811 | 41.86264 |

TABLE 61A-continued

| Cell type | Group | | Replicates | | Group | Replicates |
|---|---|---|---|---|---|---|
| | | | | TNFa | | |
| Raji | 11 | 2228.672 | 3952.296 | 5817.774 | | |
| | 12 | 3639.337 | 7400.496 | 9585.174 | | |
| | 13 | 4699.947 | 13583.39 | 10646.23 | | |
| Raji CD20KO | 11 | 343.0228 | 138.8956 | 455.7918 | | |
| | 12 | 666.3561 | 1570.956 | 2033.204 | | |
| | 13 | 904.006 | 2134.385 | 1311.669 | | |
| Namalwa | 11 | 712.1625 | 1751.303 | 1156.45 | | |
| | 12 | 1605.915 | 5712.698 | 1989.63 | | |
| | 13 | 1850.41 | 7176.859 | 1563.88 | | |
| Nalm6 | 11 | 1952.569 | 90.90757 | 194.5827 | | |
| | 12 | 1909.742 | 237.1462 | 229.7622 | | |
| | 13 | 623.5514 | 305.8666 | 204.3989 | | |
| T cells alone | 11 | 53.96276 | 48.59063 | 37.73721 | | |
| | 12 | 73.1479 | 38.83681 | 45.07434 | | |
| | 13 | 59.63715 | 65.16515 | 32.03268 | | |

TABLE 61B

| Cell type | Group | Replicates | | | Group | Replicates | | |
|---|---|---|---|---|---|---|---|---|
| | | | | IL-2 | | | | |
| Raji | 1 | 322.5795 | 320.5048 | 350.4306 | 2 | 2073.658 | 100.1265 | 1416.118 |
| | | | | | 3 | 20921.12 | 8886.709 | 26954.08 |
| | | | | | 4 | 10616.69 | 2267.245 | 8153.757 |
| Raji CD20KO | 1 | 144.0881 | 141.6475 | 157.9271 | 2 | 114.382 | 35.60637 | 55.48347 |
| | | | | | 3 | 6247.868 | 1515.275 | 6207.359 |
| | | | | | 4 | 3882.511 | 839.9909 | 3086.204 |
| Namalwa | 1 | 143.7966 | 154.0605 | 106.577 | 2 | 85.0148 | 24.75363 | 71.28991 |
| | | | | | 3 | 2232.844 | 952.9922 | 4293.162 |
| | | | | | 4 | 668.272 | 175.3299 | 638.2828 |
| Nalm6 | 1 | 83.28817 | 95.77933 | 86.58723 | 2 | 39.02308 | 28.937 | 30.45196 |
| | | | | | 3 | 345.5094 | 81.29567 | 483.7254 |
| | | | | | 4 | 55.70095 | 10.65965 | 45.28578 |
| T cells alone | 1 | 2.475707 | 2.907949 | 3.047796 | 2 | 7.311224 | 14.58527 | 15.62037 |
| | | | | | 3 | 2.694135 | 186.4649 | 6.853129 |
| | | | | | 4 | 2.898734 | 7.362667 | 5.307659 |
| Raji | 5 | 3510.081 | 9491.165 | 16208.74 | 8 | 9435.531 | 3440.359 | 7830.216 |
| | 6 | 3804.56 | 15811.23 | 31095.21 | 9 | 36918.38 | 16658.88 | 38763.1 |
| | 7 | 1753.378 | 7711.317 | 11902.51 | 10 | 14906.08 | 5990.056 | 18862.47 |
| Raji CD20KO | 5 | 2277.17 | 1268.5 | 1623.264 | 8 | 70.68176 | 108.5994 | 239.3027 |
| | 6 | 5142.875 | 3411.332 | 4541.088 | 9 | 1584.179 | 2889.009 | 8581.598 |
| | 7 | 2575.962 | 1500.105 | 1613.56 | 10 | 666.248 | 3000.571 | 9240.457 |
| Namalwa | 5 | 2547.378 | 3062.228 | 1450.611 | 8 | 303.5536 | 593.7966 | 1560.495 |
| | 6 | 6034.566 | 10971.02 | 6869.738 | 9 | 2305.998 | 3875.078 | 11899.19 |
| | 7 | 2975.146 | 4558.808 | 1835.84 | 10 | 595.2925 | 1550.197 | 4864.39 |
| Nalm6 | 5 | 132.1701 | 71.77628 | 102.7936 | 8 | 72.12333 | 50.96007 | 80.62564 |
| | 6 | 183.3285 | 176.8246 | 267.3849 | 9 | 823.2917 | 299.8667 | 901.03 |
| | 7 | 51.11399 | 50.24134 | 57.06661 | 10 | 221.3179 | 102.692 | 234.6751 |
| T cells alone | 5 | 12.70908 | 18.65894 | 16.35375 | 8 | 17.00011 | 13.59572 | 15.75731 |
| | 6 | 8.719928 | 7.591335 | 11.91575 | 9 | 8.642956 | 4.919328 | 11.89729 |
| | 7 | 5.717691 | 4.289614 | 6.980622 | 10 | 5.387739 | 3.932472 | 9.043607 |
| Raji | 11 | 823.133 | 3402.324 | 896.7429 | | | | |
| | 12 | 2799.535 | 6101.386 | 1873.887 | | | | |
| | 13 | 2180.811 | 6525.733 | 2506.268 | | | | |
| Raji CD20KO | 11 | 43.58357 | 76.1947 | 47.89087 | | | | |
| | 12 | 84.85969 | 225.7324 | 65.41539 | | | | |
| | 13 | 101.4673 | 179.8601 | 106.4787 | | | | |
| Namalwa | 11 | 96.9067 | 180.8989 | 87.23379 | | | | |
| | 12 | 228.7018 | 503.392 | 198.3201 | | | | |
| | 13 | 201.064 | 208.7059 | 125.427 | | | | |
| Nalm6 | 11 | 36.04238 | 35.06366 | 29.59289 | | | | |
| | 12 | 6.91882 | 11.08133 | 4.670726 | | | | |
| | 13 | 12.17589 | 7.01667 | 5.499756 | | | | |
| T cells alone | 11 | 14.98063 | 15.91492 | 13.15346 | | | | |
| | 12 | 5.901473 | 6.110295 | 5.688816 | | | | |
| | 13 | 4.758223 | 3.894212 | 3.511602 | | | | |

TABLE 61C

| | | IL-10 | | | | | | |
|---|---|---|---|---|---|---|---|---|
| Cell type | Group | | Replicates | | Group | | Replicates | |
| Raji | 1 | 178.0432 | 142.8539 | 120.4695 | 2 | 895.8653 | 69.6716 | 892.6929 |
| | | | | | 3 | 1097.383 | 275.2268 | 630.683 |
| | | | | | 4 | 1609.907 | 633.7046 | 1807.731 |
| Raji CD20KO | 1 | 97.01133 | 85.2923 | 53.7706 | 2 | 309.4966 | 28.25922 | 239.7828 |
| | | | | | 3 | 606.8257 | 91.35382 | 309.2822 |
| | | | | | 4 | 1253.292 | 391.0293 | 1863.251 |
| Namalwa | 1 | 33.10979 | 35.6513 | 34.88744 | 2 | 573.4806 | 68.91302 | 432.3923 |
| | | | | | 3 | 646.463 | 239.0274 | 221.7614 |
| | | | | | 4 | 1527.354 | 192.0951 | 2717.487 |
| Nalm6 | 1 | 50.10573 | 56.39945 | 79.07014 | 2 | 185.7021 | 24.16594 | 125.913 |
| | | | | | 3 | 443.9515 | 46.61747 | 273.2845 |
| | | | | | 4 | 1161.58 | 507.9296 | 1320.574 |
| T cells alone | 1 | 30.33024 | 36.6716 | 31.08655 | 2 | 30.82579 | 5.067228 | 35.02344 |
| | | | | | 3 | 32.25264 | 2.559772 | 29.35922 |
| | | | | | 4 | 64.27 | 10.88138 | 106.1506 |
| Raji | 5 | 251.3409 | 1515.368 | 1375.689 | 8 | 510.7076 | 293.819 | 798.0907 |
| | 6 | 161.179 | 290.4449 | 338.9459 | 9 | 273.8515 | 394.2801 | 513.9037 |
| | 7 | 773.2684 | 422.0451 | 1022.366 | 10 | 463.0497 | 110.0162 | 621.5802 |
| Raji CD20KO | 5 | 872.8176 | 934.0822 | 703.4425 | 8 | 47.28079 | 112.9426 | 333.4111 |
| | 6 | 1060.602 | 244.7751 | 222.7141 | 9 | 48.86976 | 422.8751 | 674.2297 |
| | 7 | 807.5648 | 530.7835 | 124.8675 | 10 | 79.00288 | 134.7437 | 641.66 |
| Namalwa | 5 | 1079.3 | 3961.233 | 446.361 | 8 | 92.83561 | 137.2657 | 913.6063 |
| | 6 | 953.3019 | 746.7817 | 191.549 | 9 | 67.28244 | 274.0883 | 832.4924 |
| | 7 | 1364.544 | 1637.356 | 531.6147 | 10 | 150.1814 | 100.8329 | 968.0775 |
| Nalm6 | 5 | 412.9091 | 114.515 | 600.812 | 8 | 317.099 | 52.03268 | 148.2565 |
| | 6 | 908.1756 | 76.49075 | 123.8227 | 9 | 394.3369 | 82.53729 | 417.2169 |
| | 7 | 853.5691 | 573.8378 | 106.7992 | 10 | 553.2771 | 50.80476 | 227.2295 |
| T cells alone | 5 | 22.4375 | 26.96257 | 45.5054 | 8 | 22.21889 | 10.15072 | 41.45767 |
| | 6 | 28.556 | 26.16897 | 37.44123 | 9 | 20.68183 | 22.8389 | 39.23846 |
| | 7 | 33.4457 | 30.93852 | 32.09581 | 10 | 17.24112 | 20.44047 | 27.8371 |
| Raji | 11 | 95.38296 | 176.1182 | 207.3491 | | | | |
| | 12 | 73.72115 | 147.9041 | 157.5053 | | | | |
| | 13 | 183.7121 | 443.0117 | 331.2405 | | | | |
| Raji CD20KO | 11 | 66.01768 | 35.65559 | 60.18955 | | | | |
| | 12 | 83.15986 | 186.4922 | 223.6873 | | | | |
| | 13 | 168.1965 | 401.8826 | 210.6137 | | | | |
| Namalwa | 11 | 69.36119 | 159.804 | 92.54174 | | | | |
| | 12 | 108.0373 | 334.7655 | 119.5407 | | | | |
| | 13 | 192.2065 | 1887.085 | 163.9822 | | | | |
| Nalm6 | 11 | 249.6969 | 34.90282 | 21.92475 | | | | |
| | 12 | 219.2402 | 53.1071 | 41.7788 | | | | |
| | 13 | 124.2308 | 84.31646 | 49.04896 | | | | |
| T cells alone | 11 | 27.12001 | 36.7858 | 18.54694 | | | | |
| | 12 | 20.80955 | 28.15541 | 15.18784 | | | | |
| | 13 | 26.48491 | 31.52268 | 22.26345 | | | | |

TABLE 61D

| | | IFNg | | | | | | |
|---|---|---|---|---|---|---|---|---|
| Cell type | Group | | Replicates | | Group | | Replicates | |
| Raji | 1 | 41464.96 | 30963.75 | 25447.23 | 2 | 1432613 | 84135.23 | 1386317 |
| | | | | | 3 | 2397286 | 821594.6 | 1846574 |
| | | | | | 4 | 2274190 | 942782.2 | 1937710 |
| Raji CD20K | 1 | 11561.27 | 8586.159 | 5026.661 | 2 | 213743.2 | 12565.5 | 131488.3 |
| | | | | | 3 | 664001.4 | 69248.71 | 373145.3 |
| | | | | | 4 | 1163951 | 304488.7 | 1465425 |
| Namalwa | 1 | 3530.81 | 1842.586 | 2716.459 | 2 | 510701.3 | 52054.34 | 360549.4 |
| | | | | | 3 | 904990.4 | 300162.3 | 336275.7 |
| | | | | | 4 | 1253120 | 116275.2 | 1855904 |
| Nalm6 | 1 | 3899.43 | 3281.217 | 6749.83 | 2 | 163300.5 | 13171.62 | 96551.14 |
| | | | | | 3 | 294888.9 | 14905.42 | 202445.1 |
| | | | | | 4 | 503047.8 | 189820.4 | 597772.9 |
| T cells alon | 1 | 1753.5 | 1876.623 | 1557.067 | 2 | 5403.774 | 1746.713 | 7399.695 |
| | | | | | 3 | 5454.525 | 6663.711 | 5861.042 |
| | | | | | 4 | 23112.12 | 5606.156 | 49759.7 |
| Raji | 5 | 575698 | 1687352 | 1965687 | 8 | 1078730 | 402925.4 | 1348360 |
| | 6 | 519005.7 | 614491.4 | 1018404 | 9 | 1803657 | 1518159 | 2003596 |
| | 7 | 1578042 | 517803 | 1788915 | 10 | 2490064 | 419647.4 | 1932058 |

TABLE 61D-continued

| Cell type | Group | Replicates | | | Group | Replicates | | |
|---|---|---|---|---|---|---|---|---|
| | | | IFNg | | | | | |
| Raji CD20K | 5 | 513259.5 | 347633.9 | 357939.6 | 8 | 24994.79 | 67790.24 | 231769.2 |
| | 6 | 784775.3 | 111826.9 | 115041.6 | 9 | 59348.85 | 419743.6 | 852087.2 |
| | 7 | 487082.8 | 204193.3 | 69028.4 | 10 | 108512.4 | 237310.2 | 1327924 |
| Namalwa | 5 | 1095254 | 1828112 | 422922.4 | 8 | 70351.05 | 121957.9 | 1029824 |
| | 6 | 1460396 | 852559.7 | 222410.3 | 9 | 100939.4 | 489723.7 | 1834780 |
| | 7 | 1421146 | 1201823 | 475557.9 | 10 | 309207.5 | 160166.7 | 1874998 |
| Nalm6 | 5 | 219984.2 | 32995.87 | 314350.1 | 8 | 220363.4 | 32273.67 | 135918 |
| | 6 | 418594.9 | 25470.36 | 50276.03 | 9 | 361549.7 | 49278.98 | 433392.1 |
| | 7 | 364977.2 | 182266.8 | 39687.06 | 10 | 554730 | 52797.1 | 337819.6 |
| T cells alon | 5 | 1805.136 | 1126.776 | 6229.361 | 8 | 5965.458 | 948.2716 | 8793.781 |
| | 6 | 10846.88 | 2035.132 | 8678.811 | 9 | 10854 | 1365.383 | 13795.46 |
| | 7 | 10220.63 | 7642.1 | 8708.371 | 10 | 7452.874 | 5353.539 | 6430.798 |
| Raji | 11 | 205423.6 | 305476.1 | 512645.3 | | | | |
| | 12 | 392821.5 | 750606.6 | 903119.7 | | | | |
| | 13 | 554100.1 | 1314131 | 1028525 | | | | |
| Raji CD20K | 11 | 34116.67 | 12335.53 | 45684.74 | | | | |
| | 12 | 69699.52 | 134538 | 208660.6 | | | | |
| | 13 | 100355.9 | 206666.2 | 149680.4 | | | | |
| Namalwa | 11 | 80511.69 | 155485.4 | 106748 | | | | |
| | 12 | 175944.5 | 544014 | 210348.9 | | | | |
| | 13 | 264515.8 | 565138.4 | 187873.3 | | | | |
| Nalm6 | 11 | 176019.5 | 5267.248 | 15715.26 | | | | |
| | 12 | 229324.8 | 24222.55 | 26877.11 | | | | |
| | 13 | 76258.82 | 31998.6 | 26876.26 | | | | |
| T cells alon | 11 | 2279.092 | 180.2089 | 392.9496 | | | | |
| | 12 | 9621.94 | 1391.83 | 1901.967 | | | | |
| | 13 | 1775.067 | 2816.077 | 947.6876 | | | | |

TABLE 62

| | Group | | | | | | | | | | | |
|---|---|---|---|---|---|---|---|---|---|---|---|---|
| Cell Type | 1 | | | | 2 | | | 3 | | | 4 | |
| Raji | 11.9 | 11.8 | 12.9 | 45 | 31 | 48.7 | 54.1 | 39.9 | 59.7 | 44.2 | 34.3 | 51.2 |
| Raji CD20KO | 12.1 | 12 | 13.2 | 24.7 | 22.4 | 30.2 | 54.7 | 36.9 | 56.4 | 45 | 37.7 | 52.2 |
| Namalwa | 6.78 | 6.78 | 6.72 | 17.9 | 18 | 32.3 | 37.5 | 26.7 | 43.1 | 36.9 | 28.7 | 41.8 |
| Nalm6 | 6.75 | 7.04 | 6.92 | 19.3 | 13.3 | 20.5 | 26.5 | 19.7 | 30.1 | 25.7 | 20.7 | 31.3 |
| T Cells Alone | 3.23 | 2.78 | 3.12 | 7.4 | 6.33 | 9.02 | 679 | 6.13 | 8.11 | 13.3 | 11.6 | 16.4 |

| Cell Type | 5 | | | | 6 | | | 7 | | | 8 | |
|---|---|---|---|---|---|---|---|---|---|---|---|---|
| Raji | 56.6 | 43.3 | 59.9 | 55.1 | 40.8 | 61.6 | 53.7 | 42.2 | 59.1 | 44.2 | 32.2 | 53.4 |
| Raji CD20KO | 45 | 33.7 | 47.8 | 44.7 | 34.5 | 48.2 | 46.5 | 35.1 | 48.5 | 26.2 | 24.8 | 29.5 |
| Namalwa | 41.4 | 26 | 42.7 | 45.1 | 31 | 50.8 | 44.1 | 28.8 | 48.5 | 33.4 | 20.7 | 35.3 |
| Nalm6 | 23.3 | 17.7 | 25.5 | 23.9 | 18.7 | 28.2 | 24.6 | 18.6 | 28.7 | 19.1 | 15.4 | 20.8 |
| T Cells Alone | 3.78 | 3.97 | 5.09 | 5.62 | 5.91 | 7.36 | 8.13 | 8.18 | 9.92 | 4.53 | 4.68 | 4.6 |

| Cell Type | 9 | | | | 10 | | | 11 | | | 12 | |
|---|---|---|---|---|---|---|---|---|---|---|---|---|
| Raji | 53.1 | 40.8 | 57.6 | 55.2 | 42.2 | 60.1 | 49.2 | 35.8 | 55.7 | 51.9 | 37.3 | 58 |
| Raji CD20KO | 48.2 | 38.8 | 53 | 56.4 | 41.8 | 56.3 | 28.2 | 25.3 | 32.6 | 42.3 | 33.8 | 48.6 |
| Namalwa | 44.2 | 30.9 | 41.2 | 42.2 | 30.6 | | 31.9 | 24.8 | | 38.9 | 33.2 | 46.5 |
| Nalm6 | 28.6 | 22.3 | 33 | 28.1 | 23.5 | 32.5 | 17.2 | 17.4 | 22.1 | 21.2 | 19.1 | 28.2 |
| T Cells Alone | 5.01 | 5.5 | 7.29 | 5.37 | 6.24 | 7.4 | 2.9 | 4.18 | 3.67 | 6.67 | 7.27 | 9.39 |

| Cell Type | 13 | | |
|---|---|---|---|
| Raji | 57 | 42 | 61.1 |
| Raji CD20KO | 41.8 | 32.7 | 49.4 |
| Namalwa | 38 | 28.1 | 43.6 |
| Nalm6 | 19.9 | 17.9 | 25.1 |
| T Cells Alone | 3.8 | 4.76 | 5.87 |

TABLE 63

| Cell Type | Group 1 | | | 2 | | | 3 | | | 4 | | |
|---|---|---|---|---|---|---|---|---|---|---|---|---|
| Raji 1:4 | 14.8 | 13.4 | 14.7 | 31.6 | 18.5 | 31.1 | 38.8 | 23.7 | 35.8 | 39.2 | 24.5 | 33.8 |
| Nannlwa 1:4 | 6.6 | 6.61 | 6.55 | 25.5 | 15.4 | 23 | 38.1 | 20.9 | 34.5 | 34.1 | 20.8 | 29.8 |
| Nalm6 1:4 | 9.92 | 9.96 | 10.7 | 21.7 | 16.2 | 19.5 | 31.2 | 22 | 27.8 | 27.5 | 20.7 | 28.5 |
| T Cells Alone | 3.23 | 2.78 | 3.12 | 7.4 | 6.33 | 9.02 | 6.79 | 6.13 | 8.11 | 13.3 | 11.6 | 16.4 |

| Cell Type | 5 | | | 6 | | | 7 | | | 8 | | |
|---|---|---|---|---|---|---|---|---|---|---|---|---|
| Raji 1:4 | 35.9 | 26.4 | 32.5 | 39.9 | 28 | 36.3 | 37.4 | 27.3 | 37.6 | 26.3 | 21.6 | 30.3 |
| Nannlwa 1:4 | 32 | 20 | 32.7 | 37.7 | 23.9 | 42.4 | 36.3 | 20.8 | 36.6 | 25.2 | 17.8 | 25.7 |
| Nalm6 1:4 | 26 | 18.7 | 26.8 | 30.3 | 20.9 | 32.8 | 27.5 | 21.1 | 28.9 | 20.3 | 16.1 | 21.3 |
| T Cells Alone | 3.78 | 3.97 | 5.09 | 5.62 | 5.91 | 7.36 | 8.13 | 8.18 | 9.92 | 453 | 4.68 | 4.6 |

| Cell Type | 9 | | | 10 | | | 11 | | | 12 | | |
|---|---|---|---|---|---|---|---|---|---|---|---|---|
| Raji 1:4 | 35.3 | 28.6 | 39.5 | 33.1 | 28.8 | 40 | 28.2 | 27.9 | 35.6 | 39.3 | 33.7 | 42 |
| Nannlwa 1:4 | 33.8 | 22 | 33.8 | 29.9 | 20.4 | 31.2 | 25 | 19.3 | 27 | 32.2 | 24.6 | 36.4 |
| Nalm6 1:4 | 27.5 | 19.9 | 29 | 26.5 | 20.8 | 26 | 20.4 | 18.6 | 21.8 | 27.4 | 19.5 | 27.9 |
| T Cells Alone | 5.01 | 5.5 | 7.29 | 537 | 6.24 | 7.4 | 2.9 | 4.18 | 3.67 | 6.67 | 7.27 | 9.39 |

| Cell Type | 13 | | |
|---|---|---|---|
| Raji 1:4 | 40 | 36.3 | 44.4 |
| Nannlwa 1:4 | 31 | 22.9 | 36.9 |
| Nalm6 1:4 | 27.8 | 22.4 | 29 |
| T Cells Alone | 3.8 | 4.76 | 5.87 |

TABLE 64

| Cell Type | Group 1 | | | 2 | | | 3 | | | 4 | | |
|---|---|---|---|---|---|---|---|---|---|---|---|---|
| Raji | 1.49 | 1.1 | 1.28 | 9.95 | 8.23 | 8.26 | 8.36 | 6.88 | 4.62 | 29.5 | 28.5 | 27.8 |
| Raji CD20KO | 6.95 | 6.65 | 6.57 | 15.9 | 14.1 | 31.3 | 19.8 | 12 | 25.4 | 39.4 | 38 | 48.7 |
| Namalwa | 1.11 | 1.26 | 1.6 | 28.7 | 28.5 | 29.1 | 23.2 | 19.4 | 19 | 41.7 | 38.6 | 39.8 |
| Nalm6 | 5.44 | 5.04 | 4.13 | 52.2 | 50.4 | 55.8 | 58.5 | 63.8 | 63 | 69.3 | 70.7 | 72.6 |
| T Cells Alone | 4.65 | 2.28 | 3.88 | 15.9 | 14.9 | 16.8 | 22.2 | 23.1 | 22.7 | 67.2 | 68.1 | 70.3 |

| Cell Type | 5 | | | 6 | | | 7 | | | 8 | | |
|---|---|---|---|---|---|---|---|---|---|---|---|---|
| Raji | 23 | 17.5 | 11.2 | 14.3 | 10.9 | 10.4 | 15.1 | 11.9 | 10.7 | 15 | 12.8 | 9.6 |
| Raji CD20KO | 34.9 | 34.3 | 51 | 21.7 | 16.3 | 30.5 | 13.8 | 11.5 | 23 | 16.3 | 19.6 | 29.8 |
| Namalwa | 39.8 | 31.7 | 38.3 | 30.3 | 22.5 | 28.1 | 30 | 25.3 | 26.2 | 28.4 | 23.7 | 24.8 |
| Nalm6 | 68.5 | 72.6 | 74.6 | 60 | 62.2 | 64.6 | 60.5 | 65.3 | 69.4 | 58.6 | 63.5 | 67.1 |
| T Cells Alone | 11.7 | 14 | 14.7 | 26.2 | 27 | 28.7 | 23.9 | 28.9 | 30.2 | 11.2 | 13.4 | 15.1 |

| Cell Type | 9 | | | 10 | | | 11 | | | 12 | | |
|---|---|---|---|---|---|---|---|---|---|---|---|---|
| Raji | 9.59 | 9.11 | 7.33 | 18.4 | 17.3 | 15.6 | 17.4 | 17.4 | 12.6 | 13.1 | 13.4 | 10.1 |
| Raji CD20KO | 21 | 14.7 | 21.4 | 33.3 | 31.1 | 37.5 | 18.6 | 19.2 | 32.1 | 28.7 | 23.7 | 35.7 |
| Namalwa | 19.5 | 14.7 | 14.6 | 32.4 | 30 | 30.8 | 38.7 | 44.1 | 40.8 | 34.2 | 33.1 | 31.7 |
| Nalm6 | 43.5 | 44.1 | 49.2 | 61.7 | 69.8 | 68.8 | 48.6 | 47.8 | 56.2 | 65.8 | 68.3 | 67.8 |
| T Cells Alone | 23.3 | 28.1 | 30 | 22.6 | 28.1 | 29 | 5.18 | 5.6 | 7.22 | 36.9 | 43.5 | 45.2 |

| Cell Type | 13 | | |
|---|---|---|---|
| Raji | 9.02 | 8.5 | 5.41 |
| Raji CD20KO | 14.4 | 10.4 | 21.3 |
| Namalwa | 16 | 17.2 | 18.3 |
| Nalm6 | 53.1 | 58 | 58.2 |
| T Cells Alone | 8.53 | 10.8 | 13.7 |

TABLE 65

| Cell Type | Group 1 | | | 2 | | | 3 | | | 4 | | |
|---|---|---|---|---|---|---|---|---|---|---|---|---|
| Raji | 1.66 | 1.42 | 1.4 | 11.3 | 9.83 | 18.6 | 12.8 | 11.2 | 18.3 | 36 | 31.4 | 44.3 |
| Namalwa | 1.2 | 1.41 | 1.05 | 18.8 | 17.4 | 25.2 | 20.8 | 19.2 | 32.8 | 33.3 | 37.8 | 44.2 |
| Nalm6 | 2.34 | 2.23 | 2.22 | 31 | 28.9 | 38.3 | 28.7 | 30.4 | 39.1 | 40.2 | 46.1 | 51.9 |

TABLE 65-continued

| | Group | | | | | | | | | | | |
|---|---|---|---|---|---|---|---|---|---|---|---|---|
| T Cells Alone | 4.65 | 2.28 | 3.88 | 15.9 | 14.9 | 16.8 | 22.2 | 23.1 | 22.7 | 67.2 | 68.1 | 70.3 |

| Cell Type | 5 | | | | 6 | | | 7 | | | 8 | |
|---|---|---|---|---|---|---|---|---|---|---|---|---|
| Raji | 18.6 | 20.5 | 25.8 | 14.8 | 13 | 21.3 | 15.6 | 13.2 | 21.2 | 11.3 | 12.7 | 20.4 |
| Namalwa | 22.5 | 25.8 | 31.3 | 23.6 | 25.6 | 34.4 | 22.2 | 22.9 | 31 | 17.1 | 16.9 | 24.8 |
| Nalm6 | 45.9 | 43.3 | 48.4 | 39.9 | 43.2 | 44.6 | 37.6 | 45.6 | 49.7 | 27.3 | 31.2 | 39.4 |
| T Cells Alone | 11.7 | 14 | 14.7 | 26.2 | 27 | 28.7 | 23.9 | 28.9 | 30.2 | 11.2 | 13.4 | 15.1 |

| Cell Type | 9 | | | 10 | | | 11 | | | 12 | | |
|---|---|---|---|---|---|---|---|---|---|---|---|---|
| Raji | 9.42 | 9.78 | 15.3 | 17.6 | 15.3 | 22.6 | 12.2 | 16.5 | 18.3 | 10.2 | 11.4 | 18.1 |
| Namalwa | 13.3 | 14.5 | 22.6 | 23.6 | 23.5 | 29.5 | 20.3 | 17.1 | 26.9 | 20.7 | 20.2 | 31 |
| Nalm6 | 30.3 | 27.4 | 34.9 | 35.6 | 36.8 | 50.7 | 32.9 | 48.3 | 65.4 | 41 | 50 | 60.7 |
| T Cells Alone | 23.3 | 28.1 | 30 | 22.6 | 28.1 | 29 | 518 | 5.6 | 7.22 | 36.9 | 43.5 | 45.2 |

| Cell Type | 13 | | |
|---|---|---|---|
| Raji | 6.57 | 8.41 | 8.1 |
| Namalwa | 9.64 | 7.92 | 14.8 |
| Nalm6 | 22.1 | 22.9 | 38.9 |
| T Cells Alone | 8.53 | 10.8 | 13.7 |

Example 18

TABLE 66

Exemplary Binding motif sequences

| SEQ ID NO | VH/VL Of Table: | Sequence |
|---|---|---|
| 251 | Table 4 | ggtaccCCCGGgCCCATGGCTCTTCCTGTGACAGCTCTTCTGCTGC<br>CCCTGGCCCTGCTTCTGCATGCTGCTAGACCTCAGGTTCAGTTG<br>CAGCAATGGGGAGCTGGCCTGTTAAAGCCCAGCGAAACCCTGT<br>CCCTCACCTGCGCTGTGTATGGCGGAAGCTTCAGCGGCTATTA<br>CTGGAGCTGGATCCGGCAGCCTCCTGGAAAAGGATTAGAATGG<br>ATCGGCGAGATAGACCACAGCGGGAGCACAAACTACAACCCC<br>AGCCTGAAATCGCGGGTTACAATCTCTGTGGACACAAGCAAGA<br>ATCAGTTCTCCCTGAAGCTGAGCAGCGTTACTGCCGCCGACAC<br>AGCTGTGTACTATTGCGCCAGAGGCGGAGGCTCCTGGTACAGC<br>AACTGGTTCGATCCTTGGGGCCAAGGCACCATGGTGACCGTTT<br>CCAGCGGCTCTACAAGCGGCAGCGGGAAACCTGGTTCTGGAGA<br>GGGCAGCACAAAGGGCGACATCCAGATGACACAGAGCCCCAG<br>CACCCTTAGCGCCTCTGTGGGAGATAGGGTTACCATTACCTGC<br>AGGGCTTCCCAGAGCATCAGCAGCTGGCTGGCATGGTATCAAC<br>AGAAGCCTGGCAAGGCTCCCAAGCTGCTCATCTATGACGCCTC<br>CAGCCTGGAAAGCGGGGTTCCCTCCAGATTTAGCGGCTCAGGC<br>TCCGGAACAGAGTTCACCCTTACCATCTCTAGCCTGCAACCCG<br>ACGACTTCGCTACTTATTACTGTCAACAAGACAGAAGCTTGCC<br>CCCCACATTCGGCGGAGGGACCAAGGTTGAGATCAAG |
| 252 | Table 5 | ggtaccCCCGGgCCCATGGCTCTTCCTGTGACAGCTCTTCTGCTGC<br>CCCTGGCCCTGCTTCTGCATGCTGCTAGACCTCAGGTTCAGTTG<br>CAGCAATGGGGAGCTGGCCTGTTAAAGCCCAGCGAAACCCTGT<br>CCCTCACCTGCGCTGTGTATGGCGGAAGCTTCAGCGGCATCCA<br>CTGGAACTGGATCCGGCAGCCTCCTGGCAAAGGCCTTGAATGG<br>ATCGGCGATATCGACACCAGCGGCTCCACCAACTACAACCCCA<br>GCCTGAAATCGAGGGTTACAATCTCTGTGGACACAAGCAAGAA<br>TCAGTTCTCCCTGAAGCTGAGCAGCGTTACTGCCGCCGACACA<br>GCTGTGTACTATTGCGCCAGACTGGGCCAGGAAAGCGCTACCT<br>ACCTTGGCATGGATGTGTGGGGGCAGGGCACCACCGTTACTGT<br>TAGCTCTGGCTCAACAAGCGGCAGCGGCAAGCCTGGCTCAGGA<br>GAAGGAAGCACAAAGGGCGACATTGTAATGACTCAGAGCCCC<br>GACAGCCTGGCCGTTAGCTTAGGCGAAAGGGCTACAATCAATT<br>GCAAGAGCAGCCAGAGCGTTCTGTACAGCAGCAACAACAAGA<br>ACTACCTCGCATGGTATCAACAGAAGCCAGGCCAGCCTCCCAA<br>GCTGCTCATCTACTGGGCTTCCACCAGAGAGAGCGGGGTTCCC<br>GATAGATTCTCCGGCTCCGGTTCTGGAACAGATTTCACGCTCAC<br>AATCAGCAGCTTACAGGCCGAGGATGTGGCTGTCTACTATTGT<br>CAGCAGTTGTACACCTACCCCTTCACATTCGGCGGAGGCACCA<br>AGGTTGAGATCAAG |

TABLE 66-continued

| | Exemplary Binding motif sequences | |
| --- | --- | --- |
| SEQ ID NO | VH/VL Of Table: | Sequence |
| 253 | Table 6 | ggtaccCCCGGgCCCATGGCTCTTCCTGTGACAGCTCTTCTGCTGC CCCTGGCCCTGCTTCTGCATGCTGCTAGACCTCAGCTTCAGCTC CAAGAGAGCGGACCTGGCTTAGTGAAGCCCAGCGAAACCCTGT CCCTCACCTGCACCGTTTCTGGCGGAAGCATCAGCAGCTCCAG CTATTACTGGGGATGGATCAGGCAGCCCCCTGGCAAGGGTTTA GAATGGATCGGCTCGATATATTACTCCGGCAGCACCTACTATA ACCCCAGCTTGAAGAGCCGGGTTACCATTTCTGTGGACACATC AAAGAACCAGTTCAGCCTGAAGCTGAGCTCTGTGACTGCCGCC GACACAGCTGTGTACTACTGTGCCAGAGAGACAGACTACTCCA GCGGCATGGGCTACGGCATGGATGTGTGGGGACAAGGAACCA CCGTTACTGTGAGCAGCGGTTCCACCAGCGGCTCAGGCAAGCC TGGCTCAGGAGAAGGAAGCACCAAGGGGGATATACAGATGAC ACAGAGCCCCTCCAGCCTGTCCGCCAGCGTTGGCGATCGTGTA ACGATCACCTGCCGGGCCTCTCAGAGCATCAACTCCTACCTCA ATTGGTATCAACAGAAGCCAGGCAAGGCCCCAAATTACTCAT CTACGCCGCCAGCAGCTTACAGAGCGGGGTTCCCTCTAGATTC TCCGGCTCCGGTTCTGGAACAGATTTCACCCTCACTATCTCCAG CTTGCAGCCCGAGGATTTCGCCACTTATTACTGTCAGCAGAGC CTGGCCGACCCCTTCACATTCGGCGGAGGCACAAAGGTTGAGA TCAAG |
| 254 | Table 7 | ggtaccCCCGGgCCCATGGCTCTTCCTGTGACAGCTCTTCTGCTGC CCCTGGCCCTGCTTCTGCATGCTGCTAGACCTCAGGTTCAGCTT GTGCAGAGCGGAGCTGAAGTTAAGAAGCCTGGCGCCTCTGTGA AGGTTAGCTGCAAGGCCAGCGGCTACACATTCAAGGAATATGG CATCTCCTGGGTTAGGCAGGCTCCCGGCCAAGGCTTAGAATGG ATGGGCTGGATCTCCGCCTACTCCGGCCACACCTACTACGCCC AGAAGCTTCAGGGCAGGGTTACCATGACCACCGACACCAGCAC CTCTACCGCCTATATGGAGCTGAGGAGCCTGAGATCGGACGAC ACAGCTGTGTATTACTGCGCCAGAGGCCCCCACTACGACGACT GGTCTGGATTTATCATCTGGTTCGACCCCTGGGGGCAGGGCAC CCTGGTCACAGTTTCTTCTGGCTCCACCAGCGGAAGCGGCAAG CCAGGCTCAGGCGAAGGATCTACAAAAGGCGACATCCAAATG ACACAGAGCCCCAGCAGCTTGAGCGCCTCCGTTGGCGACAGAG TTACAATCACCTGCAGGGCCTCTCAGAGCATCAGCAGCTATTT GAATTGGTATCAACAGAAGCCAGGAAAGGCCCCTAAGCTGCTC ATCTACGCTGCCAGCTCGCTCCAATCTGGCGTTCCTAGCAGATT TAGCGGCTCCGGCAGCGGCACAGACTTTACTCTTACCATTAGC TCCCTGCAGCCCGAGGACTTCGCTACCTACTATTGCCAGCAAA GCTACAGATTCCCTCCCACCTTTGGCCAGGGCACAAAGGTTGA GATCAAG |
| 255 | Table 8 | ggtaccCCCGGgCCCATGGCTCTTCCTGTGACAGCTCTTCTGCTGC CCCTGGCCCTGCTTCTGCATGCTGCTAGACCTCAGGTTCAGTTA CAAGAGAGCGGACCTGGCTTAGTGAAGCCCAGCGAAACCCTGT CCCTCACCTGCACCGTTTCTGGCGGAAGCATCAGCTCTCCCGAC CATTACTGGGGATGGATCAGGCAGCCCCCTGGCAAGGGTTTGG AATGGATCGGCAGCATCTACGCCAGCGGCAGCACATTCTACAA CCCCTCGCTCAAAAGCAGGGTTACTATTTCTGTGGACACAAGC AAAAATCAGTTCAGCCTGAAGCTGAGCTCTGTGACTGCCGCCG ACACAGCTGTGTACTACTGTGCCAGAGAGACAGACTACTCCAG CGGGATGGGCTACGGCATGGATGTGTGGGGACAAGGAACCAC CGTTACTGTGAGCAGCGGCTCCACAAGCGGCTCAGGCAAGCCT GGCTCAGGAGAAGGAAGCACCAAGGGGGACATTCAAATGACC CAAAGCCCCTCCAGCCTGTCCGCCAGCGTTGGCGATAGGGTTA CCATTACCTGCAGGGCCAGCCAAAGCATCAACTCCTACCTAAA TTGGTATCAACAGAAGCCAGGCAAGGCCCCCAAACTACTCATT TACGCCGCCAGCAGCTTACAGAGCGGGGTTCCCTCTAGATTCT CCGGCAGCGGTTCTGGAACAGATTTCACTCTCACAATATCTTCG CTGCAGCCCGAGGATTTCGCTACCTACTATTGCCAGCAATCCCT GGCCGACCCCTTCACATTCGGCGGAGGCACAAAGGTTGAGATC AAG |
| 256 | Table 9 | ggtaccCCCGGgCCCATGGCTCTTCCTGTGACAGCTCTTCTGCTGC CCCTGGCCCTGCTTCTGCATGCTGCTAGACCTCAGATCACATTA AAAGAGAGCGGACCTACACTGGTGAAGCCCACCCAAACGCTT ACCCTCACCTGCACCTTTAGCGGGTTCAGCTGGACACAGAGG GCGTTGGCGTTGGATGGATCAGGCAGCCTCCTGGCAAAGCCCT CGAATGGCTTGCCCTCATCTACTTCAACGACCAGAAGAGATAC AGCCCCTCCTTAAAATCTCGGCTCACAATCACCAAAGACACAA GCAAAAATCAGTTGTGCTCACCATGACCAACATGGACCCTGT GGACACCGCTGTGTACTACTGTGCCAGAGACACCGGCTACAGC AGATGGTACTACGGGATGGACGTTTGGGGCCAAGGCACCACTG TGACCGTTTCCAGCGGCTCTACAAGCGGCAGCGGGAAACCTGG |

TABLE 66-continued

| | | |
|---|---|---|

Exemplary Binding motif sequences

| SEQ ID NO | VH/VL Of Table: | Sequence |
|---|---|---|
| | | TTCTGGAGAGGGCAGCACAAAGGGCGACATCCAGATGACGCA ATCCCCCAGCTCTGTGAGCGCCTCTGTGGGAGACAGAGTTACA ATCACATGCCGGGCCTCCCAGGGCATCAGCTCTTGGCTGGCAT GGTATCAACAGAAGCCTGGCAAGGCTCCCAAGCTGCTCATCTA TGCCGCCTCCTCCTTACAATCTGGAGTTCCCTCCAGGTTCAGCG GGAGCGGCTCAGGAACAGACTTCACCCTTACCATCTCTAGCCT GCAACCCGAGGACTTCGCTACTTATTACTGTCAGCAGGCCTAC GCCTACCCCATCACATTCGGCGGAGGAACAAAGGTTGAGATCA AG |
| 257 | Table 10 | ggtaccCCCGGgCCCATGGCTCTTCCTGTGACAGCTCTTCTGCTGC CCCTGGCCCTGCTTCTGCATGCTGCTAGACCTCAGGTTCAGTTG CAGCAATGGGGAGCTGGCCTGTTAAAGCCCAGCGAAACCCTGT CCCTCACCTGCGCTGTGTATGGCGGAAGCTTCGAGAAATACTA CTGGAGCTGGATCCGGCAGCCTCCCGGCAAAGGCTTAGAATGG ATCGGCGAGATTTATCACAGCGGGCTCACCAACTACAACCCCA GCCTGAAATCTCGAGTTACAATCTCTGTGGACACAAGCAAGAA TCAGTTCTCCCTGAAGCTGAGCAGCGTTACTGCCGCCGACACA GCTGTGTACTATTGCGCCAGAGTTAGATACGACAGCAGCGACA GCTATTACTACAGCTATGACTACGGCATGGATGTGTGGGGGCA GGGCACCACCGTTACTGTCTCCTCTGGATCTACCAGCGGCAGC GGCAAGCCTGGATCTGGCGAAGGAAGCACAAAGGGCGACATT GTGCTCACCCAGAGCCCCGACAGCCTGGCTGTGTCTTTAGGCG AAAGGGCTACCATCAACTGCAAGAGCAGCCAGAGCGTTCTGTA CAGCAGCAACAACAAGAACTACCTTGCTTGGTATCAACAGAAG CCTGGCCAGCCCCCTAAGCTGCTCATCTACTGGGCCTCTAGCA GAGAGAGCGGGGTTCCCGATCGGTTTAGCGGCTCCGGCTCAGG AACCGATTTCACCCTCACTATCTCCAGCCTCCAGGCCGAGGAT GTGGCTGTCTACTATTGTCAGCAGAGCTATAGCTTCCCCTGGAC ATTCGGCGGAGGCACCAAGGTTGAGATCAAG |
| 258 | Table 11 | ggtaccCCCGGgCCCATGGCTCTTCCTGTGACAGCTCTTCTGCTGC CCCTGGCCCTGCTTCTGCATGCTGCTAGACCTCAGGTTCAGTTA CAACAATGGGGAGCTGGCCTGTTAAAGCCCAGCGAAACCCTGT CCCTCACCTGCGCTGTGTATGGCGGAAGCTTCAGCCGCTATGT GTGGAGCTGGATCCGGCAGCCTCCTGGCAAAGGCCTTGAATGG ATCGGAGAGATAGACAGCAGCGGCAAGACCAACTACAACCCC AGCCTGAAATCACGCGTTACAATCTCTGTGGACACAAGCAAGA ATCAGTTCTCCCTGAAGCTGAGCAGCGTTACTGCCGCCGACAC AGCTGTGTACTATTGCGCCAGAGTTAGATACGACAGCTCCGAC AGCTATTACTACAGCTATGACTACGGCATGGATGTGTGGGGGC AGGGCACCACCGTTACAGTTAGCTCTGGAAGCACCAGCGGCTC CGGCAAGCCTGGATCTGGTGAAGGAAGCACAAAGGGCGACAT TGTGCTCACCCAGAGCCCCGACAGCCTGGCTGTGTCTTTAGGC GAAAGGGCTACCATCAACTGCAAGAGCAGCCAGAGCGTTCTGT ACAGCAGCAACAACAAGAACTACCTTGCATGGTATCAACAGA AGCCTGGCCAGCCTCCCAAGCTGCTCATCTACTGGGCCTCTAG CAGAGAGAGCGGGGTTCCCGATCGCTTTAGCGGCAGCGGTTCT GGCACCGATTTCACTCTTACAATCAGCAGCTTACAGGCCGAGG ATGTGGCTGTCTACTATTGTCAGCAGAGCTATAGCTTCCCCTGG ACATTCGGCGGAGGCACCAAGGTTGAGATCAAG |
| 259 | Table 12 | ggtaccCCCGGgCCCATGGCTCTTCCTGTGACAGCTCTTCTGCTGC CCCTGGCCCTGCTTCTGCATGCTGCTAGACCTCAGGTTCAGTTA CAACAATGGGGAGCTGGCCTGTTAAAGCCCAGCGAAACCCTGT CCCTCACCTGCGCTGTGTATGGCGGAAGCTTCAGCGGCTACGC TTGGAGCTGGATTAGACAGCCTCCTGGCAAAGGACTAGAATGG ATCGGAGAGATCGACCACAGAGGCTTCACCAACTACAACCCCA GCCTGAAATCCAGAGTTACAATCTCTGTGGACACAAGCAAGAA TCAGTTCTCCCTGAAGCTGAGCAGCGTTACTGCCGCCGACACA GCTGTGTACTATTGCGCCAGGGTTAGATACGACAGCAGCGACA GCTATTACTACAGCTATGACTACGGCATGGATGTGTGGGGGCA GGGCACCACCGTTACGGTTAGCTCTGGATCTACCAGCGGCAGC GGCAAGCCTGGCTCAGGAGAAGGAAGCACAAAGGGCGACATT GTGCTCACCCAGAGCCCCGACAGCCTGGCCGTTTCTTTAGGCG AAAGGGCTACCATCAACTGCAAGAGCAGCCAGAGCGTTCTGTA CAGCAGCAACAACAAGAACTACCTTGCATGGTATCAACAGAA GCCAGGCCAGCCTCCCAAGCTGCTCATCTACTGGGCCTCTAGC AGAGAGAGCGGGGTTCCCGATAGATTTTCGGGATCAGGCTCCG GCACCGATTTCACTCTTACGATCAGCAGCTTACAGGCCGAGGA TGTGGCTGTCTACTATTGTCAGCAGAGCTATAGCTTCCCCTGGA CATTCGGCGGAGGCACCAAGGTTGAGATCAAG |

TABLE 66-continued

| | | |
|---|---|---|
| | | Exemplary Binding motif sequences |

| SEQ ID NO | VH/VL Of Table: | Sequence |
|---|---|---|
| 260 | Table 13 | ggtaccCCCGGgCCCATGGCTCTTCCTGTGACAGCTCTTCTGCTGC CCCTGGCCCTGCTTCTGCATGCTGCTAGACCTCAGGTTCAGTTA CAACAATGGGGAGCTGGCCTGTTAAAGCCCAGCGAAACCCTGT CCCTCACCTGCGCTGTGTATGGCGGAAGCTTCCAGAAATACTA CTGGAGCTGGATCCGGCAGCCTCCCGGCAAAGGCTTAGAATGG ATCGGAGAGATAGACACCAGCGGCTTCACCAACTACAACCCCA GCCTGAAATCTAGGGTTACAATCTCTGTGGACACAAGCAAGAA TCAGTTCTCCCTGAAGCTGAGCAGCGTTACTGCCGCCGACACA GCTGTGTACTATTGCGCCAGAGTTGGCAGATACAGCTACGGCT ACTACATCACCGCCTTCGACATTTGGGGCCAAGGCACCACTGT GACCGTTTCCAGCGGAAGCACTAGCGGCAGCGGGAAACCTGGT TCTGGAGAGGGCTCAACCAAGGGCGACATCGTGATGACACAG AGCCCCGACTCTCTGGCTGTGTCCCTGGGAGAGAGAGCCACCA TCAACTGCAAGAGCAGCCAGAGCGTTCTGTACAGCAGCAACAA CAAGAACTACCTGGCATGGTATCAACAGAAGCCTGGCCAGCCC CCTAAGCTGCTCATCTACTGGGCTTCCACCAGAGAATCAGGCG TTCCAGACAGGTTCTCCGGCTCGGGTTCAGGCACAGACTTCAC CCTTACCATCTCTTCCCTGCAGGCCGAAGATGTGGCCGTTTACT ACTGTCAGCAGCACTACAGCTTCCCTTTCACATTCGGCGGAGG CACCAAGGTTGAGATCAAG |

Example 19

TABLE 67

| | | |
|---|---|---|
| | | Exemplary hinge sequences |

| SEQ ID NO | Hinge | Sequence |
|---|---|---|
| 261 | C8K | GCAGCTGCTTTCGTGCCTGTGTTCCTGCCTGCTAAGCCCACCA CCACTCCTGCTCCAAGACCTCCTACCCCCGCTCCTACAATCGC CAGCCAACCTCTGAGCCTGAGACCGGAGGCATGCAGACCTGCG GCAGGGGGAGCAGTTCACACAAGAGGCTTGGACTTCGCTTGCG ACATCTACATCTGGGCCCCTCTGGCCGGCACATGCGGAGTTCT TCTTCTTAGCCTGGTGATCACCCTGTACTGCAACCACAGAAAC |
| 262 | C28T | GCTGCTGCATTGGATAATGAAAAATCGAACGGCACAATCATTC ATGTGAAGGGCAAACACCTGTGTCCCAGCCCCTTGTTCCCAGG ACCTAGCAAGCCTTTTTGGGTTCTCGTGGTGGTGGGCGGCGTT CTGGCTTGCTACTCTCTACTTGTAACTGTCGCATTTATTATAT TCTGGGTT |
| 263 | C28T1x | GGAGGAGGAGGATCTCTGGATAACGAGAAAAGCAACGGGACCA TCATTCATGTGAAGGGAAAACATCTGTGTCCCAGCCCCTTGTT CCCCGGACCTAGCAAGCCGTTTTGGGTTCTCGTGGTGGTGGGC GGCGTTCTGGCTTGCTACTCTCTGCTTGTGACCGTTGCCTTCA TTATCTTCTGGGTT |
| 264 | C28T2x | GGAGGAGGAGGATCTGGTGGAGGAGGTTCTCTGGACAATGAGA AATCAAATGGAACGATCATCCATGTGAAGGGGAAGCACCTCTG CCCCTCTCCCCTGTTTCCTGGTCCTAGCAAGCCCTTCTGGGTT TTGGTGGTCGTGGGCGGCGTTCTGGCTTGCTACAGCCTGTTAG TGACCGTTGCATTTATCATATTTTGGGTT |
| 265 | C28T2x_NC | GGAGGAGGAGGATCTGGTGGAGGAGGTTCTCTGGACAATGAGA AATCGAATGGGACAATCATCCATGTGAAGGGGAAGCACCTGAG CCCCTCTCCCCTGTTTCCTGGTCCTAGCAAGCCCTTCTGGGTT TTGGTGGTCGTGGGCGGCGTTCTGGCCGTTTACAGCCTGTTAG TGACCGTTGCTTTTATCATATTTTGGGTT |
| 266 | C28T2x_NG | GGAGGAGGAGGATCTGGTGGAGGAGGTTCTCTGGACAATGAAA AGAGCAATGGCACAATCATCCATGTGAAGGGGAAGCACCTGAA CGGCTCCGCCCCTGTTTCCTGGTCCTAGCAAGCCATTTTGGGTT CTCGTGGTGGTGGGCGGCGTTCTGGCCGTTTACAGCCTGTTAG TGACCGTTGCGTTCATAATCTTCTGGGTT |
| 267 | C28T3x | GGAGGAGGAGGATCTGGTGGAGGAGGTTCTGGAGGAGGCGGCT CTCTCGACAACGAAAAGAGCAATGGCACCATTATTCACGTTAA |

TABLE 67-continued

Exemplary hinge sequences

| SEQ ID NO | Hinge | Sequence |
|---|---|---|
| | | AGGCAAGCATCTGTGCCCCTCCCCCCTGTTCCCCGGACCTTCA AAACCTTTTTGGGTTCTCGTGGTGGTGGGCGGCGTTCTGGCCT GCTATTCTTTGCTGGTAACTGTAGCCTTCATTATCTTCTGGGTT |
| 268 | I4 | GAGAGCAAGTACGGACCTCCTTGTCCTCCATGTCCTGCTCCCG AGTTCGAGGGCGGACCTTCAGTGTTCCTGTTCCCCCCTAAACC CAAGGATACTCTTATGATCAGCCGGACCCCCGAGGTCACCTGT GTGGTGGTAGATGTTAGCCAGGAGGATCCCGAGGTGCAGTTCA ACTGGTACGTCGACGGCGTCGAGGTACACAACGCCAAGACCAA GCCTAGGGAGGAGCAGTTCCAGTCCACCTATAGGGTCGTGAGC GTGCTTACCGTGCTGCACCAGGACTGGTTGAACGGCAAGGAGT ACAAGTGCAAGGTGTCCAACAAGGGCCTCCCCAGCAGCATCGA GAAGACCATTAGCAAGGCAAAGGGACAGCCCCAGGGAGCCCCAG GTGTACACATTACCTCCTTCCCAGGAAGAGATGACCAAGAACC AGGTGTCGCTTACCTGCCTGGTCAAGGGCTTCTACCCCTCCGA CATTGCAGTTGAATGGGAGTCAAACGGCCAGCCGGAGAACAAT TACAAGACCACCCCCCCCAGTCTTGGACAGCGACGGCTCTTTCT TCCTCTACTCGCGGCTTACTGTAGATAAAAGTCGTTGGCAGGA GGGAAACGTGTTCAGCTGCTCTGTGATGCACGAGGCCCTCCAT AACCACTACACCCAGAAGAGCCTCTCCCTGTCTCTGGGCAAGA TGTTCTGGGTGCTGGTCGTGGTGGGCGGAGTTCTTGCTTGCTA CTCCCTGCTCGTGACCGTCGCTTTCATTATATTCTGGGTC |
| 269 | I1-2 | GAGAGAAAGTGTTGTGTTGAGTGTCCTCCTTGTCCTCCCTGCC CTGCTCCCGAGTTACTTGGCGGACCTTCAGTGTTCCTGTTCCC CCCCAAGCCCAAGGATACTCTCATGATCAGCCGGACCCCCGAG GTCACCTGTGTGGTGGTAGATGTTAGCCACGAGGACCCTGAGG TCAAGTTCAACTGGTACGTCGACGGCGTCGAGGTGCACAACGC CAAGACCCAAGCCTCGTGAAGAACAGTACCAGTCCACCTACAGA GTTGTGAGCGTGCTTACCGTGCTGCACCAGGACTGGCTGAACG GCAAGGAGTACAAGTGCAAGGTGTCCAACAAGGCCCTCCCCGC TCCCATCGAGAAGACAATCAGCAAGGCCAAGCCCTGTCCAGCC CCTGAGCTCTTAGGAGGACCTAGCGTTTTCCTTTTCCCTCCCA AGCCTAAGGACACTCTTATGATCTCCAGAACACCAGAGGTTAC CTGCGTCGTGGTGGACGTGTCCCATGAGGACCCAGAAGTCAAA TTCAATTGGTATGTAGATGGGGTCGAGGTCCACAACGCTAAGA CAAAGCCCCGCGAGGAGCAGTACAACTCTACCTACAGGGTCGT GTCCGTGCTCACAGTGCTGCATCAGGATTGGCTCAACGGGAAG GAGTATAAGTGCAAAGTGTCCAATAAGGCCCTTCCCGCCCCTA TCGAGAAAACCATCTCTAAGGCCAAATTCTGGGTGCTGGTGGT TGTGGGCGGCGTGCTTGCTTGTTACTCCCTGCTGGTCACTGTA GCTTTCATCATATTTTGGGTG |

Example 20

TABLE 68

Exemplary nucleotide sequences encoding a binding motif, hinge, and 41BB costimulatory domain

| SEQ ID NO | Sequence |
|---|---|
| 271 | ggtaccCCCGGgCCCATGGCTCTTCCTGTGACAGCTCTTCTGCTGCCCCTGGCCC TGCTTCTGCATGCTGCTAGACCTCAGCTTCAGCTCCAAGAGAGCGGACCTGG CTTAGTGAAGCCCAGCGAAACCCTGTCCCTCACCTGCACCGTTTCTGGCGGA AGCATCAGCAGCTCCAGCTATTACTGGGGATGGATCAGGCAGCCCCCTGGCA AGGGTTTAGAATGGATCGGCTCGATATATTACTCCGGCAGCACCTACTATAA CCCCAGCTTGAAGAGCCGGGTTACCATTTCTGTGGACACATCAAAGAACCAG TTCAGCCTGAAGCTGAGCTCTGTGACTGCCGCCGACACAGCTGTGTACTACT GTGCCAGAGAGACAGACTACTCCAGCGGCATGGGCTACGGCATGGATGTGT GGGGACAAGGAACCACCGTTACTGTGAGCAGCGGTTCCACCAGCGGCTCAG GCAAGCCTGGCTCAGGAGAAGGAAGCACCAAGGGGGATATACAGATGACAC AGAGCCCCTCCAGCCTGTCCGCCAGCGTTGGCGATCGTGTAACGATCACCTG CCGGGCCTCTCAGAGCATCAACTCCTACCTCAATTGGTATCAACAGAAGCCA GGCAAGGCCCCCAAATTACTCATCTACGCCGCCAGCAGCTTACAGAGCGGG GTTCCCTCTAGATTCTCCGGCTCCGGTTCTGGAACAGATTTCACCCTCACTAT CTCCAGCTTGCAGCCCGAGGATTTCGCCACTTATTACTGTCAGCAGAGCCTG GCCGACCCCTTCACATTCGGCGGAGGCACAAAGGTTGAGATCAAGGCAGCT GCTTTCGTGCCTGTGTTCCTGCCTGCTAAGCCCACCACCACTCCTGCTCCAAG ACCTCCTACCCCCGCTCCTACAATCGCCAGCCAACCTCTGAGCCTGAGACCG |

TABLE 68-continued

Exemplary nucleotide sequences encoding a binding motif, hinge,
and 41BB costimulatory domain

| SEQ ID NO | Sequence |
|---|---|
| | GAGGCATGCAGACCTGCGGCAGGGGGAGCAGTTCACACAAGAGGCTTGGAC |
| | TTCGCTTGCGACATCTACATCTGGGCCCCTCTGGCCGGCACATGCGGAGTTCT |
| | TCTTCTTAGCCTGGTGATCACCCTGTACTGCAACCACAGAAACAGATTCAGC |
| | GTTGTGAAGAGAGGCCGGAAGAAGCTGCTGTACATCTTCAAGCAGCCCTTCA |
| | TGAGACCTGTGCAGACCACACAGGAGGAAGACGGCTGCAGCTGTAGATTCC |
| | CCGAGGAAGAGGAGGGCGGCTGTGAGCTGAGAGTTAAGTTCAGCAGGAGCG |
| | CCGACGCCCCTGCCTACCAGCAAGGACAGAATCAACTGTACAACGAGCTGA |
| | ACCTGGGCAGACGGGAGGAATACGATGTGCTGGACAAGAGGAGAGGCAGA |
| | GACCCCGAGATGGGCGGCAAACCTAGAAGAAAGAACCCCCAGGAGGGCCTG |
| | TATAACGAGCTCCAGAAGGACAAGATGGCCGAGGCCTACAGCGAGATCGGC |
| | ATGAAGGGCGAAAGAAGAAGAGGCAAGGGCCACGACGGCCTCTACCAGGG |
| | CTTAAGCACAGCTACAAAGGACACCTACGACGCCCTGCACATGCAGGCCCT |
| | GCCCCCTAGATGATTAATTAAatcgat |
| 272 | ggtaccCCCGGgCCCATGGCTCTTCCTGTGACAGCTCTTCTGCTGCCCCTGGCCC |
| | TGCTTCTGCATGCTGCTAGACCTCAGGTTCAGTTACAAGAGAGCGGACCTGG |
| | CTTAGTGAAGCCCAGCGAAACCCTGTCCCTCACCTGCACCGTTTCTGGCGGA |
| | AGCATCAGCTCTCCCGACCATTACTGGGGATGGATCAGGCAGCCCCCTGGCA |
| | AGGGTTTGGAATGGATCGGCAGCATCTACGCCAGCGGCACATTCTACAA |
| | CCCCTCGCTCAAAAGCAGGGTTACTATTTCTGTGGACACAAGCAAAAATCAG |
| | TTCAGCCTGAAGCTGAGCTCTGTGACTGCCGCCGACACAGCTGTGTACTACT |
| | GTGCCAGAGAGACAGACTACTCCAGCGGGATGGGCTACGGCATGGATGTGT |
| | GGGGACAAGGAACCACCGTTACTGTGAGCAGCGGCTCCACAAGCGGCTCAG |
| | GCAAGCCTGGCTCAGGAGAAGGAAGCACCAAGGGGGACATTCAAATGACCC |
| | AAAGCCCCTCCAGCCTGTCCGCCAGCGTTGGCGATAGGGTTACCATTACCTG |
| | CAGGGCCAGCCAAAGCATCAACTCCTACCTAAATTGGTATCAACAGAAGCC |
| | AGGCAAGGCCCCCAAACTACTCATTTACGCCGCCAGCAGCTTACAGAGCGG |
| | GGTTCCCTCTAGATTCTCCGGCAGCGGTTCTGGAACAGATTTCACTCTCACAA |
| | TATCTTCGCTGCAGCCCGAGGATTTCGCTACCTACTATTGCCAGCAATCCCTG |
| | GCCGACCCCTTCACATTCGGCGGAGGCACAAAGGTTGAGATCAAGGCAGCT |
| | GCTTTCGTGCCTGTGTTCCTGCCTGCTAAGCCCACCACCACTCCTGCTCCAAG |
| | ACCTCCTACCCCCGCTCCTACAATCGCCAGCCAACCTCTGAGCCTGAGACCG |
| | GAGGCATGCAGACCTGCGGCAGGGGGAGCAGTTCACACAAGAGGCTTGGAC |
| | TTCGCTTGCGACATCTACATCTGGGCCCCTCTGGCCGGCACATGCGGAGTTCT |
| | TCTTCTTAGCCTGGTGATCACCCTGTACTGCAACCACAGAAACAGATTCAGC |
| | GTTGTGAAGAGAGGCCGGAAGAAGCTGCTGTACATCTTCAAGCAGCCCTTCA |
| | TGAGACCTGTGCAGACCACACAGGAGGAAGACGGCTGCAGCTGTAGATTCC |
| | CCGAGGAAGAGGAGGGCGGCTGTGAGCTGAGAGTTAAGTTCAGCAGGAGCG |
| | CCGACGCCCCTGCCTACCAGCAAGGACAGAATCAACTGTACAACGAGCTGA |
| | ACCTGGGCAGACGGGAGGAATACGATGTGCTGGACAAGAGGAGAGGCAGA |
| | GACCCCGAGATGGGCGGCAAACCTAGAAGAAAGAACCCCCAGGAGGGCCTG |
| | TATAACGAGCTCCAGAAGGACAAGATGGCCGAGGCCTACAGCGAGATCGGC |
| | ATGAAGGGCGAAAGAAGAAGAGGCAAGGGCCACGACGGCCTCTACCAGGG |
| | CTTAAGCACAGCTACAAAGGACACCTACGACGCCCTGCACATGCAGGCCCT |
| | GCCCCCTAGATGATTAATTAAatcgat |
| 273 | ggtaccCCCGGgCCCATGGCTCTTCCTGTGACAGCTCTTCTGCTGCCCCTGGCCC |
| | TGCTTCTGCATGCTGCTAGACCTCAGATCACATTAAAAGAGAGCGGACCTAC |
| | ACTGGTGAAGCCCACCCAAACGCTTACCCTCACCTGCACCTTTAGCGGGTTC |
| | AGCCTGGACACAGAGGGCGTTGGCGTTGGATGGATCAGGCAGCCTCCTGGC |
| | AAAGCCCTCGAATGGCTTGCCCTCATCTACTTCAACGACCAGAAGAGATACA |
| | GCCCCTCCTTAAAATCTCGGCTCACAATCACCAAAGACACAAGCAAAAATCA |
| | GGTTGTGCTCACCATGACCAACATGGACCCTGTGGACACCGCTGTGTACTAC |
| | TGTGCCAGAGACACCGGCTACAGCAGATGGTACTACGGGATGGACGTTTGG |
| | GGCCAAGGCACCACTGTGACCGTTTCCAGCGGCTCTACAAGCGGCAGCGGG |
| | AAACCTGGTTCTGGAGAGGGCAGCACAAAGGGCGACATCCAGATGACGCAA |
| | TCCCCCAGCTCTGTGAGCGCCTCTGTGGGAGACAGAGTTACAATCACATGCC |
| | GGGCCTCCCAGGGCATCAGCTCTTGGCTGGCATGGTATCAACAGAAGCCTGG |
| | CAAGGCTCCCAAGCTGCTCATCTATGCCGCCTCCTCCTTACAATCTGGAGTTC |
| | CCTCCAGGTTCAGCGGGAGCGGCTCAGGAACAGACTTCACCCTTACCATCTC |
| | TAGCCTGCAACCCGAGGACTTCGCTACTTATTACTGTCAGCAGGCCTACGCC |
| | TACCCCATCACATTCGGCGGAGGAACAAAGGTTGAGATCAAGGCAGCTGCTT |
| | TCGTGCCTGTGTTCCTGCCTGCTAAGCCCACCACCACTCCTGCTCCAAGACCT |
| | CCTACCCCCGCTCCTACAATCGCCAGCCAACCTCTGAGCCTGAGACCGGAGG |
| | CATGCAGACCTGCGGCAGGGGGAGCAGTTCACACAAGAGGCTTGGACTTCG |
| | CTTGCGACATCTACATCTGGGCCCCTCTGGCCGGCACATGCGGAGTTCTTCTT |
| | CTTAGCCTGGTGATCACCCTGTACTGCAACCACAGAAACAGATTCAGCGTTG |
| | TGAAGAGAGGCCGGAAGAAGCTGCTGTACATCTTCAAGCAGCCCTTCATGA |
| | GACCTGTGCAGACCACACAGGAGGAAGACGGCTGCAGCTGTAGATTCCCCG |
| | AGGAAGAGGAGGGCGGCTGTGAGCTGAGAGTTAAGTTCAGCAGGAGCGCCG |
| | ACGCCCCTGCCTACCAGCAAGGACAGAATCAACTGTACAACGAGCTGAACC |
| | TGGGCAGACGGGAGGAATACGATGTGCTGGACAAGAGGAGAGGCAGAGAC |
| | CCCGAGATGGGCGGCAAACCTAGAAGAAAGAACCCCCAGGAGGGCCTGTAT |
| | AACGAGCTCCAGAAGGACAAGATGGCCGAGGCCTACAGCGAGATCGGCATG |

TABLE 68-continued

Exemplary nucleotide sequences encoding a binding motif, hinge, and 41BB costimulatory domain

| SEQ ID NO | Sequence |
|---|---|
| | AAGGGCGAAAGAAGAAGAGGCAAGGGCCACGACGGCCTCTACCAGGGCTTA<br>AGCACAGCTACAAAGGACACCTACGACGCCCTGCACATGCAGGCCCTGCCC<br>CCTAGATGATTAATTAAatcgat |
| 274 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAACAATGGGGAGCTGG<br>CCTGTTAAAGCCCAGCGAAACCCTGTCCCTCACCTGCGCTGTGTATGGCGGA<br>AGCTTCCAGAAATACTACTGGAGCTGGATCCGGCAGCCTCCCGGCAAAGGCT<br>TAGAATGGATCGGAGAGATAGACACCAGCGGCTTCACCAACTACAACCCCA<br>GCCTGAAATCTAGGGTTACAATCTCTGTGGACACAAGCAAGAATCAGTTCTC<br>CCTGAAGCTGAGCAGCGTTACTGCCGCCGACACAGCTGTGTACTATTGCGCC<br>AGAGTTGGCAGATACAGCTACGGCTACTACATCACCGCCTTCGACATTTGGG<br>GCCAAGGCACCACTGTGACCGTTTCCAGCGGAAGCACTAGCGGCAGCGGGA<br>AACCTGGTTCTGGAGAGGGCTCAACCAAGGGCGACATCGTGATGACACAGA<br>GCCCCGACTCTCTGGCTGTGTCCCTGGGAGAGAGAGCCACCATCAACTGCAA<br>GAGCAGCCAGAGCGTTCTGTACAGCAGCAACAACAAGAACTACCTGGCATG<br>GTATCAACAGAAGCCTGGCCAGCCCCCTAAGCTGCTCATCTACTGGGCTTCC<br>ACCAGAGAATCAGGCGTTCCAGACAGGTTCTCCGGCTCGGGTTCAGGCACAG<br>ACTTCACCCTTACCATCTCTTCCCTGCAGGCCGAAGATGTGGCCGTTTACTAC<br>TGTCAGCAGCACTACAGCTTCCCTTTCACATTCGGCGGAGGCACCAAGGTTG<br>AGATCAAGGCAGCTGCTTTCGTGCCTGTGTTCCTGCCTGCTAAGCCCACCAC<br>CACTCCTGCTCCAAGACCTCCTACCCCCCGCTCCTACAATCGCCAGCCAACCT<br>CTGAGCCTGAGACCGGAGGCATGCAGACCTGCGGCAGGGGGAGCAGTTCAC<br>ACAAGAGGCTTGGACTTCGCTTGCGACATCTACATCTGGGCCCCTCTGGCCG<br>GCACATGCGGAGTTCTTCTTCTTAGCCTGGTGATCACCCTGTACTGCAACCAC<br>AGAAACAGATTCAGCGTTGTGAAGAGAGGCCGGAAGAAGCTGCTGTACATC<br>TTCAAGCAGCCCTTCATGAGACCTGTGCAGACCACACAGGAGGAAGACGGC<br>TGCAGCTGTAGATTCCCCGAGGAAGAGGAGGGCGGCTGTGAGCTGAGAGTT<br>AAGTTCAGCAGGAGCGCCGACGCCCCTGCCTACCAGCAAGGACAGAATCAA<br>CTGTACAACGAGCTGAACCTGGGCAGACGGGAGGAATACGATGTGCTGGAC<br>AAGAGGAGAGGCAGAGACCCCGAGATGGGCGGCAAACCTAGAAGAAAGAA<br>CCCCCAGGAGGGCCTGTATAACGAGCTCCAGAAGGACAAGATGGCCGAGGC<br>CTACAGCGAGATCGGCATGAAGGGCGAAAGAAGAAGAGGCAAGGGCCACG<br>ACGGCCTCTACCAGGGCTTAAGCACAGCTACAAAGGACACCTACGACGCCC<br>TGCACATGCAGGCCCTGCCCCCTAGATGATTAATTAAatcgat |
| 275 | ggtaccCCCGGgCCCATGGCTCTTCCTGTGACAGCTCTTCTGCTGCCCCTGGCCC<br>TGCTTCTGCATGCTGCTAGACCTCAGGTTCAGTTGCAGCAATGGGGAGCTGG<br>CCTGTTAAAGCCCAGCGAAACCCTGTCCCTCACCTGCGCTGTGTATGGCGGA<br>AGCTTCGAGAAATACTACTGGAGCTGGATCCGGCAGCCTCCCGGCAAAGGCT<br>TAGAATGGATCGGCGAGATTTATCACAGCGGGCTCACCAACTACAACCCCAG<br>CCTGAAATCTCGAGTTACAATCTCTGTGGACACAAGCAAGAATCAGTTCTCC<br>CTGAAGCTGAGCAGCGTTACTGCCGCCGACACAGCTGTGTACTATTGCGCCA<br>GAGTTAGATACGACAGCAGCGACAGCTATTACTACAGCTATGACTACGGCAT<br>GGATGTGTGGGGGCAGGGCACCACCGTTACTGTCTCCTCTGGATCTACCAGC<br>GGCAGCGGCAAGCCTGGATCTGGCGAAGGAAGCACAAAGGGCGACATTGTG<br>CTCACCCAGAGCCCCGACAGCCTGGCTGTGTCTTTAGGCGAAAGGGCTACCA<br>TCAACTGCAAGAGCAGCCAGAGCGTTCTGTACAGCAGCAACAACAAGAACT<br>ACCTTGCTTGGTATCAACAGAAGCCTGGCCAGCCCCCTAAGCTGCTCATCTA<br>CTGGGCCTCTAGCAGAGAGAGCGGGGTTCCCGATCGGTTTAGCGGCTCCGGC<br>TCAGGAACCGATTTCACCCTCACTATCTCCAGCCTCCAGGCCGAGGATGTGG<br>CTGTCTACTATTGTCAGCAGAGCTATAGCTTCCCCTGGACATTCGGCGGAGG<br>CACCAAGGTTGAGATCAAGGCAGCTGCTTTCGTGCCTGTGTTCCTGCCTGCT<br>AAGCCCACCACCACTCCTGCTCCAAGACCTCCTACCCCCGCTCCTACAATCG<br>CCAGCCAACCTCTGAGCCTGAGACCGGAGGCATGCAGACCTGCGGCAGGGG<br>GAGCAGTTCACACAAGAGGCTTGGACTTCGCTTGCGACATCTACATCTGGGC<br>CCCTCTGGCCGGCACATGCGGAGTTCTTCTTCTTAGCCTGGTGATCACCCTGT<br>ACTGCAACCACAGAAACAGATTCAGCGTTGTGAAGAGAGGCCGGAAGAAGC<br>TGCTGTACATCTTCAAGCAGCCCTTCATGAGACCTGTGCAGACCACACAGGA<br>GGAAGACGGCTGCAGCTGTAGATTCCCCGAGGAAGAGGAGGGCGGCTGTGA<br>GCTGAGAGTTAAGTTCAGCAGGAGCGCCGACGCCCCTGCCTACCAGCAAGG<br>ACAGAATCAACTGTACAACGAGCTGAACCTGGGCAGACGGGAGGAATACGA<br>TGTGCTGGACAAGAGGAGAGGCAGAGACCCCGAGATGGGCGGCAAACCTAG<br>AAGAAAGAACCCCCAGGAGGGCCTGTATAACGAGCTCCAGAAGGACAAGAT<br>GGCCGAGGCCTACAGCGAGATCGGCATGAAGGGCGAAAGAAGAAGAGGCA<br>AGGGCCACGACGGCCTCTACCAGGGCTTAAGCACAGCTACAAAGGACACCT<br>ACGACGCCCTGCACATGCAGGCCCTGCCCCCTAGATGATTAATTAAatcgat |
| 276 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAACAATGGGGAGCTGG<br>CCTGTTAAAGCCCAGCGAAACCCTGTCCCTCACCTGCGCTGTGTATGGCGGA<br>AGCTTCAGCCGCTATGTGTGGAGCTGGATCCGGCAGCCTCCTGGCAAAGGCC<br>TTGAATGGATCGGAGAGATAGACAGCAGCGGCAAGACCAACTACAACCCCA<br>GCCTGAAATCACGCGTTACAATCTCTGTGGACACAAGCAAGAATCAGTTCTC |

TABLE 68-continued

Exemplary nucleotide sequences encoding a binding motif, hinge,
and 41BB costimulatory domain

| SEQ ID NO | Sequence |
|---|---|
| | CCTGAAGCTGAGCAGCGTTACTGCCGCCGACACAGCTGTGTACTATTGCGCC<br>AGAGTTAGATACGACAGCTCCGACAGCTATTACTACAGCTATGACTACGGCA<br>TGGATGTGTGGGGGCAGGGCACCACCGTTACAGTTAGCTCTGGAAGCACCA<br>GCGGCTCCGGCAAGCCTGGATCTGGTGAAGGAAGCACAAAGGGCGACATTG<br>TGCTCACCCAGAGCCCCGACAGCCTGGCTGTGTCTTTAGGCGAAAGGGCTAC<br>CATCAACTGCAAGAGCAGCCAGAGCGTTCTGTACAGCAGCAACAACAAGAA<br>CTACCTTGCATGGTATCAACAGAAGCCTGGCCAGCCTCCCAAGCTGCTCATC<br>TACTGGGCCTCTAGCAGAGAGAGCGGGGTTCCCGATCGCTTTAGCGGCAGCG<br>GTTCTGGCACCGATTTCACTCTTACAATCAGCAGCTTACAGGCCGAGGATGT<br>GGCTGTCTACTATTGTCAGCAGAGCTATAGCTTCCCCTGGACATTCGGCGGA<br>GGCACCAAGGTTGAGATCAAGGCAGCTGCTTTCGTGCCTGTGTTCCTGCCTG<br>CTAAGCCCACCACCACTCCTGCTCCAAGACCTCCTACCCCCGCTCCTACAAT<br>CGCCAGCCAACCTCTGAGCCTGAGACCGGAGGCATGCAGACCTGCGGCAGG<br>GGGAGCAGTTCACACAAGAGGCTTGGACTTCGCTTGCGACATCTACATCTGG<br>GCCCCTCTGGCCGGCACATGCGGAGTTCTTCTTCTTAGCCTGGTGATCACCCT<br>GTACTGCAACCACAGAAACAGATTCAGCGTTGTGAAGAGAGGCCGGAAGAA<br>GCTGCTGTACATCTTCAAGCAGCCCTTCATGAGACCTGTGCAGACCACACAG<br>GAGGAAGACGGCTGCAGCTGTAGATTCCCCGAGGAAGAGGAGGGCGGCTGT<br>GAGCTGAGAGTTAAGTTCAGCAGGAGCGCCGACGCCCCTGCCTACCAGCAA<br>GGACAGAATCAACTGTACAACGAGCTGAACCTGGGCAGACGGGAGGAATAC<br>GATGTGCTGGACAAGAGGAGAGGCAGAGACCCCGAGATGGGCGGCAAACCT<br>AGAAGAAAGAACCCCCAGGAGGGCCTGTATAACGAGCTCCAGAAGGACAAG<br>ATGGCCGAGGCCTACAGCGAGATCGGCATGAAGGGCGAAAGAAGAAGAGG<br>CAAGGGCCACGACGGCCTCTACCAGGGCTTAAGCACAGCTACAAAGGACAC<br>CTACGACGCCCTGCACATGCAGGCCCTGCCCCCTAGATGATTAATTAAatcgat |
| 277 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAACAATGGGGAGCTGG<br>CCTGTTAAAGCCCAGCGAAACCCTGTCCCTCACCTGCGCTGTGTATGGCGGA<br>AGCTTCAGCGGCTACGCTTGGAGCTGGATTAGACAGCCTCCTGGCAAAGGAC<br>TAGAATGGATCGGAGAGATCGACCACAGAGGCTTCACCAACTACAACCCCA<br>GCCTGAAATCCAGAGTTACAATCTCTGTGGACACAAGCAAGAATCAGTTCTC<br>CCTGAAGCTGAGCAGCGTTACTGCCGCCGACACAGCTGTGTACTATTGCGCC<br>AGGGTTAGATACGACAGCAGCGACAGCTATTACTACAGCTATGACTACGGC<br>ATGGATGTGTGGGGGCAGGGCACCACCGTTACGGTTAGCTCTGGATCTACCA<br>GCGGCAGCGGCAAGCCTGGCTCAGGAGAAGGAAGCACAAAGGGCGACATTG<br>TGCTCACCCAGAGCCCCGACAGCCTGGCCGTTTCTTTAGGCGAAAGGGCTAC<br>CATCAACTGCAAGAGCAGCCAGAGCGTTCTGTACAGCAGCAACAACAAGAA<br>CTACCTTGCATGGTATCAACAGAAGCCAGGCCAGCCTCCCAAGCTGCTCATC<br>TACTGGGCCTCTAGCAGAGAGAGCGGGGTTCCCGATAGATTTTCGGGATCAG<br>GCTCCGGCACCGATTTCACTCTTACGATCAGCAGCTTACAGGCCGAGGATGT<br>GGCTGTCTACTATTGTCAGCAGAGCTATAGCTTCCCCTGGACATTCGGCGGA<br>GGCACCAAGGTTGAGATCAAGGCAGCTGCTTTCGTGCCTGTGTTCCTGCCTG<br>CTAAGCCCACCACCACTCCTGCTCCAAGACCTCCTACCCCCGCTCCTACAAT<br>CGCCAGCCAACCTCTGAGCCTGAGACCGGAGGCATGCAGACCTGCGGCAGG<br>GGGAGCAGTTCACACAAGAGGCTTGGACTTCGCTTGCGACATCTACATCTGG<br>GCCCCTCTGGCCGGCACATGCGGAGTTCTTCTTCTTAGCCTGGTGATCACCCT<br>GTACTGCAACCACAGAAACAGATTCAGCGTTGTGAAGAGAGGCCGGAAGAA<br>GCTGCTGTACATCTTCAAGCAGCCCTTCATGAGACCTGTGCAGACCACACAG<br>GAGGAAGACGGCTGCAGCTGTAGATTCCCCGAGGAAGAGGAGGGCGGCTGT<br>GAGCTGAGAGTTAAGTTCAGCAGGAGCGCCGACGCCCCTGCCTACCAGCAA<br>GGACAGAATCAACTGTACAACGAGCTGAACCTGGGCAGACGGGAGGAATAC<br>GATGTGCTGGACAAGAGGAGAGGCAGAGACCCCGAGATGGGCGGCAAACCT<br>AGAAGAAAGAACCCCCAGGAGGGCCTGTATAACGAGCTCCAGAAGGACAAG<br>ATGGCCGAGGCCTACAGCGAGATCGGCATGAAGGGCGAAAGAAGAAGAGG<br>CAAGGGCCACGACGGCCTCTACCAGGGCTTAAGCACAGCTACAAAGGACAC<br>CTACGACGCCCTGCACATGCAGGCCCTGCCCCCTAGATGATTAATTAAatcgat |
| 278 | ggtaccCCCGGgCCCATGGCTCTTCCTGTGACAGCTCTTCTGCTGCCCCTGGCCC<br>TGCTTCTGCATGCTGCTAGACCTCAGGTTCAGTTGCAGCAATGGGGAGCTGG<br>CCTGTTAAAGCCCAGCGAAACCCTGTCCCTCACCTGCGCTGTGTATGGCGGA<br>AGCTTCAGCGGCTATTACTGGAGCTGGATCGGCAGCCTCCTGGAAAAGGAT<br>TAGAATGGATCGGCGAGATAGACCACAGCGGGAGCACAAACTACAACCCCA<br>GCCTGAAATCGCGGGTTACAATCTCTGTGGACACAAGCAAGAATCAGTTCTC<br>CCTGAAGCTGAGCAGCGTTACTGCCGCCGACACAGCTGTGTACTATTGCGCC<br>AGAGGCGGAGGCTCCTGGTACAGCAACTGGTTCGATCCTTGGGGCCAAGGC<br>ACCATGGTGACCGTTTCCAGCGGCTCTACAAGCGGCAGCGGGAAACCTGGTT<br>CTGGAGAGGGCAGCACAAAGGGCGACATCCAGATGACACAGAGCCCCAGCA<br>CCCTTAGCGCCTCTGTGGGAGATAGGGTTACCATTACCTGCAGGGCTTCCCA<br>GAGCATCAGCAGCTGGCTGGCATGGTATCAACAGAAGCCTGGCAAGGCTCC<br>CAAGCTGCTCATCTATGACGCCTCCAGCCTGGAAAGCGGGGTTCCCTCCAGA<br>TTTAGCGGCTCAGGCTCCGGAACAGAGTTCACCCTTACCATCTCTAGCCTGC<br>AACCCGACGACTTCGCTACTTATTACTGTCAACAAGACAGAAGCTTGCCCCC<br>CACATTCGGCGGAGGGACCAAGGTTGAGATCAAGGCAGCTGCTTTCGTGCCT |

TABLE 68-continued

Exemplary nucleotide sequences encoding a binding motif, hinge,
and 41BB costimulatory domain

| SEQ ID NO | Sequence |
| --- | --- |
|  | GTGTTCCTGCCTGCTAAGCCCACCACCACTCCTGCTCCAAGACCTCCTACCCC CGCTCCTACAATCGCCAGCCAACCTCTGAGCCTGAGACCGGAGGCATGCAG ACCTGCGGCAGGGGGAGCAGTTCACACAAGAGGCTTGGACTTCGCTTGCGA CATCTACATCTGGGCCCCTCTGGCCGGCACATGCGGAGTTCTTCTTCTTAGCC TGGTGATCACCCTGTACTGCAACCACAGAAACAGATTCAGCGTTGTGAAGAG AGGCCGGAAGAAGCTGCTGTACATCTTCAAGCAGCCCTTCATGAGACCTGTG CAGACCACACAGGAGGAAGACGGCTGCAGCTGTAGATTCCCCGAGGAAGAG GAGGGCGGCTGTGAGCTGAGAGTTAAGTTCAGCAGGAGCGCCGACGCCCCT GCCTACCAGCAAGGACAGAATCAACTGTACAACGAGCTGAACCTGGGCAGA CGGGAGGAATACGATGTGCTGGACAAGAGGAGAGGCAGAGACCCCGAGAT GGGCGGCAAACCTAGAAGAAAGAACCCCCAGGAGGGCCTGTATAACGAGCT CCAGAAGGACAAGATGGCCGAGGCCTACAGCGAGATCGGCATGAAGGGCGA AAGAAGAAGAGGCAAGGGCCACGACGGCCTCTACCAGGGCTTAAGCACAGC TACAAAGGACACCTACGACGCCCTGCACATGCAGGCCCTGCCCCCTAGATGA TTAATTAAatcgat |
| 279 | ggtaccCCCGGgCCCATGGCTCTTCCTGTGACAGCTCTTCTGCTGCCCCTGGCCC TGCTTCTGCATGCTGCTAGACCTCAGGTTCAGCTTGTGCAGAGCGGAGCTGA AGTTAAGAAGCCTGGCGCCTCTGTGAAGGTTAGCTGCAAGGCCAGCGGCTAC ACATTCAAGGAATATGGCATCTCCTGGGTTAGGCAGGCTCCCGGCCAAGGCT TAGAATGGATGGGCTGGATCTCCGCCTACTCCGGCCACACCTACTACGCCCA GAAGCTTCAGGGCAGGGTTACCATGACCACCGACACCAGCACCTCTACCGCC TATATGGAGCTGAGGAGCCTGAGATCGGACGACACAGCTGTGTATTACTGCG CCAGAGGCCCCCACTACGACGACTGGTCTGGATTTATCATCTGGTTCGACCC CTGGGGGCAGGGCACCCTGGTCACAGTTTCTTCTGGCTCCACCAGCGGAAGC GGCAAGCCAGGCTCAGGCGAAGGATCTACAAAAGGCGACATCCAAATGACA CAGAGCCCCAGCAGCTTGAGCGCCTCCGTTGGCGACAGAGTTACAATCACCT GCAGGGCCTCTCAGAGCATCAGCAGCTATTTGAATTGGTATCAACAGAAGCC AGGAAAGGCCCCTAAGCTGCTCATCTACGCTGCCAGCTCGCTCCAATCTGGC GTTCCTAGCAGATTTAGCGGCTCCGGCAGCGGCACAGACTTTACTCTTACCA TTAGCTCCCTGCAGCCCGAGGACTTCGCTACCTACTATTGCCAGCAAAGCTA CAGATTCCCTCCCACCTTTGGCCAGGGCACAAAGGTTGAGATCAAGGCAGCT GCTTTCGTGCCTGTGTTCCTGCCTGCTAAGCCCACCACCACTCCTGCTCCAAG ACCTCCTACCCCCGCTCCTACAATCGCCAGCCAACCTCTGAGCCTGAGACCG GAGGCATGCAGACCTGCGGCAGGGGGAGCAGTTCACACAAGAGGCTTGGAC TTCGCTTGCGACATCTACATCTGGGCCCCTCTGGCCGGCACATGCGGAGTTCT TCTTCTTAGCCTGGTGATCACCCTGTACTGCAACCACAGAAACAGATTCAGC GTTGTGAAGAGAGGCCGGAAGAAGCTGCTGTACATCTTCAAGCAGCCCTTCA TGAGACCTGTGCAGACCACACAGGAGGAAGACGGCTGCAGCTGTAGATTCC CCGAGGAAGAGGAGGGCGGCTGTGAGCTGAGAGTTAAGTTCAGCAGGAGCG CCGACGCCCCTGCCTACCAGCAAGGACAGAATCAACTGTACAACGAGCTGA ACCTGGGCAGACGGGAGGAATACGATGTGCTGGACAAGAGGAGAGGCAGA GACCCCGAGATGGGCGGCAAACCTAGAAGAAAGAACCCCCAGGAGGGCCTG TATAACGAGCTCCAGAAGGACAAGATGGCCGAGGCCTACAGCGAGATCGGC ATGAAGGGCGAAAGAAGAAGAGGCAAGGGCCACGACGGCCTCTACCAGGG CTTAAGCACAGCTACAAAGGACACCTACGACGCCCTGCACATGCAGGCCCT GCCCCCTAGATGATTAATTAAatcgat |
| 280 | ggtaccCCCGGgCCCATGGCTCTTCCTGTGACAGCTCTTCTGCTGCCCCTGGCCC TGCTTCTGCATGCTGCTAGACCTCAGGTTCAGTTGCAGCAATGGGGAGCTGG CCTGTTAAAGCCCAGCGAAACCCTGTCCCTCACCTGCGCTGTGTATGGCGGA AGCTTCAGCGGCATCCACTGGAACTGGATCCGGCAGCCTCCTGGCAAAGGCC TTGAATGGATCGGCGATATCGACACCAGCGGCTCCACCAACTACAACCCCAG CCTGAAATCGAGGGTTACAATCTCTGTGGACACAAGCAAGAATCAGTTCTCC CTGAAGCTGAGCAGCGTTACTGCCGCCGACACAGCTGTGTACTATTGCGCCA GACTGGGCCAGGAAAGCGCTACCTACCTTGGCATGGATGTGTGGGGGCAGG GCACCACCGTTACTGTTAGCTCTGGCTCAACAAGCGGCAGCGGCAAGCCTGG CTCAGGAGAAGGAAGCACAAAGGGCGACATTGTAATGACTCAGAGCCCCGA CAGCCTGGCCGTTAGCTTAGGCGAAAGGGCTACAATCAATTGCAAGAGCAG CCAGAGCGTTCTGTACAGCAGCAACAACAAGAACTACCTCGCATGGTATCAA CAGAAGCCAGGCCAGCCTCCCAAGCTGCTCATCTACTGGGCTTCCACCAGAG AGAGCGGGGTTCCCGATAGATTCTCCGGCTCCGGTTCTGGAACAGATTTCAC GCTCACAATCAGCAGCTTACAGGCCGAGGATGTGGCTGTCTACTATTGTCAG CAGTTGTACACCTACCCCTTCACATTCGGCGGAGGCACCAAGGTTGAGATCA AGGCAGCTGCTTTCGTGCCTGTGTTCCTGCCTGCTAAGCCCACCACCACTCCT GCTCCAAGACCTCCTACCCCCGCTCCTACAATCGCCAGCCAACCTCTGAGCC TGAGACCGGAGGCATGCAGACCTGCGGCAGGGGGAGCAGTTCACACAAGAG GCTTGGACTTCGCTTGCGACATCTACATCTGGGCCCCTCTGGCCGGCACATG CGGAGTTCTTCTTCTTAGCCTGGTGATCACCCTGTACTGCAACCACAGAAAC AGATTCAGCGTTGTGAAGAGAGGCCGGAAGAAGCTGCTGTACATCTTCAAG CAGCCCTTCATGAGACCTGTGCAGACCACACAGGAGGAAGACGGCTGCAGC TGTAGATTCCCCGAGGAAGAGGAGGGCGGCTGTGAGCTGAGAGTTAAGTTC AGCAGGAGCGCCGACGCCCCTGCCTACCAGCAAGGACAGAATCAACTGTAC AACGAGCTGAACCTGGGCAGACGGGAGGAATACGATGTGCTGGACAAGAGG |

TABLE 68-continued

Exemplary nucleotide sequences encoding a binding motif, hinge,
and 41BB costimulatory domain

| SEQ ID NO | Sequence |
|---|---|
| | AGAGGCAGAGACCCCGAGATGGGCGGCAAACCTAGAAGAAAGAACCCCCA<br>GGAGGGCCTGTATAACGAGCTCCAGAAGGACAAGATGGCCGAGGCCTACAG<br>CGAGATCGGCATGAAGGGCGAAAGAAGAAGAGGCAAGGGCCACGACGGCC<br>TCTACCAGGGCTTAAGCACAGCTACAAAGGACACCTACGACGCCCTGCACAT<br>GCAGGCCCTGCCCCCTAGATGATTAATTAAatcgat |
| 281 | ggtaccCCCGGgCCCATGGCTCTTCCTGTGACAGCTCTTCTGCTGCCCCTGGCCC<br>TGCTTCTGCATGCTGCTAGACCTCAGCTTCAGCTCCAAGAGAGCGGACCTGG<br>CTTAGTGAAGCCCAGCGAAACCCTGTCCCTCACCTGCACCGTTTCTGGCGGA<br>AGCATCAGCAGCTCCAGCTATTACTGGGGATGGATCAGGCAGCCCCCTGGCA<br>AGGGTTTAGAATGGATCGGCTCGATATATTACTCCGGCAGCACCTACTATAA<br>CCCCAGCTTGAAGAGCCGGGTTACCATTTCTGTGGACACATCAAAGAACCAG<br>TTCAGCCTGAAGCTGAGCTCTGTGACTGCCGCCGACACAGCTGTGTACTACT<br>GTGCCAGAGAGACAGACTACTCCAGCGGCATGGGCTACGGCATGGATGTGT<br>GGGGACAAGGAACCACCGTTACTGTGAGCAGCGGTTCCACCAGCGGCTCAG<br>GCAAGCCTGGCTCAGGAGAAGGAAGCACCAAGGGGGATATACAGATGACAC<br>AGAGCCCCTCCAGCCTGTCCGCCAGCGTTGGCGATCGTGTAACGATCACCTG<br>CCGGGCCTCTCAGAGCATCAACTCCTACCTCAATTGGTATCAACAGAAGCCA<br>GGCAAGGCCCCAAATTACTCATCTACGCCGCCAGCAGCTTACAGAGCGGG<br>GTTCCCTCTAGATTCTCCGGCTCCGGTTCTGGAACAGATTTCACCCTCACTAT<br>CTCCAGCTTGCAGCCCGAGGATTTCGCCCACTTATTACTGTCAGCAGAGCCTG<br>GCCGACCCCTTCACATTCGGCGGAGGCACAAAGGTTGAGATCAAGGCTGCTG<br>CATTGGATAATGAAAAATCGAACGGCACAATCATTCATGTGAAGGGCAAAC<br>ACCTGTGTCCCAGCCCCTTGTTCCCAGGACCTAGCAAGCCTTTTTGGGTTCTC<br>GTGGTGGTGGGCGGCGTTCTGGCTTGCTACTCTCTACTTGTAACTGTCGCATT<br>TATTATATTCTGGGTTAGATTCAGCGTTGTGAAGAGAGGCCGGAAGAAGCTG<br>CTGTACATCTTCAAGCAGCCCTTCATGAGACCTGTGCAGACCACACAGGAGG<br>AAGACGGCTGCAGCTGTAGATTCCCCGAGGAAGAGGAGGGCGGCTGTGAGC<br>TGAGAGTTAAGTTCAGCAGGAGCGCCGACGCCCCTGCCTACCAGCAAGGAC<br>AGAATCAACTGTACAACGAGCTGAACCTGGGCAGACGGGAGGAATACGATG<br>TGCTGGACAAGAGGAGAGGCAGAGACCCCGAGATGGGCGGCAAACCTAGA<br>AGAAAGAACCCCCAGGAGGGCCTGTATAACGAGCTCCAGAAGGACAAGATG<br>GCCGAGGCCTACAGCGAGATCGGCATGAAGGGCGAAAGAAGAAGAGGCAA<br>GGGCCACGACGGCCTCTACCAGGGCTTAAGCACAGCTACAAAGGACACCTA<br>CGACGCCCTGCACATGCAGGCCCTGCCCCCTAGATGATTAATTAAatcgat |
| 282 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAAGAGAGCGGACCTGG<br>CTTAGTGAAGCCCAGCGAAACCCTGTCCCTCACCTGCACCGTTTCTGGCGGA<br>AGCATCAGCTCTCCCGACCATTACTGGGGATGGATCAGGCAGCCCCCTGGCA<br>AGGGTTTGGAATGGATCGGCAGCATCTACGCCAGCGGCAGCACATTCTACAA<br>CCCCTCGCTCAAAAGCAGGGTTACTATTTCTGTGGACACAAGCAAAATCAG<br>TTCAGCCTGAAGCTGAGCTCTGTGACTGCCGCCGACACAGCTGTGTACTACT<br>GTGCCAGAGAGACAGACTACTCCAGCGGGATGGGCTACGGCATGGATGTGT<br>GGGGACAAGGAACCACCGTTACTGTGAGCAGCGGCTCCACAAGCGGCTCAG<br>GCAAGCCTGGCTCAGGAGAAGGAAGCACCAAGGGGGACATTCAAATGACCC<br>AAAGCCCCTCCAGCCTGTCCGCCAGCGTTGGCGATAGGGTTACCATTACCTG<br>CAGGGCCAGCCAAAGCATCAACTCCTACCTAAATTGGTATCAACAGAAGCC<br>AGGCAAGGCCCCCAAACTACTCATTTACGCCGCCAGCAGCTTACAGAGCGG<br>GGTTCCCTCTAGATTCTCCGGCAGCGGTTCTGGAACAGATTTCACTCTCACAA<br>TATCTTCGCTGCAGCCCGAGGATTTCGCTACCTACTATTGCCAGCAATCCCTG<br>GCCGACCCCTTCACATTCGGCGGAGGCACAAAGGTTGAGATCAAGGCTGCTG<br>CATTGGATAATGAAAAATCGAACGGCACAATCATTCATGTGAAGGGCAAAC<br>ACCTGTGTCCCAGCCCCTTGTTCCCAGGACCTAGCAAGCCTTTTTGGGTTCTC<br>GTGGTGGTGGGCGGCGTTCTGGCTTGCTACTCTCTACTTGTAACTGTCGCATT<br>TATTATATTCTGGGTTAGATTCAGCGTTGTGAAGAGAGGCCGGAAGAAGCTG<br>CTGTACATCTTCAAGCAGCCCTTCATGAGACCTGTGCAGACCACACAGGAGG<br>AAGACGGCTGCAGCTGTAGATTCCCCGAGGAAGAGGAGGGCGGCTGTGAGC<br>TGAGAGTTAAGTTCAGCAGGAGCGCCGACGCCCCTGCCTACCAGCAAGGAC<br>AGAATCAACTGTACAACGAGCTGAACCTGGGCAGACGGGAGGAATACGATG<br>TGCTGGACAAGAGGAGAGGCAGAGACCCCGAGATGGGCGGCAAACCTAGA<br>AGAAAGAACCCCCAGGAGGGCCTGTATAACGAGCTCCAGAAGGACAAGATG<br>GCCGAGGCCTACAGCGAGATCGGCATGAAGGGCGAAAGAAGAAGAGGCAA<br>GGGCCACGACGGCCTCTACCAGGGCTTAAGCACAGCTACAAAGGACACCTA<br>CGACGCCCTGCACATGCAGGCCCTGCCCCCTAGATGATTAATTAAatcgat |
| 283 | ggtaccCCCGGgCCCATGGCTCTTCCTGTGACAGCTCTTCTGCTGCCCCTGGCCC<br>TGCTTCTGCATGCTGCTAGACCTCAGATCACATTAAAAGAGAGCGGACCTAC<br>ACTGGTGAAGCCCACCCAAACGCTTACCCTCACCTGCACCTTTAGCGGGTTC<br>AGCCTGGACACAGAGGGCGTTGGCGTTGGATGGATCAGGCAGCCTCCTGGC<br>AAAGCCCTCGAATGGCTTGCCCTCATCTACTTCAACGACCAGAAGAGATACA<br>GCCCCTCCTTAAAATCTCGGCTCACAATCACCAAAGACACAAGCAAAAATCA<br>GGTTGTGCTCACCATGACCAACATGGACCCTGTGGACACCGCTGTGTACTAC<br>TGTGCCAGAGACACCGGCTACAGCAGATGGTACTACGGGATGGACGTTTGG |

TABLE 68-continued

Exemplary nucleotide sequences encoding a binding motif, hinge, and 41BB costimulatory domain

| SEQ ID NO | Sequence |
|---|---|
| | GGCCAAGGCACCACTGTGACCGTTTCCAGCGGCTCTACAAGCGGCAGCGGG AAACCTGGTTCTGGAGAGGGCAGCACAAAGGGCGACATCCAGATGACGCAA TCCCCCAGCTCTGTGAGCGCCTCTGTGGGAGACAGAGTTACAATCACATGCC GGGCCTCCCAGGGCATCAGCTCTTGGCTGGCATGGTATCAACAGAAGCCTGG CAAGGCTCCCAAGCTGCTCATCTATGCCGCCTCCTCCTTACAATCTGGAGTTC CCTCCAGGTTCAGCGGGGAGCGGCTCAGGAACAGACTTCACCCTTACCATCTC TAGCCTGCAACCCGAGGACTTCGCTACTTATTACTGTCAGCAGGCCTACGCC TACCCCATCACATTCGGCGGAGGAACAAAGGTTGAGATCAAGGCTGCTGCAT TGGATAATGAAAAATCGAACGGCACAATCATTCATGTGAAGGGCAAACACC TGTGTCCCAGCCCCTTGTTCCCAGGACCTAGCAAGCCTTTTTGGGTTCTCGTG GTGGTGGGCGGCGTTCTGGCTTGCTACTCTCTACTTGTAACTGTCGCATTTAT TATATTCTGGGTTAGATTCAGCGTTGTGAAGAGAGGCCGGAAGAAGCTGCTG TACATCTTCAAGCAGCCCTTCATGAGACCTGTGCAGACCACACAGGAGGAAG ACGGCTGCAGCTGTAGATTCCCCGAGGAAGAGGAGGGCGGCTGTGAGCTGA GAGTTAAGTTCAGCAGGAGCGCCGACGCCCCTGCCTACCAGCAAGGACAGA ATCAACTGTACAACGAGCTGAACCTGGGCAGACGGGAGGAATACGATGTGC TGGACAAGAGGAGAGGCAGAGACCCCGAGATGGGCGGCAAACCTAGAAGA AAGAACCCCCAGGAGGGCCTGTATAACGAGCTCCAGAAGGACAAGATGGCC GAGGCCTACAGCGAGATCGGCATGAAGGGCGAAAGAAGAAGAGGCAAGGG CCACGACGGCCTCTACCAGGGCTTAAGCACAGCTACAAAGGACACCTACGA CGCCCTGCACATGCAGGCCCTGCCCCCTAGATGATTAATTAAatcgat |
| 284 | ggtaccCCCGGgCCCATGGCTCTTCCTGTGACAGCTCTTCTGCTGCCCCTGGCCC TGCTTCTGCATGCTGCTAGACCTCAGGTTCAGTTACAACAATGGGGAGCTGG CCTGTTAAAGCCCAGCGAAACCCTGTCCCTCACCTGCGCTGTGTATGGCGGA AGCTTCCAGAAATACTACTGGAGCTGGATCCGGCAGCCTCCCGGCAAAGGCT TAGAATGGATCGGAGAGATAGAACACCAGCGGCTTCACCAACTACAACCCCA GCCTGAAATCTAGGGTTACAATCTCTGTGGACACAAGCAAGAATCAGTTCTC CCTGAAGCTGAGCAGCGTTACTGCCGCCGACACAGCTGTGTACTATTGCGCC AGAGTTGGCAGATACAGCTACGGCTACTACATCACCGCCTTCGACATTTGGG GCCAAGGCACCACTGTGACCGTTTCCAGCGGAAGCACTAGCGGCAGCGGGA AACCTGGTTCTGGAGAGGGCTCAACCAAGGGCGACATCGTGATGACACAGA GCCCCGACTCTCTGGCTGTGTCCCTGGGAGAGAGAGCCACCATCAACTGCAA GAGCAGCCAGAGCGTTCTGTACAGCAGCAACAACAAGAACTACCTGGCATG GTATCAACAGAAGCCTGGCCAGCCCCCTAAGCTGCTCATCTACTGGGCTTCC ACCAGAGAATCAGGCGTTCCAGACAGGTTCTCCGGCTCGGGTTCAGGCACAG ACTTCACCCTTACCATCTCTTCCCTGCAGGCCGAAGATGTGGCCGTTTACTAC TGTCAGCAGCACTACAGCTTCCCTTTCACATTCGGCGGAGGCACCAAGGTTG AGATCAAGGCTGCTGCATTGGATAATGAAAAATCGAACGGCACAATCATTC ATGTGAAGGGCAAACACCTGTGTCCCAGCCCCTTGTTCCCAGGACCTAGCAA GCCTTTTTGGGTTCTCGTGGTGGTGGGCGGCGTTCTGGCTTGCTACTCTCTAC TTGTAACTGTCGCATTTATTATATTCTGGGTTAGATTCAGCGTTGTGAAGAGA GGCCGGAAGAAGCTGCTGTACATCTTCAAGCAGCCCTTCATGAGACCTGTGC AGACCACACAGGAGGAAGACGGCTGCAGCTGTAGATTCCCCGAGGAAGAGG AGGGCGGCTGTGAGCTGAGAGTTAAGTTCAGCAGGAGCGCCGACGCCCCTG CCTACCAGCAAGGACAGAATCAACTGTACAACGAGCTGAACCTGGGCAGAC GGGAGGAATACGATGTGCTGGACAAGAGGAGAGGCAGAGACCCCGAGATG GGCGGCAAACCTAGAAGAAAGAACCCCCAGGAGGGCCTGTATAACGAGCTC CAGAAGGACAAGATGGCCGAGGCCTACAGCGAGATCGGCATGAAGGGCGA AAGAAGAAGAGGCAAGGGCCACGACGGCCTCTACCAGGGCTTAAGCACAGC TACAAAGGACACCTACGACGCCCTGCACATGCAGGCCCTGCCCCCTAGATGA TTAATTAAatcgat |
| 285 | ggtaccCCCGGgCCCATGGCTCTTCCTGTGACAGCTCTTCTGCTGCCCCTGGCCC TGCTTCTGCATGCTGCTAGACCTCAGGTTCAGTTGCAGCAATGGGGAGCTGG CCTGTTAAAGCCCAGCGAAACCCTGTCCCTCACCTGCGCTGTGTATGGCGGA AGCTTCGAGAAATACTACTGGAGCTGGATCCGGCAGCCTCCCGGCAAAGGCT TAGAATGGATCGGCGAGATTTATCACAGCGGGCTCACCAACTACAACCCCAG CCTGAAATCTCGAGTTACAATCTCTGTGGACACAAGCAAGAATCAGTTCTCC CTGAAGCTGAGCAGCGTTACTGCCGCCGACACAGCTGTGTACTATTGCGCCA GAGTTAGATACGACAGCAGCGACAGCTATTACTACAGCTATGACTACGGCAT GGATGTGTGGGGGCAGGGCACCACCGTTACTGTCTCCTCTGGATCTACCAGC GGCAGCGGCAAGCCTGGATCTGGCGAAGGAAGCACAAAGGGCGACATTGTG CTCACCCAGAGCCCCGACAGCCTGGCTGTGTCTTTAGGCGAAAGGGCTACCA TCAACTGCAAGAGCAGCCAGAGCGTTCTGTACAGCAGCAACAACAAGAACT ACCTTGCTTGGTATCAACAGAAGCCTGGCCAGCCCCCTAAGCTGCTCATCTA CTGGGCCTCTAGCAGAGAGAGCGGGGTTCCCGATCGGTTTAGCGGCTCCGGC TCAGGAACCGATTTCACCCTCACTATCTCCAGCCTCCAGGCCGAGGATGTGG CTGTCTACTATTGTCAGCAGAGCTATAGCTTCCCCTGGACATTCGGCGGAGG CACCAAGGTTGAGATCAAGGCTGCTGCATTGGATAATGAAAAATCGAACGG CACAATCATTCATGTGAAGGGCAAACACCTGTGTCCCAGCCCCTTGTTCCCA GGACCTAGCAAGCCTTTTTGGGTTCTCGTGGTGGTGGGCGGCGTTCTGGCTT GCTACTCTCTACTTGTAACTGTCGCATTTATTATATTCTGGGTTAGATTCAGC GTTGTGAAGAGAGGCCGGAAGAAGCTGCTGTACATCTTCAAGCAGCCCTTCA |

TABLE 68-continued

Exemplary nucleotide sequences encoding a binding motif, hinge,
and 41BB costimulatory domain SEQ ID
NO    Sequence

```
        TGAGACCTGTGCAGACCACACAGGAGGAAGACGGCTGCAGCTGTAGATTCC
        CCGAGGAAGAGGAGGGCGGCTGTGAGCTGAGAGTTAAGTTCAGCAGGAGCG
        CCGACGCCCCTGCCTACCAGCAAGGACAGAATCAACTGTACAACGAGCTGA
        ACCTGGGCAGACGGGAGGAATACGATGTGCTGGACAAGAGGAGAGGCAGA
        GACCCCGAGATGGGCGGCAAACCTAGAAGAAAGAACCCCCAGGAGGGCCTG
        TATAACGAGCTCCAGAAGGACAAGATGGCCGAGGCCTACAGCGAGATCGGC
        ATGAAGGGCGAAAGAAGAAGAGGCAAGGGCCACGACGGCCTCTACCAGGG
        CTTAAGCACAGCTACAAAGGACACCTACGACGCCCTGCACATGCAGGCCCT
        GCCCCCTAGATGATTAATTAAatcgat 286    ggtaccCCCGGGcCCCATGGCTCTTCCTGTGACAGCTCTTCTGCTGCCCCTGGCCC
        TGCTTCTGCATGCTGCTAGACCTCAGGTTCAGTTACAACAATGGGGAGCTGG
        CCTGTTAAAGCCCAGCGAAACCCTGTCCCTCACCTGCGCTGTGTATGGCGGA
        AGCTTCAGCCGCTATGTGTGGAGCTGGATCCGGCAGCCTCCTGGCAAAGGCC
        TTGAATGGATCGGAGAGATAGACAGCAGCGGCAAGACCAACTACAACCCCA
        GCCTGAAATCACGCGTTACAATCTCTGTGGACACAAGCAAGAATCAGTTCTC
        CCTGAAGCTGAGCAGCGTTACTGCCGCCGACACAGCTGTGTACTATTGCGCC
        AGAGTTAGATACGACAGCTCCGACAGCTATTACTACAGCTATGACTACGGCA
        TGGATGTGTGGGGGCAGGGCACCACCGTTACAGTTAGCTCTGGAAGCACCA
        GCGGCTCCGGCAAGCCTGGATCTGGTGAAGGAAGCACAAAGGGCGACATTG
        TGCTCACCCAGAGCCCCGACAGCCTGGCTGTGTCTTTAGGCGAAAGGGCTAC
        CATCAACTGCAAGAGCAGCCAGAGCGTTCTGTACAGCAGCAACAACAAGAA
        CTACCTTGCATGGTATCAACAGAAGCCTGGCCAGCCTCCCAAGCTGCTCATC
        TACTGGGCCTCTAGCAGAGAGAGCGGGGTTCCCGATCGCTTTAGCGGCAGCG
        GTTCTGGCACCGATTTCACTCTTACAATCAGCAGCTTACAGGCCGAGGATGT
        GGCTGTCTACTATTGTCAGCAGAGCTATAGCTTCCCCTGGACATTCGGCGGA
        GGCACCAAGGTTGAGATCAAGGCTGCTGCATTGGATAATGAAAAATCGAAC
        GGCACAATCATTCATGTGAAGGGCAAACACCTGTGTCCCAGCCCCTTGTTCC
        CAGGACCTAGCAAGCCTTTTTGGGTTCTCGTGGTGGTGGGCGGCGTTCTGGC
        TTGCTACTCTCTACTTGTAACTGTCGCATTTATTATATTCTGGGTTAGATTCA
        GCGTTGTGAAGAGAGGCCGGAAGAAGCTGCTGTACATCTTCAAGCAGCCCTT
        CATGAGACCTGTGCAGACCACACAGGAGGAAGACGGCTGCAGCTGTAGATT
        CCCCGAGGAAGAGGAGGGCGGCTGTGAGCTGAGAGTTAAGTTCAGCAGGAG
        CGCCGACGCCCCTGCCTACCAGCAAGGACAGAATCAACTGTACAACGAGCT
        GAACCTGGGCAGACGGGAGGAATACGATGTGCTGGACAAGAGGAGAGGCA
        GAGACCCCGAGATGGGCGGCAAACCTAGAAGAAAGAACCCCCAGGAGGGC
        CTGTATAACGAGCTCCAGAAGGACAAGATGGCCGAGGCCTACAGCGAGATC
        GGCATGAAGGGCGAAAGAAGAAGAGGCAAGGGCCACGACGGCCTCTACCA
        GGGCTTAAGCACAGCTACAAAGGACACCTACGACGCCCTGCACATGCAGGC
        CCTGCCCCCTAGATGATTAATTAAatcgat 287    ggtaccCCCGGGcCCCATGGCTCTTCCTGTGACAGCTCTTCTGCTGCCCCTGGCCC
        TGCTTCTGCATGCTGCTAGACCTCAGGTTCAGTTACAACAATGGGGAGCTGG
        CCTGTTAAAGCCCAGCGAAACCCTGTCCCTCACCTGCGCTGTGTATGGCGGA
        AGCTTCAGCGGCTACGCTTGGAGCTGGATTAGACAGCCTCCTGGCAAAGGAC
        TAGAATGGATCGGAGAGATCGACCACAGAGGCTTCACCAACTACAACCCCA
        GCCTGAAATCCAGAGTTACAATCTCTGTGGACACAAGCAAGAATCAGTTCTC
        CCTGAAGCTGAGCAGCGTTACTGCCGCCGACACAGCTGTGTACTATTGCGCC
        AGGGTTAGATACGACAGCAGCGACAGCTATTACTACAGCTATGACTACGGC
        ATGGATGTGTGGGGGCAGGGCACCACCGTTACGGTTAGCTCTGGATCTACCA
        GCGGCAGCGGCAAGCCTGGCTCAGGAGAAGGAAGCACAAAGGGCGACATTG
        TGCTCACCCAGAGCCCCGACAGCCTGGCCGTTTCTTTAGGCGAAAGGGCTAC
        CATCAACTGCAAGAGCAGCCAGAGCGTTCTGTACAGCAGCAACAACAAGAA
        CTACCTTGCATGGTATCAACAGAAGCCAGGCCAGCCTCCCAAGCTGCTCATC
        TACTGGGCCTCTAGCAGAGAGAGCGGGGTTCCCGATAGATTTTCGGGATCAG
        GCTCCGGCACCGATTTCACTCTTACGATCAGCAGCTTACAGGCCGAGGATGT
        GGCTGTCTACTATTGTCAGCAGAGCTATAGCTTCCCCTGGACATTCGGCGGA
        GGCACCAAGGTTGAGATCAAGGCTGCTGCATTGGATAATGAAAAATCGAAC
        GGCACAATCATTCATGTGAAGGGCAAACACCTGTGTCCCAGCCCCTTGTTCC
        CAGGACCTAGCAAGCCTTTTTGGGTTCTCGTGGTGGTGGGCGGCGTTCTGGC
        TTGCTACTCTCTACTTGTAACTGTCGCATTTATTATATTCTGGGTTAGATTCA
        GCGTTGTGAAGAGAGGCCGGAAGAAGCTGCTGTACATCTTCAAGCAGCCCTT
        CATGAGACCTGTGCAGACCACACAGGAGGAAGACGGCTGCAGCTGTAGATT
        CCCCGAGGAAGAGGAGGGCGGCTGTGAGCTGAGAGTTAAGTTCAGCAGGAG
        CGCCGACGCCCCTGCCTACCAGCAAGGACAGAATCAACTGTACAACGAGCT
        GAACCTGGGCAGACGGGAGGAATACGATGTGCTGGACAAGAGGAGAGGCA
        GAGACCCCGAGATGGGCGGCAAACCTAGAAGAAAGAACCCCCAGGAGGGC
        CTGTATAACGAGCTCCAGAAGGACAAGATGGCCGAGGCCTACAGCGAGATC
        GGCATGAAGGGCGAAAGAAGAAGAGGCAAGGGCCACGACGGCCTCTACCA
        GGGCTTAAGCACAGCTACAAAGGACACCTACGACGCCCTGCACATGCAGGC
        CCTGCCCCCTAGATGATTAATTAAatcgat 288    ggtaccCCCGGGcCCCATGGCTCTTCCTGTGACAGCTCTTCTGCTGCCCCTGGCCC
        TGCTTCTGCATGCTGCTAGACCTCAGGTTCAGTTGCAGCAATGGGGAGCTGG
```

TABLE 68-continued

Exemplary nucleotide sequences encoding a binding motif, hinge,
and 41BB costimulatory domain

| SEQ ID NO | Sequence |
|---|---|
| | CCTGTTAAAGCCCAGCGAAACCCTGTCCCTCACCTGCGCTGTGTATGGCGGA<br>AGCTTCAGCGGCTATTACTGGAGCTGGATCCGGCAGCCTCCTGGAAAAGGAT<br>TAGAATGGATCGGCGAGATAGACCACAGCGGGAGCACAAACTACAACCCCA<br>GCCTGAAATCGCGGGTTACAATCTCTGTGGACACAAGCAAGAATCAGTTCTC<br>CCTGAAGCTGAGCAGCGTTACTGCCGCCGACACAGCTGTGTACTATTGCGCC<br>AGAGGCGGAGGCTCCTGGTACAGCAACTGGTTCGATCCTTGGGGCCAAGGC<br>ACCATGGTGACCGTTTCCAGCGGCTCTACAAGCGGCAGCGGGAAACCTGGTT<br>CTGGAGAGGGCAGCACAAAGGGCGACATCCAGATGACACAGAGCCCCAGCA<br>CCCTTAGCGCCTCTGTGGGAGATAGGGTTACCATTACCTGCAGGGCTTCCCA<br>GAGCATCAGCAGCTGGCTGGCATGGTATCAACAGAAGCCTGGCAAGGCTCC<br>CAAGCTGCTCATCTATGACGCCTCCAGCCTGGAAAGCGGGGTTCCCTCCAGA<br>TTTAGCGGCTCAGGCTCCGGAACAGAGTTCACCCTTACCATCTCTAGCCTGC<br>AACCCGACGACTTCGCTACTTATTACTGTCAACAAGACAGAAGCTTGCCCCC<br>CACATTCGGCGGAGGGACCAAGGTTGAGATCAAGGCTGCTGCATTGGATAA<br>TGAAAAATCGAACGGCACAATCATTCATGTGAAGGGCAAACACCTGTGTCCC<br>AGCCCCTTGTTCCCAGGACCTAGCAAGCCTTTTTGGGTTCTCGTGGTGGTGGG<br>CGGCGTTCTGGCTTGCTACTCTCTACTTGTAACTGTCGCATTTATTATATTCTG<br>GGTTAGATTCAGCGTTGTGAAGAGAGGCCGGAAGAAGCTGCTGTACATCTTC<br>AAGCAGCCCTTCATGAGACCTGTGCAGACCACACAGGAGGAAGACGGCTGC<br>AGCTGTAGATTCCCCGAGGAAGAGGAGGGCGGCTGTGAGCTGAGAGTTAAG<br>TTCAGCAGGAGCGCCGACGCCCCTGCCTACCAGCAAGGACAGAATCAACTG<br>TACAACGAGCTGAACCTGGGCAGACGGGAGGAATACGATGTGCTGGACAAG<br>AGGAGAGGCAGAGACCCCGAGATGGGCGGCAAACCTAGAAGAAAAGAACCC<br>CCAGGAGGGCCTGTATAACGAGCTCCAGAAGGACAAGATGGCCGAGGCCTA<br>CAGCGAGATCGGCATGAAGGGCGAAAGAAGAAGAGGCAAGGGCCACGACG<br>GCCTCTACCAGGGCTTAAGCACAGCTACAAAGGACACCTACGACGCCCTGC<br>ACATGCAGGCCCTGCCCCCTAGATGATTAATTAAatcgat |
| 289 | ggtaccCCCGGgCCCATGGCTCTTCCTGTGACAGCTCTTCTGCTGCCCCTGGCCC<br>TGCTTCTGCATGCTGCTAGACCTCAGGTTCAGCTTGTGCAGAGCGGAGCTGA<br>AGTTAAGAAGCCTGGCGCCTCTGTGAAGGTTAGCTGCAAGGCCAGCGGCTAC<br>ACATTCAAGGAATATGGCATCTCCTGGGTTAGGCAGGCTCCCGGCCAAGGCT<br>TAGAATGGATGGGCTGGATCTCCGCCTACTCCGGCCACACCTACTACGCCCA<br>GAAGCTTCAGGGCAGGGTTACCATGACCACCGACACCAGCACCTCTACCGCC<br>TATATGGAGCTGAGGAGCCTGAGATCGGACGACACAGCTGTGTATTACTGCG<br>CCAGAGGCCCCCACTACGACGACTGGTCTGGATTTATCATCTGGTTCGACCC<br>CTGGGGGCAGGGCACCCTGGTCACAGTTTCTTCTGGCTCCACCAGCGGAAGC<br>GGCAAGCCAGGCTCAGGCGAAGGATCTACAAAAGGCGACATCCAAATGACA<br>CAGAGCCCCAGCAGCTTGAGCGCCTCCGTTGGCGACAGAGTTACAATCACCT<br>GCAGGGCCTCTCAGAGCATCAGCAGCTATTTGAATTGGTATCAACAGAAGCC<br>AGGAAAGGCCCCTAAGCTGCTCATCTACGCTGCCAGCTCGCTCCAATCTGGC<br>GTTCCTAGCAGATTTAGCGGCTCCGGCAGCGGCACAGACTTTACTCTTACCA<br>TTAGCTCCCTGCAGCCCGAGGACTTCGCTACCTACTATTGCCAGCAAAGCTA<br>CAGATTCCCTCCCACCTTTGGCCAGGGCACAAAGGTTGAGATCAAGGCTGCT<br>GCATTGGATAATGAAAAATCGAACGGCACAATCATTCATGTGAAGGGCAAA<br>CACCTGTGTCCCAGCCCCTTGTTCCCAGGACCTAGCAAGCCTTTTTGGGTTCT<br>CGTGGTGGTGGGCGGCGTTCTGGCTTGCTACTCTCTACTTGTAACTGTCGCAT<br>TTATTATATTCTGGGGTTAGATTCAGCGTTGTGAAGAGAGGCCGGAAGAAGCT<br>GCTGTACATCTTCAAGCAGCCCTTCATGAGACCTGTGCAGACCACACAGGAG<br>GAAGACGGCTGCAGCTGTAGATTCCCCGAGGAAGAGGAGGGCGGCTGTGAG<br>CTGAGAGTTAAGTTCAGCAGGAGCGCCGACGCCCCTGCCTACCAGCAAGGA<br>CAGAATCAACTGTACAACGAGCTGAACCTGGGCAGACGGGAGGAATACGAT<br>GTGCTGGACAAGAGGAGAGGCAGAGACCCCGAGATGGGCGGCAAACCTAG<br>AAGAAAGAACCCCCAGGAGGGCCTGTATAACGAGCTCCAGAAGGACAAGAT<br>GGCCGAGGCCTACAGCGAGATCGGCATGAAGGGCGAAAGAAGAAGAGGCA<br>AGGGCCACGACGGCCTCTACCAGGGCTTAAGCACAGCTACAAAGGACACCT<br>ACGACGCCCTGCACATGCAGGCCCTGCCCCCTAGATGATTAATTAAatcgat |
| 290 | ggtaccCCCGGgCCCATGGCTCTTCCTGTGACAGCTCTTCTGCTGCCCCTGGCCC<br>TGCTTCTGCATGCTGCTAGACCTCAGGTTCAGTTGCAGCAATGGGGAGCTGG<br>CCTGTTAAAGCCCAGCGAAACCCTGTCCCTCACCTGCGCTGTGTATGGCGGA<br>AGCTTCAGCGGCATCCACTGGAACTGGATCCGGCAGCCTCCTGGCAAAGGCC<br>TTGAATGGATCGGCGATATCGACACCAGCGGCTCCACCAACTACAACCCCAG<br>CCTGAAATCGAGGGTTACAATCTCTGTGGACACAAGCAAGAATCAGTTCTCC<br>CTGAAGCTGAGCAGCGTTACTGCCGCCGACACAGCTGTGTACTATTGCGCCA<br>GACTGGGCAGGAAAGCGCTACCTACCTTGGCATGGATGTGTGGGGGCAGG<br>GCACCACCGTTACTGTTAGCTCTGGCTCAACAAGCGGCAGCGGCAAGCCTGG<br>CTCAGGAGAAGGAAGCACAAAGGGCGACATTGTAATGACTCAGAGCCCCGA<br>CAGCCTGGCCGTTAGCTTAGGCGAAAGGGCTACAATCAATTGCAAGAGCAG<br>CCAGAGCGTTCTGTACAGCAGCAACAACAAGAACTACCTCGCATGGTATCAA<br>CAGAAGCCAGGCCAGCCTCCCAAGCTGCTCATCTACTGGGCTTCCACCAGAG<br>AGAGCGGGGTTCCCGATAGAATTCTCCGGCTCCGGTTCTGGAACAGATTTCAC<br>GCTCACAATCAGCAGCTTACAGGCCGAGGATGTGGCTGTCTACTATTGTCAG<br>CAGTTGTACACCTACCCCTTCACATTCGGCGGAGGCACCAAGGTTGAGATCA |

TABLE 68-continued

Exemplary nucleotide sequences encoding a binding motif, hinge,
and 41BB costimulatory domain SEQ ID
NO        Sequence AGGCTGCTGCATTGGATAATGAAAAATCGAACGGCACAATCATTCATGTGAA
          GGGCAAACACCTGTGTCCCAGCCCCTTGTTCCCAGGACCTAGCAAGCCTTTT
          TGGGTTCTCGTGGTGGTGGGCGGCGTTCTGGCTTGCTACTCTCTACTTGTAAC
          TGTCGCATTTATTATATTCTGGGTTAGATTCAGCGTTGTGAAGAGAGGCCGG
          AAGAAGCTGCTGTACATCTTCAAGCAGCCCTTCATGAGACCTGTGCAGACCA
          CACAGGAGGAAGACGGCTGCAGCTGTAGATTCCCCGAGGAAGAGGAGGGCG
          GCTGTGAGCTGAGAGTTAAGTTCAGCAGGAGCGCCGACGCCCCTGCCTACCA
          GCAAGGACAGAATCAACTGTACAACGAGCTGAACCTGGGCAGACGGGAGGA
          ATACGATGTGCTGGACAAGAGGAGAGGCAGAGACCCCGAGATGGGCGGCAA
          ACCTAGAAGAAAGAACCCCCAGGAGGGCCTGTATAACGAGCTCCAGAAGGA
          CAAGATGGCCGAGGCCTACAGCGAGATCGGCATGAAGGGCGAAAGAAGAA
          GAGGCAAGGGCCACGACGGCCTCTACCAGGGCTTAAGCACAGCTACAAAGG
          ACACCTACGACGCCCTGCACATGCAGGCCCTGCCCCCTAGATGATTAATTAA
          atcgat 271       ggtaccCCCGGgCCCATGGCTCTTCCTGTGACAGCTCTTCTGCTGCCCCTGGCCC
          TGCTTCTGCATGCTGCTAGACCTCAGCTTCAGCTCCAAGAGAGCGGACCTGG
          CTTAGTGAAGCCCAGCGAAACCCTGTCCCTCACCTGCACCGTTTCTGGCGGA
          AGCATCAGCAGCTCCAGCTATTACTGGGGATGGATCAGGCAGCCCCCTGGCA
          AGGGTTTAGAATGGATCGGCTCGATATATTACTCCGGCAGCACCTACTATAA
          CCCCAGCTTGAAGAGCCGGGTTACCATTTCTGTGGACACATCAAAGAACCAG
          TTCAGCCTGAAGCTGAGCTCTGTGACTGCCGCCGACACAGCTGTGTACTACT
          GTGCCAGAGAGACAGACTACTCCAGCGGCATGGGCTACGGCATGGATGTGT
          GGGGACAAGGAACCACCGTTACTGTGAGCAGCGGTTCCACCAGCGGCTCAG
          GCAAGCCTGGCTCAGGAGAAGGAAGCACCAAGGGGGATATACAGATGACAC
          AGAGCCCCTCCAGCCTGTCCGCCAGCGTTGGCGATCGTGTAACGATCACCTG
          CCGGGCCTCTCAGAGCATCAACTCCTACCTCAATTGGTATCAACAGAAGCCA
          GGCAAGGCCCCCAAATTACTCATCTACGCCGCCAGCAGCTTACAGAGCGGG
          GTTCCCTCTAGATTCTCCGGCTCCGGTTCTGGAACAGATTTCACCCTCACTAT
          CTCCAGCTTGCAGCCCGAGGATTTCGCCACTTATTACTGTCAGCAGAGCCTG
          GCCGACCCCTTCACATTCGGCGGAGGCACAAAGGTTGAGATCAAGGCAGCT
          GCTTTCGTGCCTGTGTTCCTGCCTGCTAAGCCCACCACCACTCCTGTCTCCAAG
          ACCTCCTACCCCGCTCCTACAATCGCCAGCCAACCTCTGAGCCTGAGACCG
          GAGGCATGCAGACCTGCGGCAGGGGGAGCAGTTCACACAAGAGGCTTGGAC
          TTCGCTTGCGACATCTACATCTGGGCCCCTCTGGCCGGCACATGCGGAGTTCT
          TCTTCTTAGCCTGGTGATCACCCTGTACTGCAACCACAGAAACAGATTCAGC
          GTTGTGAAGAGAGGCCGGAAGAAGCTGCTGTACATCTTCAAGCAGCCCTTCA
          TGAGACCTGTGCAGACCACACAGGAGGAAGACGGCTGCAGCTGTAGATTCC
          CCGAGGAAGAGGAGGGCGGCTGTGAGCTGAGAGTTAAGTTCAGCAGGAGCG
          CCGACGCCCCTGCCTACCAGCAAGGACAGAATCAACTGTACAACGAGCTGA
          ACCTGGGCAGACGGGAGGAATACGATGTGCTGGACAAGAGGAGAGGCAGA
          GACCCCGAGATGGGCGGCAAACCTAGAAGAAAGAACCCCCAGGAGGGCCTG
          TATAACGAGCTCCAGAAGGACAAGATGGCCGAGGCCTACAGCGAGATCGGC
          ATGAAGGGCGAAAGAAGAAGAGGCAAGGGCCACGACGGCCTCTACCAGGG
          CTTAAGCACAGCTACAAAGGACACCTACGACGCCCTGCACATGCAGGCCCT
          GCCCCCTAGATGATTAATTAAatcgat 272       ggtaccCCCGGgCCCATGGCTCTTCCTGTGACAGCTCTTCTGCTGCCCCTGGCCC
          TGCTTCTGCATGCTGCTAGACCTCAGGTTCAGTTACAAGAGAGCGGACCTGG
          CTTAGTGAAGCCCAGCGAAACCCTGTCCCTCACCTGCACCGTTTCTGGCGGA
          AGCATCAGCTCTCCCGACCATTACTGGGGATGGATCAGGCAGCCCCCTGGCA
          AGGGTTTGGAATGGATCGGCAGCATCTACGCCAGCGGCAGCACATTCTACAA
          CCCCTCGCTCAAAAGCAGGGTTACTATTTCTGTGGACACAAGCAAAAATCAG
          TTCAGCCTGAAGCTGAGCTCTGTGACTGCCGCCGACACAGCTGTGTACTACT
          GTGCCAGAGAGACAGACTACTCCAGCGGGATGGGCTACGGCATGGATGTGT
          GGGGACAAGGAACCACCGTTACTGTGAGCAGCGGCTCCACAAGCGGCTCAG
          GCAAGCCTGGCTCAGGAGAAGGAAGCACCAAGGGGGACATTCAAATGACCC
          AAAGCCCCTCCAGCCTGTCCGCCAGCGTTGGCGATAGGGTTACCATTACCTG
          CAGGGCCAGCCAAAGCATCAACTCCTACCTAAATTGGTATCAACAGAAGCC
          AGGCAAGGCCCCCAAACTACTCATTTACGCCGCCAGCAGCTTACAGAGCGG
          GGTTCCCTCTAGATTCTCCGGCAGCGGTTCTGGAACAGATTTCACTCTCACAA
          TATCTTCGCTGCAGCCCGAGGATTTCGCTACCTACTATTGCCAGCAATCCCTG
          GCCGACCCCTTCACATTCGGCGGAGGCACAAAGGTTGAGATCAAGGCAGCT
          GCTTTCGTGCCTGTGTTCCTGCCTGCTAAGCCCACCACCACTCCTGCTCCAAG
          ACCTCCTACCCCGCTCCTACAATCGCCAGCCAACCTCTGAGCCTGAGACCG
          GAGGCATGCAGACCTGCGGCAGGGGGAGCAGTTCACACAAGAGGCTTGGAC
          TTCGCTTGCGACATCTACATCTGGGCCCCTCTGGCCGGCACATGCGGAGTTCT
          TCTTCTTAGCCTGGTGATCACCCTGTACTGCAACCACAGAAACAGATTCAGC
          GTTGTGAAGAGAGGCCGGAAGAAGCTGCTGTACATCTTCAAGCAGCCCTTCA
          TGAGACCTGTGCAGACCACACAGGAGGAAGACGGCTGCAGCTGTAGATTCC
          CCGAGGAAGAGGAGGGCGGCTGTGAGCTGAGAGTTAAGTTCAGCAGGAGCG
          CCGACGCCCCTGCCTACCAGCAAGGACAGAATCAACTGTACAACGAGCTGA
          ACCTGGGCAGACGGGAGGAATACGATGTGCTGGACAAGAGGAGAGGCAGA
          GACCCCGAGATGGGCGGCAAACCTAGAAGAAAGAACCCCCAGGAGGGCCTG TABLE 68-continued Exemplary nucleotide sequences encoding a binding motif, hinge,
and 41BB costimulatory domain

| SEQ ID NO | Sequence |
|---|---|
| | TATAACGAGCTCCAGAAGGACAAGATGGCCGAGGCCTACAGCGAGATCGGC ATGAAGGGCGAAAGAAGAAGAGGCAAGGGCCACGACGGCCTCTACCAGGG CTTAAGCACAGCTACAAAGGACACCTACGACGCCCTGCACATGCAGGCCCT GCCCCCTAGATGATTAATTAAatcgat |
| 273 | ggtaccCCCGGgCCCATGGCTCTTCCTGTGACAGCTCTTCTGCTGCCCCTGGCCC TGCTTCTGCATGCTGCTAGACCTCAGATCACATTAAAAGAGAGCGGACCTAC ACTGGTGAAGCCCACCCAAACGCTTACCCTCACCTGCACCTTTAGCGGGTTC AGCCTGGACACAGAGGGCGTTGGCGTTGGATGGATCAGGCAGCCTCCTGGC AAAGCCCTCGAATGGCTTGCCCTCATCTACTTCAACGACCAGAAGAGATACA GCCCCTCCTTAAAATCTCGGCTCACAATCACCAAAGACACAAGCAAAAATCA GGTTGTGCTCACCATGACCAACATGGACCCTGTGGACACCGCTGTGTACTAC TGTGCCAGAGACACCGGCTACAGCAGATGGTACTACGGGATGGACGTTTGG GGCCAAGGCACCACTGTGACCGTTTCCAGCGGCTCTACAAGCGGCAGCGGG AAACCTGGTTCTGGAGAGGGCAGCACAAAGGGCGACATCCAGATGACGCAA TCCCCCAGCTCTGTGAGCGCCTCTGTGGGAGACAGAGTTACAATCACATGCC GGGCCTCCCAGGGCATCAGCTCTTGGCTGGCATGGTATCAACAGAAGCCTGG CAAGGCTCCCAAGCTGCTCATCTATGCCGCCTCCTCCTTACAATCTGGAGTTC CCTCCAGGTTCAGCGGGAGCGGCTCAGGAACAGACTTCACCCTTACCATCTC TAGCCTGCAACCCGAGGACTTCGCTACTTATTACTGTCAGCAGGCCTACGCC TACCCCATCACATTCGGCGGAGGAACAAAGGTTGAGATCAAGGCAGCTGCTT TCGTGCCTGTGTTCCTGCCTGCTAAGCCCACCACCACTCCTGCTCCAAGACCT CCTACCCCCGCTCCTACAATCGCCAGCCAACCTCTGAGCCTGAGACCGGAGG CATGCAGACCTGCGGCAGGGGGAGCAGTTCACACAAGAGGCTTGGACTTCG CTTGCGACATCTACATCTGGGCCCCTCTGGCCGGCACATGCGGAGTTCTTCTT CTTAGCCTGGTGATCACCCTGTACTGCAACCACAGAAACAGATTCAGCGTTG TGAAGAGAGGCCGGAAGAAGCTGCTGTACATCTTCAAGCAGCCCTTCATGA GACCTGTGCAGACCACACAGGAGGAAGACGGCTGCAGCTGTAGATTCCCCG AGGAAGAGGAGGGCGGCTGTGAGCTGAGAGTTAAGTTCAGCAGGAGCGCCG ACGCCCCTGCCTACCAGCAAGGACAGAATCAACTGTACAACGAGCTGAACC TGGGCAGACGGGAGGAATACGATGTGCTGGACAAGAGGAGAGGCAGAGAC CCCGAGATGGGCGGCAAACCTAGAAGAAAGAACCCCCAGGAGGGCCTGTAT AACGAGCTCCAGAAGGACAAGATGGCCGAGGCCTACAGCGAGATCGGCATG AAGGGCGAAAGAAGAAGAGGCAAGGGCCACGACGGCCTCTACCAGGGCTTA AGCACAGCTACAAAGGACACCTACGACGCCCTGCACATGCAGGCCCTGCCC CCTAGATGATTAATTAAatcgat |
| 274 | ggtaccCCCGGgCCCATGGCTCTTCCTGTGACAGCTCTTCTGCTGCCCCTGGCCC TGCTTCTGCATGCTGCTAGACCTCAGGTTCAGTTACAACAATGGGGAGCTGG CCTGTTAAAGCCCAGCGAAACCCTGTCCCTCACCTGCGCTGTGTATGGCGGA AGCTTCCAGAAATACTACTGGAGCTGGATCCGGCAGCCTCCCGGCAAAGGCT TAGAATGGATCGGAGAGATAGACACCAGCGGCTTCACCAACTACAACCCCA GCCTGAAATCTAGGGTTACAATCTCTGTGGACACAAGCAAGAATCAGTTCTC CCTGAAGCTGAGCAGCGTTACTGCCGCCGACACAGCTGTGTACTATTGCGCC AGAGTTGGCAGATACAGCTACGGCTACTACATCACCGCCTTCGACATTTGGG GCCAAGGCACCACTGTGACCGTTTCCAGCGGAAGCACTAGCGGCAGCGGGA AACCTGGTTCTGGAGAGGGCTCAACCAAGGGCGACATCGTGATGACACAGA GCCCCGACTCTCTGGCTGTGTCCCTGGGAGAGAGAGCCACCATCAACTGCAA GAGCAGCCAGAGCGTTCTGTACAGCAGCAACAACAAGAACTACCTGGCATG GTATCAACAGAAGCCTGGCCAGCCCCCTAAGCTGCTCATCTACTGGGCTTCC ACCAGAGAATCAGGCGTTCCAGACAGGTTCTCCGGCTCGGGTTCAGGCACAG ACTTCACCCTTACCATCTCTTCCCTGCAGGCCGAAGATGTGGCCGTTTACTAC TGTCAGCAGCACTACAGCTTCCCTTTCACATTCGGCGGAGGCACCAAGGTTG AGATCAAGGCAGCTGCTTTCGTGCCTGTGTTCCTGCCTGCTAAGCCCACCAC CACTCCTGCTCCAAGACCTCCTACCCCCGCTCCTACAATCGCCAGCCAACCT CTGAGCCTGAGACCGGAGGCATGCAGACCTGCGGCAGGGGGAGCAGTTCAC ACAAGAGGCTTGGACTTCGCTTGCGACATCTACATCTGGGCCCCTCTGGCCG GCACATGCGGAGTTCTTCTTCTTAGCCTGGTGATCACCCTGTACTGCAACCAC AGAAACAGATTCAGCGTTGTGAAGAGAGGCCGGAAGAAGCTGCTGTACATC TTCAAGCAGCCCTTCATGAGACCTGTGCAGACCACACAGGAGGAAGACGGC TGCAGCTGTAGATTCCCCGAGGAAGAGGAGGGCGGCTGTGAGCTGAGAGTT AAGTTCAGCAGGAGCGCCGACGCCCCTGCCTACCAGCAAGGACAGAATCAA CTGTACAACGAGCTGAACCTGGGCAGACGGGAGGAATACGATGTGCTGGAC AAGAGGAGAGGCAGAGACCCCGAGATGGGCGGCAAACCTAGAAGAAAGAA CCCCCAGGAGGGCCTGTATAACGAGCTCCAGAAGGACAAGATGGCCGAGGC CTACAGCGAGATCGGCATGAAGGGCGAAAGAAGAAGAGGCAAGGGCCACG ACGGCCTCTACCAGGGCTTAAGCACAGCTACAAAGGACACCTACGACGCCC TGCACATGCAGGCCCTGCCCCCTAGATGATTAATTAAatcgat |

Example 21

TABLE 69

Exemplary anti-CD20/anti-CD19 bicistronic CAR nucleotide and
amino acid sequences set forth in SEQ ID NOs: 291 and 292.

SEQ ID
NO: 291
```
ATGCTGCTGCTGGTGACATCTCTGCTGCTTTGCGAGCTGCCCCACCCT
GCCTTCCTGCTTATCCCCGACATTCAGATGACCCAGACCACCAGCAGC
CTGAGCGCCAGCTTAGGAGATAGAGTTACCATCAGCTGCAGAGCCAG
CCAGGACATCAGCAAATACCTGAACTGGTATCAGCAGAAGCCCGACG
GCACTGTGAAACTGCTTATTTACCACACCTCCAGACTGCACAGCGGCG
TTCCCAGCAGATTCTCTGGCAGCGGATCTGGAACCGACTACAGCCTCA
CCATCTCCAACCTGGAGCAGGAGGACATCGCCACCTACTTCTGCCAGC
AGGGCAACACACTGCCCTACACCTTCGGAGGAGGAACCAAGCTGGAG
ATCACCGGGGGAGGAGGCTCTGGAGGCGGCGGATCAGGAGGAGGGG
GATCTGAGGTTAAGCTGCAGGAGAGCGGCCCTGGCCTGGTGGCTCCT
AGCCAATCTTTATCTGTGACCTGCACTGTGTCCGGCGTTAGCCTGCCC
GATTATGGCGTTTCCTGGATCAGACAGCCCCCCAGAAAGGGCCTGGA
ATGGCTGGGCGTTATCTGGGGCAGCGAGACCACATACTACAACAGCG
CCCTGAAGAGCAGACTTACGATTATCAAGGACAACAGCAAGAGCCAG
GTTTTCCTGAAGATGAACAGCCTGCAGACCGACGACACCGCCATCTAC
TACTGCGCTAAGCACTACTACTACGGCGGCAGCTACGCCATGGACTAC
TGGGGCCAGGGAACAAGCGTTACCGTTAGCAGCGCTGCTGCACTGGA
CAACGAGAAGAGCAACGGCACCATCATCCACGTTAAGGGCAAGCACC
TGTGCCCCAGCCCTCTGTTCCCTGGACCTTCTAAGCCTTTCTGGGTTCT
GGTGGTGGTCGGCGGCGTTTTAGCCTGTTACAGCCTTCTGGTGACTGT
GGCCTTCATCATCTTTTGGGTTAGAAGCAAGAGAAGCAGACTGCTCCA
CAGCGACTACATGAACATGACCCCCAGACGGCCTGGCCCCACCAGAA
AGCATTACCAGCCCTACGCTCCTCCCAGAGACTTCGCCGCCTACAGGA
GCAGAGTTAAATTCAGCAGATCCGCCGATGCCCCCGCTTACCAACAG
GGACAAAACCAGCTGTACAATGAGCTCAACCTGGGGAGAAGAGAAG
AATACGACGTTCTGGATAAGAGAAGGGGCAGAGATCCCGAAATGGGG
GGCAAGCCCAGACGCAAGAACCCTCAGGAGGGGCTTTACAACGAACT
GCAGAAGGATAAGATGGCTGAGGCTTACTCGGAGATTGGGATGAAGG
GGGAGAGAAGGCGGGGCAAGGGACACGATGGCTTATACCAGGGGCT
GAGCACCGCCACCAAGGACACATACGACGCTCTTCATATGCAGGCTC
TGCCCCCAAGAAGGGCTAAGAGATCTGGCTCTGGCGAGGGCAGAGGC
AGCTTGCTTACATGTGGCGATGTGGAGGAGAACCCCGGGCCCATGGC
TCTTCCTGTGACAGCTCTTCTGCTGCCCCTGGCCCTGCTTCTGCATGCT
GCTAGACCTCAGCTTCAGCTCCAAGAGAGCGGACCTGGCTTAGTGAA
GCCCAGCGAAACCCTGTCCCTCACCTGCACCGTTTCTGGCGGAAGCAT
CAGCAGCTCCAGCTATTACTGGGGATGGATCAGGCAGCCCCCCTGGCA
AGGGTTTAGAATGGATCGGCTCGATATATTACTCCGGCAGCACCTACT
ATAACCCCAGCTTGAAGAGCCGGGTTACCATTTCTGTGGACACATCAA
AGAACCAGTTCAGCCTGAAGCTGAGCTCTGTGACTGCCGCCGACACA
GCTGTGTACTACTGTGCCAGAGAGACAGACTACTCCAGCGGCATGGG
CTACGGCATGGATGTGTGGGGACAAGGAACCACCGTTACTGTGAGCA
GCGGTTCCACCAGCGGCTCAGGCAAGCCTGGCTCAGGAGAAGGAAGC
ACCAAGGGGGATATACAGATGACACAGAGCCCCTCCAGCCTGTCCGC
CAGCGTTGGCGATCGTGTAACGATCACCTGCCGGGCCTCTCAGAGCAT
CAACTCCTACCTCAATTGGTATCAACAGAAGCCAGGCAAGGCCCCCA
AATTACTCATCTACGCCGCCAGCAGCTTACAGAGCGGGGTTCCCTCTA
GATTCTCCGGCTCCGGTTCTGGAACAGATTTCACCCTCACTATCTCCA
GCTTGCAGCCCGAGGATTTCGCCACTTATTACTGTCAGCAGAGCCTGG
CCGACCCCTTCACATTCGGCGGAGGCACAAAGGTTGAGATCAAGGCA
GCTGCTTTCGTGCCTGTGTTCCTGCCTGCTAAGCCCACCACCACTCCTG
CTCCAAGACCTCCTACCCCCGCTCCTACAATCGCCAGCCAACCTCTGA
GCCTGAGACCGGAGGCATGCAGACCTGCGGCAGGGGGAGCAGTTCAC
ACAAGAGGCTTGGACTTCGCTTGCGACATCTACATCTGGGCCCCTCTG
GCCGGCACATGCGGAGTTCTTCTTCTTAGCCTGGTGATCACCCTGTAC
TGCAACCACAGAAACAGATTCAGCGTTGTGAAGAGAGGCCGGAAGAA
GCTGCTGTACATCTTCAAGCAGCCCTTCATGAGACCTGTGCAGACCAC
ACAGGAGGAAGACGGCTGCAGCTGTGATTCCCCGAGGAAGAGGAG
GGCGGCTGTGAGCTGAGAGTTAAGTTCAGCAGGAGCGCCGACGCCCC
TGCCTACCAGCAAGGACAGAATCAACTGTACAACGAGCTGAACCTGG
GCAGACGGGAGGAATACGATGTGCTGGACAAGAGGAGAGGCAGAGA
CCCCGAGATGGGCGGCAAACCTAGAAGAAAGAACCCCCAGGAGGGC
CTGTATAACGAGCTCCAGAAGGACAAGATGGCCGAGGCCTACAGCGA
GATCGGCATGAAGGGCGAAAGAAGAAGAGGCAAGGGCCACGACGGC
CTCTACCAGGGCTTAAGCACAGCTACAAAGGACACCTACGACGCCCT
GCACATGCAGGCCCTGCCCCCTAGATGA
```

SEQ ID
NO: 292
```
MLLLVTSLLLCELPHPAFLLIPDIQMTQTTSSLSASLGDRVTISCRASQDIS
KYLNWYQQKPDGTVKLLIYHTSRLHSGVPSRFSGSGSGTDYSLTISNLEQ
EDIATYFCQQGNTLPYTFGGGTKLEITGGGSGGGGSGGGSEVKLQESG
PGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAM
DYWGQGTSVTVSSAAALDNEKSNGTIIHVKGKHLCPSPLFPGPSKPFWVL
VVVGGVLACYSLLVTVAFIIFWVRSKRSRLLHSDYMNMTPRRPGPTRKH
YQPYAPPRDFAAYRSRVKFSRSADAPAYQQGQNQLYNELNLGRREEYD
```

TABLE 69-continued

Exemplary anti-CD20/anti-CD19 bicistronic CAR nucleotide and
amino acid sequences set forth in SEQ ID NOs: 291 and 292.

```
VLDKRRGRDPEMGGKPRRKNPQEGLYNELQKDKMAEAYSEIGMKGERR
RGKGHDGLYQGLSTATKDTYDALHMQALPPRRAKRSGSGEGRGSLLTC
GDVEENPGPMALPVTALLLPLALLLHAARPQLQLQESGPGLVKPSETLSL
TCTVSGGSISSSSYYVVGWIRQPPGKGLEWIGSIYYSGSTYYNPSLKSRVTI
SVDTSKNQFSLKLSSVTAADTAVYYCARETDYSSGMGYGMDVWGQGTT
VTVSSGSTSGSGKPGSGEGSTKGDIQMTQSPSSLSASVGDRVTITCRASQS
INSYLNWYQQKPGKAPKLLIYAASSLQSGVPSRFSGSGSGTDFTLTISSLQ
PEDFATYYCQQSLADPFTFGGGTKVEIKAAAFVPVFLPAKPTTTPAPRPPT
PAPTIASQPLSLRPEACRPAAGGAVHTRGLDFACDIYIWAPLAGTCGVLL
LSLVITLYCNHRNRFSVVKRGRKKLLYIFKQPFMRPVQTTQEEDGCSCRF
PEEEEGGCELRVKFSRSADAPAYQQGQNQLYNELNLGRREEYDVLDKRR
GRDPEMGGKPRRKNPQEGLYNELQKDKMAEAYSEIGMKGERRRGKGH
DGLYQGLSTATKDTYDALHMQALPPR
```

Example 22

TABLE 70

Exemplary anti-CD20/anti-CD19 bispecific CAR and components thereof

| | SEQ ID NO: | Sequence |
|---|---|---|
| Bispecific CAR (nt sequence) | 293 | ATGCTTCTCCTGGTGACAAGCCTTCTGCTCTGTGAGTTAC CACACCCAGCATTCCTCCTGATCCCAGACATCCAGATGA CCCAGTCTCCATCCTCCCTGTCTGCATCTGTAGGAGACAG AGTCACCATCACTTGCCGGGCAAGTCAGAGCATTAACAG CTATTTAAATTGGTATCAGCAGAAACCAGGGAAAGCCCC TAAGCTCCTGATCTATGCTGCATCCAGTTTGCAAAGTGGG GTCCCATCAAGGTTCAGTGGCAGTGGATCTGGGACAGAT TTCACTCTCACCATCAGCAGTCTGCAACCTGAAGATTTTG CAACTTACTACTGCCAGCAAAGCCTCGCCGACCCTTTCAC TTTTGGCGGAGGGACCAAGGTTGAGATCAAAGGGGGGG GTGGAAGTGGGAAGCCTGGCAGCGGCGAGGGCGGCAGT CAGCTGCAGCTGCAGGAGTCGGGCCCAGGACTGGTGAAG CCTTCGGAGACCCTGTCCCTCACCTGCACTGTCTCTGGTG GCTCCATCAGCAGTAGTAGTTACTACTGGGGCTGGATCC GCCAGCCCCAGGGAAGGGGCTGGAGTGGATTGGGAGT ATCTATTATAGTGGGAGCACCTACTACAACCCGTCCCTCA AGAGTCGAGTCACCATATCCGTAGACACGTCCAAGAACC AGTTCTCCCTGAAGCTGAGTTCTGTGACCGCCGCAGACA CGGCGGTGTACTACTGCGCCAGAGAGACTGACTACAGCA GCGGAATGGGATACGGAATGGACGTATGGGGCCAGGGA ACAACTGTCACCGTCTCCTCAGGCGGTGGCGGCAGTGGG AAGCCTGGCAGCGATATTCAAATGACCCAGTCCCCGTCC TCCCTGAGTGCCTCCGTCGGTGACCGTGTTACGATTACCT GCCGTGCGAGCCAAGACATCTCTAAATACCTGAACTGGT ATCAGCAAAAACCGGATCAGGCACCGAAACTGCTGATCA AACATACCTCACGTCTGCACTCGGGTGTGCCGAGCCGCTT TAGTGGTTCCGGCTCAGGTACCGATTACACCCTGACGATC AGCTCTCTGCAGCCGGAAGACTTTGCCACGTATTACTGCC AGCAAGGTAATACCCTGCCGTATACGTTCGGCCAAGGTA CCAAACTGGAAATCAAAGGGGGGGGTGGAAGTGGGGGC GGTGGCAGCGGCGGTGGCGGCAGTGAAGTGCAGCTGGTT GAAAGCGGTGGTGGTCTGGTTCAACCGGGTCGTTCCCTG CGTCTGTCATGTACGGCGAGTGGTGTCTCCCTGCCGGACT ATGGCGTGTCCTGGATTCGTCAGCCGCCGGGTAAAGGCC TGGAATGGATTGGTGTCATCTGGGGCAGTGAAACCACGT ATTACAACTCGGCCCTGAAAAGCCGTTTCACCATCTCTCG CGATAACAGTAAAAATACGCTGTACCTGCAGATGAATAG CCTGCGCGCGGAAGACACCGCCGTTTACTACTGCGCAAA ACATTACTACTACGGTGGCAGCTATGCTATGGATTACTGG GGTCAAGGCACGCTGGTCACCGTTTCGTCAGCCGCTGCC CTAGACAATGAGAAGAGCAATGGAACCATTATCCATGTG AAAGGGAAACACCTTTGTCCAAGTCCCCTATTTCCCGGA CCTTCTAAGCCCTTTTGGGTGCTGGTGGTGGTTGGGGGAG TCCTGGCTTGCTATAGCTTGCTAGTAACAGTGGCCTTTAT TATTTTCTGGGTGAGGAGTAAGAGGAGCAGGCTCCTGCA CAGTGACTACATGAACATGACTCCCCGCCGCCCCGGGCC CACCCGCAAGCATTACCAGCCCTATGCCCACCACGCGA CTTCGCAGCCTATCGCTCCAGAGTGAAGTTCAGCAGGAG CGCAGAGCGCCCCCGCGTACCAGCAGGGCCAGAACCAGCT CTATAACGAGCTCAATCTAGGACGAAGAGAGGAGTACGA |

TABLE 70-continued

Exemplary anti-CD20/anti-CD19 bispecific CAR and components thereof

| | SEQ ID NO: | Sequence |
|---|---|---|
| | | TGTTTTGGACAAGAGACGTGGCCGGGACCCTGAGATGGG GGGAAAGCCGAGAAGGAAGAACCCTCAGGAAGGCCTGT ACAATGAACTGCAGAAAGATAAGATGGCGGAGGCCTAC AGTGAGATTGGGATGAAAGGCGAGCGCCGGAGGGGCAA GGGGCACGATGGCCTTTACCAGGGTCTCAGTACAGCCAC CAAGGACACCTACGACGCCCTTCACATGCAGGCCCTGCC CCCTCGATGA |
| Bispecific CAR (AA sequence) | 294 | MLLLVTSLLLCELPHPAFLLIPDIQMTQSPSSLSASVGDRVTI TCRASQSINSYLNWYQQKPGKAPKLLIYAASSLQSGVPSRFS GSGSGTDFTLTISSLQPEDFATYYCQQSLADPFTFGGGTKVE IKGGGGSGKPGSGEGGSQLQLQESGPGLVKPSETLSLTCTVS GGSISSSSYYWGWIRQPPGKGLEWIGSIYYSGSTYYNPSLKS RVTISVDTSKNQFSLKLSSVTAADTAVYYCARETDYSSGMG YGMDVWGQGTTVTVSSGGGGGSGKPGSDIQMTQSPSSLSAS VGDRVTITCRASQDISKYLNWYQQKPDQAPKLLIKHTSRLH SGVPSRFSGSGSGTDYTLTISSLQPEDFATYYCQQGNTLPYT FGQGTKLEIKGGGGSGGGGSGGGGSEVQLVESGGGLVQPG RSLRLSCTASGVSLPDYGVSWIRQPPGKGLEWIGVIWGSETT YYNSALKSRFTISRDNSKNTLYLQMNSLRAEDTAVYYCAK HYYYGGSYAMDYWGQGTLVTVSSAAALDNEKSNGTIIHV KGKHLCPSPLFPGPSKPFWVLVVVGGVLACYSLLVTVAFIIF WVRSKRSRLLHSDYMNMTPRRPGPTRKHYQPYAPPRDFAA YRSRVKFSRSADAPAYQQGQNQLYNELNLGRREEYDVLDK RRGRDPEMGGKPRRKNPQEGLYNELQKDKMAEAYSEIGM KGERRRGKGHDGLYQGLSTATKDTYDALHMQALPPR |
| CSF2RA Signal Peptide | 295 | MLLLVTSLLLCELPHPAFLLIP |
| Ab3 VL | 296 | DIQMTQSPSSLSASVGDRVTITCRASQSINSYLNWYQQKPG KAPKLLIYAASSLQSGVPSRFSGSGSGTDFTLTISSLQPEDFA TYYCQQSLADPFTFGGGTKVEIK |
| KL2 linker | 297 | GGGGSGKPGSGEGGS |
| Ab3 VH | 298 | QLQLQESGPGLVKPSETLSLTCTVSGGSISSSSYYWGWIRQP PGKGLEWIGSIYYSGSTYYNPSLKSRVTISVDTSKNQFSLKL SSVTAADTAVYYCARETDYSSGMGYGMDVWGQGTTVTVSS |
| truncated linker | 299 | GGGGSGKPGS |
| Anti-CD19 VL | 300 | DIQMTQSPSSLSASVGDRVTITCRASQDISKYLNWYQQKPDQAPK LLIKHTSRLHSGVPSRFSGSGSGTDYTLTISSLQPEDFATYYCQQG NTLPYTFGQGTKLEIK |
| G4S linker | 301 | GGGGSGGGGSGGGGS |
| Anti-CD19 VH | 302 | EVQLVESGGGLVQPGRSLRLSCTASGVSLPDYGVSWIRQPPGKGL EWIGVIWGSETTYYNSALKSRFTISRDNSKNTLYLQMNSLRAEDT AVYYCAKHYYYGGSYAMDYWGQGTLVTVSS |
| CD28T extracellular region | 303 | LDNEKSNGTIIHVKGKHLCPSPLFPGPSKP |
| CD28 transmembrane region | 304 | FWVLVVVGGVLACYSLLVTVAFIIFWV |
| CD28 intracellular region | 305 | RSKRSRLLHSDYMNMTPRRPGPTRKHYQPYAPPRDFAAYR S |
| CD3z | 306 | RVKFSRSADAPAYQQGQNQLYNELNLGRREEYDVLDKRRG RDPEMGGKPRRKNPQEGLYNELQKDKMAEAYSEIGMKGE RRRGKGHDGLYQGLSTATKDTYDALHMQALPPR |

Example 23

TABLE 71

| | | |
|---|---|---|
| | Exemplary linkers | |
| | SEQ ID NO: | Sequence |
| G4S (G4Sx1) | 307 | GGGGS |
| G4Sx2 | 308 | GGGGSGGGGS |
| G4Sx3 | 309 | GGGGSGGGGSGGGGS |
| G4Sx4 | 310 | GGGGSGGGGSGGGGSGGGGS |
| IgA | 311 | PSTPPTPSPSTPPTPSPS |

TABLE 71-continued

| | | |
|---|---|---|
| | Exemplary linkers | |
| | SEQ ID NO: | Sequence |
| PAPAP | 312 | PAPAP (optionally comprising 1, 2, 3, 4, 5, 6, 7, 8, 9, or 10 adjacent copies of PAPAP) |
| EAAAK | 313 | EAAAK (optionally comprising 1, 2, 3, 4, 5, 6, 7, 8, 9, or 10 adjacent copies of EAAAK) |

While a number of embodiments have been described, it is apparent that the disclosure and examples may provide other embodiments that utilize or are encompassed by the compositions and methods described herein. Therefore, it will be appreciated that the scope of is to be defined by that which may be understood from the disclosure and the appended claims rather than by the embodiments that have been represented by way of example.

SEQUENCE LISTING

```
Sequence total quantity: 314
SEQ ID NO: 1          moltype = AA   length = 120
FEATURE               Location/Qualifiers
REGION                1..120
                      note = Description of Artificial Sequence: Synthetic
                      polypeptide
source                1..120
                      mol_type = protein
                      organism = synthetic construct
SEQUENCE: 1
QVQLQQWGAG LLKPSETLSL TCAVYGGSFS GYYWSWIRQP PGKGLEWIGE IDHSGSTNYN   60
PSLKSRVTIS VDTSKNQFSL KLSSVTAADT AVYYCARGGG SWYSNWFDPW GQGTMVTVSS  120

SEQ ID NO: 2          moltype = DNA   length = 360
FEATURE               Location/Qualifiers
misc_feature          1..360
                      note = Description of Artificial Sequence: Synthetic
                      polynucleotide
source                1..360
                      mol_type = other DNA
                      organism = synthetic construct
SEQUENCE: 2
caggtgcagc tacagcagtg gggcgcagga ctgttgaagc cttcggagac cctgtccctc   60
acctgcgctg tctatggtgg gtccttcagt ggttactact ggagctggat ccgccagccc  120
ccagggaagg ggctggagtg gattggggaa atcgaccata gtggaagcac caactacaac  180
ccgtccctca agagtcgagt caccatatca gtagacacgt ccaagaacca gttctccctg  240
aagctgagct ctgtgaccgc cgcggacacg gcggtgtact actgcgccag aggtggagga  300
agttggtaca gcaactggtt cgacccatgg ggacagggta caatggtcac cgtctcctca  360

SEQ ID NO: 3          moltype = AA   length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 3
GGSFSGYY                                                              8

SEQ ID NO: 4          moltype = AA   length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 4
GYYWS                                                                 5
```

-continued

```
SEQ ID NO: 5          moltype = AA   length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 5
GGSFSG                                                             6

SEQ ID NO: 6          moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 6
IDHSGST                                                            7

SEQ ID NO: 7          moltype = AA   length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 7
EIDHSGSTNY NPSLKS                                                  16

SEQ ID NO: 8          moltype = AA   length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 8
DHSGS                                                              5

SEQ ID NO: 9          moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 9
ARGGGSWYSN WFDP                                                    14

SEQ ID NO: 10         moltype = AA   length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 10
GGGSWYSNWF DP                                                      12

SEQ ID NO: 11         moltype = AA   length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 11
GGGSWYSNWF DP                                                      12

SEQ ID NO: 12         moltype = AA   length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 12
```

```
DIQMTQSPST LSASVGDRVT ITCRASQSIS SWLAWYQQKP GKAPKLLIYD ASSLESGVPS    60
RFSGSGSGTE FTLTISSLQP DDFATYYCQQ DRSLPPTFGG GTKVEIK                  107

SEQ ID NO: 13              moltype = DNA   length = 321
FEATURE                    Location/Qualifiers
misc_feature               1..321
                           note = Description of Artificial Sequence: Synthetic
                            polynucleotide
source                     1..321
                           mol_type = other DNA
                           organism = synthetic construct
SEQUENCE: 13
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctatgat gcctccagtt tggaaagtgg ggtcccatca   180
aggttcagcg gcagtggatc tgggacagaa ttcactctca ccatcagcag cctgcagcct   240
gatgattttg caacttatta ctgccagcag gaccgaagtc tccctcctac ttttggcgga   300
gggaccaagg ttgagatcaa a                                             321

SEQ ID NO: 14              moltype = AA   length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 14
RASQSISSWL A                                                          11

SEQ ID NO: 15              moltype = AA   length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 15
RASQSISSWL A                                                          11

SEQ ID NO: 16              moltype = AA   length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 16
RASQSISSWL A                                                          11

SEQ ID NO: 17              moltype = AA   length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 17
DASSLES                                                               7

SEQ ID NO: 18              moltype = AA   length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 18
DASSLES                                                               7

SEQ ID NO: 19              moltype = AA   length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 19
DASSLES                                                               7
```

```
SEQ ID NO: 20            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 20
QQDRSLPPT                                                                         9

SEQ ID NO: 21            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 21
QQDRSLPPT                                                                         9

SEQ ID NO: 22            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 22
QQDRSLPPT                                                                         9

SEQ ID NO: 23            moltype = AA   length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 23
QVQLQQWGAG LLKPSETLSL TCAVYGGSFS GIHWNWIRQP PGKGLEWIGD IDTSGSTNYN    60
PSLKSRVTIS VDTSKNQFSL KLSSVTAADT AVYYCARLGQ ESATYLGMDV WGQGTTVTVS   120
S                                                                   121

SEQ ID NO: 24            moltype = DNA   length = 363
FEATURE                  Location/Qualifiers
misc_feature             1..363
                         note = Description of Artificial Sequence: Synthetic
                          polynucleotide
source                   1..363
                         mol_type = other DNA
                         organism = synthetic construct
SEQUENCE: 24
caggtgcagc tacagcagtg gggcgcagga ctgttgaagc cttcggagac cctgtccctc    60
acctgcgctg tctatggtgg gtccttcagt ggtatccact ggaactggat ccgccagccc   120
ccagggaagg ggctggagtg gattggggac atcgacacaa gtggaagcac caactacaac   180
ccgtccctca agagtcgagt caccatatcc gtagacacgt ccaagaacca gttctccctg   240
aagctgagtt ctgtgaccgc cgcagacacg gcggtgtact actgcgccag attgggacag   300
gagtcagcca cctatctcgg aatggacgta tggggccagg gaacaactgt caccgtctcc   360
tca                                                                 363

SEQ ID NO: 25            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 25
GGSFSGIH                                                                          8

SEQ ID NO: 26            moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 26
GIHWN                                                                             5
```

```
SEQ ID NO: 27            moltype = AA   length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 27
GGSFSG                                                                       6

SEQ ID NO: 28            moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 28
IDTSGST                                                                      7

SEQ ID NO: 29            moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 29
DIDTSGSTNY NPSLKS                                                            16

SEQ ID NO: 30            moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 30
DTSGS                                                                        5

SEQ ID NO: 31            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 31
ARLGQESATY LGMDV                                                            15

SEQ ID NO: 32            moltype = AA   length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 32
LGQESATYLG MDV                                                              13

SEQ ID NO: 33            moltype = AA   length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 33
LGQESATYLG MDV                                                              13

SEQ ID NO: 34            moltype = AA   length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
```

```
SEQUENCE: 34
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQLYTY PFTFGGGTKV EIK         113

SEQ ID NO: 35         moltype = DNA   length = 339
FEATURE               Location/Qualifiers
misc_feature          1..339
                      note = Description of Artificial Sequence: Synthetic
                       polynucleotide
source                1..339
                      mol_type = other DNA
                      organism = synthetic construct
SEQUENCE: 35
gacatcgtga tgacccagtc tccagactcc ctggctgtgt ctctgggcga gagggccacc  60
atcaactgca agtccagcca gagtgtttta tacagctcca acaataagaa ctacttagct  120
tggtaccagc agaaaccagg acagcctcct aagctgctca tttactgggc atctacccgg  180
gaatccgggg tccctgaccg attcagtggc agcgggtctg ggacagattt cactctcacc  240
atcagcagcc tgcaggctga agatgtggca gtttattact gtcagcagct ctacacctac  300
cctttcactt ttggcggagg gaccaaggtt gagatcaaa                         339

SEQ ID NO: 36         moltype = AA   length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 36
KSSQSVLYSS NNKNYLA                                                  17

SEQ ID NO: 37         moltype = AA   length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 37
KSSQSVLYSS NNKNYLA                                                  17

SEQ ID NO: 38         moltype = AA   length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 38
KSSQSVLYSS NNKNYLA                                                  17

SEQ ID NO: 39         moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 39
WASTRES                                                            7

SEQ ID NO: 40         moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 40
WASTRES                                                            7

SEQ ID NO: 41         moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 41
WASTRES                                                            7
```

```
SEQ ID NO: 42          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 42
QQLYTYPFT                                                      9

SEQ ID NO: 43          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 43
QQLYTYPFT                                                      9

SEQ ID NO: 44          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 44
QQLYTYPFT                                                      9

SEQ ID NO: 45          moltype = AA  length = 124
FEATURE                Location/Qualifiers
REGION                 1..124
                       note = Description of Artificial Sequence: Synthetic
                        polypeptide
source                 1..124
                       mol_type = protein
                       organism = synthetic construct
SEQUENCE: 45
QLQLQESGPG LVKPSETLSL TCTVSGGSIS SSSYYWGWIR QPPGKGLEWI GSIYYSGSTY  60
YNPSLKSRVT ISVDTSKNQF SLKLSSVTAA DTAVYYCARE TDYSSGMGYG MDVWGQGTTV  120
TVSS                                                              124

SEQ ID NO: 46          moltype = DNA  length = 372
FEATURE                Location/Qualifiers
misc_feature           1..372
                       note = Description of Artificial Sequence: Synthetic
                        polynucleotide
source                 1..372
                       mol_type = other DNA
                       organism = synthetic construct
SEQUENCE: 46
cagctgcagc tgcaggagtc gggcccagga ctggtgaagc cttcggagac cctgtccctc  60
acctgcactg tctctggtgg ctccatcagc agtagtagtt actactgggg ctggatccgc  120
cagccccag ggaaggggct ggagtggatt gggagtatct attatagtgg gagcacctac  180
tacaacccgt ccctcaagag tcgagtcacc atatccgtag acacgtccaa gaaccagttc  240
tccctgaagc tgagttctgt gaccgccgca gacacggcgg tgtactactg cgccagagag  300
actgactaca gcagcggaat gggatacgga atggacgtat ggggccaggg aacaactgtc  360
accgtctcct ca                                                    372

SEQ ID NO: 47          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 47
GGSISSSSYY                                                     10

SEQ ID NO: 48          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 48
```

-continued

```
SSSYYWG                                                      7

SEQ ID NO: 49         moltype = AA   length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 49
GGSISSSS                                                     8

SEQ ID NO: 50         moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 50
IYYSGST                                                      7

SEQ ID NO: 51         moltype = AA   length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 51
SIYYSGSTYY NPSLKS                                            16

SEQ ID NO: 52         moltype = AA   length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 52
YYSGS                                                        5

SEQ ID NO: 53         moltype = AA   length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 53
ARETDYSSGM GYGMDV                                            16

SEQ ID NO: 54         moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 54
ETDYSSGMGY GMDV                                              14

SEQ ID NO: 55         moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 55
ETDYSSGMGY GMDV                                              14

SEQ ID NO: 56         moltype = AA   length = 107
FEATURE               Location/Qualifiers
REGION                1..107
                      note = Description of Artificial Sequence: Synthetic
                       polypeptide
source                1..107
                      mol_type = protein
```

```
                        organism = synthetic construct
SEQUENCE: 56
DIQMTQSPSS LSASVGDRVT ITCRASQSIN SYLNWYQQKP GKAPKLLIYA ASSLQSGVPS  60
RFSGSGSGTD FTLTISSLQP EDFATYYCQQ SLADPFTFGG GTKVEIK                107

SEQ ID NO: 57          moltype = DNA   length = 321
FEATURE                Location/Qualifiers
misc_feature           1..321
                       note = Description of Artificial Sequence: Synthetic
                        polynucleotide
source                 1..321
                       mol_type = other DNA
                       organism = synthetic construct
SEQUENCE: 57
gacatccaga tgacccagtc tccatcctcc ctgtctgcat ctgtaggaga cagagtcacc  60
atcacttgcc gggcaagtca gagcattaac agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgccagcaa agcctcgccg accctttcac ttttggcgga  300
gggaccaagg ttgagatcaa a                                           321

SEQ ID NO: 58          moltype = AA   length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 58
RASQSINSYL N                                                               11

SEQ ID NO: 59          moltype = AA   length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 59
RASQSINSYL N                                                               11

SEQ ID NO: 60          moltype = AA   length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 60
RASQSINSYL N                                                               11

SEQ ID NO: 61          moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 61
AASSLQS                                                                    7

SEQ ID NO: 62          moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 62
AASSLQS                                                                    7

SEQ ID NO: 63          moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 63
```

```
AASSLQS                                                          7

SEQ ID NO: 64          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 64
QQSLADPFT                                                        9

SEQ ID NO: 65          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 65
QQSLADPFT                                                        9

SEQ ID NO: 66          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 66
QQSLADPFT                                                        9

SEQ ID NO: 67          moltype = AA   length = 125
FEATURE                Location/Qualifiers
REGION                 1..125
                       note = Description of Artificial Sequence: Synthetic
                        polypeptide
source                 1..125
                       mol_type = protein
                       organism = synthetic construct
SEQUENCE: 67
QVQLVQSGAE VKKPGASVKV SCKASGYTFK EYGISWVRQA PGQGLEWMGW ISAYSGHTYY   60
AQKLQGRVTM TTDTSTSTAY MELRSLRSDD TAVYYCARGP HYDDWSGFII WFDPWGQGTL  120
VTVSS                                                            125

SEQ ID NO: 68          moltype = DNA   length = 375
FEATURE                Location/Qualifiers
misc_feature           1..375
                       note = Description of Artificial Sequence: Synthetic
                        polynucleotide
source                 1..375
                       mol_type = other DNA
                       organism = synthetic construct
SEQUENCE: 68
caggttcagc tggtgcagtc tggagctgag gtgaagaagc ctggggcctc agtgaaggtc   60
tcctgcaagg cttctggtta cacctttaaa gaatatggta tcagctgggt gcgacaggcc  120
cctggacaag ggcttgagtg gatgggatgg atcagcgctt acagtggtca cacatactat  180
gcacagaagc tccagggcag agtcaccatg accacagaca catccacgag cacagcctac  240
atggagctga ggagcctgag atctgacgac acggcggtgt actactgcgc cagagggcct  300
cactacgacg actggagcgg atttatcata tggttcgacc catggggaca gggtacattg  360
gtcaccgtct cctca                                                 375

SEQ ID NO: 69          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 69
GYTFKEYG                                                         8

SEQ ID NO: 70          moltype = AA   length = 5
FEATURE                Location/Qualifiers
REGION                 1..5
                       note = Description of Artificial Sequence: Synthetic peptide
source                 1..5
                       mol_type = protein
                       organism = synthetic construct
```

```
SEQUENCE: 70
EYGIS                                                              5

SEQ ID NO: 71         moltype = AA  length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 71
GYTFKE                                                             6

SEQ ID NO: 72         moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 72
ISAYSGHT                                                           8

SEQ ID NO: 73         moltype = AA  length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 73
WISAYSGHTY YAQKLQ                                                  16

SEQ ID NO: 74         moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 74
SAYSG                                                              5

SEQ ID NO: 75         moltype = AA  length = 18
FEATURE               Location/Qualifiers
REGION                1..18
                      note = Description of Artificial Sequence: Synthetic peptide
source                1..18
                      mol_type = protein
                      organism = synthetic construct
SEQUENCE: 75
ARGPHYDDWS GFIIWFDP                                                18

SEQ ID NO: 76         moltype = AA  length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 76
GPHYDDWSGF IIWFDP                                                  16

SEQ ID NO: 77         moltype = AA  length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 77
GPHYDDWSGF IIWFDP                                                  16

SEQ ID NO: 78         moltype = AA  length = 107
FEATURE               Location/Qualifiers
REGION                1..107
                      note = Description of Artificial Sequence: Synthetic
                       polypeptide
source                1..107
```

```
                              mol_type = protein
                              organism = synthetic construct
SEQUENCE: 78
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYRFPPTFGQ GTKVEIK                 107

SEQ ID NO: 79            moltype = DNA   length = 321
FEATURE                  Location/Qualifiers
misc_feature             1..321
                         note = Description of Artificial Sequence: Synthetic
                          polynucleotide
source                   1..321
                         mol_type = other DNA
                         organism = synthetic construct
SEQUENCE: 79
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaaagccc ctaagctcct gatctatgct gcatccagtt tgcaaagtgg ggtcccttca  180
aggttcagtg gcagtggatc tgggacagat ttcactctca ccatcagcag tctgcaacct  240
gaagattttg caacttacta ctgtcaacag agttacaggt ttcctcctac ctttggccaa  300
gggaccaagg ttgagatcaa a                                            321

SEQ ID NO: 80            moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 80
RASQSISSYL N                                                        11

SEQ ID NO: 81            moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 81
RASQSISSYL N                                                        11

SEQ ID NO: 82            moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 82
RASQSISSYL N                                                        11

SEQ ID NO: 83            moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 83
AASSLQS                                                             7

SEQ ID NO: 84            moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 84
AASSLQS                                                             7

SEQ ID NO: 85            moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
```

-continued

```
SEQUENCE: 85
AASSLQS                                                                          7

SEQ ID NO: 86            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 86
QQSYRFPPT                                                                        9

SEQ ID NO: 87            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 87
QQSYRFPPT                                                                        9

SEQ ID NO: 88            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 88
QQSYRFPPT                                                                        9

SEQ ID NO: 89            moltype = AA  length = 124
FEATURE                  Location/Qualifiers
REGION                   1..124
                         note = Description of Artificial Sequence: Synthetic
                          polypeptide
source                   1..124
                         mol_type = protein
                         organism = synthetic construct
SEQUENCE: 89
QVQLQESGPG LVKPSETLSL TCTVSGGSIS SPDHYWGWIR QPPGKGLEWI GSIYASGSTF    60
YNPSLKSRVT ISVDTSKNQF SLKLSSVTAA DTAVYYCARE TDYSSGMGYG MDVWGQGTTV    120
TVSS                                                                 124

SEQ ID NO: 90            moltype = DNA  length = 372
FEATURE                  Location/Qualifiers
misc_feature            1..372
                         note = Description of Artificial Sequence: Synthetic
                          polynucleotide
source                   1..372
                         mol_type = other DNA
                         organism = synthetic construct
SEQUENCE: 90
caggtgcagc tgcaggagtc gggcccagga ctggtgaagc cttcggagac cctgtccctc    60
acctgcactg tctctggtgg ctccatcagc agtcccgacc actactgggg ctggatccgc    120
cagcccccag ggaaggggct ggagtggatt gggtccatct acgccagtgg gagcaccttc    180
tacaacccgt ccctcaagag tcgagtcacc atatccgtag acacgtccaa gaaccagttc    240
tccctgaagc tgagctctgt gaccgccgcg gacacggcgg tgtactactg cgccagagag    300
actgactaca gcagcggaat gggatacgga atggacgtat ggggccaggg aacaactgtc    360
accgtctcct ca                                                        372

SEQ ID NO: 91            moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 91
GGSISSPDHY                                                                       10

SEQ ID NO: 92            moltype = AA  length = 7
FEATURE                  Location/Qualifiers
REGION                   1..7
                         note = Description of Artificial Sequence: Synthetic peptide
source                   1..7
                         mol_type = protein
```

```
SEQUENCE: 92
SPDHYWG                                                                   7

SEQ ID NO: 93          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 93
GGSISSPD                                                                  8

SEQ ID NO: 94          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 94
IYASGST                                                                   7

SEQ ID NO: 95          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 95
SIYASGSTFY NPSLKS                                                         16

SEQ ID NO: 96          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 96
YASGS                                                                     5

SEQ ID NO: 97          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 97
ARETDYSSGM GYGMDV                                                         16

SEQ ID NO: 98          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 98
ETDYSSGMGY GMDV                                                           14

SEQ ID NO: 99          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 99
ETDYSSGMGY GMDV                                                           14

SEQ ID NO: 100         moltype = AA  length = 107
FEATURE                Location/Qualifiers
REGION                 1..107
                       note = Description of Artificial Sequence: Synthetic
                        polypeptide
```

```
source                   1..107
                         mol_type = protein
                         organism = synthetic construct
SEQUENCE: 100
DIQMTQSPSS LSASVGDRVT ITCRASQSIN SYLNWYQQKP GKAPKLLIYA ASSLQSGVPS  60
RFSGSGSGTD FTLTISSLQP EDFATYYCQQ SLADPFTFGG GTKVEIK               107

SEQ ID NO: 101           moltype = DNA   length = 321
FEATURE                  Location/Qualifiers
misc_feature             1..321
                         note = Description of Artificial Sequence: Synthetic
                          polynucleotide
source                   1..321
                         mol_type = other DNA
                         organism = synthetic construct
SEQUENCE: 101
gacatccaga tgacccagtc tccatcctcc ctgtctgcat ctgtaggaga cagagtcacc  60
atcacttgcc gggcaagtca gagcattaac agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgccagcaa agcctcgccg acccttcac ttttggcgga  300
gggaccaagg ttgagatcaa a                                           321

SEQ ID NO: 102           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 102
RASQSINSYL N                                                       11

SEQ ID NO: 103           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 103
RASQSINSYL N                                                       11

SEQ ID NO: 104           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 104
RASQSINSYL N                                                       11

SEQ ID NO: 105           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 105
AASSLQS                                                            7

SEQ ID NO: 106           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 106
AASSLQS                                                            7

SEQ ID NO: 107           moltype = AA   length = 7
FEATURE                  Location/Qualifiers
REGION                   1..7
                         note = Description of Artificial Sequence: Synthetic peptide
source                   1..7
                         mol_type = protein
```

-continued

```
                        organism = synthetic construct
SEQUENCE: 107
AASSLQS                                                          7

SEQ ID NO: 108         moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 108
QQSLADPFT                                                        9

SEQ ID NO: 109         moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 109
QQSLADPFT                                                        9

SEQ ID NO: 110         moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 110
QQSLADPFT                                                        9

SEQ ID NO: 111         moltype = AA   length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 111
QITLKESGPT LVKPTQTLTL TCTFSGFSLD TEGVGVGWIR QPPGKALEWL ALIYFNDQKR   60
YSPSLKSRLT ITKDTSKNQV VLTMTNMDPV DTAVYYCARD TGYSRWYYGM DVWGQGTTVT  120
VSS                                                              123

SEQ ID NO: 112         moltype = DNA   length = 369
FEATURE                Location/Qualifiers
misc_feature           1..369
                       note = Description of Artificial Sequence: Synthetic
                        polynucleotide
source                 1..369
                       mol_type = other DNA
                       organism = synthetic construct
SEQUENCE: 112
cagatcacct tgaaggagtc tggtcctacg ctggtgaaac ccacacagac cctcacgctg   60
acctgcacct tctctgggtt ctcactcgac actgaaggag tgggtgtggg ctggatccgt  120
cagcccccag gaaaggccct ggagtggctt gcactcattt atttcaatga tcaaaagcgc  180
tacagcccat ctctgaagag caggctcacc atcaccaagg acacctccaa aaaccaggtg  240
gtccttacaa tgaccaacat ggaccctgtg gacacggcgg tgtactactg cgccagagac  300
acgggataca gccgatggta ctacggcatg gatgtatggg gccagggaac aactgtcacc  360
gtctcctca                                                        369

SEQ ID NO: 113         moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 113
GFSLDTEGVG                                                       10

SEQ ID NO: 114         moltype = AA   length = 7
FEATURE                Location/Qualifiers
REGION                 1..7
                       note = Description of Artificial Sequence: Synthetic peptide
source                 1..7
```

-continued

```
                             mol_type = protein
                             organism = synthetic construct
SEQUENCE: 114
TEGVGVG                                                          7

SEQ ID NO: 115              moltype = AA   length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 115
GFSLDTEG                                                         8

SEQ ID NO: 116              moltype = AA   length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 116
IYFNDQK                                                          7

SEQ ID NO: 117              moltype = AA   length = 16
FEATURE                     Location/Qualifiers
REGION                      1..16
                            note = Description of Artificial Sequence: Synthetic peptide
source                      1..16
                            mol_type = protein
                            organism = synthetic construct
SEQUENCE: 117
LIYFNDQKRY SPSLKS                                                16

SEQ ID NO: 118              moltype = AA   length = 5
FEATURE                     Location/Qualifiers
REGION                      1..5
                            note = Description of Artificial Sequence: Synthetic peptide
source                      1..5
                            mol_type = protein
                            organism = synthetic construct
SEQUENCE: 118
YFNDQ                                                            5

SEQ ID NO: 119              moltype = AA   length = 15
FEATURE                     Location/Qualifiers
REGION                      1..15
                            note = Description of Artificial Sequence: Synthetic peptide
source                      1..15
                            mol_type = protein
                            organism = synthetic construct
SEQUENCE: 119
ARDTGYSRWY YGMDV                                                 15

SEQ ID NO: 120              moltype = AA   length = 13
FEATURE                     Location/Qualifiers
REGION                      1..13
                            note = Description of Artificial Sequence: Synthetic peptide
source                      1..13
                            mol_type = protein
                            organism = synthetic construct
SEQUENCE: 120
DTGYSRWYYG MDV                                                   13

SEQ ID NO: 121              moltype = AA   length = 13
FEATURE                     Location/Qualifiers
REGION                      1..13
                            note = Description of Artificial Sequence: Synthetic peptide
source                      1..13
                            mol_type = protein
                            organism = synthetic construct
SEQUENCE: 121
DTGYSRWYYG MDV                                                   13

SEQ ID NO: 122              moltype = AA   length = 107
FEATURE                     Location/Qualifiers
REGION                      1..107
                            note = Description of Artificial Sequence: Synthetic
```

```
                         polypeptide
source                   1..107
                         mol_type = protein
                         organism = synthetic construct
SEQUENCE: 122
DIQMTQSPSS VSASVGDRVT ITCRASQGIS SWLAWYQQKP GKAPKLLIYA ASSLQSGVPS  60
RFSGSGSGTD FTLTISSLQP EDFATYYCQQ AYAYPITFGG GTKVEIK              107

SEQ ID NO: 123           moltype = DNA  length = 321
FEATURE                  Location/Qualifiers
misc_feature             1..321
                         note = Description of Artificial Sequence: Synthetic
                          polynucleotide
source                   1..321
                         mol_type = other DNA
                         organism = synthetic construct
SEQUENCE: 123
gacatccaga tgacccagtc tccatcttcc gtgtctgcat ctgtaggaga cagagtcacc  60
atcacttgtc gggcgagtca gggtattagc agctggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagatttg  caacttatta ctgtcagcag gcatacgcct accctatcac ttttggcgga 300
gggaccaagg ttgagatcaa a                                           321

SEQ ID NO: 124           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 124
RASQGISSWL A                                                        11

SEQ ID NO: 125           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 125
RASQGISSWL A                                                        11

SEQ ID NO: 126           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 126
RASQGISSWL A                                                        11

SEQ ID NO: 127           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 127
AASSLQS                                                             7

SEQ ID NO: 128           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 128
AASSLQS                                                             7

SEQ ID NO: 129           moltype = AA  length = 7
FEATURE                  Location/Qualifiers
REGION                   1..7
                         note = Description of Artificial Sequence: Synthetic peptide
source                   1..7
```

-continued

```
                          mol_type = protein
                          organism = synthetic construct
SEQUENCE: 129
AASSLQS                                                           7

SEQ ID NO: 130           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 130
QQAYAYPIT                                                         9

SEQ ID NO: 131           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 131
QQAYAYPIT                                                         9

SEQ ID NO: 132           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 132
QQAYAYPIT                                                         9

SEQ ID NO: 133           moltype = AA   length = 127
FEATURE                  Location/Qualifiers
REGION                   1..127
                         note = Description of Artificial Sequence: Synthetic
                          polypeptide
source                   1..127
                         mol_type = protein
                         organism = synthetic construct
SEQUENCE: 133
QVQLQQWGAG LLKPSETLSL TCAVYGGSFE KYYWSWIRQP PGKGLEWIGE IYHSGLTNYN  60
PSLKSRVTIS VDTSKNQFSL KLSSVTAADT AVYYCARVRY DSSDSYYYSY DYGMDVWGQG  120
TTVTVSS                                                           127

SEQ ID NO: 134           moltype = DNA   length = 381
FEATURE                  Location/Qualifiers
misc_feature             1..381
                         note = Description of Artificial Sequence: Synthetic
                          polynucleotide
source                   1..381
                         mol_type = other DNA
                         organism = synthetic construct
SEQUENCE: 134
caggtgcagc tacagcagtg gggcgcagga ctgttgaagc cttcggagac cctgtccctc  60
acctgcgctg tctatggtgg gtccttcgaa aaatactact ggagctggat ccgccagccc  120
ccaggggaagg ggctggagtg gattggggaa atctaccata gtggactcac caactacaac  180
ccgtccctca agagtcgagt caccatatca gtagacacgt ccaagaacca gttctccctg  240
aagctgagct ctgtgaccgc cgcggacacg gcggtgtact actgcgccag ggtcagatac  300
gacagcagcg actcctacta ctatagctac gattatggaa tggacgtatg gggccaggga  360
acaactgtca ccgtctcctc a                                            381

SEQ ID NO: 135           moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 135
GGSFEKYY                                                          8

SEQ ID NO: 136           moltype = AA   length = 5
FEATURE                  Location/Qualifiers
REGION                   1..5
                         note = Description of Artificial Sequence: Synthetic peptide
```

```
source                    1..5
                          mol_type = protein
                          organism = synthetic construct
SEQUENCE: 136
KYYWS                                                            5

SEQ ID NO: 137            moltype = AA   length = 6
FEATURE                   Location/Qualifiers
REGION                    1..6
                          note = Description of Artificial Sequence: Synthetic peptide
source                    1..6
                          mol_type = protein
                          organism = synthetic construct
SEQUENCE: 137
GGSFEK                                                           6

SEQ ID NO: 138            moltype = AA   length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 138
IYHSGLT                                                          7

SEQ ID NO: 139            moltype = AA   length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 139
EIYHSGLTNY NPSLKS                                                16

SEQ ID NO: 140            moltype = AA   length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 140
YHSGL                                                            5

SEQ ID NO: 141            moltype = AA   length = 21
FEATURE                   Location/Qualifiers
REGION                    1..21
                          note = Description of Artificial Sequence: Synthetic peptide
source                    1..21
                          mol_type = protein
                          organism = synthetic construct
SEQUENCE: 141
ARVRYDSSDS YYYSYDYGMD V                                          21

SEQ ID NO: 142            moltype = AA   length = 19
FEATURE                   Location/Qualifiers
REGION                    1..19
                          note = Description of Artificial Sequence: Synthetic peptide
source                    1..19
                          mol_type = protein
                          organism = synthetic construct
SEQUENCE: 142
VRYDSSDSYY YSYDYGMDV                                             19

SEQ ID NO: 143            moltype = AA   length = 19
FEATURE                   Location/Qualifiers
REGION                    1..19
                          note = Description of Artificial Sequence: Synthetic peptide
source                    1..19
                          mol_type = protein
                          organism = synthetic construct
SEQUENCE: 143
VRYDSSDSYY YSYDYGMDV                                             19

SEQ ID NO: 144            moltype = AA   length = 113
FEATURE                   Location/Qualifiers
REGION                    1..113
```

-continued

```
                        note = Description of Artificial Sequence: Synthetic
                         polypeptide
source                  1..113
                        mol_type = protein
                        organism = synthetic construct
SEQUENCE: 144
DIVLTQSPDS LAVSLGERAT INCKSSQSVL YSSNNKNYLA WYQQKPGQPP KLLIYWASSR  60
ESGVPDRFSG SGSGTDFTLT ISSLQAEDVA VYYCQQSYSF PWTFGGGTKV EIK         113

SEQ ID NO: 145          moltype = DNA   length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 145
gacatcgtgc tgacccagtc tccagactcc ctggctgtgt ctctgggcga gagggccacc  60
atcaactgca agtccagcca gagtgtttta tacagctcca acaataagaa ctacttagct  120
tggtaccagc agaaaccagg acagcctcct aagctgctca tttactgggc atctagccgg  180
gaatccgggg tccctgaccg attcagtggc agcgggtctg ggacagattt cactctcacc  240
atcagcagcc tgcaggctga agatgtggca gtttattact gtcagcagtc ctactccttc  300
ccttggactt ttggcggagg gaccaaggtt gagatcaaa                         339

SEQ ID NO: 146          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 146
KSSQSVLYSS NNKNYLA                                                 17

SEQ ID NO: 147          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 147
KSSQSVLYSS NNKNYLA                                                 17

SEQ ID NO: 148          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 148
KSSQSVLYSS NNKNYLA                                                 17

SEQ ID NO: 149          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 149
WASSRES                                                            7

SEQ ID NO: 150          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 150
WASSRES                                                            7

SEQ ID NO: 151          moltype = AA   length = 7
FEATURE                 Location/Qualifiers
REGION                  1..7
                        note = Description of Artificial Sequence: Synthetic peptide
```

-continued

```
source                  1..7
                        mol_type = protein
                        organism = synthetic construct
SEQUENCE: 151
WASSRES                                                              7

SEQ ID NO: 152          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 152
QQSYSFPWT                                                            9

SEQ ID NO: 153          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 153
QQSYSFPWT                                                            9

SEQ ID NO: 154          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 154
QQSYSFPWT                                                            9

SEQ ID NO: 155          moltype = AA   length = 127
FEATURE                 Location/Qualifiers
REGION                  1..127
                        note = Description of Artificial Sequence: Synthetic
                         polypeptide
source                  1..127
                        mol_type = protein
                        organism = synthetic construct
SEQUENCE: 155
QVQLQQWGAG LLKPSETLSL TCAVYGGSFS RYVWSWIRQP PGKGLEWIGE IDSSGKTNYN  60
PSLKSRVTIS VDTSKNQFSL KLSSVTAADT AVYYCARVRY DSSDSYYYSY DYGMDVWGQG  120
TTVTVSS                                                            127

SEQ ID NO: 156          moltype = DNA   length = 381
FEATURE                 Location/Qualifiers
misc_feature            1..381
                        note = Description of Artificial Sequence: Synthetic
                         polynucleotide
source                  1..381
                        mol_type = other DNA
                        organism = synthetic construct
SEQUENCE: 156
caggtgcagc tacagcagtg gggcgcagga ctgttgaagc cttcggagac cctgtccctc  60
acctgcgctg tctatggtgg gtccttcagt cgatacgtat ggagctggat ccgccagccc  120
ccagggaagg ggctggagtg gattggggaa atcgactcca gtggaaaaac caactacaac  180
ccgtccctca agagtcgagt caccatatca gtagacacgt ccaagaacca gttctccctg  240
aagctgagct ctgtgaccgc cgcggacacg gcggtgtact actgcgccag ggtcagatac  300
gacagcagcg actcctacta ctatagctac gattatggaa tggacgtatg gggccaggga  360
acaactgtca ccgtctcctc a                                            381

SEQ ID NO: 157          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 157
GGSFSRYV                                                            8

SEQ ID NO: 158          moltype = AA   length = 5
FEATURE                 Location/Qualifiers
REGION                  1..5
```

-continued

```
                           note = Description of Artificial Sequence: Synthetic peptide
source                     1..5
                           mol_type = protein
                           organism = synthetic construct
SEQUENCE: 158
RYVWS                                                                 5

SEQ ID NO: 159             moltype = AA   length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 159
GGSFSR                                                                6

SEQ ID NO: 160             moltype = AA   length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 160
IDSSGKT                                                               7

SEQ ID NO: 161             moltype = AA   length = 16
FEATURE                    Location/Qualifiers
REGION                     1..16
                           note = Description of Artificial Sequence: Synthetic peptide
source                     1..16
                           mol_type = protein
                           organism = synthetic construct
SEQUENCE: 161
EIDSSGKTNY NPSLKS                                                     16

SEQ ID NO: 162             moltype = AA   length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 162
DSSGK                                                                 5

SEQ ID NO: 163             moltype = AA   length = 21
FEATURE                    Location/Qualifiers
REGION                     1..21
                           note = Description of Artificial Sequence: Synthetic peptide
source                     1..21
                           mol_type = protein
                           organism = synthetic construct
SEQUENCE: 163
ARVRYDSSDS YYYSYDYGMD V                                               21

SEQ ID NO: 164             moltype = AA   length = 19
FEATURE                    Location/Qualifiers
REGION                     1..19
                           note = Description of Artificial Sequence: Synthetic peptide
source                     1..19
                           mol_type = protein
                           organism = synthetic construct
SEQUENCE: 164
VRYDSSDSYY YSYDYGMDV                                                  19

SEQ ID NO: 165             moltype = AA   length = 19
FEATURE                    Location/Qualifiers
REGION                     1..19
                           note = Description of Artificial Sequence: Synthetic peptide
source                     1..19
                           mol_type = protein
                           organism = synthetic construct
SEQUENCE: 165
VRYDSSDSYY YSYDYGMDV                                                  19

SEQ ID NO: 166             moltype = AA   length = 113
FEATURE                    Location/Qualifiers
```

-continued

```
REGION                  1..113
                        note = Description of Artificial Sequence: Synthetic
                         polypeptide
source                  1..113
                        mol_type = protein
                        organism = synthetic construct
SEQUENCE: 166
DIVLTQSPDS LAVSLGERAT INCKSSQSVL YSSNNKNYLA WYQQKPGQPP KLLIYWASSR  60
ESGVPDRFSG SGSGTDFTLT ISSLQAEDVA VYYCQQSYSF PWTFGGGTKV EIK        113

SEQ ID NO: 167          moltype = DNA   length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 167
gacatcgtgc tgacccagtc tccagactcc ctggctgtgt ctctgggcga gagggccacc   60
atcaactgca agtccagcca gagtgtttta tacagctcca acaataagaa ctacttagct  120
tggtaccagc agaaaccagg acagcctcct aagctgctca tttactgggc atctagccgg  180
gaatccgggg tccctgaccg attcagtggc agcgggtctg ggacagattt cactctcacc  240
atcagcagcc tgcaggctga agatgtggca gtttattact gtcagcagtc ctactccttc  300
ccttggactt ttggcggagg gaccaaggtt gagatcaaa                         339

SEQ ID NO: 168          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 168
KSSQSVLYSS NNKNYLA                                                   17

SEQ ID NO: 169          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 169
KSSQSVLYSS NNKNYLA                                                   17

SEQ ID NO: 170          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 170
KSSQSVLYSS NNKNYLA                                                   17

SEQ ID NO: 171          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 171
WASSRES                                                              7

SEQ ID NO: 172          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 172
WASSRES                                                              7

SEQ ID NO: 173          moltype = AA   length = 7
FEATURE                 Location/Qualifiers
REGION                  1..7
```

-continued

```
                            note = Description of Artificial Sequence: Synthetic peptide
source                      1..7
                            mol_type = protein
                            organism = synthetic construct
SEQUENCE: 173
WASSRES                                                                           7

SEQ ID NO: 174              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 174
QQSYSFPWT                                                                         9

SEQ ID NO: 175              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 175
QQSYSFPWT                                                                         9

SEQ ID NO: 176              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 176
QQSYSFPWT                                                                         9

SEQ ID NO: 177              moltype = AA  length = 127
FEATURE                     Location/Qualifiers
REGION                      1..127
                            note = Description of Artificial Sequence: Synthetic
                             polypeptide
source                      1..127
                            mol_type = protein
                            organism = synthetic construct
SEQUENCE: 177
QVQLQQWGAG LLKPSETLSL TCAVYGGSFS GYAWSWIRQP PGKGLEWIGE IDHRGFTNYN   60
PSLKSRVTIS VDTSKNQFSL KLSSVTAADT AVYYCARVRY DSSDSYYYSY DYGMDVWGQG  120
TTVTVSS                                                                         127

SEQ ID NO: 178              moltype = DNA  length = 381
FEATURE                     Location/Qualifiers
misc_feature               1..381
                            note = Description of Artificial Sequence: Synthetic
                             polynucleotide
source                      1..381
                            mol_type = other DNA
                            organism = synthetic construct
SEQUENCE: 178
caggtgcagc tacagcagtg gggcgcagga ctgttgaagc cttcggagac cctgtccctc   60
acctgcgctg tctatggtgg gtccttctcc ggttacgcat ggagctggat ccgccagccc  120
ccagggaagg ggctggagtg gattggggaa atcgaccatc gaggattcac caactacaac  180
ccgtccctca agagtcgagt caccatatca gtagacacgt ccaagaacca gttctccctg  240
aagctgagct ctgtgaccgc cgcggacacg gcggtgtact actgcgccag ggtcagatac  300
gacagcagcg actcctacta ctatagctac gattatggaa tggacgtatg gggccaggga  360
acaactgtca ccgtctcctc a                                             381

SEQ ID NO: 179              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 179
GGSFSGYA                                                                          8

SEQ ID NO: 180              moltype = AA  length = 5
FEATURE                     Location/Qualifiers
```

-continued

```
REGION                  1..5
                        note = Description of Artificial Sequence: Synthetic peptide
source                  1..5
                        mol_type = protein
                        organism = synthetic construct
SEQUENCE: 180
GYAWS                                                                    5

SEQ ID NO: 181          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 181
GGSFSG                                                                   6

SEQ ID NO: 182          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 182
IDHRGFT                                                                  7

SEQ ID NO: 183          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 183
EIDHRGFTNY NPSLKS                                                        16

SEQ ID NO: 184          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 184
DHRGF                                                                    5

SEQ ID NO: 185          moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 185
ARVRYDSSDS YYYSYDYGMD V                                                  21

SEQ ID NO: 186          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 186
VRYDSSDSYY YSYDYGMDV                                                     19

SEQ ID NO: 187          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 187
VRYDSSDSYY YSYDYGMDV                                                     19

SEQ ID NO: 188          moltype = AA  length = 113
```

```
FEATURE              Location/Qualifiers
REGION               1..113
                     note = Description of Artificial Sequence: Synthetic
                      polypeptide
source               1..113
                     mol_type = protein
                     organism = synthetic construct
SEQUENCE: 188
DIVLTQSPDS LAVSLGERAT INCKSSQSVL YSSNNKNYLA WYQQKPGQPP KLLIYWASSR  60
ESGVPDRFSG SGSGTDFTLT ISSLQAEDVA VYYCQQSYSF PWTFGGGTKV EIK         113

SEQ ID NO: 189       moltype = DNA   length = 339
FEATURE              Location/Qualifiers
misc_feature         1..339
                     note = Description of Artificial Sequence: Synthetic
                      polynucleotide
source               1..339
                     mol_type = other DNA
                     organism = synthetic construct
SEQUENCE: 189
gacatcgtgc tgacccagtc tccagactcc ctggctgtgt ctctgggcga gagggccacc  60
atcaactgca agtccagcca gagtgtttta tacagctcca acaataagaa ctacttagct  120
tggtaccagc agaaaccagg acagcctcct aagctgctca tttactgggc atctagccgg  180
gaatccgggg tccctgaccg attcagtggc agcgggtctg ggacagattt cactctcacc  240
atcagcagc tgcaggctga agatgtggca gtttattact gtcagcagtc ctactccttc  300
ccttggactt ttggcggagg gaccaaggtt gagatcaaa                        339

SEQ ID NO: 190       moltype = AA   length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 190
KSSQSVLYSS NNKNYLA                                                       17

SEQ ID NO: 191       moltype = AA   length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 191
KSSQSVLYSS NNKNYLA                                                       17

SEQ ID NO: 192       moltype = AA   length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 192
KSSQSVLYSS NNKNYLA                                                       17

SEQ ID NO: 193       moltype = AA   length = 7
FEATURE              Location/Qualifiers
REGION               1..7
                     note = Description of Artificial Sequence: Synthetic peptide
source               1..7
                     mol_type = protein
                     organism = synthetic construct
SEQUENCE: 193
WASSRES                                                                   7

SEQ ID NO: 194       moltype = AA   length = 7
FEATURE              Location/Qualifiers
REGION               1..7
                     note = Description of Artificial Sequence: Synthetic peptide
source               1..7
                     mol_type = protein
                     organism = synthetic construct
SEQUENCE: 194
WASSRES                                                                   7

SEQ ID NO: 195       moltype = AA   length = 7
FEATURE              Location/Qualifiers
```

-continued

```
REGION                  1..7
                        note = Description of Artificial Sequence: Synthetic peptide
source                  1..7
                        mol_type = protein
                        organism = synthetic construct
SEQUENCE: 195
WASSRES                                                                           7

SEQ ID NO: 196          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 196
QQSYSFPWT                                                                         9

SEQ ID NO: 197          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 197
QQSYSFPWT                                                                         9

SEQ ID NO: 198          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 198
QQSYSFPWT                                                                         9

SEQ ID NO: 199          moltype = AA   length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 199
QVQLQQWGAG LLKPSETLSL TCAVYGGSFQ KYYWSWIRQP PGKGLEWIGE IDTSGFTNYN    60
PSLKSRVTIS VDTSKNQFSL KLSSVTAADT AVYYCARVGR YSYGYYITAF DIWGQGTTVT    120
VSS                                                                   123

SEQ ID NO: 200          moltype = DNA   length = 369
FEATURE                 Location/Qualifiers
misc_feature            1..369
                        note = Description of Artificial Sequence: Synthetic
                         polynucleotide
source                  1..369
                        mol_type = other DNA
                        organism = synthetic construct
SEQUENCE: 200
caggtgcagc tacagcagtg gggcgcagga ctgttgaagc cttcggagac cctgtccctc    60
acctgcgctg tctatggtgg gtccttccaa aaatactact ggagctggat ccgccagccc    120
ccagggaagg ggctggagtg gattgggaa atcgacacca gtggattcac caactacaac    180
ccgtccctca agagtcgagt caccatatca gtagacacgt ccaagaacca gttctccctg    240
aagctgagct ctgtgaccgc cgcggacacg gcggtgtact actgcgccag agtgggaagg    300
tacagctacg gatactatat caccgcattc gacatatggg gtcagggtac aactgtcacc    360
gtctcctca                                                            369

SEQ ID NO: 201          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 201
GGSFQKYY                                                                          8

SEQ ID NO: 202          moltype = AA   length = 5
```

| FEATURE | Location/Qualifiers |
|---|---|
| REGION | 1..5 |
| | note = Description of Artificial Sequence: Synthetic peptide |
| source | 1..5 |
| | mol_type = protein |
| | organism = synthetic construct |

SEQUENCE: 202
KYYWS                                                                   5

SEQ ID NO: 203     moltype = AA   length = 6
FEATURE            Location/Qualifiers
REGION             1..6
                   note = Description of Artificial Sequence: Synthetic peptide
source             1..6
                   mol_type = protein
                   organism = synthetic construct SEQUENCE: 203
GGSFQK                                                                  6

SEQ ID NO: 204     moltype = AA   length = 7
FEATURE            Location/Qualifiers
REGION             1..7
                   note = Description of Artificial Sequence: Synthetic peptide
source             1..7
                   mol_type = protein
                   organism = synthetic construct SEQUENCE: 204
IDTSGFT                                                                 7

SEQ ID NO: 205     moltype = AA   length = 16
FEATURE            Location/Qualifiers
REGION             1..16
                   note = Description of Artificial Sequence: Synthetic peptide
source             1..16
                   mol_type = protein
                   organism = synthetic construct SEQUENCE: 205
EIDTSGFTNY NPSLKS                                                       16

SEQ ID NO: 206     moltype = AA   length = 5
FEATURE            Location/Qualifiers
REGION             1..5
                   note = Description of Artificial Sequence: Synthetic peptide
source             1..5
                   mol_type = protein
                   organism = synthetic construct SEQUENCE: 206
DTSGF                                                                   5

SEQ ID NO: 207     moltype = AA   length = 17
FEATURE            Location/Qualifiers
REGION             1..17
                   note = Description of Artificial Sequence: Synthetic peptide
source             1..17
                   mol_type = protein
                   organism = synthetic construct SEQUENCE: 207
ARVGRYSYGY YITAFDI                                                      17

SEQ ID NO: 208     moltype = AA   length = 15
FEATURE            Location/Qualifiers
REGION             1..15
                   note = Description of Artificial Sequence: Synthetic peptide
source             1..15
                   mol_type = protein
                   organism = synthetic construct SEQUENCE: 208
VGRYSYGYYI TAFDI                                                        15

SEQ ID NO: 209     moltype = AA   length = 15
FEATURE            Location/Qualifiers
REGION             1..15
                   note = Description of Artificial Sequence: Synthetic peptide
source             1..15
                   mol_type = protein
                   organism = synthetic construct SEQUENCE: 209
VGRYSYGYYI TAFDI                                                        15

-continued

```
SEQ ID NO: 210          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 210
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQHYSF PFTFGGGTKV EIK         113

SEQ ID NO: 211          moltype = DNA  length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 211
gacatcgtga tgacccagtc tccagactcc ctggctgtgt ctctgggcga gagggccacc  60
atcaactgca agtccagcca gagtgtttta tacagctcca acaataagaa ctacttagct  120
tggtaccagc agaaaccagg acagcctcct aagctgctca tttactgggc atctacccgg  180
gaatccgggg tccctgaccg attcagtggc agcgggtctg ggacagattt cactctcacc  240
atcagcagcc tgcaggctga agatgtggca gtttattact gtcagcagca ctactccttc  300
cctttcactt ttggcggagg gaccaaggtt gagatcaaa                         339

SEQ ID NO: 212          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 212
KSSQSVLYSS NNKNYLA                                                 17

SEQ ID NO: 213          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 213
KSSQSVLYSS NNKNYLA                                                 17

SEQ ID NO: 214          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 214
KSSQSVLYSS NNKNYLA                                                 17

SEQ ID NO: 215          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 215
WASTRES                                                            7

SEQ ID NO: 216          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 216
WASTRES                                                            7

SEQ ID NO: 217          moltype = AA  length = 7
```

-continued

```
FEATURE               Location/Qualifiers
REGION                1..7
                      note = Description of Artificial Sequence: Synthetic peptide
source                1..7
                      mol_type = protein
                      organism = synthetic construct
SEQUENCE: 217
WASTRES                                                                    7

SEQ ID NO: 218        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 218
QQHYSFPFT                                                                  9

SEQ ID NO: 219        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 219
QQHYSFPFT                                                                  9

SEQ ID NO: 220        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 220
QQHYSFPFT                                                                  9

SEQ ID NO: 221        moltype = AA  length = 120
FEATURE               Location/Qualifiers
REGION                1..120
                      note = Description of Artificial Sequence: Synthetic
                       polypeptide
source                1..120
                      mol_type = protein
                      organism = synthetic construct
SEQUENCE: 221
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVSS  120

SEQ ID NO: 222        moltype = DNA  length = 360
FEATURE               Location/Qualifiers
misc_feature          1..360
                      note = Description of Artificial Sequence: Synthetic
                       polynucleotide
source                1..360
                      mol_type = other DNA
                      organism = synthetic construct
SEQUENCE: 222
gaggtgaaac tgcaggagtc aggacctggc ctggtggcgc cctcacagag cctgtccgtc  60
acatgcactg tctcaggggt ctcattaccc gactatggtg taagctggat cgccagcct  120
ccacgaaagg gtctggagtg gctgggagta atatgggta gtgaaaccac atactataat  180
tcagctctca aatccagact gaccatcatc aaggacaact ccaagagcca agtttttctta  240
aaaatgaaca gtctgcaaac tgatgacaca gccattact actgtgccaa acattattac  300
tacggtggta gctatgctat ggactactgg ggtcaaggaa cctcagtcac cgtctcctca  360

SEQ ID NO: 223        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 223
GVSLPDYG                                                                   8

SEQ ID NO: 224        moltype = AA  length = 5
FEATURE               Location/Qualifiers
```

-continued

```
REGION                  1..5
                        note = Description of Artificial Sequence: Synthetic peptide
source                  1..5
                        mol_type = protein
                        organism = synthetic construct
SEQUENCE: 224
DYGVS                                                              5

SEQ ID NO: 225          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 225
GVSLPDY                                                            7

SEQ ID NO: 226          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 226
IWGSETT                                                            7

SEQ ID NO: 227          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 227
VIWGSETTYY NSALKS                                                  16

SEQ ID NO: 228          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 228
WGSET                                                              5

SEQ ID NO: 229          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 229
AKHYYYGGSY AMDY                                                    14

SEQ ID NO: 230          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 230
HYYYGGSYAM DY                                                      12

SEQ ID NO: 231          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 231
HYYYGGSYAM DY                                                      12

SEQ ID NO: 232          moltype = AA  length = 107
```

```
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 232
DIQMTQTTSS LSASLGDRVT ISCRASQDIS KYLNWYQQKP DGTVKLLIYH TSRLHSGVPS   60
RFSGSGSGTD YSLTISNLEQ EDIATYFCQQ GNTLPYTFGG GTKLEIT                107

SEQ ID NO: 233          moltype = DNA   length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 233
gacatccaga tgacacagac tacatcctcc ctgtctgcct ctctgggaga cagagtcacc   60
atcagttgca gggcaagtca ggacattagt aaatatttaa attggtatca gcagaaacca  120
gatggaactg ttaaactcct gatctaccat acatcaagat tacactcagg agtcccatca  180
aggttcagtg gcagtgggtc tggaacagat tattctctca ccattagcaa cctggagcaa  240
gaagatattg ccacttactt ttgccaacag ggtaatacgc ttccgtacac gttcggaggg  300
gggactaagt tggaaataac a                                            321

SEQ ID NO: 234          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 234
RASQDISKYL N                                                         11

SEQ ID NO: 235          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 235
RASQDISKYL N                                                         11

SEQ ID NO: 236          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 236
RASQDISKYL N                                                         11

SEQ ID NO: 237          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 237
HTSRLHS                                                               7

SEQ ID NO: 238          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 238
HTSRLHS                                                               7

SEQ ID NO: 239          moltype = AA   length = 7
FEATURE                 Location/Qualifiers
```

-continued

```
REGION                1..7
                      note = Description of Artificial Sequence: Synthetic peptide
source                1..7
                      mol_type = protein
                      organism = synthetic construct
SEQUENCE: 239
HTSRLHS                                                            7

SEQ ID NO: 240        moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 240
QQGNTLPYT                                                          9

SEQ ID NO: 241        moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 241
QQGNTLPYT                                                          9

SEQ ID NO: 242        moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 242
QQGNTLPYT                                                          9

SEQ ID NO: 243        moltype = AA   length = 245
FEATURE               Location/Qualifiers
REGION                1..245
                      note = Description of Artificial Sequence: Synthetic
                       polypeptide
source                1..245
                      mol_type = protein
                      organism = synthetic construct
SEQUENCE: 243
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSS                                                              245

SEQ ID NO: 244        moltype = DNA   length = 735
FEATURE               Location/Qualifiers
misc_feature          1..735
                      note = Description of Artificial Sequence: Synthetic
                       polynucleotide
source                1..735
                      mol_type = other DNA
                      organism = synthetic construct
SEQUENCE: 244
gacatccaga tgacacagac tacatcctcc ctgtctgcct ctctgggaga cagagtcacc  60
atcagttgca gggcaagtca ggacattagt aaatatttaa attggtatca gcagaaacca  120
gatggaactg ttaaactcct gatctaccat acatcaagat tacactcagg agtcccatca  180
aggttcagtg gcagtgggtc tggaacagat tattctctca ccattagcaa cctggagcaa  240
gaagatattg ccacttactt ttgccaacag ggtaatacgc ttccgtacac gttcggaggg  300
gggactaagt tggaaataac aggctccacc tctggatccg gcaagcccgg atctggcgag  360
ggatccacca agggcgaggt gaaactgcag agtcaggcac ctggcctggt ggcgccctca  420
cagagcctgt ccgtcacatg cactgtctcg ggggtctcat tacccgacta tggtgtaagc  480
tggattcgcc agcctccacg aaagggtctg gagtggctgg gagtaatatg gggtagtgaa  540
accacatact ataattcagc tctcaaatcc agactgacca tcatcaagga caactccaag  600
agccaagttt tcttaaaaat gaacagtctg caaactgatg acacagccat ttactactgt  660
gccaaacatt attactacgg tggtagctat gctatggact actggggtca aggaacctca  720
gtcaccgtct cctca                                                  735

SEQ ID NO: 245        moltype = AA   length = 22
FEATURE               Location/Qualifiers
REGION                1..22
```

```
                              note = Description of Artificial Sequence: Synthetic peptide
source                        1..22
                              mol_type = protein
                              organism = synthetic construct
SEQUENCE: 245
MLLLVTSLLL CELPHPAFLL IP                                             22

SEQ ID NO: 246                moltype = DNA   length = 66
FEATURE                       Location/Qualifiers
misc_feature                  1..66
                              note = Description of Artificial Sequence: Synthetic
                               oligonucleotide
source                        1..66
                              mol_type = other DNA
                              organism = synthetic construct
SEQUENCE: 246
atgcttctcc tggtgacaag ccttctgctc tgtgagttac cacacccagc attcctcctg   60
atccca                                                              66

SEQ ID NO: 247                moltype = AA   length = 18
FEATURE                       Location/Qualifiers
REGION                        1..18
                              note = Description of Artificial Sequence: Synthetic peptide
source                        1..18
                              mol_type = protein
                              organism = synthetic construct
SEQUENCE: 247
GSTSGSGKPG SGEGSTKG                                                  18

SEQ ID NO: 248                moltype = DNA   length = 54
FEATURE                       Location/Qualifiers
misc_feature                  1..54
                              note = Description of Artificial Sequence: Synthetic
                               oligonucleotide
source                        1..54
                              mol_type = other DNA
                              organism = synthetic construct
SEQUENCE: 248
ggctccacct ctggatccgg caagcccgga tctggcgagg gatccaccaa gggc          54

SEQ ID NO: 249                moltype = AA   length = 19
FEATURE                       Location/Qualifiers
REGION                        1..19
                              note = Description of Artificial Sequence: Synthetic peptide
source                        1..19
                              mol_type = protein
                              organism = synthetic construct
SEQUENCE: 249
MEWTWVFLFL LSVTAGVHS                                                 19

SEQ ID NO: 250                moltype = AA   length = 21
FEATURE                       Location/Qualifiers
REGION                        1..21
                              note = Description of Artificial Sequence: Synthetic peptide
source                        1..21
                              mol_type = protein
                              organism = synthetic construct
SEQUENCE: 250
MALPVTALLL PLALLLHAAR P                                              21

SEQ ID NO: 251                moltype = DNA   length = 813
FEATURE                       Location/Qualifiers
misc_feature                  1..813
                              note = Description of Artificial Sequence: Synthetic
                               polynucleotide
source                        1..813
                              mol_type = other DNA
                              organism = synthetic construct
SEQUENCE: 251
ggtacccccg ggcccatggc tcttcctgtg acagctcttc tgctgccct ggccctgctt    60
ctgcatgctg ctagacctca ggttcagttg cagcaatggg gagctggcct gttaaagccc   120
agcgaaaccc tgtccctcac ctgcgctgtg tatggcggaa gcttcagcgg ctattactgg   180
agctggatcc ggcagcctcc tggaaaagga ttagaatgga tcggcgagat agaccacagc   240
gggagcacaa actacaaccc cagcctgaaa tcgcgggtta caatctctgt ggacacaagc   300
aagaatcagt tctccctgaa gctgagcagc gttactgccg ccgacacagc tgtgtactat   360
tgcgccagag gcgaggctc ctggtacagc aactggttcg atccttgggg ccaaggcacc    420
atggtgaccg tttccagcgg ctctacaagc ggcagcggga aacctggttc tggagagggc   480
agcacaaagg gcgacatcca gatgacacag agccccagca cccttagcgc ctctgtggga   540
gatagggtta ccattacctg cagggcttcc cagagcatca gcagctggct ggcatggtat   600
```

-continued

```
caacagaagc ctggcaaggc tcccaagctg ctcatctatg acgcctccag cctggaaagc    660
ggggttccct ccagatttag cggctcaggc tccggaacag agttcaccct taccatctct    720
agcctgcaac ccgacgactt cgctacttat tactgtcaac aagacagaag cttgcccccc    780
acattcggcg agggaccaa ggttgagatc aag                                  813

SEQ ID NO: 252         moltype = DNA  length = 834
FEATURE                Location/Qualifiers
misc_feature           1..834
                       note = Description of Artificial Sequence: Synthetic
                        polynucleotide
source                 1..834
                       mol_type = other DNA
                       organism = synthetic construct
SEQUENCE: 252
ggtaccccg ggcccatggc tcttcctgtg acagctcttc tgctgcccct ggccctgctt    60
ctgcatgctg ctagacctca ggttcagttg cagcaatggg gagctggcct gttaaagccc    120
agcgaaaccc tgtccctcac ctgcgctgtg tatggcggaa gcttcagcgg catccactgg    180
aactggatcc ggcagcctcc tggcaaaggc cttgaatgga tcggcgatat cgacaccagc    240
ggctccacca actacaaccc cagcctgaaa tcgagggtta caatctctgt ggacacaagc    300
aagaatcagt tctccctgaa gctgagcagc gttactgccg ccgacacagc tgtgtactat    360
tgcgccgagac tgggccagga aagcgctacc taccttggca tggatgtgtg ggggcagggc    420
accaccgtta ctgttagctc tggctcaaca agcggcaggc gcaagcctgg ctcaggagaa    480
ggaagcacaa agggcgacat tgtaatgact cagagccccg acagcctggc cgttagctta    540
ggcgaaaggg ctacaatcaa ttgcaagagc agccagagcg ttctgtacag cagcaacaac    600
aagaactacc tcgcatggta tcaacagaag ccaggccagc ctcccaagct gctcatctac    660
tgggcttcca ccagagagag cggggttccc gatagattct ccggctccgg ttctggaaca    720
gatttcacgc tcacaatcag cagcttacag gccgaggatg tggctgtcta ctattgtcag    780
cagttgtaca cctacccctt cacattcggc ggaggcacca aggttgagat caag           834

SEQ ID NO: 253         moltype = DNA  length = 825
FEATURE                Location/Qualifiers
misc_feature           1..825
                       note = Description of Artificial Sequence: Synthetic
                        polynucleotide
source                 1..825
                       mol_type = other DNA
                       organism = synthetic construct
SEQUENCE: 253
ggtaccccg ggcccatggc tcttcctgtg acagctcttc tgctgcccct ggccctgctt    60
ctgcatgctg ctagacctca gcttcagctc caagagagcg gacctggctt agtgaagccc    120
agcgaaaccc tgtccctcac ctgcaccgtt tctggcggaa gcatcagcag ctccagctat    180
tactgggat ggatcaggca gccccctggc aagggtttag aatggatcgg ctcgatatat    240
tactccggca gcacctacta taaccccagc ttgaagagcc gggttaccat ttctgtggac    300
acatcaaaga accagttcag cctgaagctg agctctgtga ctgccgccga cacagctgtg    360
tactactgtg ccagagagac agactactcc agcggcatgg ctacggcat ggatgtgtgg    420
ggacaaggaa ccaccgttac tgtgagcagc ggttccacca gcggctcagg caagcctggc    480
tcaggagaag gaagcaccaa gggggatata cagatgacac agagcccctc cagcctgtcc    540
gccagcgttg gcgatcgtgt aacgatcacc tgccgggcct ctcagagcat caactcctac    600
ctcaattggt atcaacagaa gccaggcaag gcccccaaat tactcatcta cgccgccagc    660
agcttacaga gcggggttcc ctctagattc tccggctccg ttctggaac agatttcacc    720
ctcactatct ccagcttgca gcccgaggat ttcgccactt attactgtca gcagagcctg    780
gccgacccct tcacattcgg cggaggcaca aggttgaga tcaag                      825

SEQ ID NO: 254         moltype = DNA  length = 828
FEATURE                Location/Qualifiers
misc_feature           1..828
                       note = Description of Artificial Sequence: Synthetic
                        polynucleotide
source                 1..828
                       mol_type = other DNA
                       organism = synthetic construct
SEQUENCE: 254
ggtaccccg ggcccatggc tcttcctgtg acagctcttc tgctgcccct ggccctgctt    60
ctgcatgctg ctagacctca ggttcagctt gtgcagagcg gagctgaagt taagagcct    120
ggcgcctctg tgaaggttag ctgcaaggc agcggctaca cattcaagga atatggcatc    180
tcctgggtta ggcaggctcc cggccaaggc ttagaatgga tgggctggat ctccgcctac    240
tccgccaca cctactacgc ccagaagctt cagggcaggg ttaccatgac caccgacacc    300
agcacctcta ccgcctatat ggagctgagg agcctgagat cggacgacac agctgtgtat    360
tactgcgcca gaggcccca ctacgacgac tggtctggat ttatcatctg gttcgacccc    420
tggggcagg gcaccctggt cacagtttct tctggctcca ccagcggaag cggcaagcca    480
ggctcaggcg aaggatctac aaaaggcgac atccaaatga cacagagccc cagcagcttg    540
agcgcctccg ttggcgacag agttacaatc acctgcaggg cctctcagag catcagcagc    600
tatttgaatt ggtatcaaca gaagccagga aaggcccta agctgctcat ctacgctgcc    660
agctcgctcc aatctggcgt tcctagcaga tttagcggct ccggcagcgg cacagacttt    720
actcttacca ttagctccct gcagcccgag gacttcgcta cctactattg ccagcaaagc    780
tacagattcc ctcccacctt tggccagggc acaaaggttg agatcaag                  828

SEQ ID NO: 255         moltype = DNA  length = 825
FEATURE                Location/Qualifiers
```

-continued

```
misc_feature          1..825
                      note = Description of Artificial Sequence: Synthetic
                       polynucleotide
source                1..825
                      mol_type = other DNA
                      organism = synthetic construct
SEQUENCE: 255
ggtaccccg ggcccatggc tcttcctgtg acagctcttc tgctgcccct ggccctgctt     60
ctgcatgctg ctagacctca ggttcagtta caagagagcg gacctggctt agtgaagccc   120
agcgaaaccc tgtccctcac ctgcaccgtt tctggcggaa gcatcagctc tcccgaccat   180
tactggggat ggatcaggca gcccctggc aaggggtttg aatggatcgg cagcatctac    240
gccagcggca gcacattcta caaccctcg ctcaaaagca gggttactat ttctgtggac    300
acaagcaaaa atcagttcag cctgaagctg agctctgtga ctgccgccga cacagctgtg   360
tactactgtg ccagagagac agactactcc agcgggatgg gctacggcat ggatgtgtgg   420
ggacaaggaa ccaccgttac tgtgagcagc ggctccacaa gcggctcagg caagcctggc   480
tcaggagaag gaagcaccaa gggggacatt caaatgaccc aaagcccctc cagcctgtcc   540
gccagcgttg gcgataggvt taccattacc tgcagggcca gccaaagcat caactcctac   600
ctaaattggt atcaacagaa gccaggcaag gcccccaaac tactcattta cgccgccagc   660
agcttacaga gcgggvttcc ctctagattc tccggcagcg gttctggaac agatttcact   720
ctcacaatat cttcgctgca gcccgaggat ttcgctacct actattgcca gcaatccctg   780
gccgacccct tcacattcgg cggaggcaca aaggttgaga tcaag                   825

SEQ ID NO: 256          moltype = DNA  length = 822
FEATURE                 Location/Qualifiers
misc_feature          1..822
                      note = Description of Artificial Sequence: Synthetic
                       polynucleotide
source                1..822
                      mol_type = other DNA
                      organism = synthetic construct
SEQUENCE: 256
ggtaccccg ggcccatggc tcttcctgtg acagctcttc tgctgcccct ggccctgctt     60
ctgcatgctg ctagacctca gatcacatta aaagagagcg gacctacact ggtgaagccc   120
acccaaacgc ttaccctcac ctgcacctt agcgggttca gcctggacac agagggcgtt    180
ggcgttggat ggatcaggca gcctcctggc aaagccctcg aatggcttgc cctcatctac   240
ttcaacgacc agaagagata cagccctcc ttaaaatctc ggctcacaat caccaaagac    300
acaagcaaaa atcaggttgt gctcaccatg accaacatgg accctgtgga caccgctgtg   360
tactactgtg ccagagacac cggctacagc agatggtact acgggatgga cgtttggggc   420
caaggcacca ctgtgaccgt ttccagcggc tctacaagcg gcagcgggaa acctggttct   480
ggagagggca gcacaaaggg cgacatccag atgacgcaat cccccagctc tgtgagcgcc   540
tctgtgggag acagagttac aatcacatgc cgggcctccc agggcatcag ctcttggctg   600
gcatggtatc aacagaagcc tggcaaggct cccaagctgc tcatctatgc cgcctcctcc   660
ttacaatctg gagttccctc caggttcagc gggagcggat caggaacaga cttcaccctt   720
accatctcta gcctgcaacc cgaggacttc gctacttatt actgtcagca ggcctacgcc   780
taccccatca cattcggcgg aggaacaaag gttgagatca ag                       822

SEQ ID NO: 257          moltype = DNA  length = 852
FEATURE                 Location/Qualifiers
misc_feature          1..852
                      note = Description of Artificial Sequence: Synthetic
                       polynucleotide
source                1..852
                      mol_type = other DNA
                      organism = synthetic construct
SEQUENCE: 257
ggtaccccg ggcccatggc tcttcctgtg acagctcttc tgctgcccct ggccctgctt     60
ctgcatgctg ctagacctca ggttcagttg cagcaatggg gagctggcct gttaaagccc   120
agcgaaaccc tgtccctcac ctgcgctgtg tatggcggaa gcttcgagaa atactactgg   180
agctggatcc ggcagcctcc cggcaaaggc ttagaatgga tcggcgagat ttatcacagc   240
gggctcacca actacaaccc cagcctgaaa tctcggvtta caatctctgt ggacacaagc   300
aagaatcagt tctccctgaa gctgagcagc gttactgccg ccgacacagc tgtgtactat   360
tgcgccagag ttagatacga cagcagcgac agctattact acagctatga ctacggcatg   420
gatgtgtggg gcagggcac caccgttact gtctcctctg gatctaccag cggcagcggc   480
aagcctggat ctggcgaagg aagcacaaag ggcgacattg tgctcacca gagcccccgac   540
agcctggctg tgtctttagg cgaaagggct accatcaact gcaagagcag ccagagcgtt   600
ctgtacagca gcaacaacaa gaactacctt gcttggtatc aacagaagcc tggccagccc   660
cctaagctgc tcatctactg ggcctctagc agagagagcg gggttcccga tcggtttagc   720
ggctccggct caggaaccga tttcacccctc actatctcca gcctccaggc cgaggatgtg   780
gctgtctact attgtcagca gagctatagc ttcccctgga cattcggcgg aggcaccaag   840
gttgagatca ag                                                        852

SEQ ID NO: 258          moltype = DNA  length = 852
FEATURE                 Location/Qualifiers
misc_feature          1..852
                      note = Description of Artificial Sequence: Synthetic
                       polynucleotide
source                1..852
                      mol_type = other DNA
                      organism = synthetic construct
```

```
SEQUENCE: 258
ggtaccccg ggcccatggc tcttcctgtg acagctcttc tgctgcccct ggccctgctt    60
ctgcatgctg ctagacctca ggttcagtta caacaatggg gagctggcct gttaaagccc   120
agcgaaaccc tgtccctcac ctgcgctgtg tatggcggaa gcttcagccg ctatgtgtgg   180
agctggatcc ggcagcctcc tggcaaaggc cttgaatgga tcggagagat agacagcagc   240
ggcaagacca actacaaccc cagcctgaaa tcacgcgtta caatctctgt ggacacaagc   300
aagaatcagt tctccctgaa gctgagcagc gttactgccg ccgacacagc tgtgtactat   360
tgcgccagag ttagatacga cagctccgac agctattact acagctatga ctacggcatg   420
gatgtgtggg ggcagggcac caccgttaca gttagctctg gaagcaccag cggctccggc   480
aagcctggat ctggtgaagg aagcacaaag ggcgacattg tgctcaccca gagccccgac   540
agcctggctg tgtctttagg cgaaagggct accatcaact gcaagagcag ccagagcgtt   600
ctgtacagca gcaacaacaa gaactacctt gcatggtatc aacagaagcc tggccagcct   660
cccaagctgc tcatctactg ggcctctagc agagagagcg gggttcccga tcgctttagc   720
ggcagcggtt ctggcaccga tttcactctt acaatcagca gcttacaggc cgaggatgtg   780
gctgtctact attgtcagca gagctatagc ttcccctgga cattcggcgg aggcaccaag   840
gttgagatca ag                                                       852

SEQ ID NO: 259        moltype = DNA   length = 852
FEATURE               Location/Qualifiers
misc_feature         1..852
                     note = Description of Artificial Sequence: Synthetic
                      polynucleotide
source               1..852
                     mol_type = other DNA
                     organism = synthetic construct
SEQUENCE: 259
ggtaccccg ggcccatggc tcttcctgtg acagctcttc tgctgcccct ggccctgctt    60
ctgcatgctg ctagacctca ggttcagtta caacaatggg gagctggcct gttaaagccc   120
agcgaaaccc tgtccctcac ctgcgctgtg tatggcggaa gcttcagcgg ctacgcttgg   180
agctggatta gacagcctcc tggcaaagga ctagaatgga tcggagagat cgaccacagc   240
ggcttcacca actacaaccc cagcctgaaa tccagagtta caatctctgt ggacacaagc   300
aagaatcagt tctccctgaa gctgagcagc gttactgccg ccgacacagc tgtgtactat   360
tgcgccaggt ttagatacga cagcagcgac agctattact acagctatga ctacggcatg   420
gatgtgtggg ggcagggcac caccgttacg gttagctctg gatctaccag cggcagcggc   480
aagcctggct caggagaagg aagcacaaag ggcgacattg tgctcaccca gagccccgac   540
agcctggccg tttctttagg cgaaagggct accatcaact gcaagagcag ccagagcgtt   600
ctgtacagca gcaacaacaa gaactacctt gcatggtatc aacagaagcc aggccagcct   660
cccaagctgc tcatctactg ggcctctagc agagagagcg gggttcccga tagattttcg   720
ggatcaggct ccggcaccga tttcactctt acgatcagca gcttacaggc cgaggatgtg   780
gctgtctact attgtcagca gagctatagc ttcccctgga cattcggcgg aggcaccaag   840
gttgagatca ag                                                       852

SEQ ID NO: 260        moltype = DNA   length = 840
FEATURE               Location/Qualifiers
misc_feature         1..840
                     note = Description of Artificial Sequence: Synthetic
                      polynucleotide
source               1..840
                     mol_type = other DNA
                     organism = synthetic construct
SEQUENCE: 260
ggtaccccg ggcccatggc tcttcctgtg acagctcttc tgctgcccct ggccctgctt    60
ctgcatgctg ctagacctca ggttcagtta caacaatggg gagctggcct gttaaagccc   120
agcgaaaccc tgtccctcac ctgcgctgtg tatggcggaa gcttccagaa atactactgg   180
agctggatcc ggcagcctcc cggcaaaggc ttagaatgga tcggagagat agacaccagc   240
ggcttcacca actacaaccc cagcctgaaa tctagggtta caatctctgt ggacacaagc   300
aagaatcagt tctccctgaa gctgagcagc gttactgccg ccgacacagc tgtgtactat   360
tgcgccagag ttggcagata cagctacggc tactacatca ccgccttcga catttggggc   420
caaggcacca ctgtgaccgt ttccagcgga agcactagcg gcagcgggaa acctggttct   480
ggagagggct caaccaaggg cgacatcgtg atgacacaga gccccgactc tctggctctg   540
tccctgggag agagagccac catcaactgc aagagcagcc agagcgttct gtacagcagc   600
aacaacaaga actacctggc atggtatcaa cagaagcctg ccagcccccc taagctgctc   660
atctactggg cttccaccag agaatcaggc gttccagaca ggttctccgg ctcgggttca   720
ggcacagact caccccttac catctcttcc ctgcaggccg aagatgtggc cgtttactac   780
tgtcagcagc actacagctt ccctttcaca ttcggcggag gcaccaaggt tgagatcaag   840

SEQ ID NO: 261        moltype = DNA   length = 258
FEATURE               Location/Qualifiers
misc_feature         1..258
                     note = Description of Artificial Sequence: Synthetic
                      polynucleotide
source               1..258
                     mol_type = other DNA
                     organism = synthetic construct
SEQUENCE: 261
gcagctgctt tcgtgcctgt gttcctgcct gctaagccca ccaccactcc tgctccaaga    60
cctcctaccc ccgctcctac aatcgccagc caacctctga gcctgagacc ggaggcatgc   120
agacctgcgg cagggggagc agttcacaca agaggcttgg acttcgcttg cgacatctac   180
atctgggccc ctctggccgg cacatgcgga gttcttcttc ttagcctggt gatcaccctg   240
```

-continued

```
tactgcaacc acagaaac                                             258

SEQ ID NO: 262          moltype = DNA   length = 180
FEATURE                 Location/Qualifiers
misc_feature            1..180
                        note = Description of Artificial Sequence: Synthetic
                         polynucleotide
source                  1..180
                        mol_type = other DNA
                        organism = synthetic construct
SEQUENCE: 262
gctgctgcat tggataatga aaaatcgaac ggcacaatca ttcatgtgaa gggcaaacac   60
ctgtgtccca gccccttgtt cccaggacct agcaagcctt tttgggttct cgtggtggtg  120
ggcggcgttc tggcttgcta ctctctactt gtaactgtcg catttattat attctgggtt  180

SEQ ID NO: 263          moltype = DNA   length = 186
FEATURE                 Location/Qualifiers
misc_feature            1..186
                        note = Description of Artificial Sequence: Synthetic
                         polynucleotide
source                  1..186
                        mol_type = other DNA
                        organism = synthetic construct
SEQUENCE: 263
ggaggaggag gatctctgga taacgagaaa agcaacggga ccatcattca tgtgaaggga   60
aaacatctgt gtcccagccc cttgttcccc ggacctagca gccgtttttg ggttctcgtg  120
gtggtgggcg gcgttctggc ttgctactct ctgcttgtga ccgttgcctt cattatcttc  180
tgggtt                                                            186

SEQ ID NO: 264          moltype = DNA   length = 201
FEATURE                 Location/Qualifiers
misc_feature            1..201
                        note = Description of Artificial Sequence: Synthetic
                         polynucleotide
source                  1..201
                        mol_type = other DNA
                        organism = synthetic construct
SEQUENCE: 264
ggaggaggag gatctggtgg aggaggttct ctggacaatg agaaatcaaa tggaacgatc   60
atccatgtga aggggaagca cctctgcccc tctccctgt ttcctggtcc tagcaagccc   120
ttctgggttt tggtggtcgt gggcggcgtt ctggcttgct acagcctgtt agtgaccgtt  180
gcatttatca tattttgggt t                                            201

SEQ ID NO: 265          moltype = DNA   length = 201
FEATURE                 Location/Qualifiers
misc_feature            1..201
                        note = Description of Artificial Sequence: Synthetic
                         polynucleotide
source                  1..201
                        mol_type = other DNA
                        organism = synthetic construct
SEQUENCE: 265
ggaggaggag gatctggtgg aggaggttct ctggacaatg agaaatcgaa tgggacaatc   60
atccatgtga aggggaagca cctgagcccc tctccctgt ttcctggtcc tagcaagccc   120
ttctgggttt tggtggtcgt gggcggcgtt ctggccgttt acagcctgtt agtgaccgtt  180
gctttttatca tattttgggt t                                           201

SEQ ID NO: 266          moltype = DNA   length = 201
FEATURE                 Location/Qualifiers
misc_feature            1..201
                        note = Description of Artificial Sequence: Synthetic
                         polynucleotide
source                  1..201
                        mol_type = other DNA
                        organism = synthetic construct
SEQUENCE: 266
ggaggaggag gatctggtgg aggaggttct ctggacaatg aaaagagcaa tggcacaatc   60
atccatgtga aggggaagca cctgaacggc tccgccctgt ttcctggtcc tagcaagcca  120
ttttgggttc tcgtggtggt gggcggcgtt ctggccgttt acagcctgtt agtgaccgtt  180
gcgttcataa tcttctgggt t                                            201

SEQ ID NO: 267          moltype = DNA   length = 216
FEATURE                 Location/Qualifiers
misc_feature            1..216
                        note = Description of Artificial Sequence: Synthetic
                         polynucleotide
source                  1..216
                        mol_type = other DNA
                        organism = synthetic construct
```

```
SEQUENCE: 267
ggaggaggag gatctggtgg aggaggttct ggaggaggcg gctctctcga caacgaaaag    60
agcaatggca ccattattca cgttaaaggc aagcatctgt gccctcccc cctgttcccc     120
ggaccttcaa aaccttttg ggttctcgtg gtggtgggcg gcgttctggc ctgctattct     180
ttgctggtaa ctgtagcctt cattatcttc tgggtt                              216

SEQ ID NO: 268           moltype = DNA   length = 771
FEATURE                  Location/Qualifiers
misc_feature             1..771
                         note = Description of Artificial Sequence: Synthetic
                          polynucleotide
source                   1..771
                         mol_type = other DNA
                         organism = synthetic construct
SEQUENCE: 268
gagagcaagt acggacctcc ttgtcctcca tgtcctgctc ccgagttcga gggcggacct     60
tcagtgttcc tgttcccccc taaacccaag gatactctta tgatcagccg gaccccccgag   120
gtcacctgtg tggtggtaga tgttagccag gaggatcccg aggtgcagtt caactggtac     180
gtcgacggcg tcgaggtaca caacgccaag accaagccta gggaggagca gttccagtcc     240
acctataggg tcgtgagcgt gcttaccgtg ctgcaccagg actggttgaa cggcaaggag     300
tacaagtgca aggtgtccaa caagggcctc cccagcagca tcgagaagac cattagcaag     360
gcaaaggac agcccaggga gcccaggtg tacacattac ctccttccca ggaagagatg      420
accaagaacc aggtgtcgct tacctgcctg gtcaagggct tctacccctc cgacattgca     480
gttgaatggg agtcaaacgg ccagccggag aacaattaca agaccacccc cccagtcttg    540
gacagcgacg gctctttctt cctctactcg cggcttactg tagataaaag tcgttggcag    600
gagggaaacg tgttcagctg ctctgtgatg cacgaggccc tccataacca ctacacccag    660
aagagcctct ccctgtctct gggcaagatg ttctgggtgc tggtcgtggt gggcggagtt    720
cttgcttgct actccctgct cgtgaccgtc gctttcatta tattctgggt c             771

SEQ ID NO: 269           moltype = DNA   length = 795
FEATURE                  Location/Qualifiers
misc_feature             1..795
                         note = Description of Artificial Sequence: Synthetic
                          polynucleotide
source                   1..795
                         mol_type = other DNA
                         organism = synthetic construct
SEQUENCE: 269
gagagaaagt gttgtgttga gtgtcctcct tgtcctccct gccctgctcc cgagttactt     60
ggcggacctt cagtgttcct gttccccccc aagcccaagg atactctcat gatcagccgg    120
accccccgagg tcacctgtgt ggtggtagat gttagccacg aggacctga ggtcaagttc     180
aactggtacg tcgacggcgt cgaggtgcac aacgccaaga ccaagcctcg tgaagaacag    240
taccagtcca cctacagagt tgtgagcgtg cttaccgtgc tgcaccagga ctggctgaac    300
ggcaaggagt acaagtgcaa ggtgtccaac aaggccctcc ccgctcccat cgagaagaca    360
atcagcaagg ccaagccctg tccagccccct gagctcttag gaggacctag cgttttcctt    420
ttccctccca agcctaagga cactcttatg atctccagaa caccagaggt tacctgcgtc    480
gtggtgacg tgtcccatga ggacccagaa gtcaaattca attggtatgt agatggggtc     540
gaggtccaca acgctaagac aaagcccgc gaggagcagt acaactctac ctacagggtc    600
gtgtccgtgc tcacagtgct gcatcaggat tggctcaacg gaaggagta taagtgcaaa    660
gtgtccaata aggcccttcc cgcccctatc gagaaaacca tctctaaggc caaattctgg    720
gtgctggtgg ttgtgggcgg cgtgcttgct tgttactccc tgctggtcac tgtagctttc    780
atcatatttt gggtg                                                      795

SEQ ID NO: 270           moltype = DNA   length = 494
FEATURE                  Location/Qualifiers
misc_feature             1..494
                         note = Description of Artificial Sequence: Synthetic
                          polynucleotide
source                   1..494
                         mol_type = other DNA
                         organism = synthetic construct
SEQUENCE: 270
agattcagcg ttgtgaagag aggccggaag aagctgctgt acatcttcaa gcagcccttc     60
atgagacctg tgcagaccac acaggaggaa gacggctgca gctgtagatt ccccgaggaa    120
gaggagggcg gctgtgagct gagagttaag ttcagcagga gcgccgacgc ccctgcctac    180
cagcaaggac agaatcaact gtacaacgag ctgaacctgg gcagacggga ggaatacgat    240
gtgctggaca gagaggagag gcagagacccc gagatgggcg gcaaacctag aagaaagaac    300
ccccaggagg gcctgtataa cgagctccag aaggacaaga tggccgaggc ctacagcgag    360
atcggcatga agggcgaaag aagaagaggc aagggccacg acggcctcta ccaggggctta    420
agcacagcta caaaggacac ctacgacgcc ctgcacatgc aggccctgcc ccctagatga    480
ttaattaaat cgat                                                       494

SEQ ID NO: 271           moltype = DNA   length = 1577
FEATURE                  Location/Qualifiers
misc_feature             1..1577
                         note = Description of Artificial Sequence: Synthetic
                          polynucleotide
source                   1..1577
                         mol_type = other DNA
```

```
                       organism = synthetic construct
SEQUENCE: 271
ggtacccccg ggcccatggc tcttcctgtg acagctcttc tgctgccect ggccctgctt   60
ctgcatgctg ctagacctca gcttcagctc caagagagcg gacctggctt agtgaagccc  120
agcgaaaccc tgtccctcac ctgcaccgtt tctggcggaa gcatcagcag ctccagctat  180
tactggggat ggatcaggca gcccectggc aagggtttag aatggatcgg ctcgatatat  240
tactccggca gcacctacta taaccccagc ttgaagagcc gggttaccat ttctgtggac  300
acatcaaaga accagttcag cctgaagctg agctctgtga ctgccgccga cacagctgtg  360
tactactgtg ccagagagac agactactcc agcggcatgg gctacggcat ggatgtgtgg  420
ggacaaggaa ccaccgttac tgtgagcagc ggttccacca gcggctcagg caagcctggc  480
tcaggagaag gaagcaccaa gggggatata cagatgacac agagccccctc cagcctgtcc  540
gccagcgttg gcgatcgtgt aacgatcacc tgccgggcct ctcagagcat caactcctac  600
ctcaattggt atcaacagaa gccaggcaag gcccccaaat tactcatcta cgccgccagc  660
agcttacaga gcggggttcc ctctagattc tccggctccg gttctggaac agatttcacc  720
ctcactatct ccagcttgca gcccgaggat ttcgccactt attactgtca gcagagcctg  780
gccgacccct tcacattcgg cggaggcaca aaggttgaga tcaaggcagc tgctttcgtg  840
cctgtgttcc tgcctgctaa gcccaccacc actcctgctc caagacctcc tacccccgct  900
cctacaatcg ccagccaacc tctgagcctg agaccggagg catgcagacc tgcggcaggg  960
ggagcagttc acacaagagg cttggacttc gcttgcgaca tctacatctg ggcccctctg 1020
gccggcacat gcggagttct tcttcttagc ctggtgatca ccctgtactg caaccacaga 1080
aacagattca gcgttgtgaa gagaggccgg aagaagctgc tgtacatctt caagcagccc 1140
ttcatgagac ctgtgcagac cacacaggag gaagacgact gcagctgtag attccccgag 1200
gaagaggagg gcggctgtga gctgagagtt aagttcagca ggagcgccga cgcccctgcc 1260
taccagcaag gacagaatca actgtacaac gagctgaacc tgggcagacg ggaggaatac 1320
gatgtgctgg acaagaggag aggcagagac cccgagatgg gcggcaaacc tagaagaaag 1380
aaccccccagg agggcctgta taacgagctc cagaaggaca agatggccga ggcctacagc 1440
gagatcggca tgaagggcga aagaagaaga ggcaagggcc acgacggcct ctaccagggc 1500
ttaagcacag ctacaaagga cacctacgac gccctgcaca tgcaggccct gccccctaga 1560
tgattaatta aatcgat                                                1577

SEQ ID NO: 272         moltype = DNA  length = 1577
FEATURE                Location/Qualifiers
misc_feature           1..1577
                       note = Description of Artificial Sequence: Synthetic
                        polynucleotide
source                 1..1577
                       mol_type = other DNA
                       organism = synthetic construct
SEQUENCE: 272
ggtacccccg ggcccatggc tcttcctgtg acagctcttc tgctgccect ggccctgctt   60
ctgcatgctg ctagacctca ggttcagtta caagagagcg gacctggctt agtgaagccc  120
agcgaaaccc tgtccctcac ctgcaccgtt tctggcggaa gcatcagctc tcccgaccat  180
tactggggat ggatcaggca gcccectggc aagggtttag aatggatcgg cagcatctac  240
gccagcggca gcacattcta caaccccctcg ctcaaaagca gggttactat ttctgtggac  300
acaagcaaaa atcagttcag cctgaagctg agctctgtga ctgccgccga cacagctgtg  360
tactactgtg ccagagagac agactactcc agcgggatgg gctacggcat ggatgtgtgg  420
ggacaaggaa ccaccgttac tgtgagcagc ggctccacca gcggctcagg caagcctggc  480
tcaggagaag gaagcaccaa gggggacatt caaatgaccc aaagcccctc cagcctgtcc  540
gccagcgttg gcgatagggt taccattacc tgcagggcca gccaaagcat caactcctac  600
ctaaattggt atcaacagaa gccaggcaag gcccccaaac tactcattta cgccgccagc  660
agcttacaga gcggggttcc ctctagattc tccggcagcg gttctggaac agatttcact  720
ctcacaatat cttcgctgca gcccgaggat ttcgctacct actattgcca gcaatccctg  780
gccgacccct tcacattcgg cggaggcaca aaggttgaga tcaaggcagc tgctttcgtg  840
cctgtgttcc tgcctgctaa gcccaccacc actcctgctc caagacctcc tacccccgct  900
cctacaatcg ccagccaacc tctgagcctg agaccggagg catgcagacc tgcggcaggg  960
ggagcagttc acacaagagg cttggacttc gcttgcgaca tctacatctg ggcccctctg 1020
gccggcacat gcggagttct tcttcttagc ctggtgatca ccctgtactg caaccacaga 1080
aacagattca gcgttgtgaa gagaggccgg aagaagctgc tgtacatctt caagcagccc 1140
ttcatgagac ctgtgcagac cacacaggag gaagacggct gcagctgtag attccccgag 1200
gaagaggagg gcggctgtga gctgagagtt aagttcagca ggagcgccga cgcccctgcc 1260
taccagcaag gacagaatca actgtacaac gagctgaacc tgggcagacg ggaggaatac 1320
gatgtgctgg acaagaggag aggcagagac cccgagatgg gcggcaaacc tagaagaaag 1380
aacccccagg agggcctgta taacgagctc cagaaggaca agatggccga ggcctacagc 1440
gagatcggca tgaagggcga aagaagaaga ggcaagggcc acgacggcct ctaccagggc 1500
ttaagcacag ctacaaagga cacctacgac gccctgcaca tgcaggccct gccccctaga 1560
tgattaatta aatcgat                                                1577

SEQ ID NO: 273         moltype = DNA  length = 1574
FEATURE                Location/Qualifiers
misc_feature           1..1574
                       note = Description of Artificial Sequence: Synthetic
                        polynucleotide
source                 1..1574
                       mol_type = other DNA
                       organism = synthetic construct
SEQUENCE: 273
ggtacccccg ggcccatggc tcttcctgtg acagctcttc tgctgccect ggccctgctt   60
ctgcatgctg ctagacctca gatcacatta aaagagagcg gacctacact ggtgaagccc  120
acccaaacgc ttaccctcac ctgcaccttt agcgggttca gcctggacac agaggggcgtt  180
```

-continued

```
ggcgttggat ggatcaggca gcctcctggc aaagccctcg aatggcttgc cctcatctac   240
ttcaacgacc agaagagata cagcccctcc ttaaaatctc ggctcacaat caccaaagac   300
acaagcaaaa atcaggttgt gctcaccatg accaacatgg accctgtgga caccgctgtg   360
tactactgtg ccagagacac cggctacagc agatggtact acgggatgga cgtttggggc   420
caaggcacca ctgtgaccgt ttccagcggg tctacaacgg gcagcgggaa acctggttct   480
ggagagggca gcacaaaggg cgacatccag atgacgcaat cccccagctc tgtgagcgcc   540
tctgtgggag acagagttac aatcacatgc cgggcctccc agggcatcag ctcttggctg   600
gcatggtatc aacagaagcc tggcaaggct cccaagctgc tcatctatgc cgcctcctcc   660
ttacaatctg gagttccctc caggttcagc gggagcggct caggaacaga cttcaccctt   720
accatctcta gcctgcaacc cgaggacttc gctacttatt actgtcagca ggcctacgcc   780
taccccatca cattcggcgg aggaacaaag gttgagatca aggcagctgc tttcgtgcct   840
gtgttcctgc ctgctaagcc caccaccact cctgctccaa gacctcctac ccccgctcct   900
acaatcgcca gccaacctct gagcctgaga ccggaggcat gcagacctgc ggcaggggga   960
gcagttcaca caagaggctt ggacttcgct tgcgacatct acatctggtg ccctctgctc   1020
ggcacatgcg gagttcttct tcttagcctg gtgatcaccc tgtactgcaa ccacagaaac   1080
agattcagcg ttgtgaagag aggccggaag aagctgctgt acatcttcaa gcagcccttc   1140
atgagacctg tgcagaccac acaggaggaa gacggctgca gctgtagatt ccccgaggaa   1200
gaggagggcg gctgtgagct gagagttaag ttcagcagga gcgccgacgc ccctgcctac   1260
cagcaaggac agaatcaact gtacaacgag ctgaacctgg gcagacggga ggaatacgat   1320
gtgctggaca gaggagagg cagagacccc gagatgggcg gcaaacctag aagaaagaac   1380
ccccaggagg gcctgtataa cgagctccag aaggacaaga tggccgaggc ctacagcgag   1440
atcggcatga agggcgaaag aagaagaggc aagggccacg acggcctcta ccagggctta   1500
agcacagcta caaaggacac ctacgacgcc ctgcacatgc aggccctgcc ccctagatga   1560
ttaattaaat cgat                                                     1574
```

SEQ ID NO: 274          moltype = DNA  length = 1592
FEATURE                 Location/Qualifiers
misc_feature            1..1592
                        note = Description of Artificial Sequence: Synthetic
                         polynucleotide
source                  1..1592
                        mol_type = other DNA
                        organism = synthetic construct
SEQUENCE: 274

```
ggtaccccg ggcccatggc tcttcctgtg acagctcttc tgctgcccct ggccctgctt   60
ctgcatgctg ctagacctca ggttcagtta caacaatggg gagctggcct gttaaagccc   120
agcgaaaccc tgtccctcac ctgcgctgtg tatggcggaa gcttccagaa atactactgg   180
agctggatcc ggcagcctcc cggcaaaggc ttagaatgga tcggagagat agacaccagc   240
ggcttcacca actacaaccc cagcctgaaa tctagggtta caatctctgt ggacacaagc   300
aagaatcagt tctccctgaa gctgagcagc gttactgccg ccgacacagc tgtgtactat   360
tgcgccagag ttggcagata cagctacggc tactacatca ccgccttcga catttggggc   420
caaggcacca ctgtgaccgt ttccagcgga agcactagcg gcagcgggaa acctggttct   480
ggagagggct caaccaaggg cgacatcgtg atgacacaga gcccccgactc tctggctgtg   540
tccctgggag agagagccac catcaactgc aagagcagcc agagcgttct gtacagcagc   600
aacaacaaga actacctggc atggtatcaa cagaagcctg gccagccccc taagctgctc   660
atctactggg cttccaccag agaatcaggc gttccagaca ggttctccgg ctcggggttca   720
ggcacagact tcaccttac catctcttcc ctgcagcaga aagatgtggc cgtttactac   780
tgtcagcagc actacagctt cccttttcaca ttcggcggag gcaccaaggt tgagatcaag   840
gcagctgctt tcgtgcctgt gttcctgcct gctaagccca ccaccactcc tgctccaaga   900
cctcctaccc ccgctcctac aatcgccagc caacctctga gcctgagacc ggaggcatgc   960
agacctgcag gggggagc agttcacaca agaggcttg acttcgcttg cgacatctac   1020
atctgggccc ctctgccgg cacatgcgga gttcttcttc ttagcctggt gatcaccctg   1080
tactgcaacc acagaaacag attcagcgtt gtgaagagag gccggaagaa gctgctgtac   1140
atcttcaagc agcccttcat gagacctgtg cagaccacac aggaggaaga cggctgcagc   1200
tgtagattcc ccgaggaaga ggaggcggc tgtgagctga gagttaagtt cagcaggagc   1260
gccgacgccc ctgcctacca gcaaggacag aatcaactgt acaacgagct gaacctgggc   1320
agacgggagg aatacgatgt gctggacaag aggagaggca gagccccga gatgggcggc   1380
aaacctagaa gaaagaaccc ccaggagggc ctgtataacg agctccagaa ggacaagatg   1440
gccgaggcct acagcgagat cggcatgaag ggcgaaagaa agaaagcaa gggccacgac   1500
ggcctctacc agggcttaag cacagctaca aaggacacct acgacgccct gcacatgcag   1560
gccctgcccc ctagatgatt aattaaatcg at                                 1592
```

SEQ ID NO: 275          moltype = DNA  length = 1604
FEATURE                 Location/Qualifiers
misc_feature            1..1604
                        note = Description of Artificial Sequence: Synthetic
                         polynucleotide
source                  1..1604
                        mol_type = other DNA
                        organism = synthetic construct
SEQUENCE: 275

```
ggtaccccg ggcccatggc tcttcctgtg acagctcttc tgctgcccct ggccctgctt   60
ctgcatgctg ctagacctca ggttcagttg cagcaatggg gagctggcct gttaaagccc   120
agcgaaaccc tgtccctcac ctgcgctgtg tatggcggaa gcttcgagaa atactactgg   180
agctggatcc ggcagcctcc cggcaaaggc ttagaatgga tcggcgagat ttatcacagc   240
gggctcacca actacaaccc cagcctgaaa tctcgagtta caatctctgt ggacacaagc   300
aagaatcagt tctccctgaa gctgagcagc gttactgccg ccgacacagc tgtgtactat   360
tgcgccagag ttagatacga cagcagcgac agctattact acagctatga ctacggcatg   420
gatgtgtggg gccagggcac caccgttact gtctcctctg gatctaccag cggcagcggc   480
```

```
aagcctggat ctggcgaagg aagcacaaag ggcgacattg tgctcaccca gagccccgac   540
agcctggctg tgtctttagg cgaaagggct accatcaact gcaagagcag ccagagcgtt   600
ctgtacagca gcaacaacaa gaactacctt gcttggtatc aacagaagcc tggccagccc   660
cctaagctgc tcatctactg ggcctctagc agagagagcg gggttcccga tcggtttagc   720
ggctccggct caggaaccga tttcaccctc actatctcca gcctccaggc cgaggatgtg   780
gctgtctact attgtcagca gagctatagc ttcccctgga cattcggcgg aggcaccaag   840
gttgagatca aggcagctgc tttcgtgcct gtgttcctgc ctgctaagcc caccaccact   900
cctgctccaa gacctcctac ccccgctcct acaatcgcca gccaacctct gagcctgaga   960
ccggaggcat gcagacctgc ggcaggggga gcagttcaca caagaggctt ggacttcgct  1020
tgcgacatct acatctgggc ccctctggcc ggcacatgcg gagttcttct tcttagcctg  1080
gtgatcaccc tgtactgcaa ccacagaaac agattcagcg ttgtgaagag aggccggaag  1140
aagctgctgt acatcttcaa gcagcccttc atgagacctg tgcagaccac acaggaggaa  1200
gacggctgca gctgtagatt ccccgaggaa gaggagggcg gctgtgagct gagagttaag  1260
ttcagcagga gcgccgacgc ccctgcctac cagcaaggac agaatcaact gtacaacgag  1320
ctgaacctgg gcagacggga ggaatacgat gtgctggaca agaggagagg cagagacccc  1380
gagatgggcg gcaaacctag aagaaagaac ccccaggagg gcctgtataa cgagctccag  1440
aaggacaaga tggccgaggc ctacagcgag atcggcatga agggcgaaag aagaagaggc  1500
aagggccacg acggcctcta ccagggctta agcacagcta caaaggacac ctacgacgcc  1560
ctgcacatgc aggccctgcc ccctagatga ttaattaaat cgat                   1604

SEQ ID NO: 276               moltype = DNA  length = 1604
FEATURE                      Location/Qualifiers
misc_feature                 1..1604
                             note = Description of Artificial Sequence: Synthetic
                             polynucleotide
source                       1..1604
                             mol_type = other DNA
                             organism = synthetic construct SEQUENCE: 276
ggtaccccg ggcccatggc tcttcctgtg acagctcttc tgctgcccct ggccctgctt    60
ctgcatgctg ctagacctca ggttcagtta caacaatggg gagctggcct gttaaagccc   120
agcgaaaccc tgtccctcac ctgcgctgtg tatggcggaa gcttcagccg ctatgtgtgg   180
agctggatcc ggcagcctcc tggcaaaggc cttgaatgga tcggagagat agacagcagc   240
ggcaagacca actacaaccc cagcctgaaa tcacgcgtta caatctctgt ggacacaagc   300
aagaatcagt tctccctgaa gctgagcagc gttactgccg ccgacacagc tgtgtactat   360
tgcgccagag ttagatacga cagctccgac agctattact acagctatga ctacggcatg   420
gatgtgtggg ggcagggcac caccgttaca gttagctctg gaagcaccag cggctccggc   480
aagcctggat ctggtgaagg aagcacaaag ggcgacattg tgctcaccca gagccccgac   540
agcctggctg tgtctttagg cgaaagggct accatcaact gcaagagcag ccagagcgtt   600
ctgtacagca gcaacaacaa gaactacctt gcatggtatc aacagaagcc tggccagcct   660
cccaagctgc tcatctactg ggcctctagc agagagagcg gggttcccga tcgctttagc   720
ggcagcggtt ctggcaccga tttcactctt acaatcagca gcttacaggc cgaggatgtg   780
gctgtctact attgtcagca gagctatagc ttcccctgga cattcggcgg aggcaccaag   840
gttgagatca aggcagctgc tttcgtgcct gtgttcctgc ctgctaagcc caccaccact   900
cctgctccaa gacctcctac ccccgctcct acaatcgcca gccaacctct gagcctgaga   960
ccggaggcat gcagacctgc ggcaggggga gcagttcaca caagaggctt ggacttcgct  1020
tgcgacatct acatctgggc ccctctggcc ggcacatgcg gagttcttct tcttagcctg  1080
gtgatcaccc tgtactgcaa ccacagaaac agattcagcg ttgtgaagag aggccggaag  1140
aagctgctgt acatcttcaa gcagcccttc atgagacctg tgcagaccac acaggaggaa  1200
gacggctgca gctgtagatt ccccgaggaa gaggagggcg gctgtgagct gagagttaag  1260
ttcagcagga gcgccgacgc ccctgcctac cagcaaggac agaatcaact gtacaacgag  1320
ctgaacctgg gcagacggga ggaatacgat gtgctggaca agaggagagg cagagacccc  1380
gagatgggcg gcaaacctag aagaaagaac ccccaggagg gcctgtataa cgagctccag  1440
aaggacaaga tggccgaggc ctacagcgag atcggcatga agggcgaaag aagaagaggc  1500
aagggccacg acggcctcta ccagggctta agcacagcta caaaggacac ctacgacgcc  1560
ctgcacatgc aggccctgcc ccctagatga ttaattaaat cgat                   1604

SEQ ID NO: 277               moltype = DNA  length = 1604
FEATURE                      Location/Qualifiers
misc_feature                 1..1604
                             note = Description of Artificial Sequence: Synthetic
                             polynucleotide
source                       1..1604
                             mol_type = other DNA
                             organism = synthetic construct SEQUENCE: 277
ggtaccccg ggcccatggc tcttcctgtg acagctcttc tgctgcccct ggccctgctt    60
ctgcatgctg ctagacctca ggttcagtta caacaatggg gagctggcct gttaaagccc   120
agcgaaaccc tgtccctcac ctgcgctgtg tatggcggaa gcttcagccg ctacgcttgg   180
agctggatta gacagcctcc tggcaaagga ctagaatgga tcggagagat cgaccacaga   240
ggcttcacca actacaaccc cagcctgaaa tccagagtta caatctctgt ggacacaagc   300
aagaatcagt tctccctgaa gctgagcagc gttactgccg ccgacacagc tgtgtactat   360
tgcgccaggg ttagatacga cagcagcgac agctattact acagctatga ctacggcatg   420
gatgtgtggg ggcagggcac caccgttacg gttagctctg gatctaccag cggcagcgga   480
aagcctggct caggagaagg aagcacaaag ggcgacattg tgctcaccca gagccccgac   540
agcctggccg tttctttagg cgaaagggct accatcaact gcaagagcag ccagagcgtt   600
ctgtacagca gcaacaacaa gaactacctt gcatggtatc aacagaagcc aggccagcct   660
cccaagctgc tcatctactg ggcctctagc agagagagcg gggttcccga tagattttcg   720
ggatcaggct ccggcaccga tttcactctt acgatcagca gcttacaggc cgaggatgtg   780
```

-continued

```
gctgtctact attgtcagca gagctatagc ttccctgga cattcggcgg aggcaccaag    840
gttgagatca aggcagctgc tttcgtgcct gtgttcctgc ctgctaagcc caccaccact    900
cctgctccaa gacctcctac ccccgctcct acaatcgcca gccaacctct gagcctgaga    960
ccggaggcat gcagacctgc ggcagggga gcagttcaca caagaggctt ggacttcgct   1020
tgcgacatct acatctgggc ccctctggcc ggcacatgcg gagttcttct tcttagcctg   1080
gtgatcaccc tgtactgcaa ccacagaaac agattcagcg ttgtgaagag aggccggaag   1140
aagctgctgt acatcttcaa gcagcccttc atgagacctg tgcagaccac acaggaggaa   1200
gacggctgca gctgtagatt ccccgaggaa gaggaggggcg gctgtgagct gagagttaag   1260
ttcagcagga gcgccgacgc ccctgcctac cagcaaggac agaatcaact gtacaacgag   1320
ctgaacctgg gcagacggga ggaatacgat gtgctggaca agaggagagg cagagacccc   1380
gagatgggcg gcaaacctag aagaaagaac ccccaggagg gcctgtataa cgagctccag   1440
aaggacaaga tggccgaggc ctacagcgag atcggcatga agggcaaag aagaagaggc   1500
aagggccacg acggcctcta ccagggctta agcacagcta caaaggacac ctacgacgcc   1560
ctgcacatgc aggccctgcc ccctagatga ttaattaaat cgat                   1604

SEQ ID NO: 278          moltype = DNA  length = 1565
FEATURE                 Location/Qualifiers
misc_feature            1..1565
                        note = Description of Artificial Sequence: Synthetic
                         polynucleotide
source                  1..1565
                        mol_type = other DNA
                        organism = synthetic construct
SEQUENCE: 278
ggtaccccg ggcccatggc tcttcctgtg acagctcttc tgctgcccct ggccctgctt    60
ctgcatgctg ctagacctca ggttcagttg cagcaatggg gagctggcct gttaaagccc   120
agcgaaaccc tgtccctcac ctgcgctgtg tatggcggaa gcttcagcgg ctattactgg   180
agctggatcc ggcagcctcc tggaaaagga ttagaatgga tcggcgagat agaccacagc   240
gggagcacaa actacaaccc cagcctgaaa tcgcgggtta caatctctgt ggacacaagc   300
aagaatcagt tctccctgaa gctgagcagc gttactgccg ccgacacagc tgtgtactat   360
tgcgccagag gcggaggctc ctggtacagc aactggttcg atccttgggg ccaaggcacc   420
atggtgaccg tttccagcgg ctctacaagc ggcagcggga aacctggttc tggagagggc   480
agcacaaagg gcgacatcca gatgacacag agccccagca cccttagcgc ctctgtggga   540
gatagggtta ccattacctg cagggcttcc cagagcatca gcagctggct ggcatggtat   600
caacagaagc ctggcaaggc tcccaagctg ctcatctatg acgcctccag cctggaaagc   660
ggggttccct ccagatttag cggctcaggc tccggaacag agttcaccct taccatctct   720
agcctgcaac ccgacgactt cgctacttat tactgtcaac aagacagaag cttgcccccc   780
acattcggcg gagggaccaa ggttgagatc aaggcagctg ctttcgtgcc tgtgttcctg   840
cctgctaagc ccaccaccac tcctgctcca agacctcctc cccccgctcc tacaatcgcc   900
agccaacctc tgagcctgag accggaggca tgcagacctg cggcagggg agcagttcac   960
acaagaggct tggacttcgc ttgcgacatc tacatctggg ccctctggc cggcacatgc   1020
ggagttcttc ttcttagcct ggtgatcacc ctgtactgca accacagaaa cagattcagc   1080
gttgtgaaga gaggccggaa gaagctgctg tacatctca gcagcccctt catgagaccc   1140
gtgcagacca cacaggagga agacggctgc agctgtagat tccccgagga agaggagggc   1200
ggctgtgagc tgagagttaa gttcagcagg agcgccgacg cccctgccta ccagcaagga   1260
cagaatcaac tgtacaacga gctgaacctg ggcagacggg aggaatacga tgtgctggac   1320
aagaggagag gcagagaccc cgagatgggc ggcaaaccta gaagaaagaa ccccccaggag   1380
ggcctgtata cgagctcca gaaggacaag atggccgagg cctacagcga gatcggcatg   1440
aagggcgaaa gaagaagagg caagggccac gacggcctct accagggctt aagcacagct   1500
acaaaggaca cctacgacgc cctgcacatg caggccctgc ccctagatg attaattaaa   1560
tcgat                                                             1565

SEQ ID NO: 279          moltype = DNA  length = 1580
FEATURE                 Location/Qualifiers
misc_feature            1..1580
                        note = Description of Artificial Sequence: Synthetic
                         polynucleotide
source                  1..1580
                        mol_type = other DNA
                        organism = synthetic construct
SEQUENCE: 279
ggtaccccg ggcccatggc tcttcctgtg acagctcttc tgctgcccct ggccctgctt    60
ctgcatgctg ctagacctca ggttcagctt gtgcagagcg gagctgaagt taagaagcct   120
ggcgcctctg tgaaggttag ctgcaaggcc agcggctaca cattcaagga atatgccatc   180
tcctgggtta ggcaggctcc cggccaaggc ttagaatgga tgggctggat ctccgcctac   240
tccggccaca cctactacgc ccagaagctt cagggcaggg ttaccatgac caccgacacc   300
agcacctcta ccgcctatat ggagctgagc agcctgagat cggacgacac agctgtgtat   360
tactgcgcca gaggccccca ctacgacgac tggtctggat ttatcatctg gttcgacccc   420
tgggggcagg gcaccctggt cacagtttct tctggctcca ccagcggaag cggcaagccc   480
ggctcaggcg aaggatctac aaaaggcgac atccaaatga cacagagccc cagcagcttg   540
agcgcctccg ttggcgacag agttacaatc acctgcaggg cctctcagag catcagcagc   600
tatttgaatt ggtatcaaca gaagccagga aaggccccta agctgctcat ctacgctgcc   660
agctcgctca atctggcgt tcctagcaga tttagcggct ccggcagcgg cacagacttt   720
actcttacca ttagctccct gcagcccgag gacttcgcta cctactattg ccagcaaagc   780
tacagattcc ctcccacctt ggcagggc acaaaggttg agatcaaggc agctgctttc   840
gtgcctgtgt tcctgcctgc taagcccacc accactcctg ctccaagacc tcctacccc   900
gctcctacaa tcgccagcca acctctgagc ctgagaccgg aggcatgcag acctgcggca   960
gggggagcag ttcacacaag aggcttggac ttcgcttgcg acatctacat ctgggccct   1020
ctggccggca catgcggagt tcttcttctt agcctggtga tcaccctgta ctgcaaccac   1080
```

```
agaaacagat tcagcgttgt gaagagaggc cggaagaagc tgctgtacat cttcaagcag  1140
cccttcatga gacctgtgca gaccacacag gaggaagacg gctgcagctg tagattcccc  1200
gaggaagagg agggcggctg tgagctgaga gttaagttca gcaggagcgc cgacgcccct  1260
gcctaccagc aaggacagaa tcaactgtac aacgagctga acctgggcag acgggaggaa  1320
tacgatgtgc tggacaagag gagaggcaga gaccccgcaa acctagaaga                1380
aagaaccccc aggagggcct gtataacgag ctccagaagg acaagatggc cgaggcctac  1440
agcgagatcg gcatgaaggg cgaaagaaga agaggcaagg gccacgacgg cctctaccag  1500
ggcttaagca cagctacaaa ggacacctac gacgccctgc acatgcaggc cctgccccct  1560
agatgattaa ttaaatcgat                                                 1580
```

```
SEQ ID NO: 280        moltype = DNA   length = 1586
FEATURE               Location/Qualifiers
misc_feature          1..1586
                      note = Description of Artificial Sequence: Synthetic
                       polynucleotide
source                1..1586
                      mol_type = other DNA
                      organism = synthetic construct
SEQUENCE: 280
ggtacccccg ggcccatggc tcttcctgtg acagctcttc tgctgcccct ggccctgctt  60
ctgcatgctc ctagacctca ggttcagttg cagcaatggg gagctggcct gttaaagccc  120
agcgaaaccc tgtccctcac ctgcgctgtg tatggcggaa gcttcagcgg catccactgg  180
aactggatcc ggcagcctcc tggcaaaggc cttgaatgga tcggcgatat cgacaccagc  240
ggctccacca actacaaccc cagcctgaaa tcgagggtta caatctctgt ggacacaagc  300
aagaatcagt tctccctgaa gctgagcagc gttactgccg ccgacacagc tgtgtactat  360
tgcgccagac tgggccagga aagcgctacc taccttggca tggatgtgtg ggggcagggc  420
accaccgtta ctgttagctc tggctcaaca agcggcagcg gcaagctggg ctcaggagaa  480
ggaagcacaa agggcgacat tgtaatgact cagagccccg acagcctggc cgttagctta  540
ggcgaaaggg ctacaatcaa ttgcaagagc agccagagcg ttctgtacag cagcaacaac  600
aagaactacc tcgcatggta tcaacagaag ccaggccagc ctcccaagct gctcatctac  660
tgggcttcca ccagagagag cggggttcca gatagattct ccggctccgg ttctggaaca  720
gatttcacgc tcacaatcag cagcttacag gccgaggatg tggctgtcta ctattgtcag  780
cagttgtaca cctaccccctt cacattcggc ggaggcacca aggttgagat caaggcagct  840
gctttcgtgc ctgtgttcct gcctgctaag cccaccacca ctcctgctcc aagacctcct  900
accccggctc ctacaatcgc cagccaacct ctgagcctga gaccggaggc atgcagacct  960
gcggcagggg gagcagttca cacaagaggc ttggacttcg cttgcgacat ctacatctgg  1020
gcccctctgg ccggcacatg cggagttctt cttcttagcc tggtgatcac cctgtactgc  1080
aaccacagaa acagattcag cgttgtgaag agaggccgga gaagctgct gtacatcttc  1140
aagcagccct tcatgagacc tgtgcagacc acacaggagg aagacggctg cagctgtaga  1200
ttccccgagg aagaggaggg cggctgtgag ctgagagtta gttcagcag gagcgccgac  1260
gcccctgcct accagcaagg acagaatcaa ctgtacaacg agctgaacct gggcagacgg  1320
gaggaatacg atgtgctgga caagaggaga ggcagagacc ccgagatggg cggcaaacct  1380
agaagaaaga accccccagga gggcctgtat aacgagctcc agaaggacaa gatggccgag  1440
gcctacagcg agatcggcat gaagggcgaa agaagaagag gcaagggcca cgacggcctc  1500
taccagggct taagcacagc tacaaaggac acctacgacg ccctgcacat gcaggccctg  1560
ccccctagat gattaattaa atcgat                                          1586
```

```
SEQ ID NO: 281        moltype = DNA   length = 1499
FEATURE               Location/Qualifiers
misc_feature          1..1499
                      note = Description of Artificial Sequence: Synthetic
                       polynucleotide
source                1..1499
                      mol_type = other DNA
                      organism = synthetic construct
SEQUENCE: 281
ggtacccccg ggcccatggc tcttcctgtg acagctcttc tgctgcccct ggccctgctt  60
ctgcatgctg ctagacctca gcttcagctc caagagagcg gacctggctt agtgaagccc  120
agcgaaaccc tgtccctcac ctgcaccgtt tctggcggaa gcatcagcag ctccagctat  180
tactggggat ggatcaggca gcccctggc aagggtttag aatggatcgg ctcgatatat  240
tactccggca gcacctacta taaccccagc ttgaagagcc gggttaccat ttctgtggac  300
acatcaaaga accagttcag cctgaagctg agctctgtga ctgccgccga cacagctgtg  360
tactactgtg ccagagagac agactactcc agcggcatgg ctacggcat ggatgtgtgg  420
ggacaaggaa ccaccgttac tgtgagcagc ggttccacca agggctcagg caagacctgg  480
tcaggagaag gaagcaccaa gggggatata cagatgacac agagcccctc cagcctgtcc  540
gccagcgttg gcgatcgtgt aacgatcacc tgccgggcct ctcagagcat caactcctac  600
ctcaattggt atcaacagaa gccaggcaag gcccccaaat tactcatcta cgccgccagc  660
agcttacaga gcggggttcc ctctagattc tccggctccg gttctggaac agatttcacc  720
ctcactatct ccagcttgca gcccgaggat ttcgccactt attactgtca gcagagctac  780
gccgacccct tcacattcgg cggaggcaca aaggttgaga tcaaggctgc tgcattggat  840
aatgaaaaat cgaacggcac aatcattcat gtgaagggca aacacctgtg tcccagcccc  900
ttgttcccag acctagcaa gccttttttgg gttctcgtgg tggtgggcgg cgttctggct  960
tgctactctc tacttgtaac tgtcgcattt attatattct gggttagatt cagcgttgtg  1020
aagagaggc ggaagaagct gctgtacatc ttcaagcag ccctttatga acctgtgtg  1080
accacacagg aggaagacgg ctgcagctgt agattccccg aggaagagga gggcggctgt  1140
gagctgagag ttaagttcag caggagcgcc gacgcccctg cctaccagca aggacagaat  1200
caactgtaca acgagctgaa cctgggcaga cgggaggaat acgatgtgct ggacaagagg  1260
agaggcagag accccgagat gggcggcaaa cctagaagaa gaaccccca ggagggcctg  1320
tataacgagc tccagaagga caagatggcc gaggcctaca gcgagatcgg catgaagggc  1380
```

```
gaaagaagaa gaggcaaggg ccacgacggc ctctaccagg gcttaagcac agctacaaag 1440
gacacctacg acgccctgca catgcaggcc ctgcccccta gatgattaat taaatcgat  1499

SEQ ID NO: 282        moltype = DNA  length = 1499
FEATURE               Location/Qualifiers
misc_feature          1..1499
                      note = Description of Artificial Sequence: Synthetic
                      polynucleotide
source                1..1499
                      mol_type = other DNA
                      organism = synthetic construct
SEQUENCE: 282
ggtacccccg ggcccatggc tcttcctgtg acagctcttc tgctgcccct ggccctgctt  60
ctgcatgctg ctagacctca ggttcagtta caagagacg gacctggctt agtgaagccc  120
agcgaaaccc tgtccctcac ctgcaccgtt tctggcggaa gcatcagctc tcccgaccat  180
tactggggat ggatcaggca gccccctggc aagggtttgg aatggatcgg cagcatctac  240
gccagcggca gcacattcta caaccccctcg ctcaaaagca gggttactat ttctgtggac  300
acaagcaaaa atcagttcag cctgaagctg agctctgtga ctgccgccga cacagctgtg  360
tactactgtg ccagagagac agactactcc agcgggatgg gctacggcat ggatgtgtgg  420
ggacaaggaa ccaccgttac tgtgagcagc ggctccacaa gcggctcagg caagcctggc  480
tcaggagaag gaagcaccaa gggggacatt caaatgaccc aaagcccctc cagcctgtcc  540
gccagcgttg gcgatagggt taccattacc tgcagggcca gcaaagcat caactcctac  600
ctaaattggt atcaacagaa gccaggcaag gccccccaaac tactcattta cgccgccagc  660
agcttacaga gcggggttcc ctctagattc tccggcagcg gttctggaac agatttcact  720
ctcacaatat cttcgctgca gcccgaggat ttcgctacct actattgcca gcaatccctg  780
gccgacccct tcacattcgg cggaggcaca aaggttgaa tcaaggctgc tgcattggat  840
aatgaaaaat cgaacggcac aatcattcat gtgaagggca aacacctgtg tcccagcccc  900
ttgttcccag gacctagcaa gccttttttgg gttctcgtgg tggtgggcgg cgttctggct  960
tgctactctc tacttgtaac tgtcgcattt attatattct gggttagatt cagcgttgtg  1020
aagagaggcc ggaagaagct gctgtacatc ttcaagcagc ccttcatgag acctgtgcag  1080
accacacagg aggaagacg ctgcagctgt agattccccg aggaagagga gggcggctgt  1140
gagctgagag ttaagttcag caggagcgcc gacgcccctg cctaccagca aggacagaat  1200
caactgtaca acgagctgaa cctgggcaga cgggaggaat acgatgtgct ggacaagagg  1260
agaggcagag accccgagat gggcggcaaa cctagaagaa agaacccca ggagggcctg  1320
tataacgagc tccagaagga caagatggcc gaggcctaca gcgagatcgg catgaagggc  1380
gaaagaagaa gaggcaaggg ccacgacggc ctctaccagg gcttaagcac agctacaaag  1440
gacacctacg acgccctgca catgcaggcc ctgcccccta gatgattaat taaatcgat  1499

SEQ ID NO: 283        moltype = DNA  length = 1496
FEATURE               Location/Qualifiers
misc_feature          1..1496
                      note = Description of Artificial Sequence: Synthetic
                      polynucleotide
source                1..1496
                      mol_type = other DNA
                      organism = synthetic construct
SEQUENCE: 283
ggtacccccg ggcccatggc tcttcctgtg acagctcttc tgctgcccct ggccctgctt  60
ctgcatgctg ctagacctca gatcacatta aaagagagcg gacctacact ggtgaagccc  120
acccaaacgc ttaccctcac ctgcaccttt agcgggttca gcctggacac agagggcgtt  180
ggcgttggat ggatcaggca gcctcctggc aaagccctcg aatggcttgc cctcatctac  240
ttcaacgacc agaagagata cagccccctcc ttaaaatctc ggctcacaat caccaaagac  300
acaagcaaaa atcaggttgt gctcaccatg accaacatgg accctgtgga caccgctgtg  360
tactactgtg ccagagacac cggctacagc agatggtact acgggatgga cgtttggggc  420
caaggcacca ctgtgaccgt ttccagcggc tctacaagcg gcagcgggaa acctggttct  480
ggagagggca gcacaaaggg cgacatccag atgacgcaat cccccagctc tgtgagcgcc  540
tctgtgggag acagagttac aatcacatgc cgggcctccc agggcatcag ctcttggctg  600
gcatggtatc aacagaagcc tggcaaggct cccaagctgc tcatctatgc cgcctcctcc  660
ttacaatctg gagttccctc caggttcagc gggagcggct caggaacaga cttcacccctt  720
accatctcta gcctgcaacc cgaggacttc gctacttatt actgtcagca ggctacgcc  780
taccccatca cattcggcgg aggaacaaag gttgagatca aggctgctgc attggataat  840
gaaaaatcga acggcacaat cattcatgtg aagggcaaac acctgtgtcc cagcccctttg  900
ttcccaggac ctagcaagcc ttttttgggtt ctcgtggtgg tgggcggcgt tctggcttgc  960
tactctctac ttgtaactgt cgcatttatt atattctgtt tagattcag cgttgtgaag  1020
agaggccgga agaagctgct gtacatcttc aagcagccct tcatgagacc tgtgcagacc  1080
acacaggagg aagacggctg cagctgtaga ttccccgagg aagaggaggg cggctgtgag  1140
ctgagagtta agttcagcag gagcgccgac gcccctgcct accagcaagg acagaatcaa  1200
ctgtacaacg agctgaacct gggcagacgg gaggaatacg atgtgctgga caagaggaga  1260
ggcagagacc ccgagatggg cggcaaacct agaagaaaga accccagga gggcctgtat  1320
aacgagctcc agaaggacaa gatggccgag gcctacagcg agatcggcat gaagggcgaa  1380
agaagaagag gcaagggcca cgacggcctc taccagggct aagcacagc tacaaaggac  1440
acctacgacg ccctgcacat gcaggccctg cccccctagat gattaattaa atcgat       1496

SEQ ID NO: 284        moltype = DNA  length = 1514
FEATURE               Location/Qualifiers
misc_feature          1..1514
                      note = Description of Artificial Sequence: Synthetic
                      polynucleotide
source                1..1514
```

```
                              mol_type = other DNA
                              organism = synthetic construct
SEQUENCE: 284
ggtaccccg ggcccatggc tcttcctgtg acagctcttc tgctgccct ggccctgctt    60
ctgcatgctg ctagacctca ggttcagtta caacaatggg gagctggcct gttaaagccc   120
agcgaaaccc tgtccctcac ctgcgctgtg tatggcggaa gcttccagaa atactactgg   180
agctggatcc ggcagcctcc cggcaaaggc ttagaatgga tcggagagat agacaccagc   240
ggcttcacca actacaaccc cagcctgaaa tctagggtta caatctctgt ggacacaagc   300
aagaatcagt tctccctgaa gctgagcagc gttactgccg ccgacacagc tgtgtactat   360
tgcgccagag ttggcagata cagctacggc tactacatca ccgccttcga catttggggc   420
caaggcacca ctgtgaccgt ttccagcgga agcactagcg gcagcgggaa acctggttct   480
ggagagggct caaccaaggg cgacatcgtg atgacacaga gccccgactc tctggctgtg   540
tccctgggag agagagccac catcaactgc aagagcagcc agagcgttct gtacagcagc   600
aacaacaaga actacctggc atggtatcaa cagaagcctg gccagccccc taagctgctc   660
atctactggg cttccaccag agaatcaggc gttccagaca ggttctccgg ctcgggttca   720
ggcacagact tcacccttac catctcttcc ctgcaggccg aagatgtggc cgtttactac   780
tgtcagcagc actacagctt ccctttcaca ttcggcggag gcaccaaggt tgagatcaag   840
gctgctgcat tggataatga aaaatcgaac ggcacaatca ttcatgtgaa gggcaaacac   900
ctgtgtccca gcccccttgtt cccaggacct agcaagcctt tttgggttct cgtggtggtg   960
ggcggcgttc tggcttgcta ctctctactt gtaactgtcg catttattat attctgggtt  1020
agattcagcg ttgtgaagag aggccggaag aagctgctgt acatcttcaa gcagcccttc  1080
atgagacctg tgcagaccac acaggaggaa gacggctgca gctgtagatt ccccgaggaa  1140
gaggagggcg gctgtgagct gagagttaag ttcagcagga gcgccgacgc ccctgcctac  1200
cagcaaggac agaatcaact gtacaacgag ctgaacctgg gcagacggga ggaatacgat  1260
gtgctggaca agaggagagg cagagacccc gagatgggcg gcaaacctag aagaaagaac  1320
ccccaggagg gcctgtataa cgagctccag aaggacaaga tggtcgagc ctacagcgag   1380
atcggcatga agggcgaaag aagaagaggc aagggccacg acggcctcta ccagggctta  1440
agcacagcta caaaggacac ctacgacgcc ctgcacatgc aggccctgcc cctagatga   1500
ttaattaaat cgat                                                    1514

SEQ ID NO: 285           moltype = DNA   length = 1526
FEATURE                  Location/Qualifiers
misc_feature            1..1526
                         note = Description of Artificial Sequence: Synthetic
                          polynucleotide
source                  1..1526
                         mol_type = other DNA
                         organism = synthetic construct
SEQUENCE: 285
ggtaccccg ggcccatggc tcttcctgtg acagctcttc tgctgccct ggccctgctt    60
ctgcatgctg ctagacctca ggttcagtta cagcaatggg gagctggcct gttaaagccc   120
agcgaaaccc tgtccctcac ctgcgctgtg tatggcggaa gcttcgagaa atactactgg   180
agctggatcc ggcagcctcc cggcaaaggc ttagaatgga tcggcgagat ttatcacagc   240
gggctcacca actacaaccc cagcctgaaa tctcgagtta caatctctgt ggacacaagc   300
aagaatcagt tctccctgaa gctgagcagc gttactgccg ccgacacagc tgtgtactat   360
tgcgccagag ttagatacga cagcagcgac agctattact acagctatga ctacggcatg   420
gatgtgtggg ggcagggcac caccgttact gtctcctctg gatctaccag cggcagcggc   480
aagcctggat ctggcgaagg aagcacaaag ggcgacattg tgctcaccca gagccccgac   540
agcctggctg tgtctttagg cgaaagggct accatcaact gcaagagcag ccagagcgtt   600
ctgtacagca gcaacaacaa gaactacctt gcttggtatc aacagaagcc tggccagccc   660
cctaagctgc tcatctactg ggcctctagc agagagagcg gggttcccga tcggtttagc   720
ggctccggct caggaaccga tttcacccctc actatctcca gcctccaggc cgaggatgtg   780
gctgtctact attgtcagca gagctatagc ttcccctgga cattcggcgg aggcaccaag   840
gttgagatca aggctgctgc attggataat gaaaaatcga acggcacaat cattcatgtg   900
aagggcaaac acctgtgtcc cagccccttg ttcccaggac ctagcaagcc tttttgggtt   960
ctcgtggtgg tgggcggcgt tctggcttgc tactctctac ttgtaactgt cgcatttatt  1020
atattctggg ttagattcag cgttgtgaag agaggccgga agaagctgct gtacatcttc  1080
aagcagccct catgagacc tgtgcagacc acacaggagg aagacggctg cagctgtaga  1140
ttccccgagg aagaggaggg cggctgtgag ctgagagtta agttcagcag gagcgccgac  1200
gcccctgcct accagcaagg acagaatcaa ctgtacaacg agctgaacct gggcagacgg  1260
gaggaatacg atgtgctgga caagaggaga ggcagagacc ccgagatggg cggcaaacct  1320
agaagaaaga acccccagga gggcctgtat aacgagctcc agaaggacaa gatggccgag  1380
gcctacagcg agatcggcat gaagggcgaa agaagaagag gcaagggcca cgacggcctc  1440
taccagggct taagcacagc tacaaaggac acctacgacg ccctgcacat gcaggccctg  1500
cccctagat gattaattaa atcgat                                        1526

SEQ ID NO: 286           moltype = DNA   length = 1526
FEATURE                  Location/Qualifiers
misc_feature            1..1526
                         note = Description of Artificial Sequence: Synthetic
                          polynucleotide
source                  1..1526
                         mol_type = other DNA
                         organism = synthetic construct
SEQUENCE: 286
ggtaccccg ggcccatggc tcttcctgtg acagctcttc tgctgccct ggccctgctt    60
ctgcatgctg ctagacctca ggttcagtta caacaatggg gagctggcct gttaaagccc   120
agcgaaaccc tgtccctcac ctgcgctgtg tatggcggaa gcttcagccg ctatgtgtgg   180
agctggatcc ggcagcctcc tggcaaaggc cttgaatgga tcggagagat agacagcagc   240
```

```
ggcaagacca actacaaccc cagcctgaaa tcacgcgtta caatctctgt ggacacaagc   300
aagaatcagt tctccctgaa gctgagcagc gttactgccg ccgacacagc tgtgtactat   360
tgcgccagag ttagatacga cagctccgac agctattact acagctatga ctacggcatg   420
gatgtgtggg ggcagggcac caccgttaca gttagctctg gaagcaccag cggctccggc   480
aagcctggat ctggtgaagg aagcacaaag ggcgacattg tgctcaccca gagccccgac   540
agcctggctg tgtctttagg cgaaagggct accatcaact gcaagagcag ccagagcgtt   600
ctgtacagca gcaacaacaa gaactacctt gcatggtatc aacagaagcc tggccagcct   660
cccaagctgc tcatctactg ggcctctagc agagagagcg gggttcccga tcgctttagc   720
ggcagcggtt ctggcaccga tttcactctt acaatcagca gcttacaggc cgaggatgtg   780
gctgtctact attgtcagca gagctatagc ttcccctgga cattcggcgg aggcaccaag   840
gttgagatca aggctgctgc attggataat gaaaaatcga acggcacaat cattcatgtg   900
aagggcaaac acctgtgtcc cagccccttg ttcccaggac ctagcaagcc ttttgggtt    960
ctcgtggtgg tgggcggcgt tctggcttgc tactctctac ttgtaactgt cgcatttatt  1020
atattctggg ttagattcag cgttgtgaag agaggccgga agaagctgct gtacatcttc  1080
aagcagccct tcatgagacc tgtgcagacc acacaggagg aagacggctg cagctgtaga  1140
ttccccgagg aagaggaggg cggctgtgag ctgagagtta agttcagcag gagcgccgac  1200
gcccctgcct accagcaagg acagaatcaa ctgtacaacg agctgaacct gggcagacgg  1260
gaggaatacg atgtgctgga caagaggaga ggcagagacc ccgagatggg cggcaaacct  1320
agaagaaaga accccaggga gggcctgtat aacgagctcc agaaggacaa gatggccgag  1380
gcctacagcg agatcggcat gaagggcgaa agaagaagag gcaagggcca cgacggcctc  1440
taccagggct taagcacagc tacaaaggac acctacgacg ccctgcacat gcaggccctg  1500
cccccctagat gattaattaa atcgat                                      1526
```

```
SEQ ID NO: 287        moltype = DNA  length = 1526
FEATURE               Location/Qualifiers
misc_feature          1..1526
                      note = Description of Artificial Sequence: Synthetic
                       polynucleotide
source                1..1526
                      mol_type = other DNA
                      organism = synthetic construct
SEQUENCE: 287
ggtaccccg ggcccatggc tcttcctgtg acagctcttc tgctgcccct ggccctgctt    60
ctgcatgctg ctagacctca ggttcagtta caacaatggg gagctggcct gttaaagccc   120
agcgaaaccc tgtccctcac ctgcgctgtg tatggcggaa gcttcagcgg ctacgcttgg   180
agctggatta gacagcctcc tggcaaagga ctagaatgga tcggagagat cgaccacaga   240
ggcttcacca actacaaccc cagcctgaaa tccagagtta caatctctgt ggacacaagc   300
aagaatcagt tctccctgaa gctgagcagc gttactgccg ccgacacagc tgtgtactat   360
tgcgccaggg ttagatacga cagcagcgac agctattact acagctatga ctacggcatg   420
gatgtgtggg ggcagggcac caccgttacg gttagctctg gatctaccag cggcagcggc   480
aagcctggct caggagaagg aagcacaaag ggcgacattg tgctcaccca gagccccgac   540
agcctggccg tttctttagg cgaaagggct accatcaact gcaagagcag ccagagcgtt   600
ctgtacagca gcaacaacaa gaactacctt gcatggtatc aacagaagcc aggccagcct   660
cccaagctgc tcatctactg ggcctctagc agagagagcg gggttcccga tagattttcg   720
ggatcaggct ccggcaccga tttcactctt acgatcagca gcttacaggc cgaggatgtg   780
gctgtctact attgtcagca gagctatagc ttccctgga cattcggcgg aggcaccaag    840
gttgagatca aggctgctgc attggataat gaaaaatcga acggcacaat cattcatgtg   900
aagggcaaac acctgtgtcc cagccccttg ttcccaggac ctagcaagcc ttttgggtt    960
ctcgtggtgg tgggcggcgt tctggcttgc tactctctac ttgtaactgt cgcatttatt  1020
atattctggg ttagattcag cgttgtgaag agaggccgga agaagctgct gtacatcttc  1080
aagcagccct tcatgagacc tgtgcagacc acacaggagg aagacggctg cagctgtaga  1140
ttccccgagg aagaggaggg cggctgtgag ctgagagtta agttcagcag gagcgccgac  1200
gcccctgcct accagcaagg acagaatcaa ctgtacaacg agctgaacct gggcagacgg  1260
gaggaatacg atgtgctgga caagaggaga ggcagagacc ccgagatggg cggcaaacct  1320
agaagaaaga accccaggga gggcctgtat aacgagctcc agaaggacaa gatggccgag  1380
gcctacagcg agatcggcat gaagggcgaa agaagaagag gcaagggcca cgacggcctc  1440
taccagggct taagcacagc tacaaaggac acctacgacg ccctgcacat gcaggccctg  1500
cccccctagat gattaattaa atcgat                                      1526
```

```
SEQ ID NO: 288        moltype = DNA  length = 1487
FEATURE               Location/Qualifiers
misc_feature          1..1487
                      note = Description of Artificial Sequence: Synthetic
                       polynucleotide
source                1..1487
                      mol_type = other DNA
                      organism = synthetic construct
SEQUENCE: 288
ggtaccccg ggcccatggc tcttcctgtg acagctcttc tgctgcccct ggccctgctt    60
ctgcatgctg ctagacctca ggttcagttg cagcaatggg gagctggcct gttaaagccc   120
agcgaaaccc tgtccctcac ctgcgctgtg tatggcggaa gcttcagcgg ctattactgg   180
agctggatcc ggcagcctcc tggaaaagga ttagaatgga tcggcgagat agaccacagc   240
gggagcacaa actacaaccc cagcctgaaa tcgcgggtta caatctctgt ggacacaagc   300
aagaatcagt tctccctgaa gctgagcagc gttactgccg ccgacacagc tgtgtactat   360
tgcgccagag cgggaggctc ctggtacagc aactggttcg atccttgggg ccaaggcacc   420
atggtgaccg tttccagcgg ctctacaagc ggcagcggga aacctggttc tggagagggc   480
agcacaaagg gcgacatcca gatgacacag agccccagca cccttagcgc ctctgtggga   540
gatagggtta ccattacctg cagggcttcc cagagcatca gcagctggct ggcatggtat   600
caacagaagc ctggcaaggc tcccaagctg ctcatctatg acgcctccag cctggaaagc   660
```

```
ggggttccct ccagatttag cggctcaggc tccggaacag agttcaccct taccatctct   720
agcctgcaac ccgacgactt cgctacttat tactgtcaac aagacagaag cttgcccccc   780
acattcggcg gagggaccaa ggttgagatc aaggctgctg cattggataa tgaaaaatcg   840
aacggcacaa tcattcatgt gaagggcaaa cacctgtgtc ccagcccctt gttcccagga   900
cctagcaagc cttttgggg tctcgtggtg gtgggcggcg ttctggcttg ctactctcta   960
cttgtaactg tcgcatttat tatattctg gttagattca gcgttgtgaa gagaggccgg  1020
aagaagctgc tgtacatctt caagcagccc ttcatgagac ctgtgcagac cacacaggag  1080
gaagacggct gcagctgtag attccccgag aagaggagg cggctgtga gctgagagtt  1140
aagttcagca ggagcgccga cgcccctgcc taccagcaag gacagaatca actgtacaac  1200
gagctgaacc tgggcagacg ggaggaatac gatgtgctgt acaagaggag aggcagagac  1260
cccgagatgg gcggcaaacc tagaagaaag aacccccagg agggcctgta taacgagctc  1320
cagaaggaca agatggccga ggcctacagc gagatcggca tgaagggcga agaagaaga  1380
ggcaagggc acgacggcct ctaccagggc ttaagcacag ctacaaagga cacctacgac  1440
gccctgcaca tgcaggccct gccccctaga tgattaatta aatcgat            1487
```

SEQ ID NO: 289          moltype = DNA   length = 1502
FEATURE                 Location/Qualifiers
misc_feature            1..1502
                        note = Description of Artificial Sequence: Synthetic
                        polynucleotide
source                  1..1502
                        mol_type = other DNA
                        organism = synthetic construct
SEQUENCE: 289

```
ggtaccccg ggcccatggc tcttcctgtg acagctcttc tgctgcccct ggccctgctt   60
ctgcatgctg ctagacctca ggttcagctt gtgcagagcg gagctgaagt taagaagct  120
ggcgcctctg tgaaggttag ctgcaaggcc agcggctaca cattcaagga atatggcatc  180
tcctgggtta ggcaggctcc cggccaaggc ttagaatgga tgggctggat ctccgcctac  240
tccgccaca cctactacgc ccagaagctt cagggcaggg ttaccatgac caccgacacc  300
agcacctcta ccgcctatat ggagctgagg agcctgagac ggacgacac agctgtgtat  360
tactgcgcca gaggccccca ctacgacgac tggtctggat ttatcatctg gttcgacccc  420
tgggggcagg gcaccctggt cacagtttct tctggctcca ccagcggaag cggcaagcca  480
ggctcaggcg aaggatctac aaaaggcgac atccaaatga cacagagccc cagcagcttg  540
agcgcctccg ttggcgacag agttacaatc acctgcaggg cctctcagag catcagcagc  600
tatttgaatt ggtatcaaca gaagccagga aaggcccta agctgctcat ctacgctgcc  660
agctcgctcc aatctggcgt tcctagcaga tttagcggct ccggcagcgg cacagacttt  720
actcttacca ttagctccct gcagcccgag gacttcgcta cctactattg ccagcaaagc  780
tacagattcc ctcccacctt tggccaggc acaaaggttg agatcaaggc tgctgcattg  840
gataatgaaa aatcgaacgg cacaatcatt catgtgaagg gcaaacacct gtgtcccagc  900
ccccttgttcc caggacctag caagcctttt tgggttctcg tggtggtggg cggcgttctg  960
gcttgctact ctctacttgt aactgtcgca tttattatat tctgggttag attcagcgtt  1020
gtgaagagag gccggaagaa gctgctgtac atcttcaagc agcccttcat gagacctgtg  1080
cagaccacac aggaggaaga cggctgcagc tgtagattcc ccgaggaaga ggaggggcgc  1140
tgtgagctga gagttaagtt cagcaggagc gccgacgccc ctgcctacca gcaaggacag  1200
aatcaactgt acaacgagct gaacctgggc agacgggagg aatacgatgt gctggacaag  1260
aggagaggca gagaccccga gatgggcggc aaacctagaa gaaagaaccc ccaggagggc  1320
ctgtataacg agctccagaa ggacaagatg gccgaggcct acagcgagat cggcatgaag  1380
ggcgaaagaa gaagaggcaa gggccacgac ggcctctacc agggcttaag cacagctaca  1440
aaggacacct acgacgccct gcacatgcag gccctgcccc ctagatgatt aattaaatcg  1500
at                                                              1502
```

SEQ ID NO: 290          moltype = DNA   length = 1508
FEATURE                 Location/Qualifiers
misc_feature            1..1508
                        note = Description of Artificial Sequence: Synthetic
                        polynucleotide
source                  1..1508
                        mol_type = other DNA
                        organism = synthetic construct
SEQUENCE: 290

```
ggtaccccg ggcccatggc tcttcctgtg acagctcttc tgctgcccct ggccctgctt   60
ctgcatgctg ctagacctca ggttcagttg cagcaatggg gagctggcct gttaaagccc  120
agcgaaaccc tgtccctcac ctgcgctgtg tatggcggaa gcttcagcgg catccactgg  180
aactggatcc ggcagcctcc tggcaaaggc cttgaatgga tcggcgatat cgacaccgac  240
ggctccacca actacaaccc cagcctgaaa tcgagggtta caatctctgt ggacacaagc  300
aagaatcagt tctccctgaa gctgagcagc gttactgccg ccgacacagc tgtgtactat  360
tgcgccgac tgggccagga aagcgctacc taccttggca tggatgtgtg ggggcagggc  420
accaccgtta ctgttagctc tggctcaaca agcggcagcg gcaagcctgg ctcaggaaa  480
ggaagcacaa agggcgacat tgtaatgact cagagccccg acagcctggc cgttagctta  540
ggcgaaaggg ctacaatcaa ttgcaagagc agccagagcg ttctgtacag cagcaacaac  600
aagaactacc tcgcatggta tcaacagaag ccaggccagc ctcccaagct gctcatctac  660
tgggcttcca ccagagagag cggggttccc gatagattct ccggctccgg ttctggaaca  720
gatttcacgc tcacaatcag cagcttacag gccgaggatg tggctgtcta ctattgtcag  780
cagttgtaca cctacccctt cacattcggc ggaggcacca aggttgagat caaggctgct  840
gcattggata tgaaaaatc gaacggcaca atcattcatg tgaagggcaa acacctgtgt  900
cccagcccct tgtccccagg acctagcaag ccttttttggg ttctcgtggt ggtgggcggc  960
gttctggctt gctactctct acttgtaact gtcgcatta ttatattctg gttagattc  1020
agcgttgtga agagaggccg gaagaagctg ctgtacatct tcaagcagcc cttcatgaga  1080
cctgtgcaga ccacacagga ggaagacggc tgcagctgta gattccccga ggaagaggag  1140
```

```
ggcggctgtg agctgagagt taagttcagc aggagcgccg acgcccctgc ctaccagcaa  1200
ggacagaatc aactgtacaa cgagctgaac ctgggcagac gggaggaata cgatgtgctg  1260
gacaagagga gaggcagaga ccccgagatg ggcggcaaac ctagaagaaa gaaccccag   1320
gagggcctgt ataacgagct ccagaaggac aagatggccg aggcctacag cgagatcggc  1380
atgaagggcg aaagaagaag aggcaagggc cacgacggcc tctaccaggg cttaagcaca  1440
gctacaaagg acacctacga cgccctgcac atgcaggccc tgcccctag atgattaatt   1500
aaatcgat                                                          1508

SEQ ID NO: 291         moltype = DNA  length = 3057
FEATURE                Location/Qualifiers
misc_feature           1..3057
                       note = Description of Artificial Sequence: Synthetic
                        polynucleotide
source                 1..3057
                       mol_type = other DNA
                       organism = synthetic construct
SEQUENCE: 291
atgctgctgc tggtgacatc tctgctgctt tgcgagctgc cccaccctgc cttcctgctt   60
atccccgaca ttcagatgac ccagaccacc agcagcctga gcgccagctt aggagataga  120
gttaccatca gctgcagagc cagccaggac atcagcaaat acctgaactg gtatcagcag  180
aagcccgacg gcactgtgaa actgcttatt taccacacct ccagactgca cagcggcgtt  240
cccagcagat tctctggcag cggatctgga accgactaca gcctcaccat ctccaacctg  300
gagcaggagg acatcgccac ctacttctgc cagcagggca acacagtgcc ctacaccttc  360
ggaggaggaa ccaagctgga gatcaccggg ggaggaggct ctggaggcgg cggatcagga  420
ggagggggat ctgaggttaa gctgcaggag agcggccctg gcctggtggc tcctagccaa  480
tctttatctg tgacctgcac tgtgtccggc gttagcctgc cggattatgg cgtttcctgg  540
atcagacagc cccccagaaa gggcctggaa tggctgggcg ttatctgggg cagcgagacc  600
acatactaca cagcgccct gaagagcaga cttacgatta tcaaggacaa cagcaagagc  660
caggttttcc tgaagatgaa cagcctgcag accgacgaca ccgccatcta ctactgcgct  720
aagcactact actacggcgg cagctacgcc atggactact ggggccaggg aacaagcgtt  780
accgttagca gcgctgctgc actggacaac gagaagagca acggcaccat catccacgtt  840
aagggcaagc acctgtgccc cagccctctg ttcctggac cttctaagcc tttctgggtt   900
ctggtggtgg tcggcggcgt tttagcctgt tacagccttc tggtgactgt ggccttcatc  960
atcttttggg ttagaagcaa gagaagcaga ctgctccaca gcgactacat gaacatgacc  1020
cccagacgga ctggcccac cagaaagcat taccagccct acgctcctcc cagagacttc  1080
gccgcctaca ggagcagagt taaattcagc agatccgccg atgcccccgc ttaccaacag  1140
ggacaaaacc agctgtacaa tgagctcaac ctggggagaa gagaagaata cgacgttctg  1200
gataagagaa ggggcagaga tcccgaaatg gggggcaagc ccagacgcaa gaaccctcag  1260
gaggggcttt acaacgaact gcagaaggat aagatgcctg aggcttactc ggagattggg  1320
atgaagggggg agagaaggcg gggcaaggga cacgatggct tataccaggg gctgagcacc  1380
gccaccaagg acacatacga cgctcttcat atgcaggctc tgcccccaag aagggctaag  1440
agatctggct ctggcgaggg cagaggcagc ttgcttacat gtggcgatgt ggaggagaac  1500
cccgggccca tggctcttcc tgtgacagct cttctgctgc ccctggccct gcttctgcat  1560
gctgctagac ctcagcttca gctccaagag agcggacctg gcttagtgaa gcccagcgaa  1620
accctgtccc tcacctgcac cgtttctggc ggaagcatca gcagctccag ctattactgg  1680
ggatggatca ggcagccccc tggcaagggt ttagaatgga tcggctcgat atattactcc  1740
ggcagcacct actataaccc cagcttgaag agccgggtta ccatttctgt ggacacatca  1800
aagaaccagt tcagcctgaa gctgagctct gtgactgccg ccgacacagc tgtgtactac  1860
tgtgccagag agacagacta ctccagcggc atgggctacg gcatggatgt gtggggacaa  1920
ggaaccaccg ttactgtgag cagcggttcc accagcggct caggcaagcc tggctcagga  1980
gaaggaagca ccaagggga tatacagatg acacagagcc cctccagcct gtccgccagc  2040
gttggcgatc gtgtaacgat cacctgccgg gcctctcaga gcatcaactc ctacctcaat  2100
tggtatcaac agaagccagg caaggccccc aaattactca tctacgccgc cagcagctta  2160
cagagcgggg ttccctctag attctccggc tccggttctg gaacagattt caccctcact  2220
atctccagct tgcagcccga ggatttcgcc acttattact gtcagcagag cctggccgac  2280
cccttcacat tcggcggagg cacaaaggtt gagatcaagg cagctgcttt cgtgcctgtg  2340
ttcctgcctg ctaagcccac caccactcct gctccaagac ctcctacccc cgctcctaca  2400
atcgccagcc aacctctgag cctgagaccg gaggcatgca gacctgcggc agggggagca  2460
gttcacacaa gaggcttgga cttcgcttgc gacatctaca tctgggcccc tctggccggc  2520
acatgcggag ttcttcttct tagcctggtg atcaccctgt actgcaacca cagaaacaga  2580
ttcagcgttg tgaagagagg ccggaagaag ctgctgtaca tcttcaagca gcccttcatg  2640
agacctgtgc agaccacaca ggaggaagac ggctgcagct gtagattccc cgaggaagag  2700
gagggcggct gtgagctgag agttaagttc agcaggagcc ccgacgcccc tgcctaccag  2760
caaggacaga atcaactgta caacgagctg aacctggggag acaggggagga atacgatgtg  2820
ctggacaaga ggagaggcag agaccccgag atgggcggca aacctagaag aaagaacccc  2880
caggagggcc tgtataacga gctccagaag gacaagatgg ccgaggccta cagcgagatc  2940
ggcatgaagg gcgaaagaag aagaggcaag ggccacgacg gcctctacca gggcttaagc  3000
acagctacaa aggacaccta cgacgccctg cacatgcagg ccctgccccc tagatga      3057

SEQ ID NO: 292         moltype = AA  length = 1018
FEATURE                Location/Qualifiers
REGION                 1..1018
                       note = Description of Artificial Sequence: Synthetic
                        polypeptide
source                 1..1018
                       mol_type = protein
                       organism = synthetic construct
SEQUENCE: 292
MLLLVTSLLL CELPHPAFLL IPDIQMTQTT SSLSASLGDR VTISCRASQD ISKYLNWYQQ   60
```

```
KPDGTVKLLI YHTSRLHSGV PSRFSGSGSG TDYSLTISNL EQEDIATYFC QQGNTLPYTF   120
GGGTKLEITG GGGSGGGGSG GGGSEVKLQE SGPGLVAPSQ SLSVTCTVSG VSLPDYGVSW   180
IRQPPRKGLE WLGVIWGSET TYYNSALKSR LTIIKDNSKS QVFLKMNSLQ TDDTAIYYCA   240
KHYYYGGSYA MDYWGQGTSV TVSSAAALDN EKSNGTIIHV KGKHLCPSPL FPGPSKPFWV   300
LVVVGGVLAC YSLLVTVAFI IFWVRSKRSR LLHSDYMNMT PRRPGPTRKH YQPYAPPRDF   360
AAYRSRVKFS RSADAPAYQQ GQNQLYNELN LGRREEYDVL DKRRGRDPEM GGKPRRKNPQ   420
EGLYNELQKD KMAEAYSEIG MKGERRRGKG HDGLYQGLST ATKDTYDALH MQALPPRRAK   480
RSGSGEGRGS LLTCGDVEEN PGPMALPVTA LLLPLALLLH AARPQLQLQE SGPGLVKPSE   540
TLSLTCTVSG GSISSSSYYW GWIRQPPGKG LEWIGSIYYS GSTYYNPSLK SRVTISVDTS   600
KNQFSLKLSS VTAADTAVYY CARETDYSSG MGYGMDVWGQ GTTVTVSSGS TSGSGKPGSG   660
EGSTKGDIQM TQSPSSLSAS VGDRVTITCR ASQSINSYLN WYQQKPGKAP KLLIYAASSL   720
QSGVPSRFSG SGSGTDFTLT ISSLQPEDFA TYYCQQSLAD PFTFGGGTKV EIKAAAFVPV   780
FLPAKPTTTP APRPPTPAPT IASQPLSLRP EACRPAAGGA VHTRGLDFAC DIYIWAPLAG   840
TCGVLLLSLV ITLYCNHRNR FSVVKRGRKK LLYIFKQPFM RPVQTTQEED GCSCRFPEEE   900
EGGCELRVKF SRSADAPAYQ QGQNQLYNEL NLGRREEYDV LDKRRGRDPE MGGKPRRKNP   960
QEGLYNELQK DKMAEAYSEI GMKGERRRGK GHDGLYQGLS TATKDTYDAL HMQALPPR   1018
```

```
SEQ ID NO: 293        moltype = DNA  length = 2202
FEATURE               Location/Qualifiers
misc_feature          1..2202
                      note = Description of Artificial Sequence: Synthetic
                      polynucleotide
source                1..2202
                      mol_type = other DNA
                      organism = synthetic construct
SEQUENCE: 293
atgcttctcc tggtgacaag ccttctgctc tgtgagttac cacacccagc attcctcctg   60
atcccagaca tccagatgac ccagtctcca tcctccctgt ctgcatctgt aggagacaga   120
gtcaccatca cttgccgggc aagtcagagc attaacagct atttaaattg gtatcagcag   180
aaaccaggga aagcccctaa gctcctgatc tatgctgcat ccagtttgca aagtggggtc   240
ccatcaaggt tcagtggcag tggatctggg acagatttca ctctcaccat cagcagtctg   300
caacctgaag attttgcaac ttactactgc cagcaaagcc tcgccgaccc tttcactttt   360
ggcggaggga ccaaggttga gatcaaaggg ggggtggaa gtgggaagcc tggcagcggc   420
gagggcggca gtcagctgca gctgcaggag tcgggcccag gactggtgaa gccttcggag   480
accctgtccc tcacctgcac tgtctctggt ggctccatca gcagtagtag ttactactgg   540
ggctggatcc gccagccccc agggaagggg ctggagtgga ttgggagtat ctattatagt   600
gggagcacct actacaaccc gtccctcaag agtcgagtca ccatatccgt agacacgtcc   660
aagaaccagt tctccctgaa gctgagttct gtgaccgccg cagacacggc ggtgtactac   720
tgcgccagag agactgacta cagcagcgga atgggatacg gaatggacgt atggggccag   780
ggaacaactg tcaccgtctc ctcaggcggg ggcggcagtg gaagcctgg cagcgatatt   840
caaatgaccc agtccccgtc ctccctgagt gcctccgtcg gtgaccgtgt tacgattacc   900
tgccgtgcga gccaagacat ctctaaatac ctgaactggt atcagcaaaa accggatcag   960
gcaccgaaac tgctgatcaa acatacctca cgtctgcact cgggtgtgcc gagccgcttt   1020
agtggttccg gctcaggtac cgattacacc ctgacgatca gctctctgca gccggaagac   1080
tttgccacgt attactgcca gcaaggtaat accctgccgt atacgttcgg ccaaggtacc   1140
aaactggaaa tcaaaggggg gggtggaagt ggggggcggtg gcagcggcgg tggcggcagt   1200
gaagtgcagc tggttgaaag cggtggtggt ctggttcaaa gcggtggtgg cctgcgtctg   1260
tcatgtacgg cgagtggtgt ctccctgccg gactatggcg tgtcctggat cgtcagccg   1320
ccgggtaaag gcctggaatg gattggtgtc atctggggca gtgaaccac gtattacaac   1380
tcggccctga aaagccgttt caccatctct cgcgataaca gtaaaaatac gctgtacctg   1440
cagatgaata gcctgcgcgc ggaagacacc gccgtttact actgcgcaaa acattactac   1500
tacggtggca gctatgctat ggattactgg ggtcaaggca cgctggtcac cgtttcgtca   1560
gccgctgccc tagacaatga gaagagcaat ggaaccatta ccatgtgaa agggaaacac   1620
ctttgtccaa gtcccctatt tcccggacct tctaagccct ttgggtgctg gtggtggtt   1680
ggggagtcc tggcttgcta tagcttgcta gtaacagtgg cctttattat tttctgggtg   1740
aggagtaaga ggagcaggct cctgcacagt gactacatga acatgactcc ccgccgcccc   1800
gggcccaccc gcaagcatta ccagccctat gccccaccac gcgacttcgc agcctatcgc   1860
tccagagtga agttcagcag gagcgcagac gcccccgcgt accagcaggg ccagaaccag   1920
ctctataacg agctcaatct aggacgaaga gaggagtacg atgtttggga caagagacgt   1980
ggccgggacc ctgagatggg gggaaagccg agaaggaaga accctcagga aggcctgtac   2040
aatgaactgc agaaagataa gatggcggag gcctacagtg agattgggat gaaaggcgag   2100
cgccggaggc gcaggggca cgatggcctt taccagggtc tcagtacagc caccaaggac   2160
acctacgacg cccttcacat gcaggccctg cccctcgat ga   2202
```

```
SEQ ID NO: 294        moltype = AA  length = 733
FEATURE               Location/Qualifiers
REGION                1..733
                      note = Description of Artificial Sequence: Synthetic
                      polypeptide
source                1..733
                      mol_type = protein
                      organism = synthetic construct
SEQUENCE: 294
MLLLVTSLLL CELPHPAFLL IPDIQMTQSP SSLSASVGDR VTITCRASQS INSYLNWYQQ   60
KPGKAPKLLI YAASSLQSGV PSRFSGSGSG TDFTLTISSL QPEDFATYYC QQSLADPFTF   120
GGGTKVEIKG GGGSGKPGSG EGGSQLQLQE SGPGLVKPSE TLSLTCTVSG GSISSSSYYW   180
GWIRQPPGKG LEWIGSIYYS GSTYYNPSLK SRVTISVDTS KNQFSLKLSS VTAADTAVYY   240
CARETDYSSG MGYGMDVWGQ GTTVTVSSGG GGSGKPGSDI QMTQSPSSLS ASVGDRVTIT   300
CRASQDISKY LNWYQQKPDQ APKLLIKHTS RLHSGVPSRF SGSGSGTDYT LTISSLQPED   360
```

```
FATYYCQQGN TLPYTFGQGT KLEIKGGGGS GGGGSGGGGS EVQLVESGGG LVQPGRSLRL   420
SCTASGVSLP DYGVSWIRQP PGKGLEWIGV IWGSETTYYN SALKSRFTIS RDNSKNTLYL   480
QMNSLRAEDT AVYYCAKHYY YGGSYAMDYW GQGTLVTVSS AAALDNEKSN GTIIHVKGKH   540
LCPSPLFPGP SKPFWVLVVV GGVLACYSLL VTVAFIIFWV RSKRSRLLHS DYMNMTPRRP   600
GPTRKHYQPY APPRDFAAYR SRVKFSRSAD APAYQQGQNQ LYNELNLGRR EEYDVLDKRR   660
GRDPEMGGKP RRKNPQEGLY NELQKDKMAE AYSEIGMKGE RRRGKGHDGL YQGLSTATKD   720
TYDALHMQAL PPR                                                      733

SEQ ID NO: 295          moltype = AA   length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 295
MLLLVTSLLL CELPHPAFLL IP                                            22

SEQ ID NO: 296          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 296
DIQMTQSPSS LSASVGDRVT ITCRASQSIN SYLNWYQQKP GKAPKLLIYA ASSLQSGVPS   60
RFSGSGSGTD FTLTISSLQP EDFATYYCQQ SLADPFTFGG GTKVEIK                 107

SEQ ID NO: 297          moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 297
GGGGSGKPGS GEGGS                                                    15

SEQ ID NO: 298          moltype = AA   length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 298
QLQLQESGPG LVKPSETLSL TCTVSGGSIS SSSYYWGWIR QPPGKGLEWI GSIYYSGSTY   60
YNPSLKSRVT ISVDTSKNQF SLKLSSVTAA DTAVYYCARE TDYSSGMGYG MDVWGQGTTV   120
TVSS                                                                124

SEQ ID NO: 299          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 299
GGGGSGKPGS                                                          10

SEQ ID NO: 300          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 300
DIQMTQSPSS LSASVGDRVT ITCRASQDIS KYLNWYQQKP DQAPKLLIKH TSRLHSGVPS   60
RFSGSGSGTD YTLTISSLQP EDFATYYCQQ GNTLPYTFGQ GTKLEIK                 107

SEQ ID NO: 301          moltype = AA   length = 15
FEATURE                 Location/Qualifiers
REGION                  1..15
                        note = Description of Artificial Sequence: Synthetic peptide
```

-continued

```
source                 1..15
                       mol_type = protein
                       organism = synthetic construct
SEQUENCE: 301
GGGGSGGGGS GGGGS                                               15

SEQ ID NO: 302         moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 302
EVQLVESGGG LVQPGRSLRL SCTASGVSLP DYGVSWIRQP PGKGLEWIGV IWGSETTYYN   60
SALKSRFTIS RDNSKNTLYL QMNSLRAEDT AVYYCAKHYY YGGSYAMDYW GQGTLVTVSS  120

SEQ ID NO: 303         moltype = AA  length = 30
FEATURE                Location/Qualifiers
REGION                 1..30
                       note = Description of Artificial Sequence: Synthetic
                        polypeptide
source                 1..30
                       mol_type = protein
                       organism = synthetic construct
SEQUENCE: 303
LDNEKSNGTI IHVKGKHLCP SPLFPGPSKP                                30

SEQ ID NO: 304         moltype = AA  length = 27
FEATURE                Location/Qualifiers
REGION                 1..27
                       note = Description of Artificial Sequence: Synthetic peptide
source                 1..27
                       mol_type = protein
                       organism = synthetic construct
SEQUENCE: 304
FWVLVVVGGV LACYSLLVTV AFIIFWV                                   27

SEQ ID NO: 305         moltype = AA  length = 41
FEATURE                Location/Qualifiers
REGION                 1..41
                       note = Description of Artificial Sequence: Synthetic
                        polypeptide
source                 1..41
                       mol_type = protein
                       organism = synthetic construct
SEQUENCE: 305
RSKRSRLLHS DYMNMTPRRP GPTRKHYQPY APPRDFAAYR S                   41

SEQ ID NO: 306         moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 306
RVKFSRSADA PAYQQGQNQL YNELNLGRRE EYDVLDKRRG RDPEMGGKPR RKNPQEGLYN   60
ELQKDKMAEA YSEIGMKGER RRGKGHDGLY QGLSTATKDT YDALHMQALP PR         112

SEQ ID NO: 307         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 307
GGGGS                                                          5

SEQ ID NO: 308         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
```

-continued

```
SEQUENCE: 308
GGGGSGGGGS                                                              10

SEQ ID NO: 309          moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 309
GGGGSGGGGS GGGGS                                                        15

SEQ ID NO: 310          moltype = AA   length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 310
GGGGSGGGGS GGGGSGGGGS                                                   20

SEQ ID NO: 311          moltype = AA   length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 311
PSTPPTPSPS TPPTPSPS                                                     18

SEQ ID NO: 312          moltype = AA   length = 50
FEATURE                 Location/Qualifiers
REGION                  1..50
                        note = Description of Artificial Sequence: Synthetic
                         polypeptide
REGION                  1..50
                        note = MISC_FEATURE - This sequence may encompass 1-10 "Pro
                         Ala Pro Ala Pro" repeating units
source                  1..50
                        mol_type = protein
                        organism = synthetic construct
SEQUENCE: 312
PAPAPPAPAP PAPAPPAPAP PAPAPPAPAP PAPAPPAPAP PAPAPPAPAP         50

SEQ ID NO: 313          moltype = AA   length = 50
FEATURE                 Location/Qualifiers
REGION                  1..50
                        note = Description of Artificial Sequence: Synthetic
                         polypeptide
REGION                  1..50
                        note = MISC_FEATURE - This sequence may encompass 1-10 "Glu
                         Ala Ala Ala Lys" repeating units
source                  1..50
                        mol_type = protein
                        organism = synthetic construct
SEQUENCE: 313
EAAAKEAAAK EAAAKEAAAK EAAAKEAAAK EAAAKEAAAK EAAAKEAAAK         50

SEQ ID NO: 314          moltype = AA   length = 8
FEATURE                 Location/Qualifiers
REGION                  1..8
                        note = Description of Artificial Sequence: Synthetic peptide
VARIANT                 2
                        note = X is Val or Ile
VARIANT                 4
                        note = X is any amino acid
source                  1..8
                        mol_type = protein
                        organism = synthetic construct
SEQUENCE: 314
DXEXNPGP                                                                 8
```

What is claimed is:

1. A polynucleotide encoding an anti-CD20 chimeric antigen receptor (CAR) comprising an anti-CD20 antigen-binding fragment, wherein the anti-CD20 antigen-binding fragment comprises a heavy chain variable domain (VH) comprising heavy chain complementarity determining regions HCDR1, HCDR2 and HCDR3, and a light chain variable domain (VL) comprising light chain complementarity determining regions LCDR1, LCDR2 and LCDR3, wherein the HCDR1, HCDR2, HCDR3, LCDR1, LCDR2 and LCDR3, respectively, comprise the amino acid sequences of SEQ ID NO:48, 51, 54, 59, 62 and 65.

2. The polynucleotide of claim 1, wherein the VH comprises the amino acid sequence of SEQ ID NO:45 and the VL comprises the amino acid sequence of SEQ ID NO:56.

3. The polynucleotide of claim 1, which further encodes an anti-CD19 CAR comprising an anti-CD19 antigen-binding fragment having specificity to CD19.

4. The polynucleotide of claim 3, wherein the anti-CD19 antigen-binding fragment comprises a VH comprising HCDR1, HCDR2, and HCDR3, and a VL comprising LCDR1, LCDR2 and LCDR3, wherein the HCDR1, HCDR2, HCDR3, LCDR1, LCDR2 and LCDR3, respectively, comprise the amino acid sequences of SEQ ID NO:224, 227, 230, 235, 238, and 241.

5. The polynucleotide of claim 4, wherein the VH of the anti-CD19 antigen-binding fragment comprises the amino acid sequence of SEQ ID NO:221, and the VL of the antigen-binding fragment comprises the amino acid sequence of SEQ ID NO:232.

6. The polynucleotide of claim 4, wherein the anti-CD20 antigen-binding fragment or the anti-CD19 antigen-binding fragment is a single chain fragment (scFv).

7. The polynucleotide of claim 4, wherein the anti-CD20 CAR and the anti-CD19 CAR each further comprise a transmembrane domain of CD8 alpha or CD28.

8. The polynucleotide of claim 7, wherein the anti-CD20 CAR and the anti-CD19 CAR each further comprise a signaling domain of 4-1BB or CD28.

9. The polynucleotide of claim 8, wherein the anti-CD20 CAR and the anti-CD19 CAR each further comprise a CD3z stimulatory domain.

10. The polynucleotide of claim 4, which further comprises a cleavable linker between the anti-CD20 CAR and the anti-CD19 CAR.

11. The polynucleotide of claim 10, wherein the cleavable linker is a 2A linker.

12. A cell comprising the polynucleotide of claim 1.

13. A polynucleotide encoding an anti-CD20 chimeric antigen receptor (CAR) comprising an anti-CD20 antigen-binding fragment, wherein the anti-CD20 antigen-binding fragment comprises a heavy chain variable domain (VH) comprising heavy chain complementarity determining regions HCDR1, HCDR2 and HCDR3, and a light chain variable domain (VL) comprising light chain complementarity determining regions LCDR1, LCDR2 and LCDR3, wherein the HCDR1, HCDR2, HCDR3, LCDR1, LCDR2 and LCDR3, respectively, comprise the amino acid sequences of SEQ ID NO:70, 73, 76, 81, 84, and 87.

14. The polynucleotide of claim 13, wherein the VH comprises the amino acid sequence of SEQ ID NO:67 and the VL comprises the amino acid sequence of SEQ ID NO:78.

15. The polynucleotide of claim 14, which further encodes an anti-CD19 CAR comprising an anti-CD19 antigen-binding fragment having specificity to CD19.

16. The polynucleotide of claim 15, wherein the anti-CD19 antigen-binding fragment comprises a VH comprising HCDR1, HCDR2, and HCDR3, and a VL comprising LCDR1, LCDR2 and LCDR3, wherein the HCDR1, HCDR2, HCDR3, LCDR1, LCDR2 and LCDR3, respectively, comprise the amino acid sequences of SEQ ID NO:224, 227, 230, 235, 238, and 241.

17. The polynucleotide of claim 16, wherein the VH of the anti-CD19 antigen-binding fragment comprises the amino acid sequence of SEQ ID NO:221, and the VL of the antigen-binding fragment comprises the amino acid sequence of SEQ ID NO:232.

18. The polynucleotide of claim 17, wherein the anti-CD20 antigen-binding fragment or the anti-CD19 antigen-binding fragment is a single chain fragment (scFv).

19. The polynucleotide of claim 18, wherein the anti-CD20 scFv and the anti-CD19 scFv each further comprises a linker between the VH and the VL.

20. The polynucleotide of claim 19, wherein the linker comprises the amino acid sequence of SEQ ID NO:247.

21. The polynucleotide of claim 20, wherein the anti-CD20 CAR further comprises a transmembrane domain of CD8 alpha.

22. The polynucleotide of claim 21, wherein the anti-CD20 CAR further comprises a signaling domain of 4-1BB.

23. The polynucleotide of claim 22, wherein the anti-CD19 CAR further comprises a transmembrane domain of CD28.

24. The polynucleotide of claim 23, wherein the anti-CD19 CAR further comprises a signaling domain of CD28.

25. The polynucleotide of claim 24, wherein the anti-CD20 CAR and the anti-CD19 CAR each further comprise a CD3z signaling domain.

26. The polynucleotide of claim 25, which further comprises a cleavable linker between the anti-CD20 CAR and the anti-CD19 CAR.

27. The polynucleotide of claim 26, wherein the cleavable linker is a 2A linker.

28. A cell comprising the polynucleotide of claim 27.

29. A method of generating an engineered cell, the method comprising transfecting or transducing a cell with a polynucleotide according to claim 27.

* * * * *